(12) United States Patent
Barnes et al.

(10) Patent No.: US 9,040,690 B2
(45) Date of Patent: May 26, 2015

(54) 2,3,5-TRISUBSTITUTED THIOPHENE COMPOUNDS AND USES THEREOF

(75) Inventors: David Barnes, Waban, MA (US); Scott Louis Cohen, Peabody, MA (US); Jiping Fu, Lafayette, CA (US); Lei Shu, Woburn, MA (US); Rui Zheng, Waltham, MA (US)

(73) Assignee: Novartis AG, Basel (CH)

( * ) Notice: Subject to any disclaimer, the term of this patent is extended or adjusted under 35 U.S.C. 154(b) by 164 days.

(21) Appl. No.: 13/810,277

(22) PCT Filed: Jul. 21, 2011

(86) PCT No.: PCT/EP2011/062545
§ 371 (c)(1),
(2), (4) Date: Jan. 15, 2013

(87) PCT Pub. No.: WO2012/010663
PCT Pub. Date: Jan. 26, 2012

(65) Prior Publication Data
US 2013/0123252 A1 May 16, 2013

Related U.S. Application Data

(60) Provisional application No. 61/366,687, filed on Jul. 22, 2010, provisional application No. 61/423,346, filed on Dec. 15, 2010.

(51) Int. Cl.
| | | |
|---|---|---|
| *A61K 31/381* | (2006.01) |
| *A61K 31/5377* | (2006.01) |
| *C07D 413/14* | (2006.01) |
| *C07D 413/04* | (2006.01) |
| *C07D 409/04* | (2006.01) |
| *C07D 409/14* | (2006.01) |
| *C07D 417/14* | (2006.01) |
| *C07D 487/04* | (2006.01) |
| *C07D 498/04* | (2006.01) |
| *A61K 31/422* | (2006.01) |
| *A61K 31/4535* | (2006.01) |
| *A61K 31/496* | (2006.01) |
| *A61K 31/506* | (2006.01) |
| *A61K 31/541* | (2006.01) |
| *A61K 31/553* | (2006.01) |
| *A61K 45/06* | (2006.01) |

(52) U.S. Cl.
CPC ............ *C07D 409/04* (2013.01); *A61K 31/381* (2013.01); *C07D 409/14* (2013.01); *C07D 413/04* (2013.01); *C07D 413/14* (2013.01); *C07D 417/14* (2013.01); *C07D 487/04* (2013.01); *C07D 498/04* (2013.01); *A61K 31/422* (2013.01); *A61K 31/4535* (2013.01); *A61K 31/496* (2013.01); *A61K 31/506* (2013.01); *A61K 31/5377* (2013.01); *A61K 31/541* (2013.01); *A61K 31/553* (2013.01); *A61K 45/06* (2013.01)

(58) Field of Classification Search
CPC . A61K 31/381; A61K 31/422; A61K 31/496; A61K 31/5377; A61K 31/553; A61K 31/4535; A61K 31/506; A61K 31/541; C07D 409/14; C07D 409/04; C07D 413/14; C07D 413/04; C07D 487/04; C07D 417/14; C07D 498/04
See application file for complete search history.

(56) References Cited

U.S. PATENT DOCUMENTS

2011/0020278 A1    1/2011  Canales

FOREIGN PATENT DOCUMENTS

| DE | 10 2004 061 746 A1 | 7/2006 |
| GB | 2 450 771 | 1/2009 |
| WO | WO 02/100851 | 12/2002 |
| WO | WO 2005/005435 | 1/2005 |
| WO | WO 2006/072347 | 7/2006 |
| WO | WO 2008/058393 | 5/2008 |
| WO | WO 2011/031669 | 3/2011 |
| WO | WO 2011/068715 | 6/2011 |

OTHER PUBLICATIONS

Lazerwith et al., "Discovery of GS-9669, a Thumb Site II Non-Nucleoside Inhibitor of NS5B for the Treatment of Genotype 1 Chronic Hepatitis C Infection" *J. Med. Chem.* 57:1893-1901, 2014.
David Barnes-Seeman et al., "Design and Synthesis of Lactam-Thiophene Carboxylic Acids as Potent Hepatitis C Virus Polymerase Inhibitors" *Bioorganic and Medicinal Chemistry Letters* 24:3979-3985, 2014.
Hanbiao Yang et al., "Cyclic Amide Bioisosterism: Strategic Application to the Design and Synthesis of HCV NS5B Polymerase Inhibitors" *Bioorganic and Medicinal Chemistry Letters* 20(15):4614-4619, 2010.
Herlihy et al., "Development of Intergenotypic Chimeric Replicons to Determine the Broad-Spectrum Antiviral Activitys of Hepatitis C Virus Polymerase Inhibitors" *Antimicrobial Agents and Chemotherapy* 52(10):3523-3531, Oct. 2008.

*Primary Examiner* — Rebecca Anderson
(74) *Attorney, Agent, or Firm* — Michael G. Smith

(57) ABSTRACT

The present invention provides a compound of formula I:

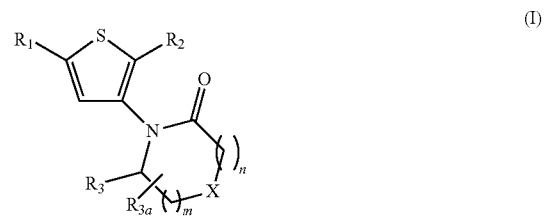

a method for manufacturing the compounds of the invention, and its therapeutic uses. The present invention further provides a combination of pharmacologically active agents and a pharmaceutical composition.

13 Claims, No Drawings

2,3,5-TRISUBSTITUTED THIOPHENE COMPOUNDS AND USES THEREOF

CROSS-REFERENCE TO RELATED APPLICATIONS

This application is the U.S. National Stage of International Application No. PCT/EP2011/062545, filed Jul. 21, 2011, which claims the benefit of priority to U.S. Provisional Application Ser. No. 61/366,687, filed on Jul. 22, 2010, and U.S. Provisional Application Ser. No. 61/423,346, filed on Dec. 15, 2010.

FIELD OF THE INVENTION

Compounds and compositions, methods for their preparation, and methods for their use in treating viral infections in patients mediated, at least in part, by a virus in the Flaviviridae family of viruses are disclosed.

STATE OF THE ART

Chronic infection with HCV is a major health problem associated with liver cirrhosis, hepatocellular carcinoma, and liver failure. An estimated 170 million chronic carriers worldwide are at risk of developing liver disease (Szabo, E. et al., *Pathol. Oncol. Res.* 2003, 9:215-221; Hoofnagle J. H., *Hepatology* 1997, 26:15S-20S). In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. Because the replicative cycle of HCV does not involve any DNA intermediate and the virus is not integrated into the host genome, HCV infection can theoretically be cured.

At present, the standard treatment for chronic HCV is pegylated interferon alpha (IFN-alpha) in combination with ribavirin and this requires at least six (6) months of treatment. IFN-alpha belongs to a family of naturally occurring small proteins with characteristic biological effects such as antiviral, immunoregulatory, and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load and there is a clear need for more effective antiviral therapy of HCV infection (Fried, M. W., et al. *N. Engl. J Med* 2002, 347:975-982).

A number of approaches are being pursued to combat the virus. These include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4a protease and the NS5b RNA-dependent RNA polymerase are considered the most promising viral targets for new drugs (see Ni, Z. J. and Wagman, A. S. *Curr. Opin. Drug Discov. Devel.* 2004, 7, 446-459; Beaulieu, P. L. and Tsantrizos, Y. S. *Curr. Opin. Investig. Drugs* 2004, 5, 838-850; and Griffith, R. C. et al., *Ann. Rep. Med. Chem* 39, 223-237, 2004). However, none of these compounds have progressed beyond clinical trials.

In view of the worldwide epidemic level of HCV and other members of the Flaviviridae family of viruses, and further in view of the limited treatment options, there is a strong need for new effective drugs for treating infections cause by these viruses.

SUMMARY OF THE INVENTION

In a first embodiment, the invention provides compounds of Formula (I), compositions thereof and methods of using same to treat viral infection. In particular, the compounds of the invention as defined by Formula (I) are useful for the treatment or prevention of hepatitis C virus infection and diseases associated with or caused by HCV infection. The structure of compounds of Formula (I) is as follows:

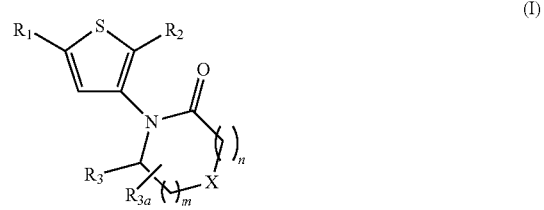

(I)

Compounds of Formula (I) includes salts thereof. Definitions for variables present in Formula (I) are defined infra.

Unless specified otherwise, the term "compounds of the present invention" refers to compounds of Formula (I) and subformulae thereof (add other additional genus structures as necessary), prodrugs thereof, salts of the compound and/or prodrugs, hydrates or solvates of the compounds, salts and/or prodrugs, as well as all stereoisomers (including diastereoisomers and enantiomers), tautomers and isotopically labeled compounds (including deuterium substitutions), as well as inherently formed moieties (e.g., polymorphs, solvates and/or hydrates).

In one embodiment provided is a pharmaceutical composition comprising a pharmaceutically acceptable carrier and a therapeutically effective amount of a compound of Formula (I).

In other embodiments provided are methods for preparing the compounds of Formula (I) and compositions thereof and for their therapeutic uses. In one embodiment provided is a method for treating a viral infection in a patient mediated at least in part by a virus in the Flaviviridae family of viruses, comprising administering to said patient a composition comprising a compound or a salt of Formula (I). In some aspects, the viral infection is mediated by hepatitis C virus.

These and other embodiments of the invention are further described in the text that follows.

DETAILED DESCRIPTION OF THE INVENTION

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 6-, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, and thiomorpholine.

The term "heterocyclyl" further refers to heterocyclic groups as defined herein substituted with 1 to 5 substituents independently selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) amido or carboxamido
(m) cyano;
(n) sulfamoyl, sulfamido or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and (x) aryl substituted with alkyl, cycloalkyl, alkoxy, hydroxy, amino, alkyl-C(O)—NH—, alkylamino, dialkylamino or halogen.

(y) alkyl substituted with cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, sulfamido, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) amido or carboxamido
(m) cyano;
(n) sulfamoyl, sulfamido or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.
(y) alkyl substituted with cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) amido or carboxamido (m) cyano;
(n) sulfamoyl, sulfamido or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.
(y) alkyl substituted with cycloalkyl, alkoxy, hydroxy, amino, alkyl-C(O)—NH—, alkylamino, dialkylamino or halogen.

In one aspect, compounds of Formula (I) are provided:

1. A compound of formula (I):

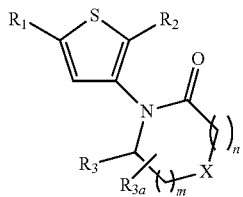

or a salt thereof, wherein m is 0, 1 or 2;

n is 0 or 1, wherein m+n is 1, 2 or 3;

$R_1$ is $C_3$-$C_{10}$alkynyl or phenyl, which phenyl is substituted with 0, 1, 2, or 3 substituents which are independently selected from the group consisting of halogen, hydroxy, cyano, $C_1$-$C_4$alkyl, halo$C_1$-$C_4$alkyl and $C_1$-$C_4$alkoxy, and which alkynyl is optionally substituted with a $C_3$-$C_7$cycloalkyl substituent, which cycloalkyl is optionally substituted with 1 or 2 independently selected $C_1$-$C_4$alkyl groups;

$R_2$ is $CO_2H$, tetrazole, C(O)N(H)S(O)$_2$CH$_3$ or a carboxylic acid isostere;

$R_3$ is $C_3$-$C_7$cycloalkyl which is substituted with 0, 1, 2 or 3 halogen atoms;

$R_{3a}$ represents 0, 1, 2, 3 or 4 residues independently selected at each occurrence from the group consisting of hydroxy, amino, cyano, halogen, $C_1$-$C_6$alkyl, $C_1$-$C_6$alkoxy, wherein each alkyl or alkoxy substituent is substituted with 0, 1 or 2 substituents independently selected from hydroxy, cyano, $C_1$-$C_4$alkoxy, $C_1$-$C_4$alkylsulfone, N(R$_{3b}$)$_2$, C(O)N (R$_{3b}$), heterocycle having 4 to 7 ring atoms and 1 or 2 ring heteroatoms selected from N, O or S and 5 or 6 member heteroaryl; or two geminal $R_{3a}$ substituents, taken in combination form a spirocyclic 3 to 6 member cycloalkyl or heterocycle;

$R_{3b}$ is independently selected at each occurrence from hydrogen, $C_1$-$C_4$alkyl, $C_1$-$C_4$alkoxy$C_1$-$C_4$alkyl and $C_1$-$C_4$alkanoyl; or N(R$_{3b}$)$_2$, taken in combination, form a 4 to 6 member heterocycle having 0 or 1 additional ring heteroatoms selected from N, O or S;

X is O, N-L-$R_4$ or CR$_5$R$_6$;

L is a bond, S(O)$_2$, C(O) or C(O)O;

$R_4$ is $C_1$-$C_6$alkyl, $C_3$-$C_7$cycloalkyl or $C_3$-$C_7$cycloalkyl$C_1$-$C_4$alkyl each of which is substituted with 0, 1 or 2 hydroxy and 0 or 1 substituents selected from cyano, S(O)$_2$—$C_1$-$C_4$alkyl, $CO_2H$, NR$_{4a}$R$_{4b}$, phenyl or pyridyl, wherein the phenyl or pyridyl substituent is substituted with 0, 1, or 2 substituents selected from $C_1$-$C_4$alkyl, halogen, NR$_{4a}$R$_{4b}$ or 5 or 6 member heteroaryl having 1 or 2 ring nitrogen atoms;

$R_4$ is naphthyl or phenyl, which phenyl is substituted with 0, 1, 2, or 3 substituents independently selected form the group consisting of halogen, cyano, $C_1$-$C_6$alkyl, halo$C_1$-$C_6$alkyl, $C_1$-$C_6$alkoxy, halo$C_1$-$C_6$alkoxy, hydroxy, hydroxy$C_1$-$C_4$alkyl, amino$C_1$-$C_4$alkyl, $C_1$-$C_6$alkyl-OC(O)NH—, $C_1$-$C_4$alkyl-C(O)NH—, NR$_{4a}$R$_{4b}$, $CO_2H$, —C(O)NR$_{4a}$R$_{4b}$, phenyl, phenoxy, heteroaryl having one or two ring nitrogen atoms and having 0, 1, or 2 $C_1$-$C_4$alkyl substituents, or two substituents combine to form a fused heterocyclic or heteroary ring, which fused heterocycle has 5, 6 or 7 ring atoms, has 1 or 2 ring heteroatoms selected from N, O or S, and which fused heterocycle is substituted with 0, 1 or 2 substituents independently selected from $C_1$-$C_6$alkyl or oxo and which fused heteroaryl has 5 or 6 ring atoms, has 1 or 2 ring heteroatoms selected from N, O or S and which fused heteroaryl is substituted with 0, 1, or 2 independently selected $C_1$-$C_4$alkyl substituents; or $R_4$ is a 5 or 6 member heteroaryl having 1 to 3 heteroatoms selected from N, O or S, which heteroaryl is substituted with 0, 1, 2 or 3 substituents independently selected from the group consisting of halogen, cyano, $C_1$-$C_6$alkyl, halo$C_1$-$C_6$alkoxy, $C_1$-$C_6$alkoxy, halo$C_1$-$C_6$alkoxy, hydroxy, NR$_{4a}$R$_{4b}$, hydroxy$C_1$-$C_4$alkyl, amino$C_1$-$C_4$alkyl, $C_1$-$C_6$alkyl-OC(O)NH—, $CO_2H$, $C_3$-$C_7$cycloalkyl, $C_5$-$C_7$cycloalkenyl, phenyl, 5 or 6 membered heteroaryl having 1 or 2 ring heteroatoms selected from N, O or S, saturated or partially unsaturated monocyclic or bicyclic heterocycle or two substituents, taken in combination form a saturated heterocyclic ring having 5 or 6 ring atoms, 1 or 2 ring heteroatoms selected from N, O or S and wherein the fused heterocyle is substituted with 0, 1, or 2 independently selected $C_1$-$C_4$alkyl substituents; and wherein the monocyclic or bicyclic heterocycle has 1 or 2 ring N, O or S atoms, 5 to 7 ring atoms in each ring and is substituted with 0, 1 or 2 substituents independently selected from the group consisting of halogen, $C_1$-$C_6$alkyl, $C_1$-$C_6$alkanoyl, $C_1$-$C_6$alkoxycarbonyl, $C_1$-$C_6$alkoxyC(O)N(H)—, $C_1$-$C_6$alkoxyC(O)N(H)CH$_2$—, amino$C_1$-$C_4$alkyl, $C_1$-$C_4$alkoxyC$_1$-$C_4$alkyl and NR$_{4a}$R$_{4b}$, and wherein the phenyl or heteroaryl substituent is substituted with 0, 1 or 2 independently selected substituents selected from halogen, $CO_2H$, cyano, $C_1$-$C_4$alkyl, $C_1$-$C_4$alkoxy, NR$_{4a}$R$_{4b}$, CH$_2$NR$_{4a}$R$_{4b}$, C(O)NR$_{4a}$R$_{4b}$, or two phenyl substituents combine to form a divalent —O—(CH$_2$)$_q$—O— substituent in which q is 1, 2, or 3; or $R_4$ is a saturated heterocycle 1 ring nitrogen and 0 or 1 additional ring heteroatom selected from N, O or S, which heterocyclic ring is substituted with 0, 1, or 2 substituents independently selected from the group consisting of $C_1$-$C_6$alkyl, $CO_2C_1$-$C_6$alkyl or $CO_2$benzyl;

$R_{4a}$ is independently selected at each occurrence from the group consisting of hydrogen and $C_1$-$C_6$alkyl, wherein the alkyl substituent is unsubstituted or substituted with hydroxy, $C_1$-$C_4$alkoxy, amino or mono- and di-$C_1$-$C_4$alkylamino;

$R_{4b}$ is independently selected at each occurrence from the group consisting of hydrogen, $C_1$-$C_6$alkyl, $C_3$-$C_7$cycloalkyl, $C_1$-$C_4$alkanoyl, and heterocycle having 4 to 7 ring atoms and 1 or 2 ring heteroatoms independently selected at each occurrence from N, O or S, wherein the alkyl substituent is unsubstituted or substituted with hydroxy, $C_1$-$C_4$alkoxy, amino or mono- and di-$C_1$-$C_4$alkylamino; or NR$_{4a}$R$_{4b}$, taken in combination, form a heterocyclic ring having one ring nitrogen atom and 0 or 1 additional ring heteroatom selected from N, O and S, which heterocyclic ring is substituted with 0, 1, 2 or 3 substituents independently selected from the group consisting of halogen, hydroxy, oxo, amino, $C_1$-$C_4$alkyl, halo$C_1$-$C_4$alkyl, hydroxy$C_1$-$C_4$alkyl, amino$C_1$-$C_4$alkyl, $C_1$-$C_4$alkoxy, $C_1$-$C_4$alkanoyl, $C_1$-$C_4$alkoxy$C_1$-$C_4$alkyl, and mono- and di-$C_1$-$C_4$alkylamino;

$R_5$ is absent or is selected from the group consisting of hydrogen and $C_1$-$C_6$alkyl;

$R_6$ is oxo, hydrogen, hydroxy, amino, N(H)-J-$R_7$;

J is absent, C(O) or S(O)$_2$; and $R_7$ is $C_1$-$C_6$alkyl, phenyl or benzyl, each of is optionally substituted with $C_1$-$C_6$alkyl, $C_1$-$C_6$alkoxy, halogen, phenyl or phenoxy.

Certain compounds of formula (I) provided by the invention include compounds of formula (Ia) and salts thereof:

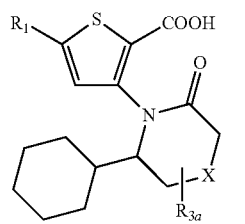

(Ia)

wherein $R_1$ is $C_3$-$C_8$alkynyl or phenyl, which phenyl is substituted with 0, 1, 2, or 3 substituents which are independently selected from the group consisting of halogen, hydroxy, cyano, $C_1$-$C_4$alkyl and $C_1$-$C_4$alkoxy, and which alkynyl is optionally substituted with a $C_3$-$C_7$cycloalkyl substituent, which cycloalkyl is optionally substituted with 1 or 2 independently selected $C_1$-$C_4$alkyl groups;

$R_{3a}$ represents 0, 1, 2, 3 or 4 residues independently selected at each occurrence from the group consisting of hydroxy, amino, $C_1$-$C_6$alkyl, $C_1$-$C_6$alkoxy, wherein each alkyl or alkoxy substituent is substituted with 0, 1 or 2 substituents independently selected from hydroxy, $C_1$-$C_4$alkoxy, $C_1$-$C_4$alkylsulfoxide and N($R_{3b}$); or two geminal $R_{3a}$ substituents, taken in combination form a spirocyclic 3 to 6 member cycloalkyl or heterocycle;

$R_{3b}$ is independently selected at each occurrence from hydrogen, $C_1$-$C_4$alkyl, $C_1$-$C_4$alkoxy$C_1$-$C_4$alkyl, or N($R_{3b}$)$_2$, taken in combination, form a 4 to 6 member heterocycle having 0 or 1 additional ring heteroatoms selected from N, O or S;

X is O, N-L-$R_4$ or CR$_5$R$_6$;

L is a bond, S(O)$_2$ or C(O);

$R_4$ is $C_1$-$C_6$alkyl or $C_3$-$C_7$cycloalkyl each of which is substituted with 0 or 1 substituents selected from CO$_2$H or NR$_{4a}$R$_{4b}$ or C1-C4 alkylphenyl, or $R_4$ is naphthyl or phenyl, which phenyl is substituted with 0, 1, 2, or 3 substituents independently selected form the group consisting of halogen, cyano, $C_1$-$C_6$alkyl, $C_1$-$C_6$alkoxy, halo$C_1$-$C_6$alkoxy, amino, hydroxy, mono- and di-$C_1$-$C_6$alkylamino, hydroxy$C_1$-$C_4$alkyl, amino$C_1$-$C_4$alkyl, $C_1$-$C_6$alkyl-OC(O)NH—, C1-C4alkyl-C(O)NH—, —C(O)NR$_{4a}$R$_{4b}$, phenyl, phenoxy, heteroaryl having one or two ring nitrogen atoms and having 0, 1, or 2 $C_1$-$C_4$alkyl substituents, or two substituents combine to form a fused heterocyclic ring, which heterocycle has 5, 6 or 7 ring atoms, 1 or 2 ring heteroatoms selected from N, O or S and which heterocycle is substituted with 0, 1 or 2 substituents independently selected from $C_1$-$C_6$alkyl; or $R_4$ is a 5 or 6 member heteroaryl having 1 to 3 heteroatoms selected from N, O or S, which heteroaryl is substituted with 0, 1, or 2 substituents independently selected from the group consisting of halogen, cyano, $C_1$-$C_6$alkyl, halo$C_1$-$C_6$alkyl, $C_1$-$C_6$alkoxy, halo$C_1$-$C_6$alkoxy, hydroxy, NR$_{4a}$R$_{4b}$, hydroxy$C_1$-$C_4$alkyl, amino$C_1$-$C_4$alkyl, $C_1$-$C_6$alkyl-OC(O)NH—, $C_3$-$C_7$cycloalkyl, $C_5$-$C_7$cycloalkenyl, phenyl, thienyl optionally substituted with CO$_2$H, or saturated or partially unsaturated monocyclic or bicyclic heterocycle which heterocycle has 1 or 2 ring N, O or S atoms, 5 to 7 ring atoms in each ring and is substituted with 0, 1 or 2 substituents independently selected from the group consisting of $C_1$-$C_6$alkyl, $C_1$-$C_6$alkanoyl, —N(H)C(O)$C_1$-$C_6$alkoxy, —CH$_2$N(H)C(O) $C_1$-$C_6$alkoxy, amino$C_1$-$C_4$alkyl, $C_1$-$C_4$alkoxy$C_1$-$C_4$alkyl and NR$_{4a}$R$_{4b}$, or two substituents on the heteroaryl ring combine to form a fused heterocyclic ring, which heterocycle has 5, 6 or 7 ring atoms, 1 or 2 ring heteroatoms selected from N, O or S and which heterocycle is substituted with 0, 1 or 2 substituents independently selected from $C_1$-$C_6$alky, and wherein the phenyl substituent is unsubstituted or substituted with halogen, $C_1$-$C_4$alkyl, or C(O)NR$_{4a}$R$_{4b}$; or $R_4$ is a saturated heterocycle 1 ring nitrogen and 1 or 1 additional ring heteroatom selected from N, O or S, which heterocyclic ring is substituted with 0, 1, or 2 substituents independently selected from the group consisting of $C_1$-$C_6$alkyl, CO$_2$$C_1$-$C_6$alkyl or CO$_2$benzyl;

$R_{4a}$ is independently selected at each occurrence from the group consisting of hydrogen and $C_1$-$C_6$alkyl, wherein the alkyl substituent is unsubstituted or substituted with hydroxy, $C_1$-$C_4$alkoxy, amino or mono- and di-$C_1$-$C_4$alkylamino;

$R_{4b}$ is independently selected at each occurrence from the group consisting of hydrogen, $C_1$-$C_6$alkyl and $C_1$-$C_4$alkanoyl, wherein the alkyl substituent is unsubstituted or substituted with hydroxy, $C_1$-$C_4$alkoxy, amino or mono- and di-$C_1$-$C_4$alkylamino; or NR$_{4a}$R$_{4b}$, taken in combination, form a heterocyclic ring having one ring nitrogen atom and 0 or 1 additional ring heteroatom selected from N, O and S, which heterocyclic ring is substituted with 0, 1, 2 or 3 substituents independently selected from the group consisting of halogen, hydroxy, amino, $C_1$-$C_4$alkyl, halo$C_1$-$C_4$alkyl, hydroxy$C_1$-$C_4$alkyl, amino$C_1$-$C_4$alkyl, $C_1$-$C_4$alkoxy, $C_1$-$C_4$alkoxy$C_1$-$C_4$alkyl, and mono- and di-$C_1$-$C_4$alkylamino;

$R_5$ is absent or is selected from the group consisting of hydrogen and $C_1$-$C_6$alkyl;

$R_6$ is oxo, hydrogen, hydroxy, amino, N(H)-J-$R_7$;

J is absent, C(O) or S(O)$_2$; and $R_7$ is $C_1$-$C_6$alkyl, phenyl or benzyl, each of is optionally substituted with $C_1$-$C_6$alkyl, $C_1$-$C_6$alkoxy, halogen, phenyl or phenoxy.

In one aspect, compounds of formula (I) include compounds of formula (II) and salts thereof:

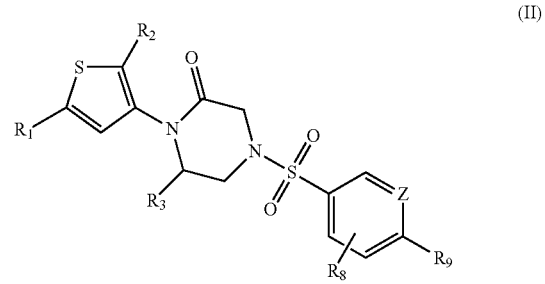

(II)

wherein

Z is CH or N;

$R_8$ is selected from hydrogen, $CO_2H$, $C_1$-$C_4$alkyl, C-$C_4$alkoxy, cyano or halogen;

$R_9$ is selected from $C_1$-$C_6$alkyl, $C_1$-$C_6$alkoxy, phenyl, $NR_{9a}R_{9b}$, N(H)—C(O)—O—$C_1$-$C_4$alkyl, and heterocycle, wherein the heterocycle has one or two rings, each ring having 5, 6, or 7 ring atoms, one ring nitrogen atom and 0 or 1 additional ring heteroatom selected from N, O or S, and wherein the heterocycle is unsubstituted or substituted with 1, 2 or 3 substituents independently selected from the group consisting of halogen, hydroxy, amino, $C_1$-$C_4$alkyl, halo$C_1$-$C_4$alkyl, hydroxy$C_1$-$C_4$alkyl, amino$C_1$-$C_4$alkyl, $C_1$-$C_4$alkoxy, $C_1$-$C_4$alkoxy$C_1$-$C_4$alkyl, and mono- and di-$C_1$-$C_4$alkylamino; or $R_8$ and $R_9$, taken in combination form a divalent residue selected from —$O(CH_2)_pO$—, —$O(CH_2)_2NH$—, or —$O(CH_2)_2N(CH_3)$—;

$R_{9a}$ is selected from the group consisting of hydrogen and $C_1$-$C_6$alkyl, wherein the alkyl substituent is unsubstituted or substituted with hydroxy, $C_1$-$C_4$alkoxy, amino or mono- and di-$C_1$-$C_4$alkylamino; and $R_{9b}$ is selected from the group consisting of hydrogen, $C_1$-$C_6$alkyl and $C_1$-$C_4$alkanoyl, wherein the alkyl substituent is unsubstituted or substituted with hydroxy, $C_1$-$C_4$alkoxy, amino or mono- and di-$C_1$-$C_4$alkylamino.

In certain aspects, compounds of formula (II) include those compounds in which $R_8$ is selected from hydrogen, $CO_2H$, methyl, methoxy or hydroxymethyl.

Certain other compounds of formula (II) include those compounds in which $R_9$ is selected from the group consisting of morpholino, piperidinyl, piperazinyl, and pyrrolidinyl, each of which is unsubstituted or substituted with one or two substituents selected from the group consisting of $C_1$-$C_4$alkyl, hydroxy$C_1$-$C_4$alkyl, amino$C_1$-$C_4$alkyl, $C_1$-$C_4$alkoxy, mono- and di-$C_1$-$C_4$alkylamino, and $C_1$-$C_4$alkoxycarbonyl.

Still other compounds of formula (II) include those compounds in which Z is N.

In yet other aspects, compounds of formula (II) include those compounds in which $R_8$ is selected from hydrogen, $CO_2H$, methyl, methoxy or hydroxymethyl;

$R_9$ is selected from the group consisting of morpholino, piperidinyl, piperazinyl, and pyrrolidinyl, each of which is unsubstituted or substituted with one or two substituents selected from the group consisting of $C_1$-$C_4$alkyl, hydroxy$C_1$-$C_4$alkyl, amino$C_1$-$C_4$alkyl, $C_1$-$C_4$alkoxy, mono- and di-$C_1$-$C_4$alkylamino, and $C_1$-$C_4$alkoxycarbonyl; and Z is N.

In certain aspects, compounds of formula (I), (Ia) or (II) include compounds of formula (IIa) and salts thereof

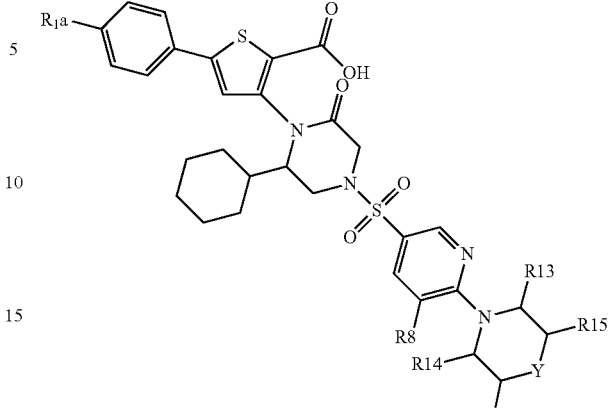

(IIa)

Wherein

Y is a bond, O, $NR_{17}$, or $CR_{17}R_{18}$;

$R_{1a}$ is H, F, Cl or $CH_3$ $R_8$ is hydrogen, methyl, $CO_2H$, or methoxy;

$R_{13}$ and $R_{14}$, are each independently selected from hydrogen or $C_1$-$C_4$alkyl;

$R_{15}$ and $R_{16}$, are each independently selected from hydrogen, $C_1$-$C_4$alkyl, hydroxy$C_1$-$C_4$alkyl, amino, or mono- and di $C_1$-$C_4$alkylamino;

$R_{17}$ is selected from hydrogen, $C_1$-$C_4$alkyl, or $C_1$-$C_4$alkoxycarbonyl; and $R_{18}$ is selected from hydrogen, $C_1$-$C_4$alkyl, $C_1$-$C_4$alkoxy, amino, or amino $C_1$-$C_4$alkyl.

In another aspect, compounds of formula (I) include compounds of formula (III) and salts thereof:

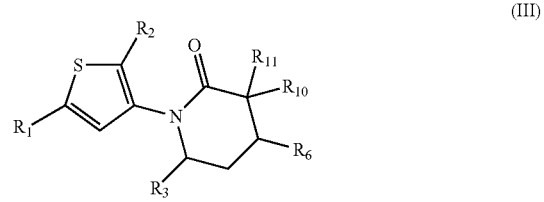

(III)

wherein $R_6$ is hydrogen, hydroxy, amino or N(H)-J-$R_7$;

J is C(O) or $S(O)_2$;

$R_7$ is (a) $C_1$-$C_4$alkyl optionally substituted with phenyl or phenoxy, or (b) phenyl optionally substituted with $C_1$-$C_4$alkyl, halogen or $C_1$-$C_4$alkoxy;

$R_{10}$ is selected from hydrogen and $C_1$-$C_6$alkyl which alkyl is unsubstituted or substituted with one or two substituents selected from OH, cyano, $SO_2CH_3$, methoxy, ethoxy, $N(R_{10a})_2$ and $C(O)(NR_{10a})_2$;

$R_{10a}$ is selected at each occurrence from the group consisting of hydrogen and $C_1$-$C_4$alkyl which is substituted with 0 or 1 substituents selected from hydroxy, methoxy or ethoxy;

$R_{11}$ is selected from the group consisting of hydrogen, fluoro, hydroxy and $C_1$-$C_4$alkyl.

In another aspect, compounds of formula (III) include those compounds in which $R_{10}$ is hydrogen or $C_1$-$C_6$alkyl substituted with one or two hydroxy substituents or one substitutent independently selected from the group consisting of cyano, $SO_2CH_3$, methoxy, ethoxy, amino, mono- and di-$C_1$-$C_2$alkylamino, $C(O)NH_2$, $C(O)N(H)Me$ and $C(O)NMe_2$. In certain other compounds of formula (III), $R_{10}$ is $C_1$-$C_6$alkyl substituted with one or two hydroxy substituents or one substitutent independently selected from the group consisting of cyano, $SO_2CH_3$, methoxy, ethoxy, amino, or mono- and di-$C_1$-$C_2$alkylamino.

In yet another aspect, compounds of formula (I) include compounds of formula (IV) and salts thereof:

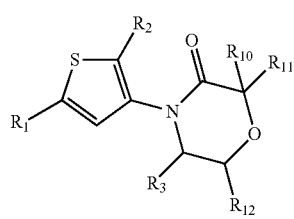

(IV)

wherein
$R_{10}$, $R_{11}$ is independently selected from hydrogen and $C_1$-$C_6$alkyl which alkyl is unsubstituted or substituted with one or two substituents selected from OH, $SO_2CH_3$, cyano, methoxy, ethoxy, $N(R_{10a})_2$ and $C(O)N(R_{10a})_2$;
$R_{10a}$ is selected at each occurrence from the group consisting of hydrogen and $C_1$-$C_4$alkyl which is substituted with 0 or 1 substituents selected from hydroxy, methoxy or ethoxy;
Or $N(R_{10a})_2$ could form a 3-6 member cycloakyl or heterocycle
$R_{12}$ is selected from the group consisting of hydrogen and $C_1$-$C_4$alkyl.

In another aspect, compounds of formula (IV) include those compounds in which $R_{10}$ is hydrogen or $C_1$-$C_6$alkyl substituted with one or two hydroxy substituents or one substituent independently selected from the group consisting of cyano, $SO_2CH_3$, methoxy, ethoxy, amino, mono- and di-$C_1$-$C_2$alkylamino, $C(O)NH_2$, $C(O)N(H)Me$ and $C(O)NMe_2$. In certain other compounds of formula (IV), $R_{10}$ is $C_1$-$C_6$alkyl substituted with one or two hydroxy substituents or one substitutent independently selected from the group consisting of cyano, $SO_2CH_3$, methoxy, ethoxy, amino, or mono- and di-$C_1$-$C_2$alkylamino.

In one aspect, compounds of formula (I), (Ia), (II), (IIa), (III) or (IV) include those compounds in which $R_1$ is tert-butylethynyl, phenyl, or phenyl para-substituted with F, Cl, or methyl. In certain instances, compounds of the identified formulae include those compounds in which $R_1$ is phenyl or tert-butylethynyl. In certain other compounds of formula (I), (Ia), (II), (IIa), (III), and/or (IV), $R_1$ is phenyl. In still other compounds of formula (I), (Ia), (II), (IIa), (III), and/or (IV), $R_1$ is tert-butylethynyl.

In another aspect, compounds of formula (I), (II), (IIa), (III) or (IV) include those compounds in which $R_2$ is $CO_2H$.

In one aspect, compounds of formula (I), (Ia), (II), (IIa), (III) or (IV) include those compounds in which $R_3$ is cyclohexyl.

In yet another aspect, compounds of (III) include those compounds in which $R_6$ is hydrogen;
$R_{10}$ is hydrogen or hydroxy$C_1$-$C_6$alkyl; and
$R_{11}$ is hydrogen, methyl, hydroxy or fluoro.

In yet another aspect, compounds of (III) include those compounds in which $R_6$ is hydrogen;
$R_{10}$ is hydroxy$C_1$-$C_6$alkyl; and
$R_{11}$ is hydrogen, methyl, hydroxy or fluoro.

In yet another aspect, compounds of (IV) include those compounds in which $R_{10}$ is hydroxy$C_1$-$C_6$alkyl;

$R_{11}$ is hydrogen or methyl; and
$R_{12}$ is hydrogen or methyl.

In certain aspects, compounds of formula (III) are provided in which $R_1$ is tert-butylethynyl, phenyl, or phenyl para-substituted with F, Cl, or methyl;
$R_2$ is $CO_2H$;
$R_3$ is cyclohexyl;
$R_6$ is hydrogen;
$R_{10}$ is hydroxy$C_1$-$C_6$alkyl; and
$R_{11}$ is hydrogen, hydroxy, methyl or fluoro.

In certain aspects, compounds of formula (III) are provided in which $R_1$ is tert-butylethynyl;
$R_2$ is $CO_2H$;
$R_3$ is cyclohexyl;
$R_6$ is hydrogen;
$R_{10}$ is hydroxy$C_1$-$C_6$alkyl; and
$R_{11}$ is hydrogen, hydroxy, methyl or fluoro.

In certain aspects, compounds of formula (IV) are provided in which $R_1$ is tert-butylethynyl;
$R_2$ is $CO_2H$;
$R_3$ is cyclohexyl;
$R_{10}$ is hydroxy$C_1$-$C_6$alkyl; and
$R_{11}$ and $R_{12}$ are independently selected from the group consisting of is hydrogen and methyl.

In certain other aspects, the invention provides compounds of Formula (V)

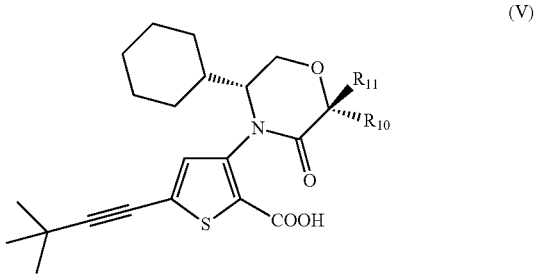

(V)

or a salt thereof, wherein
$R_{11}$ is hydrogen or methyl;
$R_{10}$ is $C_2$-$C_6$hydroxyalkyl wherein the hydroxyl group is a primary, secondary or tertiary alcohol. For example $R_{10}$ is selected from —$(CH_2)_aOH$, —$(CH_2)_bCH(CH_3)OH$ or —$(CH_2)_bC(CH_3)_2OH$, wherein a is 2, 3, or 4 and b is 1, 2, or 3. In certain compounds of Formula (V) a is 2 or 3 and b is 1 or 2.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S.

Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by HCV infection, or (ii) associated with HCV infection; or (2) reducing or inhibiting the viral replication or viral load of HCV. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of NS5b; or at least partially reducing or inhibiting the replication of HCV.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the -(amino, mono- or di-lower alkylamino, carboxy, lower alkoxycarbonyl)-lower alkyl esters, the -(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. NS5b inhibitory properties, e.g. as indicated in in vitro and in vivo tests as provided in the next sections and are therefore indicated for therapy.

In one embodiment, the invention provides a method of treating an HCV-associated disorder comprising administering to a subject in need thereof a pharmaceutically acceptable amount of a compound of the invention, such that the HCV-associated disorder is treated.

In another embodiment, the invention provides a method of treating an HIV infection comprising administering to a subject in need thereof a pharmaceutically acceptable amount of a compound of the invention.

In still another embodiment, the invention provides a method of treating, inhibiting or preventing the activity of HCV in a subject in need thereof, comprising administering to the subject a pharmaceutically acceptable amount of a compound of the invention. In one embodiment, the compounds of the invention inhibit the activity of the NS2 protease, the NS3 protease, the NS3 helicase, the NS5a protein, and/or the NS5b polymerase. In another embodiment, the interaction between the NS3 protease and NS4A cofactor is disrupted. In yet another embodiment, the compounds of the invention prevent or alter the severing of one or more of the NS4A-NS4B, NS4B-NS5A and NS5A-NS5B junctions of the HCV. In another embodiment, the invention provides a method of inhibiting the activity of a serine protease, comprising the step of contacting said serine protease with a compound of the invention. In another embodiment, the invention provides a method of treating, inhibiting or preventing the activity of HCV in a subject in need thereof, comprising administering to the subject a pharmaceutically acceptable amount of a compound of the invention, wherein the compound interacts with any target in the HCV life cycle. In one embodiment, the target of the HCV life cycle is selected from the group consisting of NS2 protease, NS3 protease, NS3 helicase, NS5a protein and NS5b polymerase.

In another embodiment, the invention provides a method of decreasing the HCV RNA load in a subject in need thereof comprising administering to the subject a pharmaceutically acceptable amount of a compound of the invention.

In another embodiment, the compounds of the invention exhibit HCV protease activity. In one embodiment, the compounds are an HCV NS3-4A protease inhibitor.

In another embodiment, the invention provides a method of treating an HCV-associated disorder in a subject, comprising administering to a subject in need thereof a pharmaceutically acceptable amount of a compound of the invention, and a pharmaceutically acceptable carrier, such that the HCV-associated disorder is treated.

In still another embodiment, the invention provides a method of treating an HCV-associated disorder comprising administering to a subject in need thereof a pharmaceutically effective amount of a compound of the invention, in combination with a pharmaceutically effective amount of an additional HCV-modulating compound, such as interferon or derivatized interferon, or a cytochrome P450 monooxygenase inhibitor, such that the HCV-associated disorder is treated. In one embodiment, the additional HCV-modulating compound is selected from the group consisting of NIM811, ITMN191, MK-7009, TMC 435350, Sch 503034 and VX-950.

In another embodiment, the invention provides a method of inhibiting hepatitis C virus replication in a cell, comprising contacting said cell with a compound of the invention.

In yet another embodiment, the invention provides a packaged HCV-associated disorder treatment, comprising an HCV-modulating compound of the invention, packaged with instructions for using an effective amount of the HCV-modulating compound to treat an HCV-associated disorder.

In certain embodiments, the HCV-associated disorder is selected from the group consisting of HCV infection, liver cirrhosis, chronic liver disease, hepatocellular carcinoma, cryoglobulinaemia, non-Hodgkin's lymphoma, liver fibrosis and a suppressed innate intracellular immune response.

In another embodiment, the invention provides a method of treating HCV infection, liver cirrhosis, chronic liver disease, hepatocellular carcinoma, cryoglobulinaemia, non-Hodgkin's lymphoma, liver fibrosis and/or a suppressed innate intracellular immune response in subject in need thereof comprising administering to the subject a pharmaceutically acceptable amount of a compound of the invention.

In one embodiment, the HCV to be treated is selected of any HCV genotype. In another embodiment, the HCV is selected from HCV genotype 1, 2 and/or 3.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the in vitro & in vivo methods provided infra.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a viral infection or disease associated with viral infection or condition mediated by hepatitis C virus. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition caused by or associated with HCV infection, wherein the medicament is prepared for administration with another therapeutic agent. The invention also provides the use of another therapeutic agent for treating a disease or condition caused by or associated with HCV infection, wherein the medicament is administered with a compound of formula (I).

The invention also provides a compound of formula (I) for use in a method of treating a disease or condition caused by or associated with HCV infection, wherein the compound of formula (I) is prepared for administration with another therapeutic agent. The invention also provides another therapeutic agent for use in a method of treating a disease or condition caused by or associated with HCV infection, wherein the other therapeutic agent is prepared for administration with a compound of formula (I). The invention also provides a compound of formula (I) for use in a method of treating a disease or condition caused by or associated with HCV infection, wherein the compound of formula (I) is administered with another therapeutic agent. The invention also provides another therapeutic agent for use in a method of treating a disease or condition caused by or associated with HCV infection, wherein the other therapeutic agent is administered with a compound of formula (I).

The invention also provides the use of a compound of formula (I) for treating a disease or condition caused by or associated with HCV infection, wherein the patient has previously (e.g. within 24 hours) been treated with another therapeutic agent. The invention also provides the use of another therapeutic agent for treating a disease or condition caused by or associated with HCV infection, wherein the patient has previously (e.g. within 24 hours) been treated with a compound of formula (I).

In one embodiment, the other therapeutic agent is selected from second therapeutic agents which are active against viruses and, in particular, against HCV. The compound and agent may be administered in a single or separate formulations. Agents active against HCV include, but are not limited to, interferon-α, pegylated interferon-α (peginterferon-α), albinterferon-α2b (albIFN, Novartis/Human Genome Science), PEG-Interferon lambda (BMS/ZymoGenetics), ribavirin, levovirin, viramidine, a combination of interferon-α and ribavirin, a combination of peginterferon-α and ribavirin, a combination of albIFN and ribavirin, a combination of interferon-α and levovirin, a combination of peginterferon-α and levovirin, and a combination of albIFN and levovirin. Interferon-α includes, but is not limited to, recombinant interferon-α2a (such as ROFERON interferon available from Hoffman-LaRoche, Nutley, N.J.), interferon-α2b (such as Intron-A interferon available from Schering Corp., Kenilworth, N.J., USA), a consensus interferon, and a purified interferon-α product. Pegylated interferon-α includes, but is not limited to, PEG IFN-α2a (such as Pegsys available from Hoffman-LaRoche, Nutley, N.J.), PEG IFN-α2b (such as PegIntron available from Schering Corp., Kenilworth, N.J., USA), For a discussion of ribavirin and its activity against HCV, see J. O. Saunders and S. A. Raybuck, "Inosine Monophosphate Dehydrogenase: Consideration of Structure, Kinetics and Therapeutic Potential," *Ann. Rep. Med. Chem.,* 35:201-210 (2000).

The agents active against hepatitis C virus also include agents that inhibit HCV NS2 or NS3 proteases, HCV NS5B polymerase, HCV NS5A protein, HCV NS3 helicase, HCV NS4B protein, HCV p7 protein, HCV NS4A protein, HCV IRES and protein translation, HCV entry, HCV assembly, HCV egress, and inosine 5'-monophosphate dehydrogenase, cyclophilins or other host factors that are required for HCV replication. Still other compounds include those disclosed in WO 2004/014313 and WO 2004/014852 and in the references cited therein.

Specific antiviral agents include BI-201335 (Boehringer Ingelheim), telaprevir (Vertex), VX-813 (Vertex), VX-500 (Vertex), boceprevir (Schering-Plough), Sch 900518 (Schering-Plough), ITMN-191/R7227 (Intermune/Roche), ITMN-5489 (Intermune), MK-7009 (Merck), TMC435 (Tibotec), BMS-650032 (Bristol-Myers-Squibb), PHX1766 (Phenomix), GS-9256 (Gilead), VCH-916 (Vertex), VCH-759 (Vertex), VCH-222/VX-222 (Vertex), ABT-333 (Abbott), ANA-598 (Anadys), PF-868,554 (Pfizer), MK-3281 (Merck), PSI-7851 (Pharmasset), R7128 (Pharmasset/Roche), R1626 (Roche), GS9190 (Gilead), BI-207127 (Boehringer Ingelheim), JTK-652 (Japan Tobacco Inc.), IDX375 (Idenix), Valopicitabine/NM283 (Idenix), IDX-184 (Idenix), AZD2836/A-831 (Arrow/AstraZeneca), AZD7295/A-689 (Arrow/AstraZeneca), BMS-790052 (Bristol-Myers-Squibb), PPI-461 (Presidio), EDP-239 (Enanta), Ceplene (Maxim Pharmaceuticals), Civacir (Nabi Biopharmaceuticals Inc, VX-497 (Vertex Pharmaceuticals Inc.), XTL-002 (XTL Biopharmaceuticals), isatoribine and its prodrugs ANA971, ANA975 and ANA773 (Anadys), NIM811 (Novartis), DEBIO-025 (DebioPharm/Novartis), SCY-635 (Scynexis), and nitazoxanide (Romark), IDN-6556 (Idun Pharmaceuticals), IP-501 (Indevus Pharmaceuticals), ISIS 14803 (ISIS Pharmaceuticals Inc.)

In some embodiments, the compositions and methods of the present invention contain a compound of the invention and interferon. In some aspects, the interferon is selected from the group consisting of interferon alpha 2B, pegylated interferon alpha, consensus interferon, interferon alpha 2A, and lymphoblastoid interferon tau.

In other embodiments the compositions and methods of the present invention contain a compound of the invention and a compound having anti-HCV activity is selected from the group consisting of interleukin 2, interleukin 6, interleukin 12, a compound that enhances the development of a type 1 helper T cell response, interfering RNA, anti-sense RNA, Imiquimod, ribavirin, an inosine 5'-monophospate dehydrogenase inhibitor, amantadine, and rimantadine.

In still other embodiments, the compound having anti-HCV activity is Ribavirin, levovirin, viramidine, thymosin alpha-1, an inhibitor of NS3 serine protease, and inhibitor of inosine monophosphate dehydrogenase, interferon-alpha, or pegylated interferon-alpha alone or in combination with Ribavirin or viramidine.

In another embodiments, the compound having anti-HCV activity is said agent active against HCV is interferon-alpha or pegylated interferon-alpha alone or in combination with Ribavirin or viramidine.

General Synthetic Methods

The compounds disclosed herein can be prepared by following the general procedures and examples set forth below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Typically, the compounds of formula (I) can be prepared according to the Schemes provided infra

General Procedures

Example A

Compound according to general structure A-3 could be synthesized by coupling reaction between fragment A-1 and fragment A-2 with CuI and trans-cyclohexane diamine as promoters followed by hydrolysis of the methyl ester under basic condition.

Scheme I

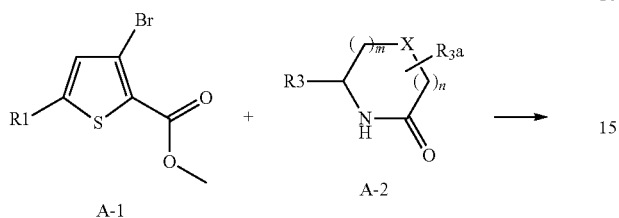

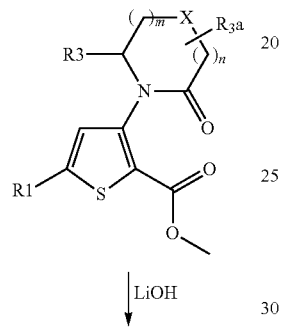

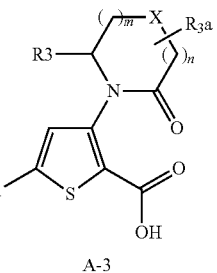

Example B

Compound according to general structure B-3 could be synthesized by following method (Scheme II). B-1 could be converted to B-2 by hydrolyzing the methyl ester under basic condition followed by cleaving Boc with HCl. B-2 could react with sulfonyl chloride to give sulfonamide B-3. Or B-2 could undergo reductive amination with aldehyde to give amine B-4.

Scheme II

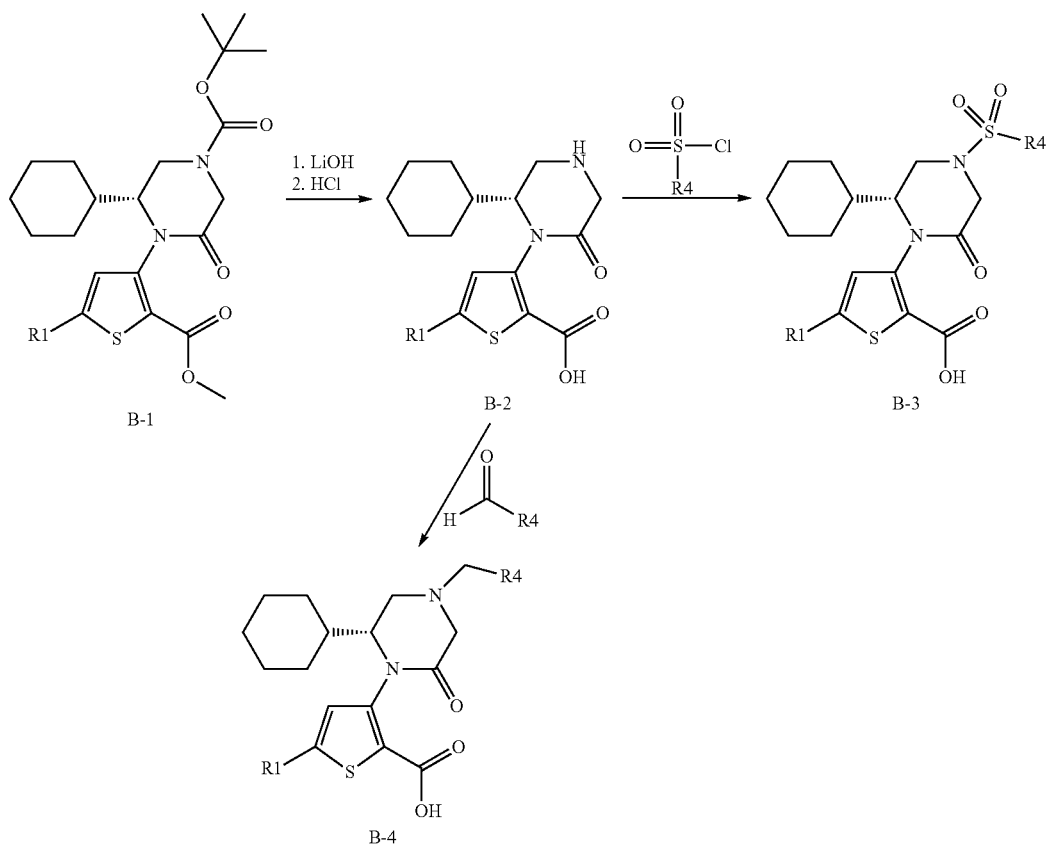

Example C

Compounds according to general structure C-3 and C-5 could be synthesized by followed method. Amine C-1 could be converted to pyridyl sulfonamide C-2 by reacting with pyridine sulfonyl chloride. Displacement of chloride with amine would provide C-3. C-1 could react with 4-fluoro phenylsulfonyl chloride to give C-4. Displacement of fluoride with amine would give C-5.

hofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Scheme III

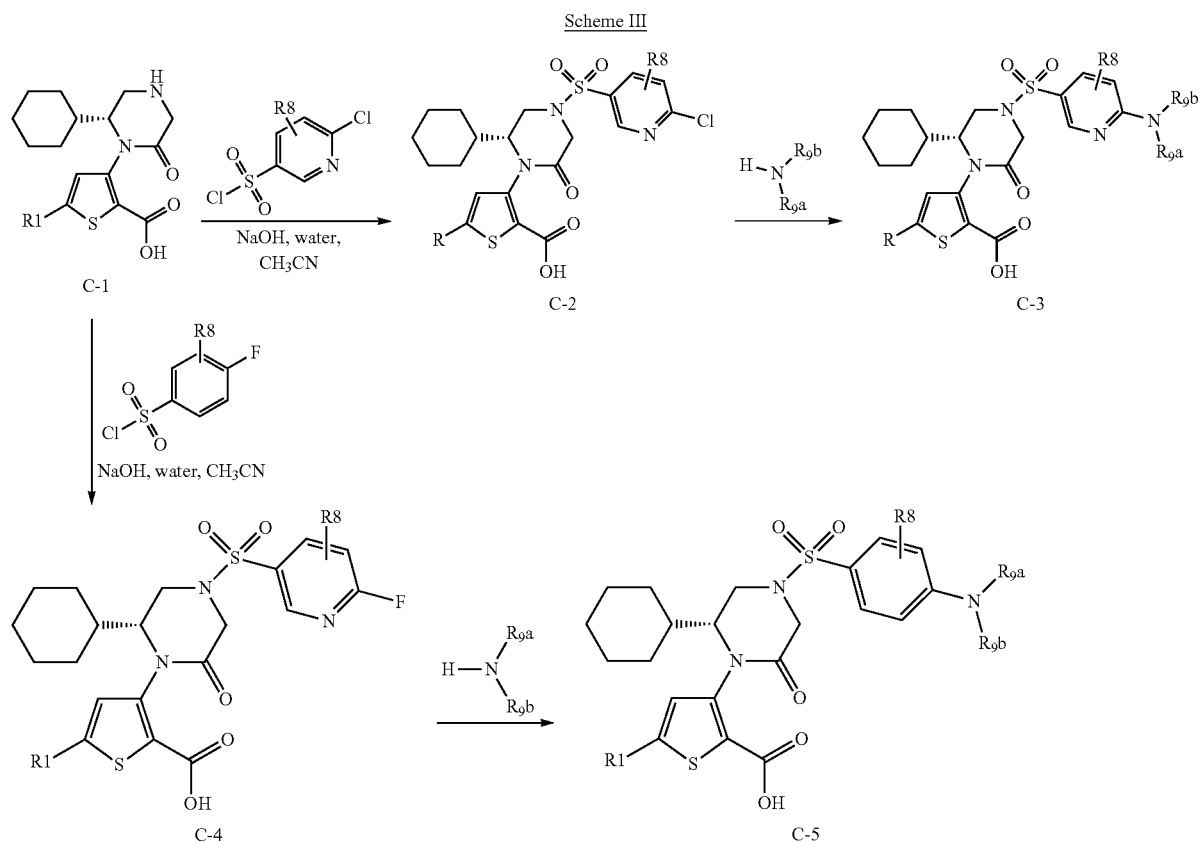

Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meieninvention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl $4^{th}$ Ed. 1952, Methods of Organic Synthesis, Thieme, Volume 21).

In one embodiment, the invention provides a method of modulating viral activity in a subject, wherein the method comprises administering to the subject a therapeutically effective amount of the compound according to the definition of formula (I). Methods of inhibiting viral replication or inhibiting viral load in a subject are provided, wherein the virus is a member of the Flaviviridae family of viruses such as hepatitis C virus.

In one embodiment, the invention provides a method of treating a disorder or a disease in a subject caused by or associated with HCV infection, wherein the method comprises administering to the subject a therapeutically effective amount of the compound according to the definition of formula (I).

In one embodiment, the invention provides a method of treating a disorder or a disease in a subject caused by or associated with HCV infection, wherein the disorder or the disease is selected from of HCV infection, liver cirrhosis, chronic liver disease, hepatocellular carcinoma, cryoglobulinaemia, non-Hodgkin's lymphoma, liver fibrosis and a suppressed innate intracellular immune response.

In one embodiment, the invention provides a compound according to the definition of formula (I), for use as a medicament.

In one embodiment, the invention provides the use of a compound according to the definition of formula (I), for the treatment of a disorder or disease in a subject caused by or associated with HCV infection.

In one embodiment, the invention provides the use of a compound according to the definition of formula (I), in the manufacture of a medicament for the treatment of a disorder or disease in a subject caused by or associated with HCV infection, wherein said disorder or disease is in particular selected from HCV infection, liver cirrhosis, chronic liver disease, hepatocellular carcinoma, cryoglobulinaemia, non-Hodgkin's lymphoma, liver fibrosis and a suppressed innate intracellular immune response.

In one embodiment, the invention provides the use of a compound according to the definition of formula (I), for the treatment of a disorder or disease in a subject caused by or associated with HCV infection, wherein the disorder or disease is selected from HCV infection, liver cirrhosis, chronic liver disease, hepatocellular carcinoma, cryoglobulinaemia, non-Hodgkin's lymphoma, liver fibrosis and a suppressed innate intracellular immune response.

In another embodiment, the invention provides compounds according to the definition of formula (I), which compounds include the exemplified compounds provided infra. Certain compounds of Formula (I) provided by the invention include compounds selected from the group consisting of:

1. 3-((S)-2-Cyclohexyl-5-oxo-pyrrolidin-1-yl)-5-phenyl-thiophene-2-carboxylic acid
2. 3-(2-Cyclohexyl-6-oxo-piperidin-1-yl)-5-phenyl-thiophene-2-carboxylic acid
3. 3-(3-Cyclohexyl-5-oxo-morpholin-4-yl)-5-phenyl-thiophene-2-carboxylic acid
4. 3-[(R)-2-Cyclohexyl-6-oxo-4-(toluene-4-sulfonyl)-piperazin-1-yl]-5-phenyl-thiophene-2-carboxylic acid
5. 3-(2-Cyclohexyl-6-oxo-piperidin-1-yl)-5-(3,3-dimethyl-but-1-ynyl)-thiophene-2-carboxylic acid
6. 3-((S)-2-Cyclohexyl-6-oxo-piperidin-1-yl)-5-(3,3-dimethyl-but-1-ynyl)-thiophene-2-carboxylic acid
7. 3-(2-Cyclohexyl-6-oxo-piperidin-1-yl)-5-(4-fluoro-phenyl)-thiophene-2-carboxylic acid
8. 3-(2-Cyclohexyl-6-oxo-piperidin-1-yl)-5-p-tolyl-thiophene-2-carboxylic acid
9. 5-(4-Chloro-phenyl)-3-(2-cyclohexyl-6-oxo-piperidin-1-yl)-thiophene-2-carboxylic acid
10. 3-[2-Cyclohexyl-4-(6-dipropylamino-pyridine-3-sulfonyl)-6-oxo-piperazin-1-yl]-5-phenyl-thiophene-2-carboxylic acid
11. 3-{(R)-2-Cyclohexyl-4-[6-((R)-2-methyl-pyrrolidin-1-yl)-pyridine-3-sulfonyl]-6-oxo-piperazin-1-yl}-5-phenyl-thiophene-2-carboxylic acid
12. 3-[(R)-2-Cyclohexyl-6-oxo-4-(6-pyrrolidin-1-yl-pyridine-3-sulfonyl)-piperazin-1-yl]-5-phenyl-thiophene-2-carboxylic acid
13. 3-{(R)-2-Cyclohexyl-4-[6-((2S,5R)-2,5-dimethyl-pyrrolidin-1-yl)-pyridine-3-sulfonyl]-6-oxo-piperazin-1-yl}-5-phenyl-thiophene-2-carboxylic acid
14. 3-[2-Cyclohexyl-6-oxo-4-(toluene-4-sulfonyl)-piperazin-1-yl]-5-(3,3-dimethyl-but-1-ynyl)-thiophene-2-carboxylic acid
15. 3-{(R)-2-Cyclohexyl-4-[6-((2R,6S)-2,6-dimethyl-morpholin-4-yl)-pyridine-3-sulfonyl]-6-oxo-piperazin-1-yl}-5-phenyl-thiophene-2-carboxylic acid
16. 3-[2-Cyclohexyl-4-(6-morpholin-4-yl-pyridine-3-sulfonyl)-6-oxo-piperazin-1-yl]-5-(3,3-dimethyl-but-1-ynyl)-thiophene-2-carboxylic acid
17. 3-[(R)-2-Cyclohexyl-4-(6-diethylamino-pyridine-3-sulfonyl)-6-oxo-piperazin-1-yl]-5-phenyl-thiophene-2-carboxylic acid
18. 3-[(R)-2-Cyclohexyl-6-oxo-4-(3,4,5,6-tetrahydro-2H-[1,2']bipyridinyl-5'-sulfonyl)-piperazin-1-yl]-5-phenyl-thiophene-2-carboxylic acid
19. 3-((R)-4-Cyclohexyl-2-oxo-oxazolidin-3-yl)-5-(3,3-dimethyl-but-1-ynyl)-thiophene-2-carboxylic acid
20. 3-[(R)-2-Cyclohexyl-4-(6-morpholin-4-yl-pyridine-3-sulfonyl)-6-oxo-piperazin-1-yl]-5-phenyl-thiophene-2-carboxylic acid
21. 3-[(R)-2-Cyclohexyl-4-(4-methoxy-benzenesulfonyl)-6-oxo-piperazin-1-yl]-5-(3,3-dimethyl-but-1-ynyl)-thiophene-2-carboxylic acid
22. 3-[(R)-2-Cyclohexyl-4-(6-methoxy-pyridine-3-sulfonyl)-6-oxo-piperazin-1-yl]-5-(3,3-dimethyl-but-1-ynyl)-thiophene-2-carboxylic acid
23. 3-[(R)-2-Cyclohexyl-4-(1-methyl-1H-pyrazole-3-sulfonyl)-6-oxo-piperazin-1-yl]-5-(3,3-dimethyl-but-1-ynyl)-thiophene-2-carboxylic acid
24. 3-{(R)-2-Cyclohexyl-4-[6-(8-oxa-3-aza-bicyclo[3.2.1]oct-3-yl)-pyridine-3-sulfonyl]-6-oxo-piperazin-1-yl}-5-p-tolyl-thiophene-2-carboxylic acid
25. 3-(2-Cyclohexyl-5-oxo-pyrrolidin-1-yl)-5-(3,3-dimethyl-but-1-ynyl)-thiophene-2-carboxylic acid
26. 3-((R)-3-Cyclohexyl-5-oxo-morpholin-4-yl)-5-(3,3-dimethyl-but-1-ynyl)-thiophene-2-carboxylic acid
27. 3-((4S,5R)-5-Cyclohexyl-3,4-dimethyl-2-oxo-imidazolidin-1-yl)-5-(3,3-dimethyl-but-1-ynyl)-thiophene-2-carboxylic acid
28. 5-(4-Chloro-phenyl)-3-((R)-3-cyclohexyl-5-oxo-morpholin-4-yl)-thiophene-2-carboxylic acid
29. 3-[(R)-5-Cyclohexyl-2-(2-morpholin-4-yl-2-oxo-ethyl)-3-oxo-morpholin-4-yl]-5-(3,3-dimethyl-but-1-ynyl)-thiophene-2-carboxylic acid
30. 3-[(R)-5-Cyclohexyl-2-(3-hydroxy-propyl)-3-oxo-morpholin-4-yl]-5-(3,3-dimethyl-but-1-ynyl)-thiophene-2-carboxylic acid
31. 3-[(R)-5-Cyclohexyl-2-(3-methanesulfonyl-propyl)-3-oxo-morpholin-4-yl]-5-(3,3-dimethyl-but-1-ynyl)-thiophene-2-carboxylic acid
32. 3-{(R)-5-Cyclohexyl-2-[(2-methoxy-ethylamino)-methyl]-3-oxo-morpholin-4-yl}-5-(3,3-dimethyl-but-1-ynyl)-thiophene-2-carboxylic acid
33. 3-(4-Cyclohexyl-2-oxo-[1,3]oxazinan-3-yl)-5-(3,3-dimethyl-but-1-ynyl)-thiophene-2-carboxylic acid
34. 3-((R)-5-Cyclohexyl-2-morpholin-4-ylmethyl-3-oxo-morpholin-4-yl)-5-(3,3-dimethyl-but-1-ynyl)-thiophene-2-carboxylic acid
35. 3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid
36. 3-((2S,5R)-2-Cyanomethyl-5-cyclohexyl-2-methyl-3-oxo-morpholin-4-yl)-5-(3,3-dimethyl-but-1-ynyl)-thiophene-2-carboxylic acid
37. 3-(6-Cyclohexyl-3-hydroxy-2-oxo-piperidin-1-yl)-5-(3,3-dimethyl-but-1-ynyl)-thiophene-2-carboxylic acid
38. 3-((R)-5-Cyclohexyl-2,2-dimethyl-3-oxo-morpholin-4-yl)-5-p-tolyl-thiophene-2-carboxylic acid
39. 3-(6-Cyclohexyl-3-hydroxy-2-oxo-piperidin-1-yl)-5-p-tolyl-thiophene-2-carboxylic acid
40. 3-[(2S,5R)-5-Cyclohexyl-2-(3-hydroxy-3-methyl-butyl)-2-methyl-3-oxo-morpholin-4-yl]-5-(3,3-dimethyl-but-1-ynyl)-thiophene-2-carboxylic acid
41. 3-[(2R,5R)-5-Cyclohexyl-2-(3-hydroxy-3-methyl-butyl)-2-methyl-3-oxo-morpholin-4-yl]-5-(3,3-dimethyl-but-1-ynyl)-thiophene-2-carboxylic acid
42. 3-[(2S,5R)-5-Cyclohexyl-2-((R)-3-hydroxy-butyl)-2-methyl-3-oxo-morpholin-4-yl]-5-(3,3-dimethyl-but-1-ynyl)-thiophene-2-carboxylic acid
43. 3-[(2R,5R)-5-Cyclohexyl-2-((R)-3-hydroxy-butyl)-2-methyl-3-oxo-morpholin-4-yl]-5-(3,3-dimethyl-but-1-ynyl)-thiophene-2-carboxylic acid
44. 3-((S)-6-Cyclohexyl-3-hydroxy-2-oxo-piperidin-1-yl)-5-(3,3-dimethyl-but-1-ynyl)-thiophene-2-carboxylic acid
45. 3-[(2R,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid
46. 3-(6-Cyclohexyl-3-hydroxy-3-methyl-2-oxo-piperidin-1-yl)-5-p-tolyl-thiophene-2-carboxylic acid
47. 3-((R)-3-Cyclohexyl-5-oxo-1,9-dioxa-4-aza-spiro[5.5]undec-4-yl)-5-(3,3-dimethyl-but-1-ynyl)-thiophene-2-carboxylic acid
48. 3-[6-Cyclohexyl-3-(3-hydroxy-propyl)-2-oxo-piperidin-1-yl]-5-(3,3-dimethyl-but-1-ynyl)-thiophene-2-carboxylic acid 49. 3-[(2S,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid
50. 3-[(2S,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid
51. 3-((R)-5-Cyclohexyl-2-hydroxymethyl-3-oxo-morpholin-4-yl)-5-(3,3-dimethyl-but-1-ynyl)-thiophene-2-carboxylic acid
52. 3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid
53. 3-[(2S,5R)-5-Cyclohexyl-2-(2,3-dihydroxy-propyl)-3-oxo-morpholin-4-yl]-5-(3,3-dimethyl-but-1-ynyl)-thiophene-2-carboxylic acid
54. 3-[(2S,5R)-5-Cyclohexyl-2-(2-hydroxy-ethyl)-3-oxo-morpholin-4-yl]-5-(3,3-dimethyl-but-1-ynyl)-thiophene-2-carboxylic acid
55. 3-[6-Cyclohexyl-3-hydroxy-3-(3-hydroxy-propyl)-2-oxo-piperidin-1-yl]-5-(3,3-dimethyl-but-1-ynyl)-thiophene-2-carboxylic acid
56. 3-[(2R,5R)-5-Cyclohexyl-2-(2,3-dihydroxy-propyl)-3-oxo-morpholin-4-yl]-5-(3,3-dimethyl-but-1-ynyl)-thiophene-2-carboxylic acid
57. 3-[(2R,5R)-5-Cyclohexyl-2-(2-hydroxy-ethyl)-3-oxo-morpholin-4-yl]-5-(3,3-dimethyl-but-1-ynyl)-thiophene-2-carboxylic acid
58. 3-[(2S,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid
59. 3-((S)-6-Cyclohexyl-3-hydroxy-2-oxo-piperidin-1-yl)-5-(3,3-dimethyl-but-1-ynyl)-thiophene-2-carboxylic acid
60. 3-[(2R,5R)-5-Cyclohexyl-2-(3-hydroxy-propyl)-3-oxo-morpholin-4-yl]-5-(3,3-dimethyl-but-1-ynyl)-thiophene-2-carboxylic acid
61. 3-[(2S,5R)-5-Cyclohexyl-2-(3-hydroxy-propyl)-3-oxo-morpholin-4-yl]-5-(3,3-dimethyl-but-1-ynyl)-thiophene-2-carboxylic acid
62. 3-[(2R,5R)-5-Cyclohexyl-2-((R)-2-hydroxy-propyl)-3-oxo-morpholin-4-yl]-5-(3,3-dimethyl-but-1-ynyl)-thiophene-2-carboxylic acid
63. 3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid
64. 3-[(S)-6-Cyclohexyl-3-(3-hydroxy-propyl)-2-oxo-piperidin-1-yl]-5-(3,3-dimethyl-but-1-ynyl)-thiophene-2-carboxylic acid
65. 3-((S)-3-Amino-6-cyclohexyl-2-oxo-piperidin-1-yl)-5-(3,3-dimethyl-but-1-ynyl)-thiophene-2-carboxylic acid
66. 3-[(S)-6-Cyclohexyl-3-(2-hydroxy-ethyl)-2-oxo-piperidin-1-yl]-5-(3,3-dimethyl-but-1-ynyl)-thiophene-2-carboxylic acid The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LIST OF ABBREVIATIONS

Ac acetyl
ACN Acetonitrile
AcOEt/EtOAc Ethyl acetate
AcOH acetic acid
aq aqueous
Ar aryl
Bn benzyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene
DCE 1,2-Dichloroethane
DCM Dichloromethane
DIPEA N-Ethyldiisopropylamine
DMAP Dimethylaminopyridine
DMF N,N'-Dimethylformamide
DMSO Dimethylsulfoxide
EI Electrospray ionisation
$Et_2O$ Diethylether
$Et_3N$ Triethylamine
Ether Diethylether
EtOH Ethanol
FC Flash Chromatography
h hour(s)
HATU O-(7-Azabenzotriazole-1-yl)-N,N,N'N'-tetramethyluronium hexafluorophosphate
HBTU O-(Benzotriazol-1-yl)-N,N,N',N'-tetramethyluronium hexafluorophosphate
HCl Hydrochloric acid
HOBt 1-Hydroxybenzotriazole
HPLC High Performance Liquid Chromatography
$H_2O$ Water
L liter(s)
LC-MS Liquid Chromatography Mass Spectrometry
Me methyl
MeI Iodomethane
MeOH Methanol
mg milligram
min minute(s)
mL milliliter
MS Mass Spectrometry
Pd/C palladium on charcoal
PG protecting group
Ph phenyl
Prep Preparative
Rf ratio of fronts
RP reverse phase
Rt Retention time
rt Room temperature
$SiO_2$ Silica gel
TBAF Tetrabutylammonium fluoride
TEA Triethylamine
TFA Trifluoroacetic acid
THF Tetrahydrofurane
TLC Thin Layer Chromatography
HPLC Methods:
  A. 4.6 mm×150 mm C18 reverse phase column, 5.0 um particle size running a gradient of 5-95% MeCN/water (0.1% formic acid) over a period of 20 min at a flow rate of 1.5 mL/min at 30° C. DAD-UV detection, 220-600 nm
B. 3 mm×100 mm C18 reverse phase column, 3.0 um particle size running a gradient of 5-95% MeCN/water (0.1% formic acid) over a period of 7.45 min at a flow rate of 1 mL/min at 40° C. DAD-UV detection, 220-600 nm.
C. 4.6 mm×50 mm C18 reverse phase column, 5.0 um particle size running a gradient of 5-95% MeCN/water (0.1% formic acid) over a period of 3.4 min at a flow rate of 2 mL/min at 40° C. DAD-UV detection, 220-600 nm.
D. 4.6 mm×50 mm C18 reverse phase column, 5.0 um particle size running a gradient of 5-95% MeCN/water (0.1% ammonium formate) over a period of 3.4 min at a flow rate of 2 mL/min at 40° C. DAD-UV detection, 220-600 nm.
E. 3.0 mm×33 mm C8 reverse phase column, 3.0 um particle size running a gradient of 5-95% MeCN/water (0.1% ammonium formate) over a period of 2.0 min at a flow rate of 2 mL/min at 50° C. DAD-UV detection, 220-600 nm.

Procedures

Example 1

Synthesis of 3-[-2-Cyclohexyl-4-(2-fluoro-benzenesulfonyl)-6-oxo-piperazin-1-yl]-5-phenyl-thiophene-2-carboxylic acid [Compound 40]

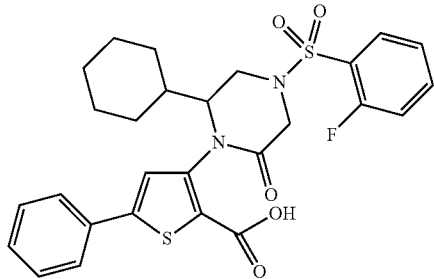 [SMILES: O=C(O)c1sc(-c2ccccc2)cc1N1C(=O)CN(S(=O)(=O)c2ccccc2F)CC1C1CCCCC1]

Step 1. Synthesis of [(R)-Cyclohexyl-(methoxy-methyl-carbamoyl)-methyl]-carbamic acid benzyl ester

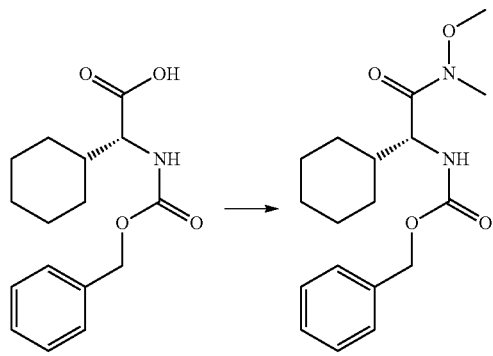 [SMILES: O=C(N[C@@H](C(=O)O)C1CCCCC1)OCc1ccccc1 ; CON(C)C(=O)[C@H](NC(=O)OCc1ccccc1)C1CCCCC1]

To a solution of (R)-benzyloxycarbonylamino-cyclohexyl-acetic acid (25 g, 88 mmol) in DMF (100 mL) at −10° C. was added HATU (36.7 g, 96 mmol, 1.0 equiv) followed by N,O-dimethyl hydroxyamine HCl salt (10.3 g, 105 mmol, 1.2 equiv). To this solution was then slowly added N-methyl morpholine (28.9 mL, 263 mmol, 3.0 equiv). The internal temperature was carefully monitored. During the addition, the internal temperature rose to 0° C. The solution was stirred at 0° C. for 2 hours after which the solution was diluted with EtOAc (500 mL) and washed with sat. aq. NaHCO$_3$ solution, water, 1.0 N aq. HCl solution and brine. The organic layer was dried over Na$_2$SO$_4$ and the solvent including DMF was removed under vacuum. The residue was diluted with EtOAc and the solution was washed with water, brine, dried (MgSO$_4$) and concentrated to give product [(R)-Cyclohexyl-(methoxy-methyl-carbamoyl)-methyl]-carbamic acid benzyl ester 26 g (yield 90%).

Step 2. Synthesis of ((R)-1-Cyclohexyl-2-oxo-ethyl)-carbamic acid benzyl ester

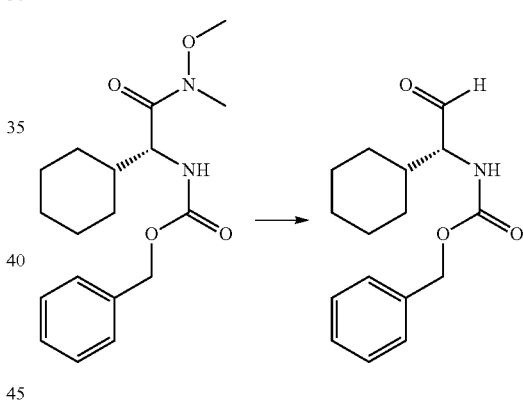

To a solution of [(R)-Cyclohexyl-(methoxy-methyl-carbamoyl)-methyl]-carbamic acid benzyl ester (27 g, 82 mmol) in THF (400 mL) at −20° C. was slowly added LiAlH$_4$ (4.06 g, 106 mmol, 1.3 equiv). LiAlH$_4$ was freshly ground from pellet purchased from Aldrich. During addition, the internal temperature was carefully monitored and did not rise above 0° C. After addition the mixture was stirred at 0° C. and the reaction was monitored by TLC and LCMS. After 1 hour, the reaction solution was cooled at −10° C. and quenched by slow addition of sat. aq. KHSO$_4$ solution until pH=5. The mixture was partitioned between water and EtOAc. The phases were separated and the organic layer was concentrated. The residue was dissolved in EtOAc and the solution was washed with water, brine, dried over Na$_2$SO$_4$ and concentrated to give product ((R)-1-Cyclohexyl-2-oxo-ethyl)-carbamic acid benzyl ester 22 g (99%). The material was continued to next step with no further purification.

Step 3. Synthesis of ((R)-2-Benzyloxycarbonylamino-2-cyclohexyl-ethylamino)-acetic acid methyl ester

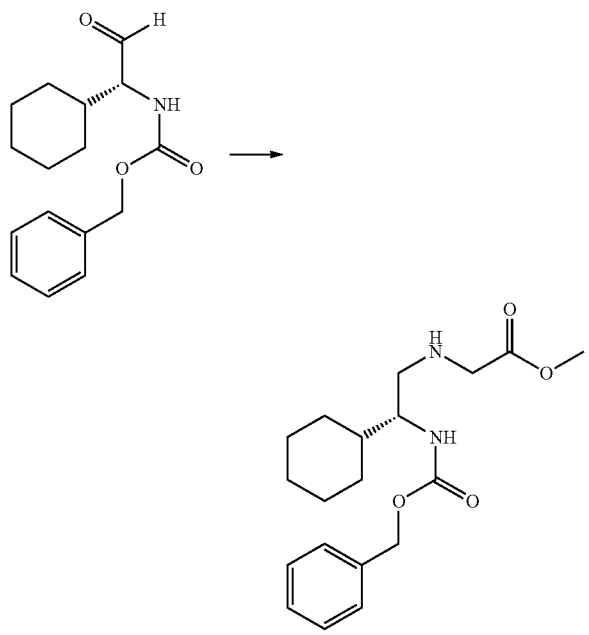

A solution of aldehyde (25 g, 91 mmol) in CH₂Cl₂ (350 mL) at 0° C. was added methyl glycine hydrochloride salt (22.8 g, 182 mmol, 2.0 equiv) followed by DIPEA (23.8 mL, 136 mmol, 1.5 equiv). To the solution was then added sodium triacetoxyborohydride (28.9 g, 136 mmol, 1.5 equiv). The mixture was stirred at room temperature for 3 hours. The reaction was quenched by addition of sat. aq. NaHCO₃ solution until pH=8. The phases were separated and the aqueous layer was extracted with CH₂Cl₂. The combined organic layer was washed with water, brine, dried (MgSO₄) and concentrated to give product ((R)-2-Benzyloxycarbonylamino-2-cyclohexyl-ethylamino)-acetic acid methyl ester (34 g, 107% yield). The crude product which contained impurity and solvent was continued to the next step with no further purification.

Step 4. Synthesis of (R)-6-Cyclohexyl-piperazin-2-one

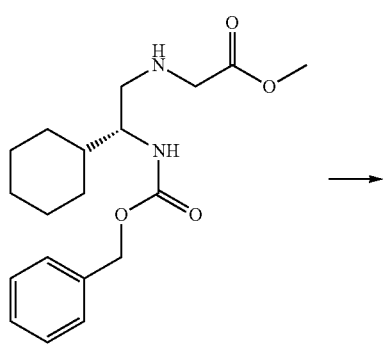

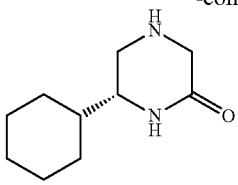

To a 2.0 L round bottom flask containing a solution of ((R)-2-Benzyloxycarbonylamino-2-cyclohexyl-ethylamino)-acetic acid methyl ester (27 g, 77 mmol) in MeOH (300 mL) under a stream of N₂ was added Pd (10% on carbon, 4.1 g, 0.05 equiv). The mixture was stirred under 1.0 atm of H₂ for 18 hours. The mixture was diluted with 100 mL of CH₂Cl₂ and filtered through Celite. The filtrate was concentrated to give crude product (R)-6-Cyclohexyl-piperazin-2-one 18 g (127%). The product, which contained impurity and solvent, was continued to the next step with no further purification.

Step 5. Synthesis of (R)-3-Cyclohexyl-5-oxo-piperazine-1-carboxylic acid tert-butyl ester

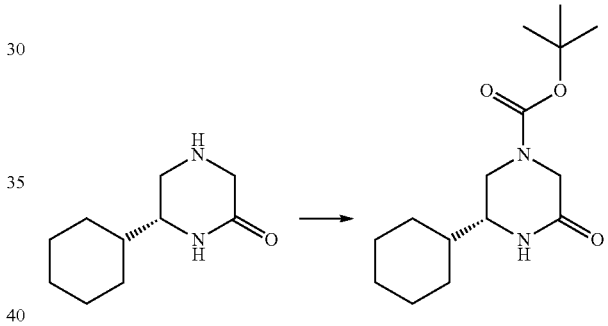

To a solution of (R)-6-Cyclohexyl-piperazin-2-one (7.3 g, 40 mmol) in CH₂Cl₂ (200 mL) was added (Boc)₂O (10.5 g, 11.1 mmol, 1.2 equiv). The solution was stirred at room temperature for 1 hour, after which the solvent was removed under vacuum. The residue was purified by silica gel column chromatography (acetone/heptane, 40%). The collected fraction was concentrated until ~100 mL solvent left. The solid was filtered and dried to give product (R)-3-Cyclohexyl-5-oxo-piperazine-1-carboxylic acid tert-butyl ester 6.7 g (59%). The ee of product was determined to be >98% by chiral SFC.

Step 6. Synthesis of 3-bromo-5-phenyl-thiophene-2-carboxylic acid methyl ester

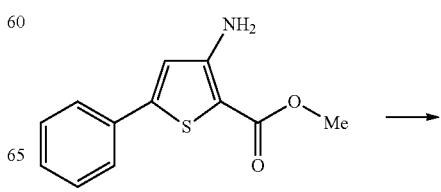

-continued

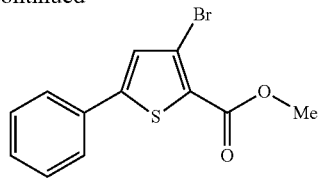

To a 250 round bottom flask equipped with refluxing condenser was added CuBr$_2$ (11.5 g, 51 mmol, 1.2 equiv), CH$_3$CN (250 mL) and t-butyl nitrite (6.63 g, 64.3 mmol, 1.5 equiv). The solution was heated at 65° C. and to this solution was added a solution of 3-amino-5-phenyl-thiophene-2-carboxylic acid methyl ester (10.0 g, 42.0 mmol) in CH$_3$CN (50 mL). The resulting mixture was heated at 65° C. for 1 hour. The reaction mixture was then cooled at room temperature and added to 1.0 N HCl aq. solution. EtOAc was added and the phases were separated. The aqueous layer was extracted with EtOAc. The organic layer was washed with water, brine, dried (Na$_2$SO$_4$) and concentrated. The residue was purified by silica gel to give product 3-bromo-5-phenyl-thiophene-2-carboxylic acid methyl ester 7.5 g.

Step 7. Synthesis of (R)-3-Cyclohexyl-4-(2-methoxycarbonyl-5-phenyl-thiophen-3-yl)-5-oxo-piperazine-1-carboxylic acid tert-butyl ester

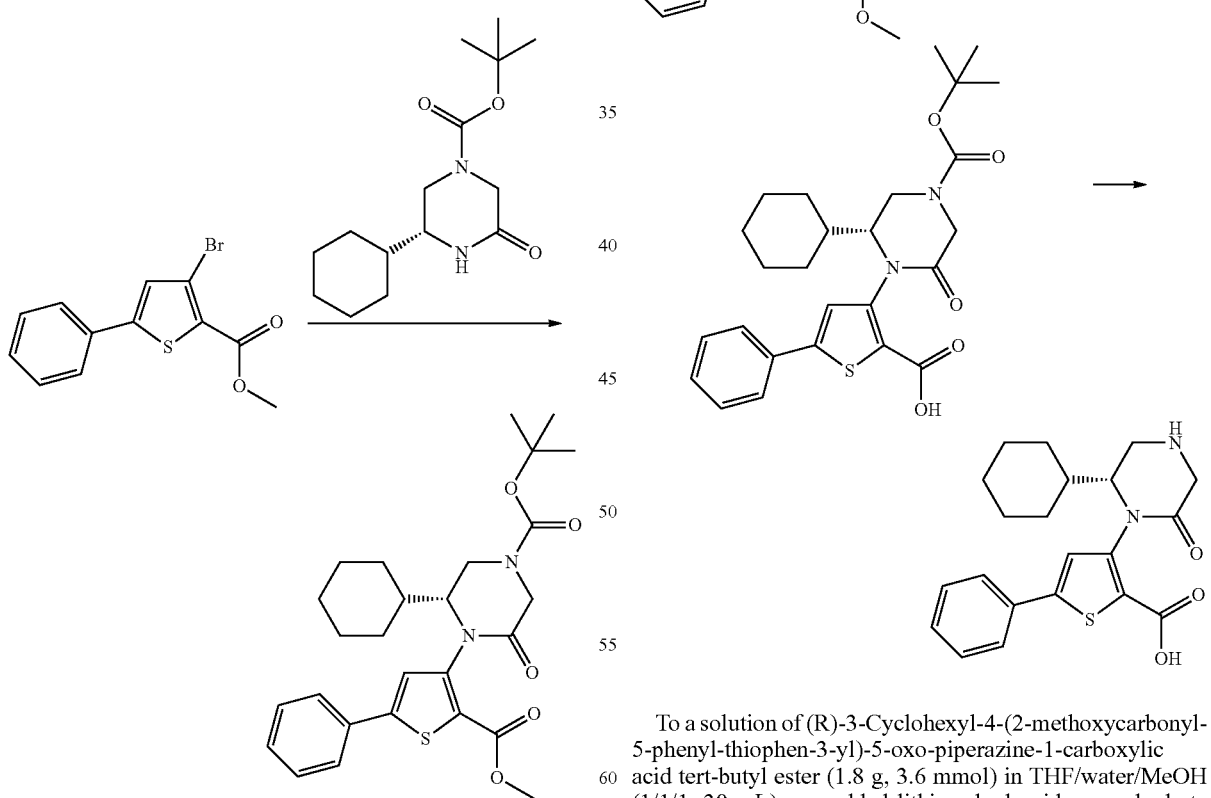

A tube was charged with trans-cyclohexanediamine (162 mg, 1.42 mmol, 0.5 equiv), K$_2$CO$_3$ (783 mg, 5.67 mmol, 2.0 equiv), 3-bromo-5-phenyl-thiophene-2-carboxylic acid methyl ester (1.01 g, 3.40 mmol, 1.2 equiv), CuI (270 mg, 1.42 mmol, 0.5 equiv), (R)-3-Cyclohexyl-5-oxo-piperazine-1-carboxylic acid tert-butyl ester (800 mg, 2.83 mmol, 1.0 equiv) and 1,4-dioxane (3.0 mL). The tube was then flushed with N$_2$ and sealed. The reaction mixtures were heated at 110° C. for 72 hours after which it was diluted with EtOAc and filtered. The filtrate was washed with 1.0 N HCl aq. solution, brine, dried (Na$_2$SO$_4$) and concentrated. The residue was purified by silica gel column chromatography (EtOAc/heptane, 50%) to give product (R)-3-Cyclohexyl-4-(2-methoxycarbonyl-5-phenyl-thiophen-3-yl)-5-oxo-piperazine-1-carboxylic acid tert-butyl ester 415 mg.

Step 8. Synthesis of 3-((R)-2-Cyclohexyl-6-oxo-piperazin-1-yl)-5-phenyl-thiophene-2-carboxylic acid

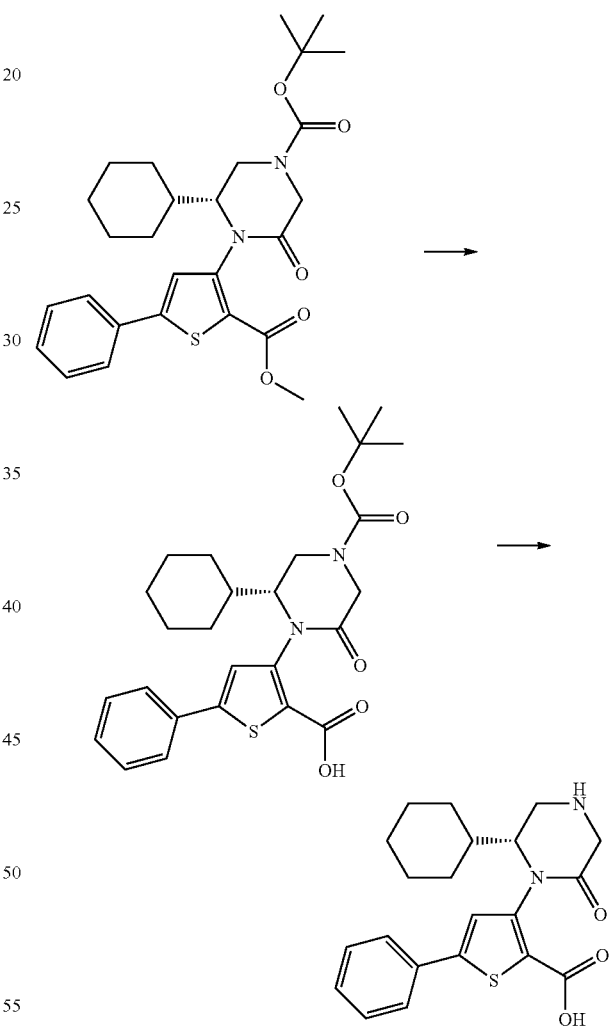

To a solution of (R)-3-Cyclohexyl-4-(2-methoxycarbonyl-5-phenyl-thiophen-3-yl)-5-oxo-piperazine-1-carboxylic acid tert-butyl ester (1.8 g, 3.6 mmol) in THF/water/MeOH (1/1/1, 30 mL) was added lithium hydroxide monohydrate (0.45 g, 10.8 mmol, 3.0 equiv) and the resulting solution was heated at 55° C. for 1 hour. The reaction was quenched by addition of 1.0 N HCl aq. solution until pH=5. The solution was then extracted with EtOAc. The organic layer was washed with brine, dried (Na$_2$SO$_4$) and concentrated to give (R)-4-(2-Carboxy-5-phenyl-thiophen-3-yl)-3-cyclohexyl-5- oxo-piperazine-1-carboxylic acid tert-butyl ester 3-((R)-2-Cyclohexyl-6-oxo-piperazin-1-yl)-5-phenyl-thiophene-2-carboxylic acid (1.7 g, 97%). The material was continued to the next step with no further purification.

To a solution of (R)-4-(2-Carboxy-5-phenyl-thiophen-3-yl)-3-cyclohexyl-5-oxo-piperazine-1-carboxylic acid tert-butyl ester (1.7 g) in 1,4-dioxane (5.0 mL) was added a solution of 4.0 N HCl in dioxane (20 mL) and the resulting mixture was stirred at room temperature of 2 hours. The solvent was then removed under vacuum to give product as HCl salt (1.4 g, 95%).

Step 9. Synthesis of racemic 3-(2-cyclohexyl-6-oxo-piperazin-1-yl)-5-phenyl-thiophene-2-carboxylic acid

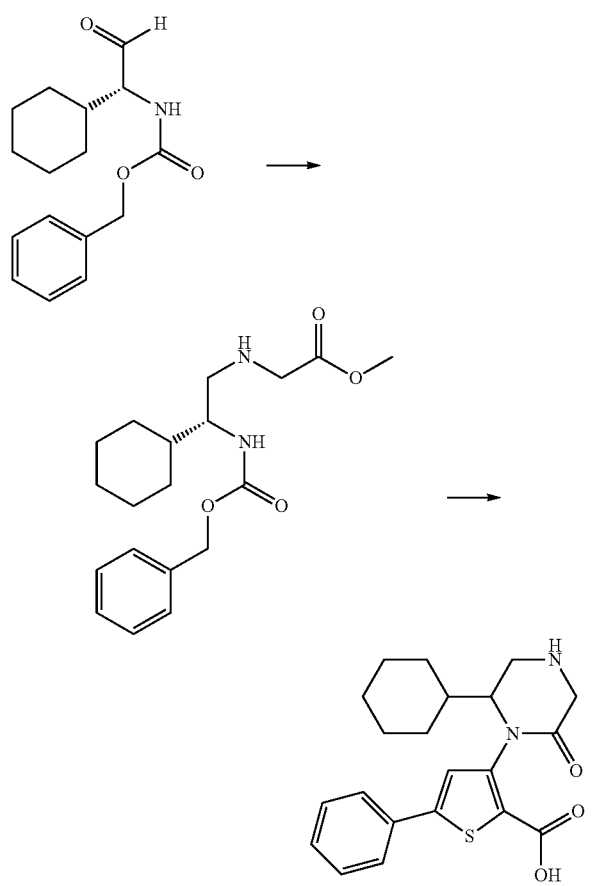

To a solution of (R)-benzyloxycarbonylamino-cyclohexyl-acetic acid (15 g, 51.5 mmol) in CH$_2$Cl$_2$ (60 mL) at 0° C. was added N-methylmorpholine (12.5 mL, 113 mmol, 2.2 equiv) and at −25° C. isobutyl chloroformate (6.76 mL, 51.5 mmol, 1.0 equiv) was added. The resulting solution was stirred at −10° C. for 1 hour, after which to this solution was added a suspension N,O-dimethyl hydroxyamine HCl salt (5.52 g, 56.5 mmol, 1.1 equiv) in CH$_2$Cl$_2$ (60 mL). The mixture was then stirred at room temperature for 3 hours, after which the solution was diluted with EtOAc (500 mL) and washed with 1.0 N aq. HCl solution and brine. The organic layer was dried over Na$_2$SO$_4$ and concentrated. Racemic 3-(2-cyclohexyl-6-oxo-piperazin-1-yl)-5-phenyl-thiophene-2-carboxylic acid was synthesized from this material following step 2-8 described above.

Step 10. Synthesis of 3-[-2-Cyclohexyl-4-(2-fluoro-benzenesulfonyl)-6-oxo-piperazin-1-yl]-5-phenyl-thiophene-2-carboxylic acid

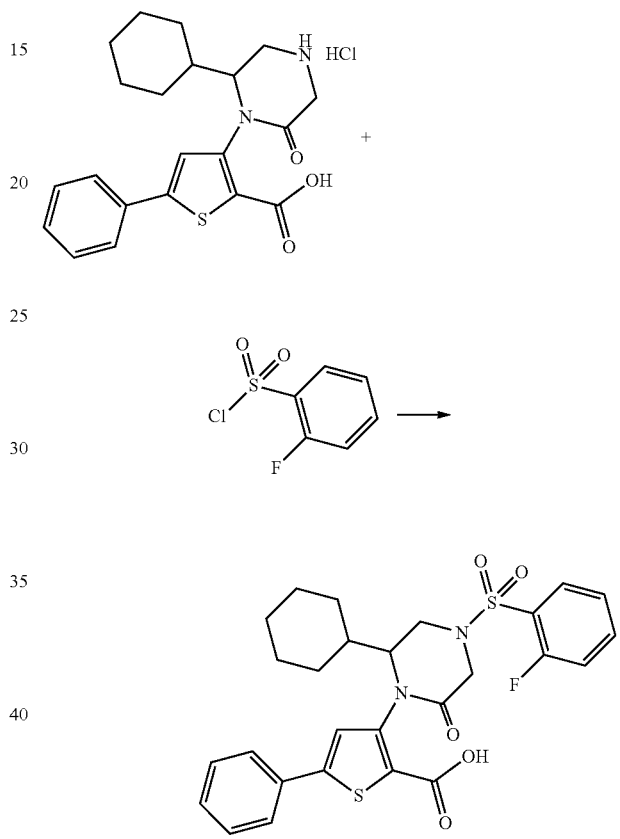

To a solution of 3-(2-cyclohexyl-6-oxo-piperazin-1-yl)-5-phenyl-thiophene-2-carboxylic acid (15.0 mg, 0.036 mmol, 1.0 equiv) in MeCN (0.2 mL) at room temperature, was added NaOH (0.40 mL, 1.5 N solution, 0.60 mmol, 16.7 equiv) and 2-fluoro-benzenesulfonyl chloride (11.4 mg, 0.059 mmol, 1.64 equiv). The mixture was stirred at room temperature for 30 minutes. The mixture was acidified with 3 N HCl (0.3 mL), and then diluted with EtOAc (10 mL). The mixture was washed with water (5 mL), brine (5 mL), then dried (over Na$_2$SO$_4$), filtered and the filtrate was concentrated under reduced pressure. The residue was purified by HPLC (0.1% NH$_4$OH) to give product (5.0 mg, 24%) as white solid. MS: 543 [M−H$^+$]. $^1$H-NMR (400 MH$_Z$, CDCl$_3$): δ 1.12 (m, 3H), 1.34 (m, 1H), 1.45-1.90 (m, 7H), 2.70-2.87 (m, 2H), 3.34 (d, 1H), 3.60-3.70 (m, 2H), 3.95 (d, 1H), 4.18 (d, 1H), 7.13 (s, 1H), 7.21 (t, 1H), 7.27 (t, 1H), 7.30-7.40 (m, 3H), 7.51-7.61 (m, 3H), 7.83 (t, 1H).

Example 2

Synthesis of 3-[(R)-2-Cyclohexyl-6-oxo-4-(6-pyrrolidin-1-yl-pyridine-3-sulfonyl)-piperazin-1-yl]-5-phenyl-thiophene-2-carboxylic acid [Compound 135]

Step 1. Synthesis of 3-[(R)-4-(6-Chloro-pyridine-3-sulfonyl)-2-cyclohexyl-6-oxo-piperazin-1-yl]-5-phenyl-thiophene-2-carboxylic acid

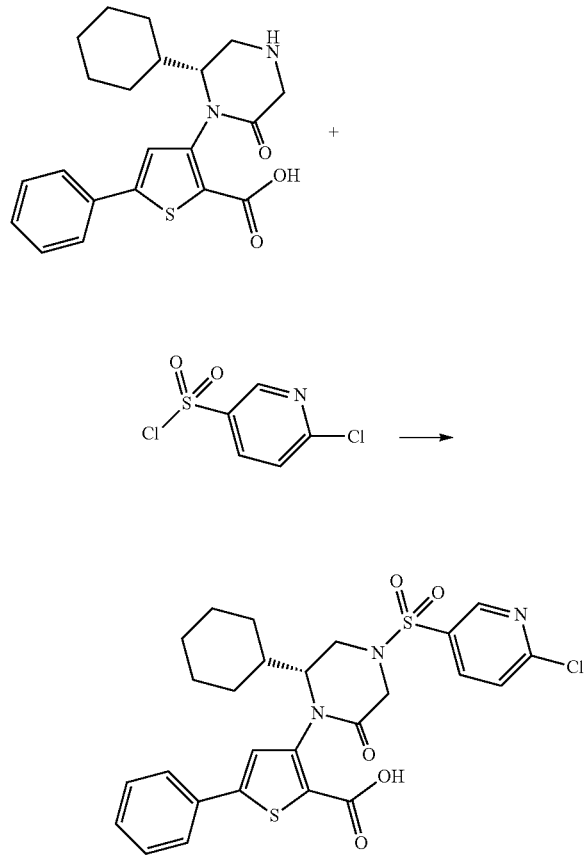

To a solution of 3-(2-cyclohexyl-6-oxo-piperazin-1-yl)-5-phenyl-thiophene-2-carboxylic acid (0.80 g, 1.90 mmol, 1.0 equiv) in MeCN (20 mL) at room temperature, was added 6-chloro-pyridine-3-sulfonyl chloride (1.10 g, 5.20 mmol, 2.7 equiv) and followed by NaOH (6.94 mL, 1.5 N solution, 10.4 mmol, 5.5 equiv) dropwise. The mixture was stirred at room temperature for 10 minutes. The mixture was acidified with 3 N HCl (2.5 mL), and then diluted with EtOAc (50 mL). The mixture was washed water (25 mL), brine (25 mL), dried (over Na$_2$SO$_4$), filtered and concentrated to give crude product (1.0 g, 94%) as yellow-green solid. MS: 560 [M−H$^+$].

Step 2. Synthesis of 3-[(R)-2-Cyclohexyl-6-oxo-4-(6-pyrrolidin-1-yl-pyridine-3-sulfonyl)-piperazin-1-yl]-5-phenyl-thiophene-2-carboxylic acid

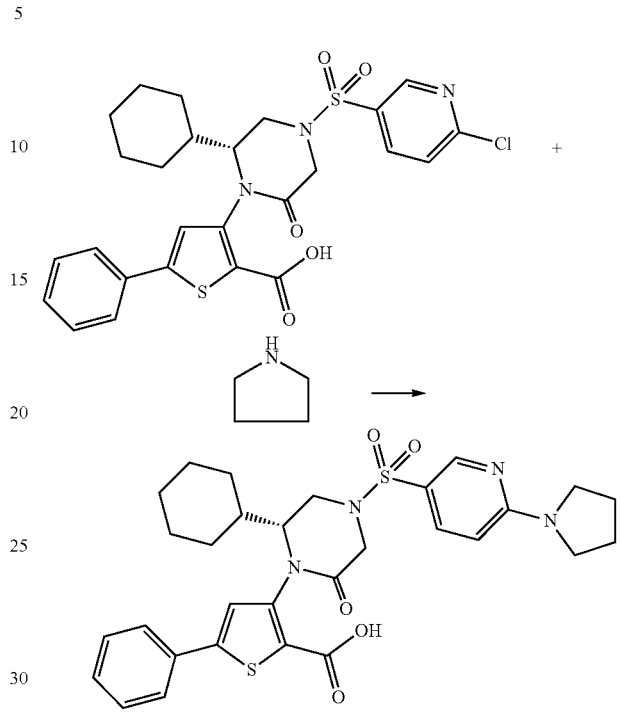

To a solution of 3-[(R)-4-(6-chloro-pyridine-3-sulfonyl)-2-cyclohexyl-6-oxo-piperazin-1-yl]-5-phenyl-thiophene-2-carboxylic acid (100 mg, 0.18 mmol, 1.0 equiv) in DMF (0.8 mL) at room temperature was added pyrrolidine (127 mg, 1.79 mmol, 10.0 equiv) and Et$_3$N (0.37 mL, 2.68 mmol, 15.0 equiv). The mixture was stirred at 70° C. for 2 hours. The mixture was then cooled to room temperature and filtered. The filtrate was concentrated and purified by HPLC (0.1% NH$_4$OH) to give product (35 mg, 33%) as white solid. MS: 595 [M−H$^+$]. $^1$H-NMR (400 MH$_Z$, MeOD): δ 1.10-1.23 (m, 5H), 1.40-2.00 (m, 10H), 3.04-3.12 (m, 2H), 3.20 (t, 2H), 3.42 (d, 2H), 3.88 (d, 1H), 3.97 (br, 1H), 4.07 (d, 1H), 6.62 (s, 1H), 7.19 (s, 1H), 7.32 (t, 1H), 7.40 (t, 2H), 7.63 (d, 2H), 7.83 (m, 1H), 8.44 (d, 1H).

Example 3

Synthesis of 3-((R)-3-Cyclohexyl-5-oxo-morpholin-4-yl)-5-(3,3-dimethyl-but-1-ynyl)-thiophene-2-carboxylic acid [Compound 236]

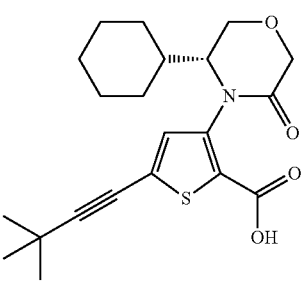 [SMILES: CC(C)(C)C#Cc1cc(N2C(=O)COC[C@H]2C2CCCCC2)c(C(=O)O)s1]

Step 1. Synthesis of (R)-5-Cyclohexyl-morpholin-3-one

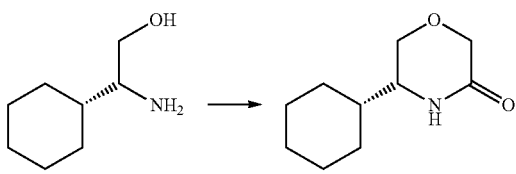

To a solution containing 3.8 g (26.5 mmol, 1.0 equiv) of (R)-2-amino-2-cyclohexyl-ethanol in 100 mL of THF was added sodium hydride (1.4 g, 58.4 mmol, 60% in mineral oil, 2.2 equiv). The reaction mixture was stirred at 25° C. for 30 minutes, at which time hydrogen evolution had ceased. The mixture was cooled at 0° C. and was added ethyl chloroacetate (3.3 g, 26.5 mmol, 1.0 equiv), dropwise, over 5 minutes. The reaction mixture was stirred for 1 hour at 25° C. and then 2 hours at reflux. The solvent was removed under vacuum and to the residue was added 1.0 N HCl aq. solution until pH=6. The mixture was extracted with ethyl acetate. The resulting organic extracts were washed with brine, dried over sodium sulfate and concentrated in vacuo. The residue was recrystallized from EtOAc/heptane to give product 2.8 g. The mother liquid was concentrated and the residue was purified by silica gel column chromatography (acetone/heptane 50%) to give product 1.3 g. Combined yield 4.1 g (84%)

Step 2. Synthesis of 5-(3,3-dimethyl-but-1-ynyl)-thiophene-2-carboxylic acid

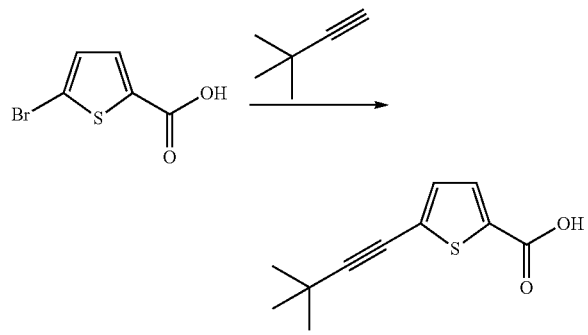

A 350 mL heavy wall round bottom flask was charged with TEA (33.7 mL, 24 mmol, 5.0 equiv), BINAP (3.0 g, 4.83 mmol, 0.1 equiv), 5-bromo-thiophene-2-carboxylic acid (48.3 mmol, 1.0 equiv), CuI (0.184 g, 0.97 mmol, 0.02 equiv), Pd$_2$dba$_3$ (2.2 g, 2.4 mmol, 0.05 equiv) and DMF (40.0 mL). The flask was flushed with N$_2$ and to the mixture was added t-butyl acetylene (15.8 g, 193 mmol, 4.0 equiv). The mixture was sealed and stirred at 70° C. for 48 hours. After cooled at room temperature, the reaction mixture was filtered and the filtrate was concentrated under vacuum. The residue was acidified with 3.0 N HCl until pH=4. The aqueous layer was extracted with EtOAc. The organic layer was washed with brine, dried over Na$_2$SO$_4$ and concentrated. The residue was purified by silical gel, EtOAc/heptane 5% to EtOAc/heptane 30% with 2% of AcOH to give product 6.5 g (yield 65%).

Step 3. Synthesis of 3-Bromo-5-(3,3-dimethyl-but-1-ynyl)-thiophene-2-carboxylic acid

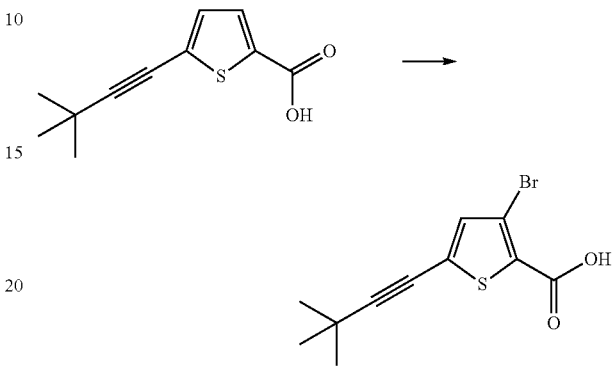

To a of solution of 5-(3,3-dimethyl-but-1-ynyl)-thiophene-2-carboxylic acid (6.5 g, 31.3 mmol, 1.0 equiv) in THF (150 mL) at −78° C. was added n-BuLi (44.9 mL, 1.6 M in heptane, 71.9 mmol, 2.3 equiv) and the resulting solution was stirred at −78° C. for 1 hour. To the solution was then added 1,2-dibromo-1,1,2,2-tetrafluoro-ethane (16.2 g, 62.5 mmol, 2.0 equiv) and the solution was allowed to warm to room temperature over 2 hours. The reaction was quenched by addition of sat. aq. NH$_4$Cl solution and the mixture was extracted with EtOAc. The organic layers were combined, washed with brine, dried over Na$_2$SO$_4$ and concentrated. The crude material was continued to the next step with no further purification.

Step 4. Synthesis of 3-Bromo-5-(3,3-dimethyl-but-1-ynyl)-thiophene-2-carboxylic acid methyl ester

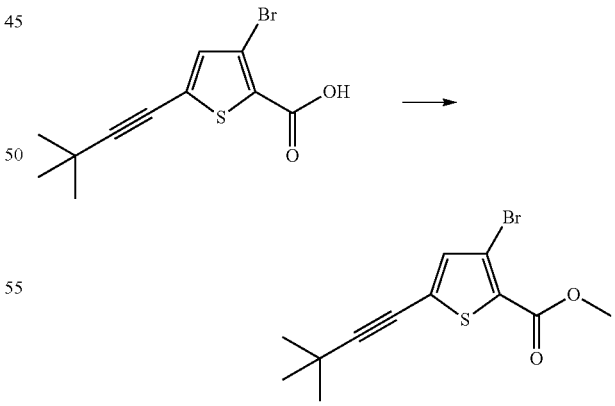

The product from previous step was dissolved in DMF (15.0 mL) and to the solution was added K$_2$CO$_3$ (8.6 g, 62.6 mmol, 2.0 equiv) and MeI (8.9 g, 62.6 mmol, 2.0 equiv). The resulting mixture was stirred at room temperature for 18 hours. The mixture was filtered and the filtrate was concentrated under vacuum. The residue was purified by silica gel column chromatography, heptane/EtOAc 15% to give product 7.0 g (74% yield for 2 steps).

Step 5. Synthesis of 3-((R)-3-Cyclohexyl-5-oxo-morpholin-4-yl)-5-(3,3-dimethyl-but-1-ynyl)-thiophene-2-carboxylic acid methyl ester

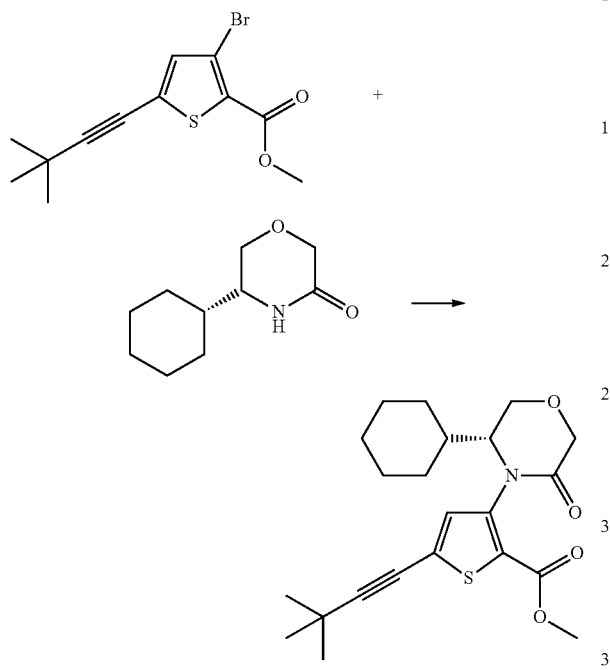

A heavy wall flask was charged with trans-cyclohexane diamine (623 mg, 5.5 mmol, 0.5 equiv), 3-bromo-5-(3,3-dimethyl-but-1-ynyl)-thiophene-2-carboxylic acid methyl ester (4.27 g, 14.2 mmol, 1.3 equiv), K$_2$CO$_3$ (3.02 g, 21.8 mmol, 2.0 equiv), CuI (1.04 g, 5.5 mmol, 0.5 equiv), 5-cyclohexyl-morpholin-3-one (2.0 g, 10.9 mmol, 1.0 equiv) and 1,4-dioxane (10.0 mL). The mixture was flushed with N$_2$ and stirred at 110° C. for 48 hours. The mixture was filtered through celite and the filtrate was concentrated under vacuum. The residue was purified by silica gel, EtOAc/heptane 50% to give product 2.8 g (yield 50%).

Step 6. Synthesis of 3-((R)-3-Cyclohexyl-5-oxo-morpholin-4-yl)-5-(3,3-dimethyl-but-1-ynyl)-thiophene-2-carboxylic acid

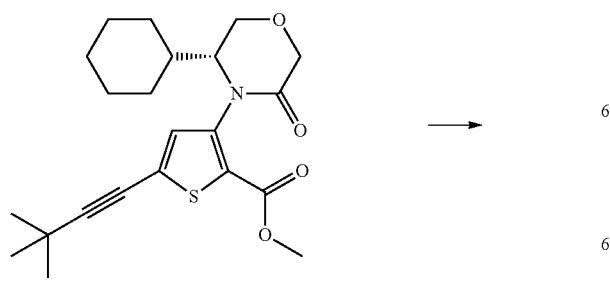

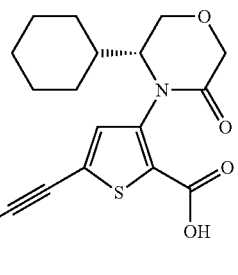

To a solution of methyl ester (35 mg, 0.087 mmol, 1.0 equiv) in THF (0.5 mL), MeOH (0.5 mL), water (0.5 mL) was added lithium hydroxide monohydrate (10.9 mg, 0.26 mmol, 3.0 equiv). The resulting mixture was stirred at 50° C. for 1 hour, after which the reaction was neutralized by addition of 1.0 N HCl aq. solution to pH=6. The mixture was extracted with EtOAc. The organic layers were combined, washed with brine, dried over Na$_2$SO$_4$ and concentrated. The residue was purified by reverse phase HPLC to give product 18 mg (yield 53%). MS: 390.1 [M+H$^+$]. $^1$H-NMR (400 MHz, CD$_3$OD): 6.87 (s, 1H), 4.19 (s, 2H), 4.05 (m, 2H), 3.82 (s, 1H), 1.43-1.90 (m, 6H), 1.06-1.39 (m, 14H)

Example 4

Synthesis of 3-[(R)-5-Cyclohexyl-2-(3-hydroxy-propyl)-3-oxo-morpholin-4-yl]-5-(3,3-dimethyl-but-1-ynyl)-thiophene-2-carboxylic acid [Compound 299]

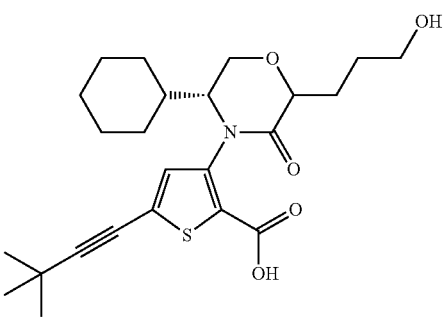 [SMILES: CC(C)(C)C#Cc1cc(N2C(=O)C(CCCO)OC[C@H]2C2CCCCC2)c(C(=O)O)s1]

Step 1. Synthesis of cyclohexyl-4-(4-methoxy-benzyl)-morpholin-3-one

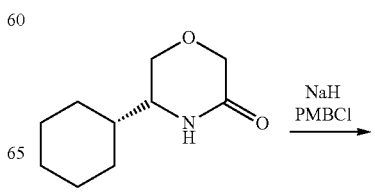

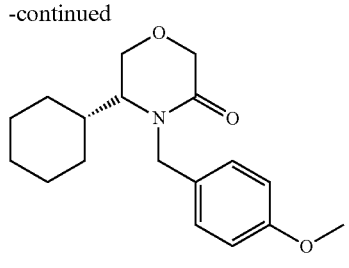

To a solution of 5-Cyclohexyl-morpholin-3-one (1.0 g, 5.5 mmol, 1.0 equiv) in DMF (15.0 mL) at 0° C. was added NaH (0.26 g, 60% in oil, 6.5 mmol, 1.2 equiv) slowly. The mixture was stirred at room temperature for 30 minutes, then it was added PMBCl (0.94 g, 6.0 mmol, 1.1 equiv). After stirred at room temperature for 2 hours, the reaction mixture was quenched by added to sat. aq. NH₄Cl solution. The mixtures were extracted with EtOAc. The organic layers were combined and washed with brine, dried over MgSO₄ and concentrated. The residue was purified by silica gel, acetone/heptane 30% to give 1.5 g (91%) of 5-Cyclohexyl-4-(4-methoxy-benzyl)-morpholin-3-one.

Step 2. Synthesis of 2-[3-(tert-Butyl-dimethyl-silanyloxy)-propyl]-5-cyclohexyl-4-(4-methoxy-benzyl)-morpholin-3-one

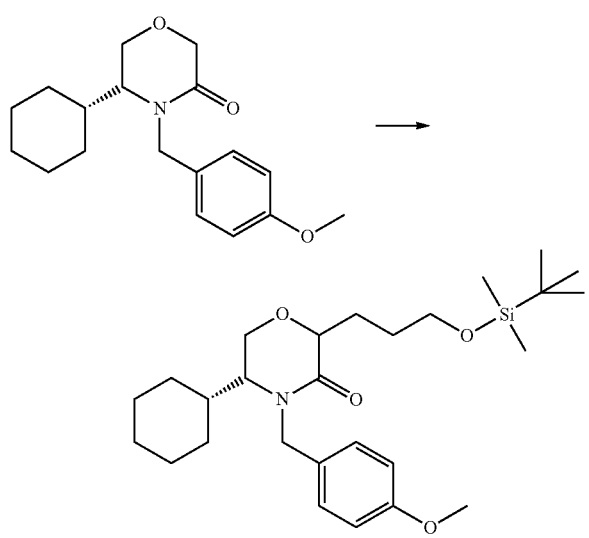

To a solution of 5-cyclohexyl-4-(4-methoxy-benzyl)-morpholin-3-one (700 mg, 2.3 mmol, 1.0 equiv) in THF (10.0 mL) at −78° C. was added n-BuLi (1.58 mL, 1.6 M in heptane, 2.54 mmol, 1.1 equiv). The resulting solution was stirred at −78° C. for 30 minutes, after which it was added a solution of tert-Butyl-(3-iodo-propoxy)-dimethyl-silane (693 mg, 2.3 mmol, 1.0 equiv) in THF (1.0 mL). The solution was stirred at −78° C. for 30 minutes and 2 hours at room temperature after which it was quenched by addition of sat. aq. NH₄Cl solution. The mixture was extracted with EtOAc. The organic layer was combined, dried over MgSO₄ and concentrated. The residue was purified by silica gel column chromatography, EtOAc/heptane 30% to give product 480 mg (yield 44%).

Step 3. Synthesis of 5-Cyclohexyl-2-(3-hydroxy-propyl)-morpholin-3-one

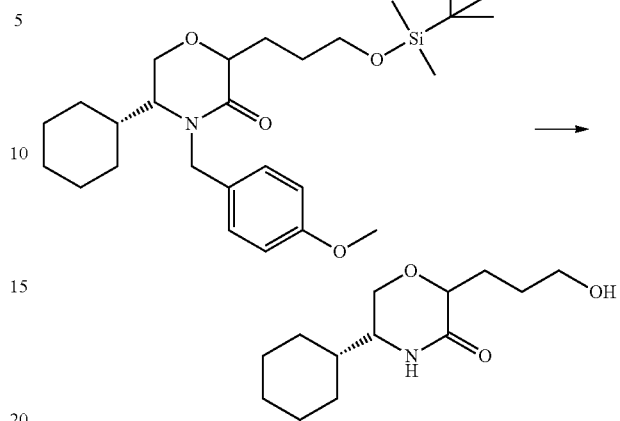

To a solution of 2-[3-(tert-Butyl-dimethyl-silanyloxy)-propyl]-5-cyclohexyl-4-(4-methoxy-benzyl)-morpholin-3-one (400 mg, 0.84 mmol, 1.0 equiv) in CH₃CN (0.3 mL) and water (0.3 mL) was added CAN (922 mg, 1.68 mmol, 2.0 equiv). The mixture was stirred at room temperature for 1 hour then second portion of CAN (900 mg) was added. After stirred at room temperature for 1 hour, the reaction mixture was diluted with EtOAc and the phases were separated. The organic layer was washed with brine, dried over Na₂SO₄ and concentrated. The residue was purified by silica gel column chromatography, EtOAc/heptane 50% to 100% EtOAc to give 5-cyclohexyl-2-(3-hydroxy-propyl)-morpholin-3-one 134 mg.

Step 4. Synthesis of 3-[(R)-5-Cyclohexyl-2-(3-hydroxy-propyl)-3-oxo-morpholin-4-yl]-5-(3,3-dimethyl-but-1-ynyl)-thiophene-2-carboxylic acid methyl ester

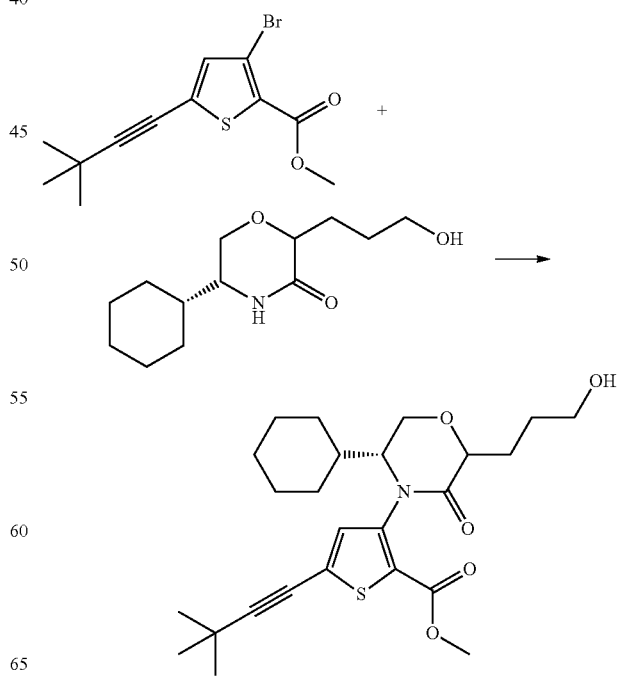

A 10 mL heavy wall vial was charged with trans-cyclohexane diamine (11.8 mg, 0.10 mmol, 0.5 equiv), 3-bromo-5-(3,3-dimethyl-but-1-ynyl)-thiophene-2-carboxylic acid methyl ester (125 mg, 0.41 mmol, 2.0 equiv), $K_2CO_3$ (57 mg, 0.41 mmol, 2.0 equiv), CuI (19.7 mg, 0.10 mmol, 0.5 equiv), 5-cyclohexyl-2-(3-hydroxy-propyl)-morpholin-3-one (50 mg, 0.21 mmol, 1.0 equiv) and 1,4-dioxane (0.5 mL). The mixture was flushed with $N_2$ and stirred at 110° C. for 24 hours. The mixture was filtered through celite and the filtrate was concentrated under vacuum. The residue was purified by silica gel, EtOAc/heptane 30% to give product 10 mg (yield 10%).

Step 5. Synthesis of 3-[(R)-5-Cyclohexyl-2-(3-hydroxy-propyl)-3-oxo-morpholin-4-yl]-5-(3,3-dimethyl-but-1-ynyl)-thiophene-2-carboxylic acid

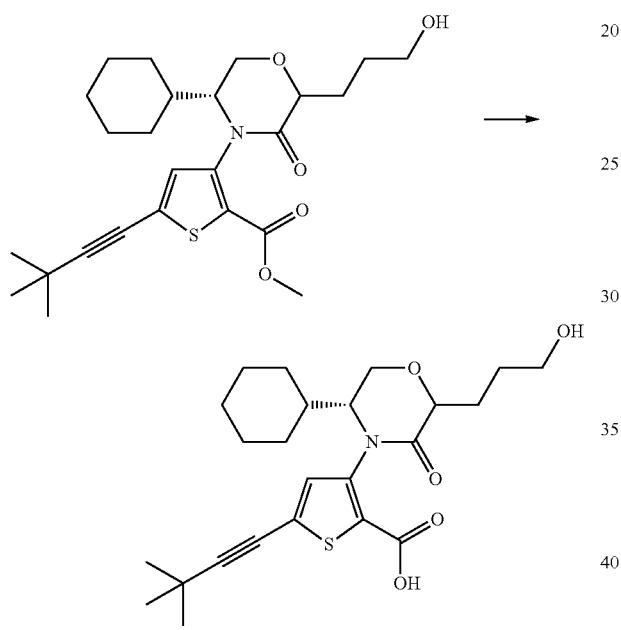

To a solution of methyl ester (10 mg, 0.022 mmol, 1.0 equiv) in THF (0.2 mL), MeOH (0.2 mL), water (0.2 mL) was added lithium hydroxide hydrate (4.5 mg, 0.11 mmol, 5.0 equiv). The resulting mixture was stirred at 50° C. for 30 minutes, after which the reaction was neutralized by addition of 1.0 N HCl aq. solution to pH=6. The mixture was extracted with EtOAc. The organic layers were combined, washed with brine, dried over $Na_2SO_4$ and concentrated. The residue was purified by reverse phase HPLC to give product 2.6 mg. MS: 448.5 [M+H$^+$]

Example 5

Synthesis of 3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid [Compound 311]

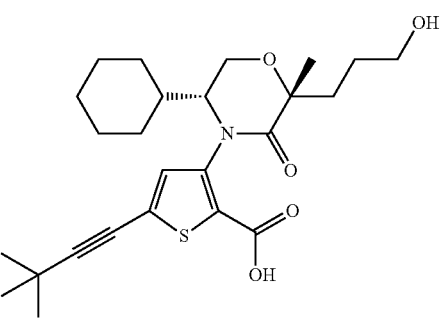 [SMILES: CC(C)(C)C#Cc1cc(N2C(=O)[C@@](C)(CCCO)OC[C@H]2C2CCCCC2)c(C(=O)O)s1]

Step 1. (R)-2-[3-(tert-Butyl-dimethyl-silanyloxy)-propyl]-5-cyclohexyl-4-(4-methoxy-benzyl)-2-methyl-morpholin-3-one

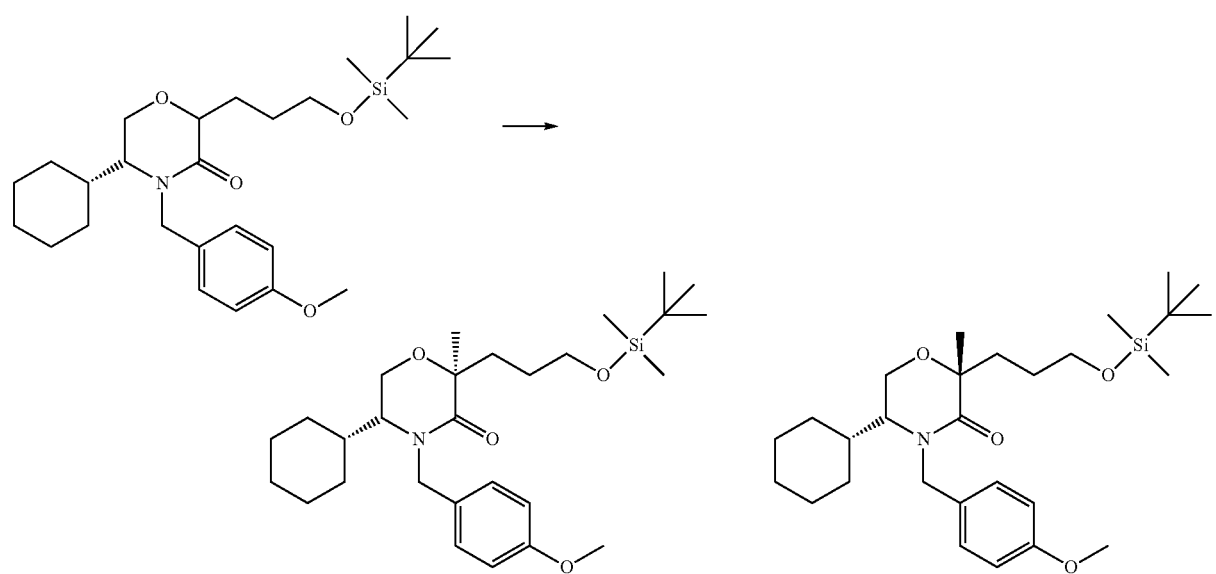

To a solution of diisopropylamine (138 mg, 1.36 mmol, 1.3 equiv) in THF (6.0 mL) at −78° C. was added n-BuLi (0.79 mL, 1.6 mL in heptane, 1.26 mmol, 1.2 equiv) and the resulting solution was stirred at −78° C. for 10 minutes. To the solution was added a solution of 2-[3-(tert-Butyl-dimethyl-silanyloxy)-propyl]-5-cyclohexyl-4-(4-methoxy-benzyl)-morpholin-3-one (500 mg, 1.05 mmol, 1.0 equiv) in THF (2 mL) and the solution was stirred at −78° C. for 30 mins. MeI was added and the solution was stirred at −78° C. for 1 hour then slowly warmed to room temperature over 2 hours. The reaction was quenched by addition of sat. aq. NH$_4$Cl solution. The mixture was extracted with EtOAc. The organic layer was washed with brine, dried over Na$_2$SO$_4$ and concentrated. The residue was purified by silica gel column chromatography, EtOAc/heptane 20% to give product (S)-2-[3-(tert-Butyl-dimethyl-silanyloxy)-propyl]-5-cyclohexyl-4-(4-methoxy-benzyl)-2-methyl-morpholin-3-one 110 mg and product (R)-2-[3-(tert-butyl-dimethyl-silanyloxy)-propyl]-5-cyclohexyl-4-(4-methoxy-benzyl)-2-methyl-morpholin-3-one 205 mg.

Step 2. Synthesis of (R)-5-cyclohexyl-2-(3-hydroxy-propyl)-2-methyl-morpholin-3-one

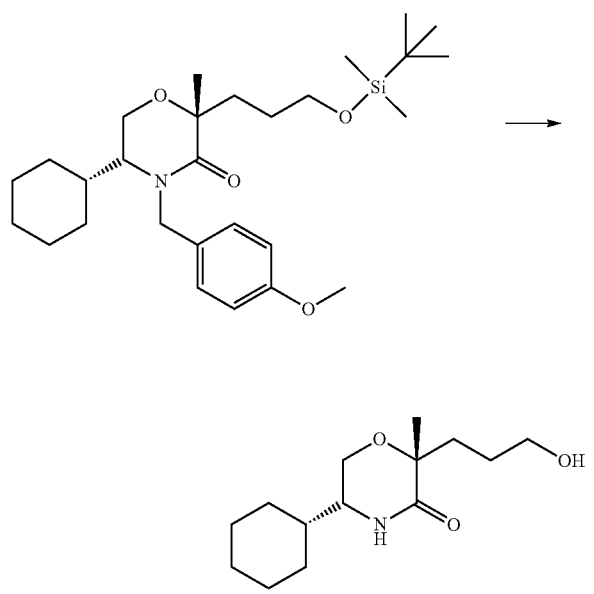

To a solution of TBS ether (200 mg, 0.41 mmol, 1.0 equiv) in CH$_3$CN (1.0 mL) and water (1.0 mL) was added CAN (461 mg, 0.82 mmol, 2.0 equiv). The mixture was stirred at room temperature for 1 hour then second portion of CAN (400 mg) was added. After stirred at room temperature for 1 hour, the reaction mixture was diluted with EtOAc and the phases were separated. The organic layer was washed with brine and dried over Na$_2$SO$_4$ and concentrated. The residue was purified by silica gel column chromatography, EtOAc/heptane 50% to 100% EtOAc to give product 45 mg (43% yield).

Step 3. Synthesis of 3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid methyl ester

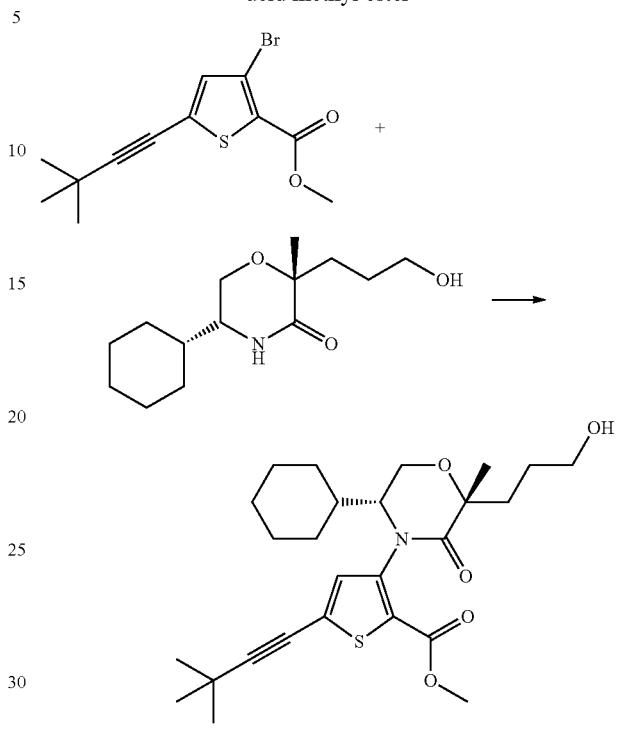

To a 10 mL vial was added trans-cyclohexane diamine (13.4 mg, 0.12 mmol, 1.0 equiv), 3-bromo-5-(3,3-dimethyl-but-1-ynyl)-thiophene-2-carboxylic acid methyl ester (70.8 mg, 0.24 mmol, 2.0 equiv), K$_2$CO$_3$ (32.5 mg, 0.24 mmol, 2.0 equiv), CuI (22 mg, 0.12 mmol, 1.0 equiv), (R)-5-cyclohexyl-2-(3-hydroxy-propyl)-2-methyl-morpholin-3-one (30 mg, 0.12 mmol, 1.0 equiv) and 1,4-dioxane (0.4 mL). The mixture was flushed with N$_2$ and stirred at 120° C. for 18 hours. The mixture was filtered through celite and the filtrate was concentrated under vacuum. The residue was purified by silica gel column chromatography, EtOAc/heptane 80% to give product 15 mg (yield 26%).

Step 4. Synthesis of 3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid

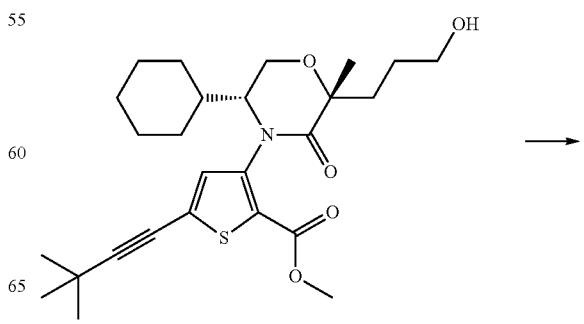

-continued

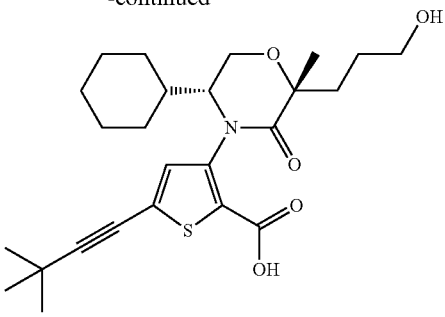

To a solution of methyl ester (15 mg, 0.032 mmol, 1.0 equiv) in THF (0.5 mL), MeOH (0.5 mL), water (0.5 mL) was added lithium hydroxide (3.8 mg, 0.16 mmol, 5.0 equiv). The resulting mixture was stirred at 50° C. for 30 minutes, after which the reaction was neutralized by addition of 1.0 N HCl aq. solution to pH=6. The mixture was extracted with EtOAc. The organic layers were combined, washed with brine, dried over $Na_2SO_4$ and concentrated. The residue was purified by reverse phase HPLC to give product 4.3 mg (yield 29%). MW: 462.2 [M+H]. $^1$H-NMR (400 MHz, MeOD): δ 6.91 (s, 1H), 4.23 (d, 1H), 3.94 (d, 1H), 3.62 (m, 1H), 3.55 (m, 2H), 1.96-1.52 (m, 10H), 1.45 (s, 3H), 1.32 (s, 9H), 1.21 (m, 4H), 1.05 (m, 1H).

Example 6

Synthesis of 3-[(2S,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid [Compound 7]

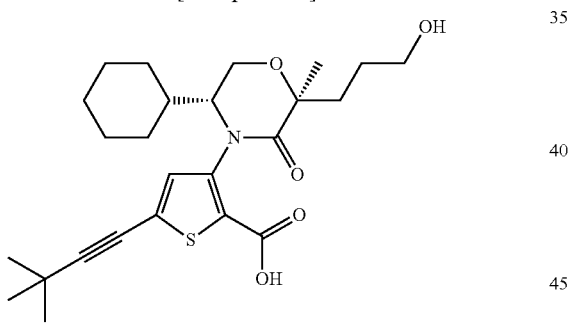

(S)-2-[3-(tert-Butyl-dimethyl-silanyloxy)-propyl]-5-cyclohexyl-4-(4-methoxy-benzyl)-2-methyl-morpholin-3-one from Example 5 step 1 was carried on according to procedure in Example 5 step 2-step 4 to provide 3-[(2S,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid. MS: 462.2[M+H$^+$]. $^1$H-NMR (400 MHz, CD$_3$OD): δ 6.93 (s, 1H), 4.12 (d, 1H), 3.91 (d, 1H), 3.66 (s, 1H), 3.54 (t, 2H), 2.14 (m, 1H), 1.91 (m, 1H), 1.44-1.85 (m, 8H), 1.41 (s, 3H), 1.06-1.37 (m, 14H).

Example 7

Synthesis of 3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid [Compound 330]

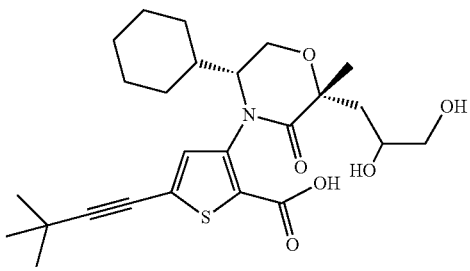 [SMILES: CC(C)(C)C#Cc1cc(N2C(=O)[C@@](C)(CC(O)CO)OC[C@H]2C2CCCCC2)c(C(=O)O)s1]

Step 1. Synthesis of 3-((R)-2-Allyl-5-cyclohexyl-3-oxo-morpholin-4-yl)-5-(3,3-dimethyl-but-1-ynyl)-thiophene-2-carboxylic acid methyl ester

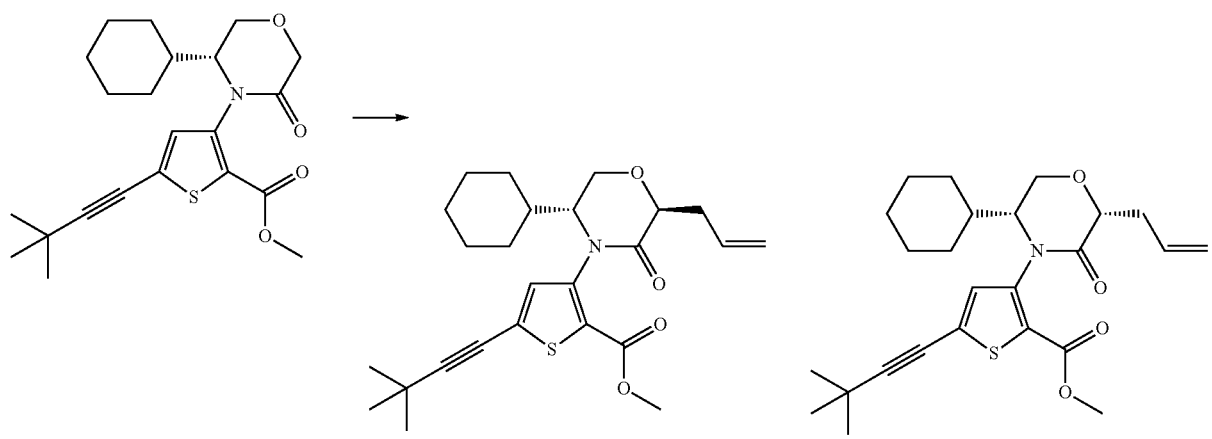

To a solution of 3-((R)-3-Cyclohexyl-5-oxo-morpholin-4-yl)-5-(3,3-dimethyl-but-1-ynyl)-thiophene-2-carboxylic acid methyl ester (600 mg, 1.49 mmol, 1.0 equiv) in THF (5.0 mL) at −78° C. was added LDA (0.82 mL, 2.0 M in THF, 1.64 mmol, 1.1 equiv) and the resulting solution was stirred at −78° C. for 20 minutes. To the solution was then added allyliodide (300 mg, 1.78 mmol, 1.2 equiv). The solution was warmed to room temperature and stirred at this temperature for 30 minutes. The reaction was quenched by addition of sat. aq. NH₄Cl solution. The mixture was extracted with EtOAc. The organic layer was washed with brine, dried over Na₂SO₄ and concentrated. The residue was purified by silica gel column chromatography, EtOAc/heptane 25% to give 3-((2S,5R)-2-Allyl-5-cyclohexyl-3-oxo-morpholin-4-yl)-5-(3,3-dimethyl-but-1-ynyl)-thiophene-2-carboxylic acid methyl 140 mg, 3-((2R,5R)-2-Allyl-5-cyclohexyl-3-oxo-morpholin-4-yl)-5-(3,3-dimethyl-but-1-ynyl)-thiophene-2-carboxylic acid methyl ester 60 mg and mixed fraction 200 mg.

Step 2. Synthesis of 3-((2S,5R)-2-Allyl-5-cyclohexyl-2-methyl-3-oxo-morpholin-4-yl)-5-(3,3-dimethyl-but-1-ynyl)-thiophene-2-carboxylic acid methyl ester and product 3-((2R,5R)-2-Allyl-5-cyclohexyl-2-methyl-3-oxo-morpholin-4-yl)-5-(3,3-dimethyl-but-1-ynyl)-thiophene-2-carboxylic acid methyl ester

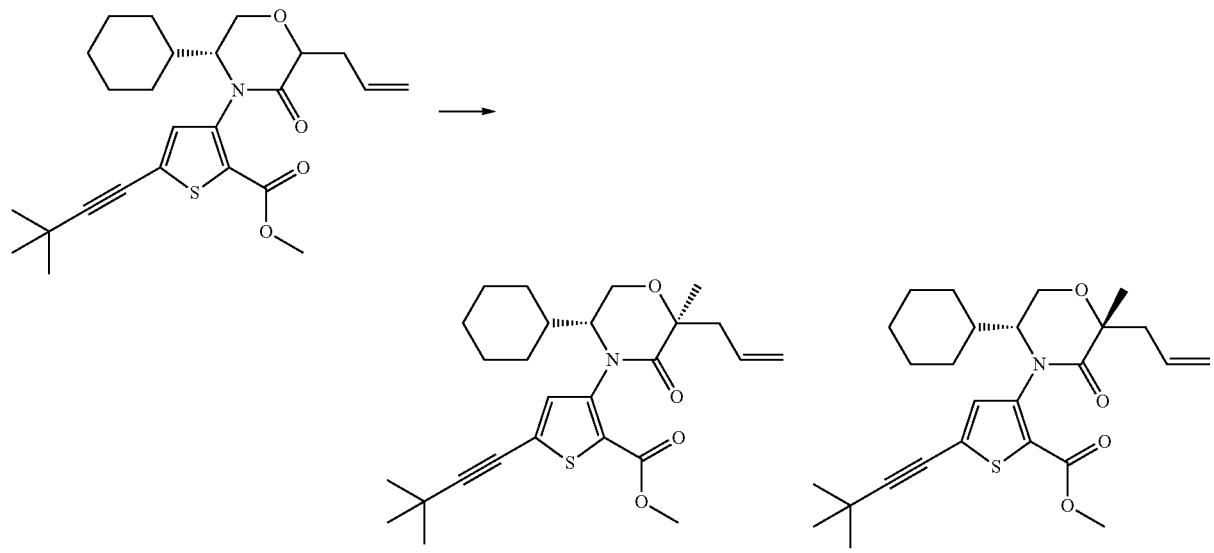

To a solution of 3-((R)-2-Allyl-5-cyclohexyl-3-oxo-morpholin-4-yl)-5-(3,3-dimethyl-but-1-ynyl)-thiophene-2-carboxylic acid methyl ester (120 mg, 0.27 mmol, 1.0 equiv) in THF (1.0 mL) at −78° C. was added LDA (0.16 mL, 2.0 M in THF, 0.32 mmol, 1.2 equiv) and the resulting solution was stirred at −78° C. for 20 minutes. To the solution was then added methyliodide (192 mg, 1.35 mmol, 5.0 equiv). The solution was warmed to room temperature and the stirred at this temperature for 30 minutes. The reaction was quenched by addition of sat. aq. NH₄Cl solution. The mixture was extracted with EtOAc. The organic layer was washed with brine, dried over Na₂SO₄ and concentrated. The residue was purified by silica gel column chromatography, EtOAc/heptane 25% to give product 3-((2S,5R)-2-Allyl-5-cyclohexyl-2-methyl-3-oxo-morpholin-4-yl)-5-(3,3-dimethyl-but-1-ynyl)-thiophene-2-carboxylic acid methyl ester 18 mg and product 3-((2R,5R)-2-Allyl-5-cyclohexyl-2-methyl-3-oxo-morpholin-4-yl)-5-(3,3-dimethyl-but-1-ynyl)-thiophene-2-carboxylic acid methyl ester 50 mg.

Step 3. Synthesis of 3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid methyl ester

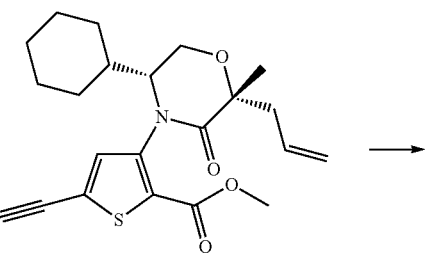

-continued

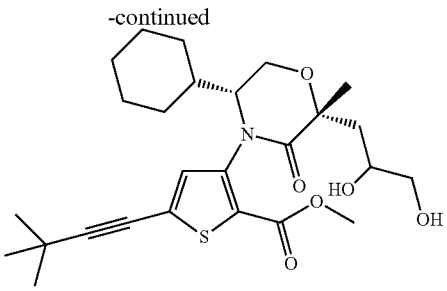

To a solution of 3-((2R,5R)-2-Allyl-5-cyclohexyl-2-methyl-3-oxo-morpholin-4-yl)-5-(3,3-dimethyl-but-1-ynyl)-thiophene-2-carboxylic acid methyl ester (0.40 g, 0.87 mmol, 1.0 equiv) in acetone (6.0 mL) was sequentially added N-methylmorpholine oxide (0.31 g, 2.63 mmol, 3.0 equiv), water (2.0 mL) and OsO₄ (0.44 g, 0.044 mmol, 0.05 equiv, 2.5 wt % in t-butanol) at 0° C. The mixture was stirred at room temperature for 60 minutes, after which the reaction was quenched by adding brine solution (0.5 mL) and EtOAc (10 mL). The organic layer was separated, dried (over Na₂SO₄) and concentrated. The crude material was continued to the next step with no further purification.

Step 4. Synthesis of 3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid

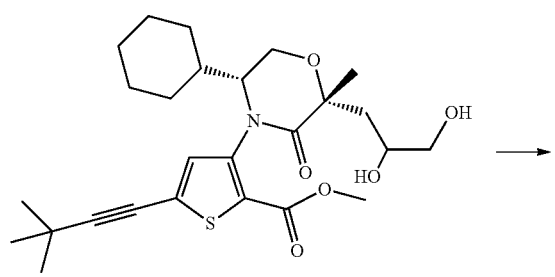

3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid methyl ester from the previous step was dissolved in 4.0 ml of THF and 0.3 mL of solution was taken out for the reaction. To the stirred solution was added THF (0.3 mL), MeOH (0.3 mL), water (0.3 mL), and LiOH.H₂O (25.6 mg, 0.61 mmol, 10.0 equiv) and the resulting solution was stirred at room temperature for 30 minutes. The reaction was quenched by addition of 3.0 N HCl aqueous solution until pH=5. To the solution was then added EtOAc and the phases were separated. The aqueous layer was extracted by EtOAc. The organic layers were combined, dried (over Na₂SO₄) and concentrated. The residue was purified by HPLC (0.1% NH₄OH, MeCN/H₂O, 10%-90%) to give product (11 mg, 37.7% yield) as white solid. MS: 478 [M–H⁺].

Example 8

Synthesis of 3-[(2R,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid [Compound 323]

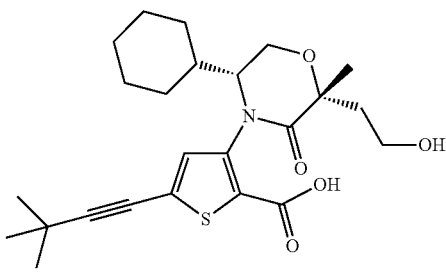 [SMILES: CC(C)(C)C#Cc1cc(N2C(=O)[C@@](C)(CCO)OC[C@H]2C2CCCCC2)c(C(=O)O)s1]

Step 1. Synthesis of 3-[(2R,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid methyl ester

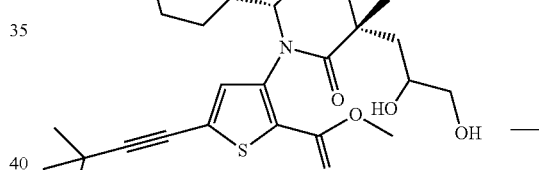

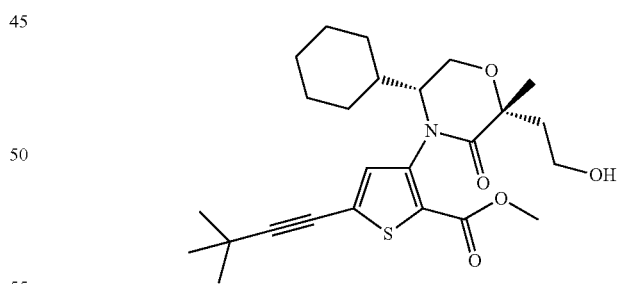

3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid methyl ester from Example 7 Step 3 was dissolved in 4 ml THF, and 3.7 mL solution was taken out for the reaction. To the stirred solution was added THF (2.3 mL), water (2.0 mL), and then sodium periodate (0.28 g, 1.31 mmol, 1.6 equiv) at 0° C. The resulting solution was stirred at room temperature for 30 minutes. And then at 0° C. another portion of sodium periodate (0.09 g, 0.44 mmol, 0.5 equiv) was added to the mixture and stirred for another 30 minutes at room temperature. The reaction was quenched by adding brine solution (0.5 mL) and EtOAc (10 mL). The organic layer was separated, dried (over Na$_2$SO$_4$) and concentrated. The residue was dissolved in ethanol (6.0 mL) and to the resulting solution at 0° C. was added sodium borohydride (0.27 g, 7.0 mmol, 8.8 equiv). The mixture was stirred at 0° C. for 15 minutes after which the reaction was quenched by adding water (2.0 mL) and EtOAc (10 mL). The organic layer was separated, dried (over Na$_2$SO$_4$) and concentrated to give product 128 mg (yield 35%). The crude product was continued to the next step with no further purification. MS: 462 [M−H$^+$].

Step 2. Synthesis of 3-[(2R,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid To a solution of methyl ester (128 mg, 0.28 mmol, 1.0 equiv) in THF (2.0 mL), MeOH (1.0 mL) and water (1.0 mL) was added LiOH.H$_2$O (93 mg, 2.22 mmol, 8.0 equiv) and the resulting solution was stirred at room temperature for 30 minutes. The reaction was quenched by addition of 3.0 N HCl aqueous solution until pH=5. To the solution was then added EtOAc and the phases were separated. The aqueous layer was extracted by EtOAc. The organic layers were combined and dried (over Na$_2$SO$_4$) and then concentrated. The residue was purified by HPLC (0.1% NH$_4$OH, MeCN/H$_2$O, 10%-90%) to give product (87 mg, 78.2% yield) as white solid. MS: 448.3 [M+H$^+$]. $^1$H-NMR (400 MHz, CD$_3$OD): 6.87 (s, 1H), 4.24 (tert, 1H), 3.93 (d, 1H), 3.62-3.82 (m, 3H), 2.08-2.21 (m, 1H), 1.88-2.04 (m, 2H), 1.56-1.87 (m, 4H), 1.43-1.56 (m, 4H), 0.98-1.35 (m, 14H)

Example 9

Synthesis of 3-[(2R,5R)-5-Cyclohexyl-2-(2-hydroxy-ethyl)-3-oxo-morpholin-4-yl]-5-(3,3-dimethyl-but-1-ynyl)-thiophene-2-carboxylic acid [Compound 8]

Step 1. Synthesis of 3-[(2R,5R)-5-Cyclohexyl-2-(2-hydroxy-ethyl)-3-oxo-morpholin-4-yl]-5-(3,3-dimethyl-but-1-ynyl)-thiophene-2-carboxylic acid methyl ester

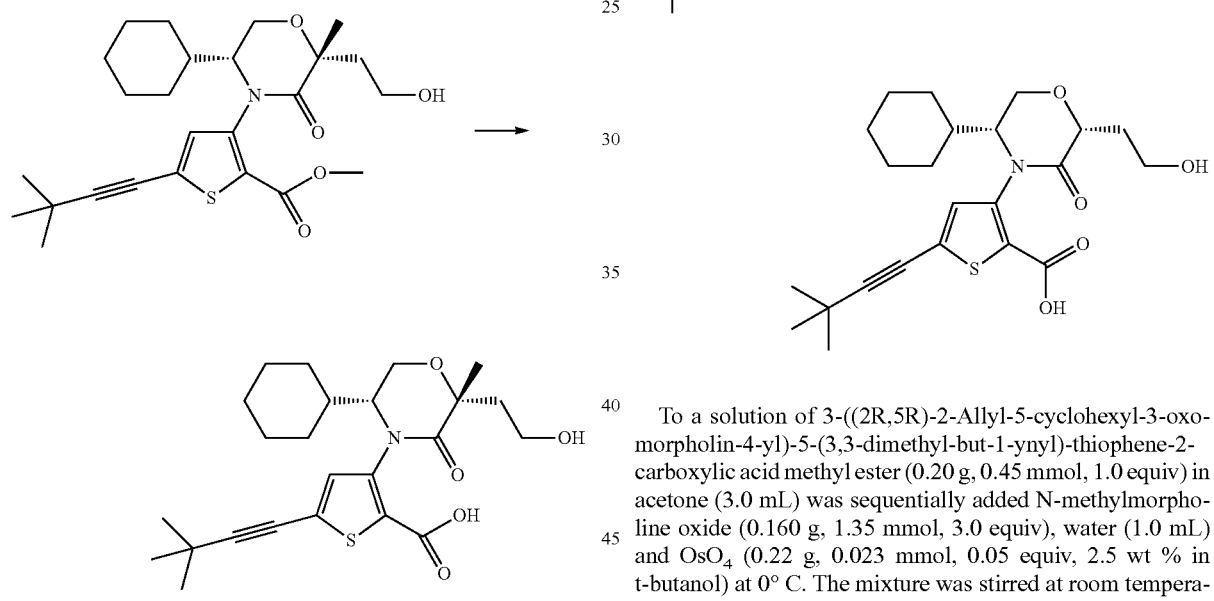

To a solution of 3-((2R,5R)-2-Allyl-5-cyclohexyl-3-oxo-morpholin-4-yl)-5-(3,3-dimethyl-but-1-ynyl)-thiophene-2-carboxylic acid methyl ester (0.20 g, 0.45 mmol, 1.0 equiv) in acetone (3.0 mL) was sequentially added N-methylmorpholine oxide (0.160 g, 1.35 mmol, 3.0 equiv), water (1.0 mL) and OsO$_4$ (0.22 g, 0.023 mmol, 0.05 equiv, 2.5 wt % in t-butanol) at 0° C. The mixture was stirred at room temperature for 60 minutes, after which the reaction was quenched by adding brine solution and EtOAc. The organic layer was separated, dried (over Na$_2$SO$_4$) and concentrated. The crude material was continued to the next step with no further purification.

The crude material from previous step was dissolved in 3.0 ml THF and water (1.0 mL) and to the solution was added sodium periodate (0.19 g, 0.92 mmol, 2.0 equiv) at 0° C. The resulting solution was stirred at room temperature for 30 minutes after which brine solution and EtOAc was added. The organic layer was separated, dried (over Na$_2$SO$_4$) and concentrated. The residue was dissolved in ethanol (3.0 mL) and to the resulting solution at 0° C. was added sodium borohydride (0.136 g, 3.6 mmol, 8.0 equiv). The mixture was stirred at 0° C. for 15 minutes after which the reaction was quenched by adding water (2.0 mL) and EtOAc (10 mL). The organic layer was separated, dried (over Na$_2$SO$_4$) and concentrated to give product 45 mg (yield 22%). The crude product was continued to the next step with no further purification.

Step 2. Synthesis of 3-[(2R,5R)-5-Cyclohexyl-2-(2-hydroxy-ethyl)-3-oxo-morpholin-4-yl]-5-(3,3-dimethyl-but-1-ynyl)-thiophene-2-carboxylic acid

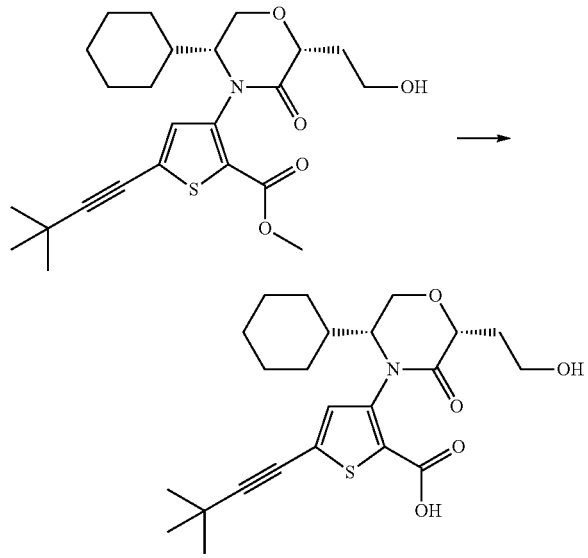

To a solution of methyl ester (45 mg, 0.10 mmol, 1.0 equiv) in THF (2.0 mL), MeOH (1.0 mL) and water (1.0 mL) was added LiOH.H$_2$O (33 mg, 0.8 mmol, 8.0 equiv) and the resulting solution was stirred at room temperature for 30 minutes. The reaction was quenched by addition of 3.0 N HCl aqueous solution until pH=5. To the solution was then added EtOAc and the phases were separated. The aqueous layer was extracted by EtOAc. The organic layers were combined and dried (over Na$_2$SO$_4$) and then concentrated. The residue was purified by reverse phase HPLC to give product (25 mg, 57% yield) as white solid.

MS: 434.2 [M+H$^+$]. $^1$H-NMR (400 MHz, CD$_3$OD): δ 6.90 (s, 1H), 4.24 (tert, 1H), 4.13 (d, 1H), 4.01 (tert, 1H), 3.73 (d, 1H), 3.71 (d, 1H), 3.66 (t, 1H), 2.21 (m, 1H), 1.41-1.98 (m, 8H), 1.05-1.37 (m, 15H).

Example 10

Synthesis of 3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid [Compound 311]

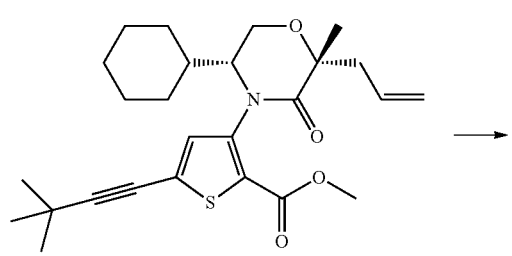

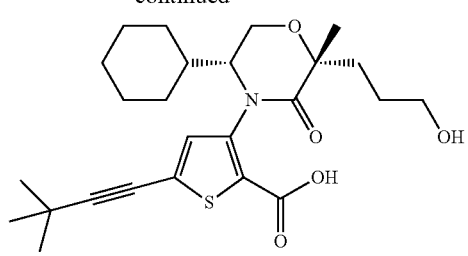

To a solution of 3-((2R,5R)-2-allyl-5-cyclohexyl-2-methyl-3-oxo-morpholin-4-yl)-5-(3,3-dimethyl-but-1-ynyl)-thiophene-2-carboxylic acid methyl ester (50 mg, 0.11 mmol, 1.0 equiv) in THF (1.0 mL) was added 9-BBN (0.5 M solution in THF, 0.55 ml, 0.27 mmol, 2.5 equiv) at 0° C. The reaction mixture was then stirred at room temperature for 2 hours. To the solution was then cooled in an ice water bath and was added EtOH, followed by aq. NaOH solution and H$_2$O$_2$ aq. solution. During addition the reaction internal temperature was kept between 5° C. and 10° C. The reaction mixture was then heated to reflux for 90 minutes. After cooled at room temperature, the reaction mixture was extracted with EtOAc. The organic layer was dried over Na$_2$SO$_4$ and concentrated in vacuo. The residue was purified by prep-HPLC to give the product 26 mg. MW: 462.2 [M+H]$^+$. $^1$H-NMR (400 MHz, MeOD): δ 6.91 (s, 1H), 4.23 (d, 1H), 3.94 (d, 1H), 3.62 (m, 1H), 3.55 (m, 2H), 1.96-1.52 (m, 10H), 1.45 (s, 3H), 1.32 (s, 9H), 1.21 (m, 4H), 1.05 (m, 1H).

Example 11

Synthesis of 3-((S)-2-Cyclohexyl-6-oxo-piperidin-1-yl)-5-(3,3-dimethyl-but-1-ynyl)-thiophene-2-carboxylic acid [Compound 35]

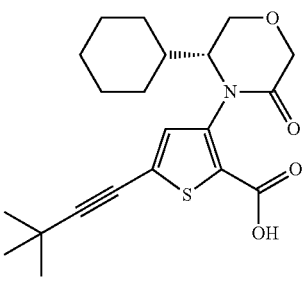 [SMILES: CC(C)(C)C#Cc1cc(N2C(=O)COC[C@H]2C2CCCCC2)c(C(=O)O)s1]

Step 1. Synthesis of (S)-5-Cyclohexyl-5-((S)-1-phenyl-ethylamino)-pentanoic acid ethyl ester

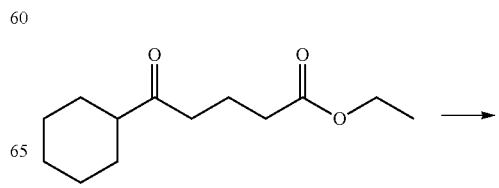

-continued

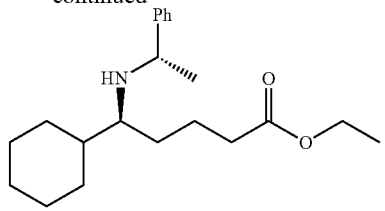

A solution of TiCl₄ in DCM (8.8 mL, 1.0 M solution in DCM, 8.8 mmol, 0.5 equiv) was added dropwisely to a vigorously stirred ice cooled solution of s-methyl benzyl amine (2.78 g, 23.0 mmol, 1.3 equiv) and TEA (10.7 g, 106 mmol, 6.0 equiv) in DCM (50 mL). The solution was heated to reflux and 5-Cyclohexyl-5-oxo-pentanoic acid ethyl ester (4.0 g, 17.6 mmol, 1.0 equiv) was added over 1 minute. The solution was then heated at reflux for 2 hours, after which, it was cooled to room temperature and diluted with ether, filtered through Celite. The cloudy solution was washed with sat. aq. NaHCO₃, brine, dried over MgSO₄ and concentrated. The residue was dissolved in EtOH (40.0 mL) and at −78° C. was added NaBH₄. After stirred at 30 minutes, the reaction mixture was warmed to 0° C. and stirred at 0° C. for 30 minutes. To the solution was then added 6.0 N aq. HCl solution until pH=3. The organic solvent was removed under vacuum and the residue was basified with sat. aq. NaHCO₃ until pH=9. The mixture was extracted with EtOAc and the organic layer was washed with brine, dried over Na₂SO₄ and concentrated. The residue was purified by silica gel, EtOAc/heptane 0-15% to give product 2.3 g (yield 39%) as the major product which eluted from the column first.

Step 2. Synthesis of
(S)-6-Cyclohexyl-piperidin-2-one

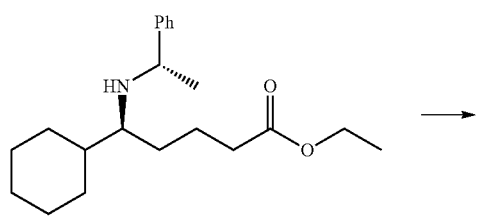

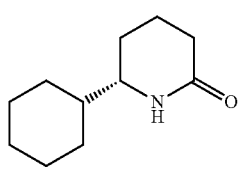

To a solution of (S)-5-Cyclohexyl-5-((S)-1-phenyl-ethylamino)-pentanoic acid ethyl ester (2.0 g, 6.0 mmol, 1.0 equiv) in MeOH (60 mL) was added Pd (1.6 g, 10% on carbon, 1.51 mmol, 0.25 equiv) and ammonium formate (3.8 g, 60.3 mmol, 10.0 equiv). The mixture was heated to reflux for 2 hours. The solution was then cooled at room temperature and filtered through Celite. The filtrate was concentrated and the residue was purified by silica gel column chromatography, acetone/heptane 50% to give product 1.05 g (96% yield).

Step 3. Synthesis of 3-((S)-2-Cyclohexyl-6-oxo-piperidin-1-yl)-5-(3,3-dimethyl-but-1-ynyl)-thiophene-2-carboxylic acid methyl ester

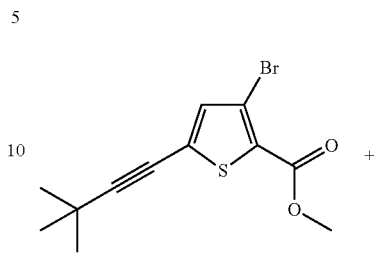

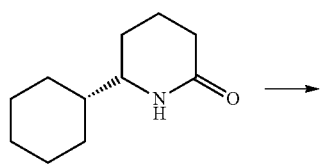

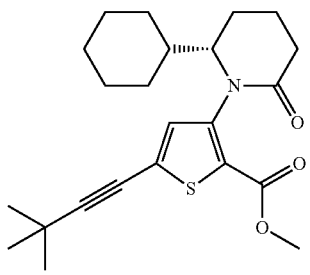

To a 10 mL vial was added trans-cyclohexane diamine (283 mg, 2.5 mmol, 0.5 equiv), 3-Bromo-5-(3,3-dimethyl-but-1-ynyl)-thiophene-2-carboxylic acid methyl ester (2.24 g, 7.4 mmol, 1.5 equiv), K₂CO₃ (1.37 g, 9.9 mmol, 2.0 equiv), CuI (473 mg, 2.5 mmol, 0.5 equiv), (S)-6-Cyclohexyl-piperidin-2-one (900 mg, 5.0 mmol, 1.0 equiv) and 1,4-dioxane (5.0 mL). The mixture was flushed with N₂ and stirred at 110° C. for 48 hours. The mixture was filtered through Celite and the filtrate was concentrated under vacuum. The residue was purified by silica gel column chromatography, EtOAc/heptane 30% to give product 800 mg (yield 40%).

Step 4. Synthesis of 3-((S)-2-Cyclohexyl-6-oxo-piperidin-1-yl)-5-(3,3-dimethyl-but-1-ynyl)-thiophene-2-carboxylic acid

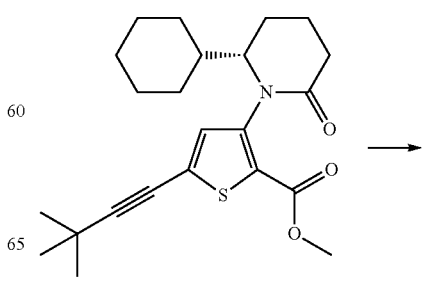

-continued

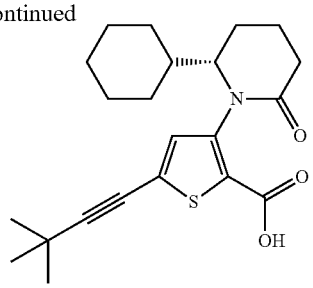

To a solution of methyl ester (10 mg, 0.025 mmol, 1.0 equiv) in THF (0.3 mL), MeOH (0.3 mL), water (0.3 mL) was added lithium hydroxide monohydrate (5.2 mg, 0.12 mmol, 5.0 equiv). The resulting mixture was stirred at 50° C. for 1 hour, after which the reaction was neutralized by addition of 1.0 N HCl aq. solution to pH=6. The mixture was extracted with EtOAc. The organic layers were combined, washed with brine, dried over $Na_2SO_4$ and concentrated. The residue was purified by reverse phase HPLC to give product 6.0 mg (yield 62%). MW: 388.4 [M+H]$^+$. $^1$H-NMR (400 MHz, MeOD): δ 7.03 (s, 1H), 3.81 (m, 1H), 2.25 (m, 1H), 1.88-1.38 (m, 6H), 1.29 (s, 9H), 1.18 (m, 4H), 1.06 (m, 4H).

Example 12

Synthesis of 3-((S)-Amino-6-cyclohexyl-2-oxo-piperidin-1-yl)-5-(3,3-dimethyl-but-1-ynyl)-thiophene-2-carboxylic acid: [Compound 322]

Step 1. Synthesis of 3-((3S,6S)-6-Cyclohexyl-3-hydroxy-2-oxo-piperidin-1-yl)-5-(3,3-dimethyl-but-1-ynyl)-thiophene-2-carboxylic acid methyl ester

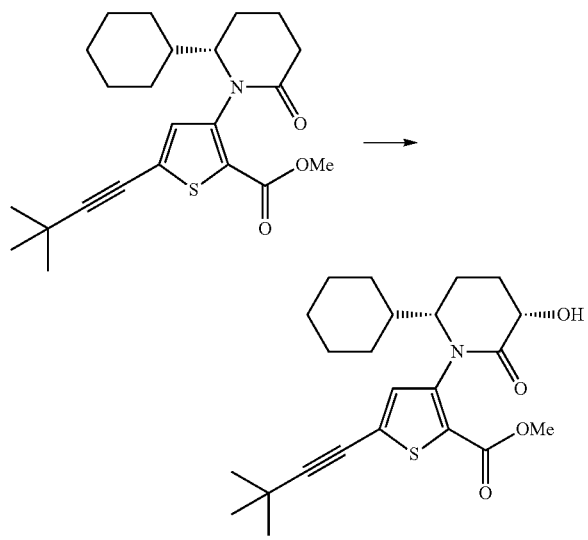

To a solution of 3-((S)-2-cyclohexyl-6-oxo-piperidin-1-yl)-5-(3,3-dimethyl-but-1-ynyl)-thiophene-2-carboxylic acid methyl ester (3.2 g, 7.97 mmol, 1.0 equiv) in THF (15.0 ml) was added NaHMDS (1.0 M in THF) at −78° C. and the resulting solution was stirred at −78° C. for 1.5 hours. To this solution was then added a solution of (S)-(+)-(camphorsulfonyl)oxaziridine (3.65 g, 15.94 mmol, 2.0 equiv) in THF (10 ml) and the reaction mixture was stirred at −78° C. for 3 hours. The reaction was quenched by addition of sat. $NH_4Cl$ aq. solution. The mixture was extracted with EtOAc and the combined organic layer was dried over $Na_2SO_4$, and concentrate. The residue was purified by silica gel column chromatography, ($Et_2O$/DCM 5%~40%) to give 1.5 g of the desired product (yield 45%). MS: 418 [M+H$^+$]

Step 2. Synthesis of 5-(3,3-Dimethyl-but-1-ynyl)-3-[(3S,6S)-6-(1-ethyl-pentyl)-3-hydroxy-2-oxo-piperidin-1-yl]-thiophene-2-carboxylic acid

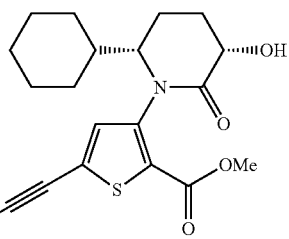

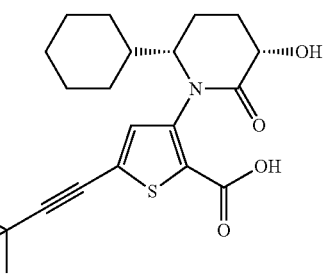

To a solution of 3-((3S,6S)-6-Cyclohexyl-3-hydroxy-2-oxo-piperidin-1-yl)-5-(3,3-dimethyl-but-1-ynyl)-thiophene-2-carboxylic acid methyl ester (1.5 g, 3.59 mmol, 1 equiv.) in THF/$H_2O$/MeOH (5.0 mL/5.0 mL/1.0 mL) was added LiOH.$H_2O$ (0.79 g, 17.56 mmol, 5.0 equiv.) at room temperature. The reaction mixture was stirred at 50° C. for 20 minutes. The reaction was then acidified to pH=5 by addition of 3.0 N HCl aq. solution and the mixture was extracted with EtOAc. The organic layer was dried over $Na_2SO_4$, and concentrated. The residue was purified by prep-HPLC (XBridge Prep C 18 5 um, 30×50 mm) in basic condition (0.1% $NH_4OH$, 10%~45% $CH_3CN$/$H_2O$, 10 min run, 40 ml/min) to give 850 mg of product (yield 57%). MS: 404 [M+H$^+$]. $^1$H-NMR (400 MHz, MeOD): δ 6.95 (s, 1H), 4.09 (m, 1H), 3.74 (m, 1H), 2.09 (m, 1H), 1.94-1.67 (m, 8H), 1.38 (m, 1H), 1.33 (s, 9H), 1.17 (m, 5H).

Example 13

Synthesis of 3-(2-Cyclohexyl-6-oxo-piperidin-1-yl)-5-(4-fluoro-phenyl)-thiophene-2-carboxylic acid [Compound 70]

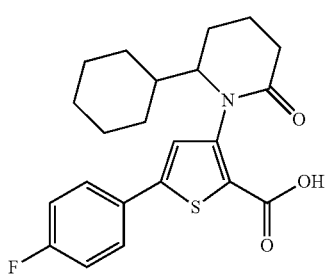 [SMILES: O=C(O)c1sc(-c2ccc(F)cc2)cc1N1C(=O)CCCC1C1CCCCC1]

Step 1. Synthesis of 3-(1-Cyclohexyl-4-ethoxycarbonyl-butylamino)-thiophene-2-carboxylic acid methyl ester

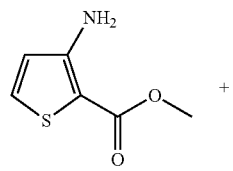

+

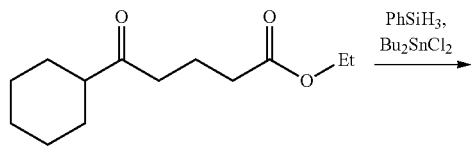

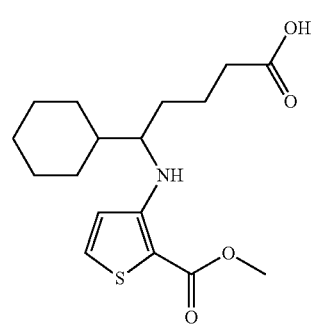

A flask was charged with 3-amino-thiophene-2-carboxylic acid methyl ester (600 mg, 3.82 mmol, 1.0 equiv), 5-cyclohexyl-5-oxo-pentanoic acid ethyl ester (864 mg, 3.82 mmol, 1.0 equiv), phenyl silane (496 mg, 4.58 mmol, 1.2 equiv), dibutyltin dichloride (116 mg, 0.38 mmol, 0.1 equiv) and dioxane (3.0 mL). The resulting solution was heated at 60° C. for 18 hours. The solution was then concentrated and the residue was purified by silica gel column chromatography, CH$_2$Cl$_2$/heptane 30% to 100%, to give 3-(1-Cyclohexyl-4-ethoxycarbonyl-butylamino)-thiophene-2-carboxylic acid methyl ester 810 mg (yield 57%).

Step 2. Synthesis of 3-(4-Carboxy-1-cyclohexyl-butylamino)-thiophene-2-carboxylic acid methyl ester

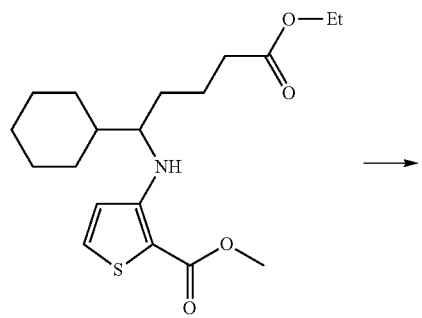

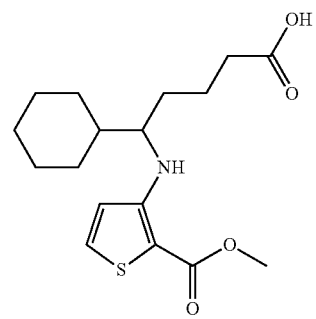

To a solution of methyl ester (300 mg, 0.82 mmol, 1.0 equiv) in THF (1.0 mL), MeOH (1.0 mL), water (1.0 mL) was added lithium hydroxide (58.6 mg, 2.45 mmol, 3.0 equiv). The resulting mixture was stirred at room temperature for 4 hours, after which the organic solvent was removed under vacuum. The resulted solution was neutralized by addition of 1.0 N HCl aq. solution until pH=6. The mixture was extracted with EtOAc. The organic layers were combined, dried over Na$_2$SO$_4$ and concentrated to give desired carboxylic acid.

Step 3. Synthesis of 3-(2-Cyclohexyl-6-oxo-piperidin-1-yl)-thiophene-2-carboxylic acid methyl ester

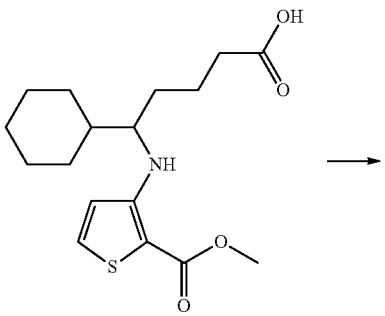

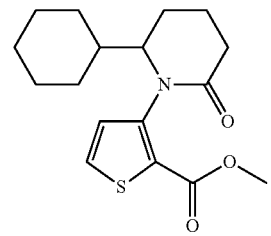

To a solution of carboxylic acid (700 mg, 2.06 mmol, 1.0 equiv) in toluene (30.0 mL) was added pyridine (816 mg, 10.3 mmol, 5.0 equiv) at 0° C. followed by thionyl chloride (245 mg, 2.06 mmol, 1.0 equiv). The solution was stirred at 0° C. for 1 hour. The reaction was quenched by addition of sat. aq. NH$_4$Cl solution. The mixture was extracted with EtOAc. The organic layers were combined, washed with brine, dried over Na$_2$SO$_4$ and concentrated. The residue was purified by silica gel, heptane/EtOAc 1/1 to give product 350 mg (yield 53%).

Step 4. Synthesis of 3-(2-Cyclohexyl-6-oxo-piperidin-1-yl)-5-(4-fluoro-phenyl)-thiophene-2-carboxylic acid methyl ester

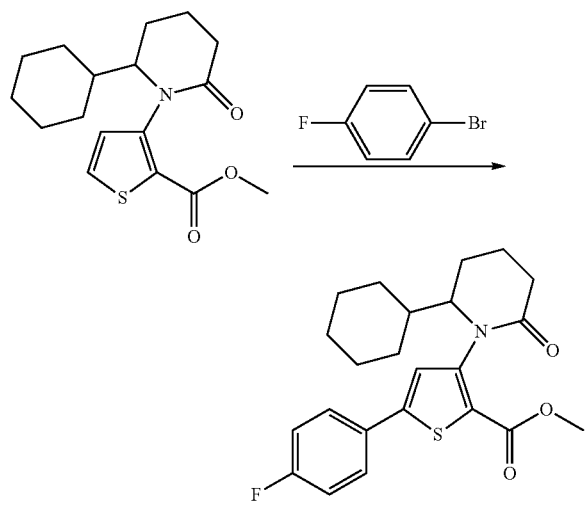

A 5 mL vial was charged with 3-(2-cyclohexyl-6-oxo-piperidin-1-yl)-thiophene-2-carboxylic acid methyl ester (32 mg, 0.10 mmol, 1.0 equiv), 1-bromo-4-fluoro benzene (17 mg, 0.10 mmol, 1.0 equiv), potassium carbonate (20.6 mg, 0.15 mmol, 1.5 equiv), tricyclophenylphosphine tetrafluoroborate (8.7 mg, 0.024 mmol, 0.24 equiv), Pd(OAc)$_2$ (2.7 mg, 0.012 mmol, 0.12 equiv), pivalic acid (6.1 mg, 0.060 mmol, 0.6 equiv) and DMA (0.3 mL). The resulted mixture was flushed with nitrogen and stirred at 100° C. for 18 hours. The mixture was loaded to silica gel column and flushed with EtOAc/heptane 67% to give product 27 mg (yield 65%).

Step 5. Synthesis of 3-(2-Cyclohexyl-6-oxo-piperidin-1-yl)-5-(4-fluoro-phenyl)-thiophene-2-carboxylic acid

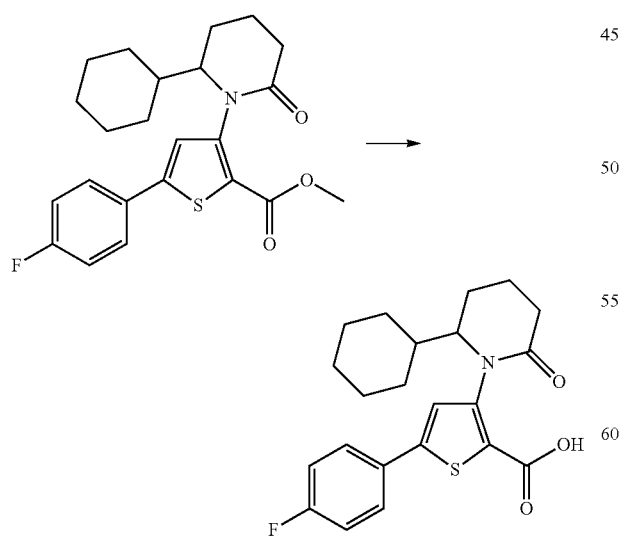

To a solution of methyl ester (20 mg, 0.048 mmol, 1.0 equiv) in THF (0.5 mL), EtOH (0.2 mL), water (0.5 mL) was added lithium hydroxide monohydrate (19 mg, 0.48 mmol, 10.0 equiv). The resulting mixture was stirred at 55° C. for 3 hours, after which the mixture was concentrated under vacuum. The residue was purified by reverse phase HPLC to give product 15.0 mg (yield 78%).

Example 14

Synthesis of 3-((R)-4-Cyclohexyl-2-oxo-oxazolidin-3-yl)-5-(3,3-dimethyl-but-1-ynyl)-thiophene-2-carboxylic acid [Compound 181]

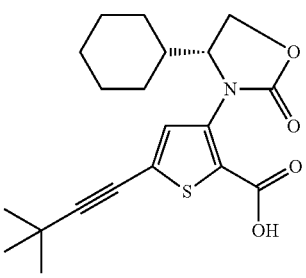 [SMILES: CC(C)(C)C#Cc1cc(N2C(=O)OC[C@H]2C2CCCCC2)c(C(=O)O)s1]

Step 1. Synthesis of (R)-4-Cyclohexyl-oxazolidin-2-one

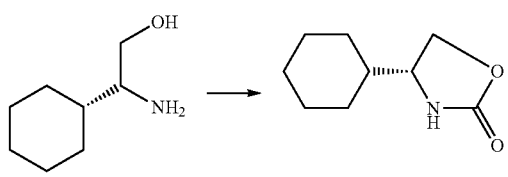

To a solution of (R)-2-Amino-2-cyclohexyl-ethanol.HCl salt (1.0 g, 5.57 mmol, 1.0 equiv) in CH$_2$Cl$_2$ (30.0 mL) at 0° C. was added DIPEA (1.94 mL, 11.1 mmol, 2.0 equiv) followed by triphosgene (4.95 g, 16.7 mmol, 3.0 equiv) and the resulting solution was stirred at room temperature for 12 hours. The solution was then concentrated and the residue was diluted with EtOAc. The solution was washed with water, brine, dried over Na$_2$SO$_4$ and concentrated. The residue was purified by silica gel column chromatography, (EtOAc 100%) to give product 520 mg.

Step 2. Synthesis of 3-((R)-4-Cyclohexyl-2-oxo-oxazolidin-3-yl)-5-(3,3-dimethyl-but-1-ynyl)-thiophene-2-carboxylic acid methyl ester

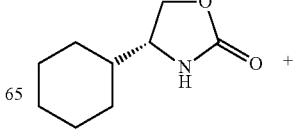

-continued

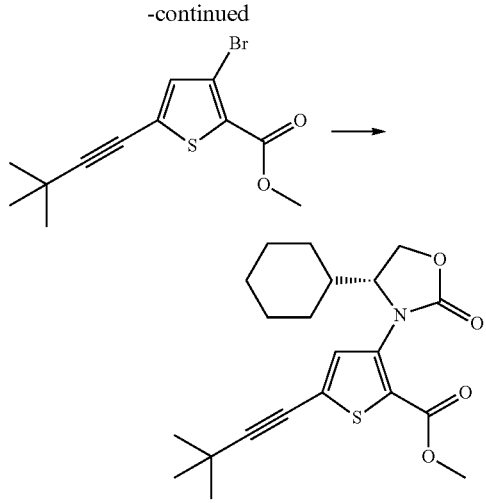

A heavy wall flask was charged with trans-cyclohexane diamine (18.9 mg, 0.17 mmol, 0.5 equiv), 3-bromo-5-(3,3-dimethyl-but-1-ynyl)-thiophene-2-carboxylic acid methyl ester (100 mg, 0.332 mmol, 1.0 equiv), $K_2CO_3$ (92 mg, 0.664 mmol, 2.0 equiv), CuI (31.6 mg, 0.166 mmol, 0.5 equiv), (R)-4-cyclohexyl-oxazolidin-2-one (56.2 mg, 0.332 mmol, 1.0 equiv) and 1,4-dioxane (0.5 mL). The mixture was flushed with $N_2$ and stirred at 110° C. for 18 hours, after which the mixture was filtered through celite and the filtrate was concentrated under vacuum. The residue was purified by silica gel, EtOAc/heptane 30% to give product 54 mg (yield 42%).

Step 3. Synthesis of 3-((R)-4-Cyclohexyl-2-oxo-oxazolidin-3-yl)-5-(3,3-dimethyl-but-1-ynyl)-thiophene-2-carboxylic acid

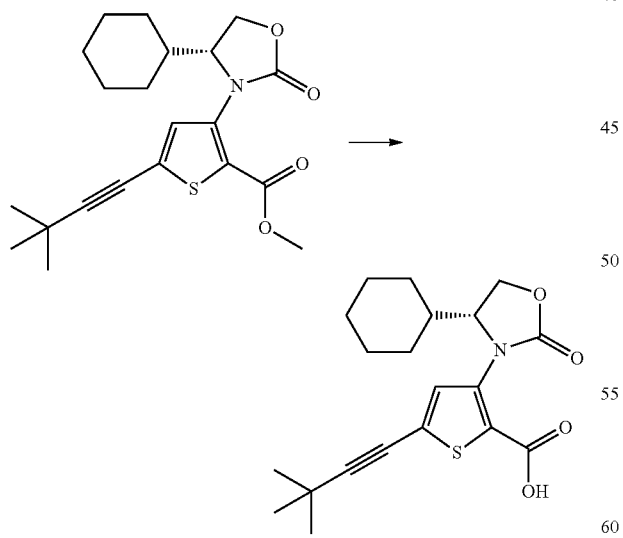

To a solution of methyl ester (50 mg, 0.128 mmol, 1.0 equiv) in THF (0.5 mL), MeOH (0.5 mL), water (0.5 mL) was added lithium hydroxide monohydrate (16.2 mg, 0.38 mmol, 3.0 equiv). The resulting mixture was stirred at 50° C. for 1 hour, after which the reaction was neutralized by addition of 1.0 N HCl aq. solution to pH=6. The mixture purified directly by reverse phase HPLC to give product 28 mg (yield 58%). MS: 376.4 [M+H⁺].

Example 15

Synthesis of 3-(2-Cyclohexyl-6-oxo-piperidin-1-yl)-5-phenyl-thiophene-2-carboxylic acid [Compound 4]

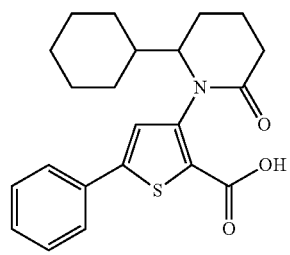 [SMILES: O=C(O)c1sc(-c2ccccc2)cc1N1C(=O)CCCC1C1CCCCC1]

Step 1. Synthesis of 3-(1-Cyclohexyl-4-ethoxycarbonyl-butylamino)-5-phenyl-thiophene-2-carboxylic acid methyl ester

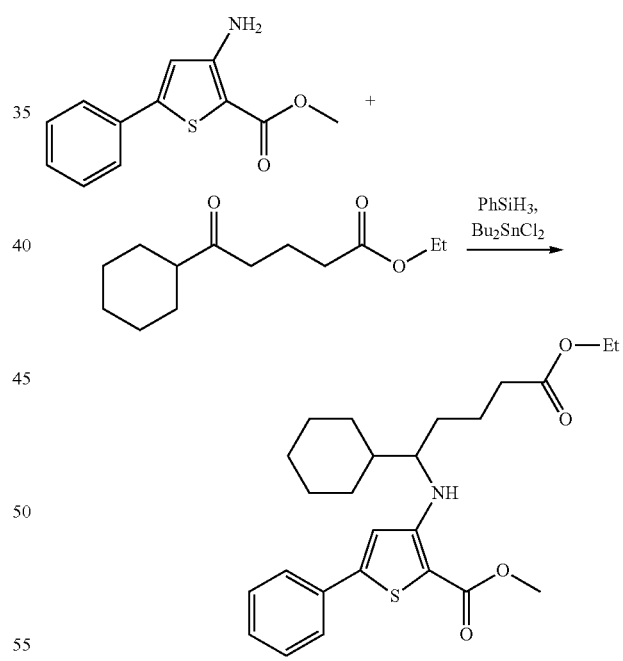

A flask was charged with 3-amino-5-phenyl-thiophene-2-carboxylic acid methyl ester (515 mg, 2.2 mmol, 1.0 equiv), 5-cyclohexyl-5-oxo-pentanoic acid ethyl ester (500 mg, 2.2 mmol, 1.0 equiv), phenyl silane (240 mg, 2.2 mmol, 1.0 equiv), dibutyltin dichloride (67 mg, 0.22 mmol, 0.1 equiv) and dioxane (2.0 mL). The resulting solution was heated at 120° C. with microwave for 2 hours. The solution was then concentrated and the residue was purified by silica gel column chromatography, EtOAc/heptane 5% to 40%, to give oil that contained starting material. The material was further purified with silica gel column chromotography, EtOH/DCM 2% to 10% to give product 150 mg (yield 15%).

Step 2. Synthesis of 3-(4-Carboxy-1-cyclohexyl-butylamino)-5-phenyl-thiophene-2-carboxylic acid methyl ester

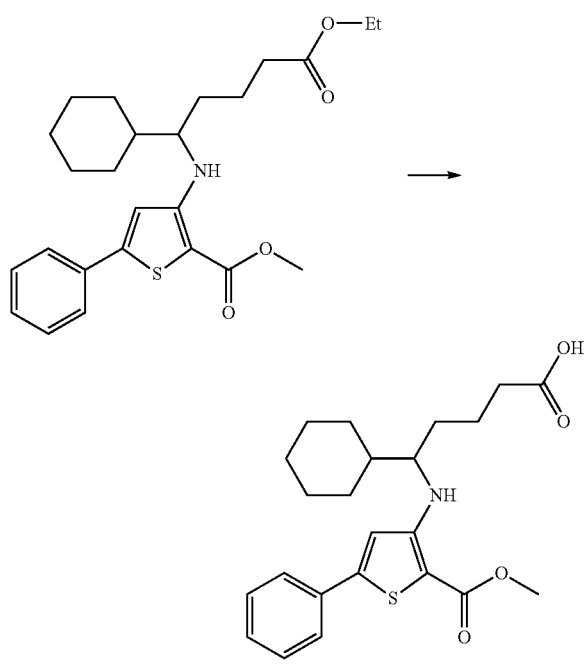

To a solution of 3-(1-Cyclohexyl-4-ethoxycarbonyl-butylamino)-5-phenyl-thiophene-2-carboxylic acid methyl ester (40 mg, 0.09 mmol, 1.0 equiv) in THF (0.4 mL), EtOH (0.2 mL), water (0.4 mL) was added lithium hydroxide (18.9 mg, 0.45 mmol, 5.0 equiv). The resulting mixture was stirred at 50° C. for 2 hours, after which the organic solvent was removed under vacuum. The resulted solution was neutralized by addition of 1.0 N HCl aq. solution until pH=6. The mixture was extracted with EtOAc. The organic layers were combined, dried over $Na_2SO_4$ and concentrated to product 30 mg (yield 83%).

Step 3. Synthesis of 3-(2-Cyclohexyl-6-oxo-piperidin-1-yl)-5-phenyl-thiophene-2-carboxylic acid methyl ester

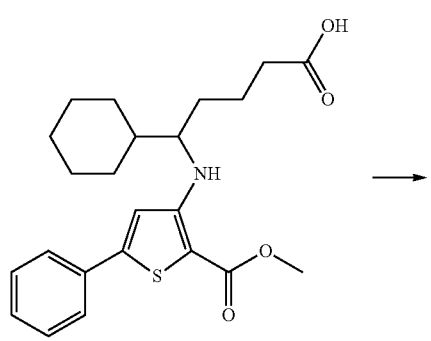

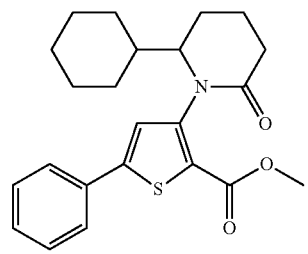

To a vial containing a solution of 3-(4-Carboxy-1-cyclohexyl-butylamino)-5-phenyl-thiophene-2-carboxylic acid methyl ester (40 mg, 0.096 mmol, 1.0 equiv) in 1,2-dioxane (1.0 mL) was added pyridine (3.8 mg, 0.048 mmol, 0.5 equiv) and $Boc_2O$ (25 mg, 0.166 mmol, 1.2 equiv). The vial was then sealed and heated at 65° C. for 18 hours. The solution was concentrated and the residue was purified by silica gel column chromatography, EtOAc/Heptane 5% to 100% to give product 15 mg (yield 39%).

Step 4. Synthesis of 3-(2-Cyclohexyl-6-oxo-piperidin-1-yl)-5-phenyl-thiophene-2-carboxylic acid

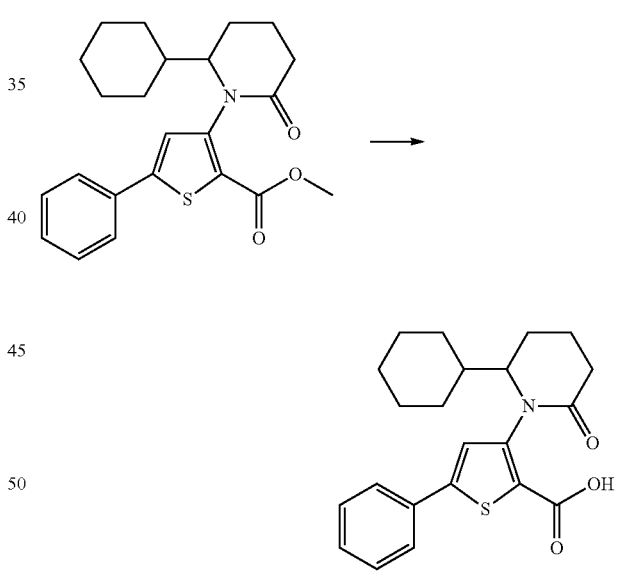

To a solution of methyl ester (15 mg, 0.038 mmol, 1.0 equiv) in THF (0.2 mL), EtOH (0.2 mL), water (0.1 mL) was added lithium hydroxide monohydrate (7.9 mg, 0.19 mmol, 5.0 equiv). The resulting mixture was stirred at 50° C. for 2 hours, after which the mixture was concentrated under vacuum. The residue was purified by reverse phase HPLC to give product 5.0 mg (yield 35%). MW: 384.1 $[M+H]^+$. $^1$H-NMR (400 MHz, $CDCl_3$): δ 7.43 (m, 2H), 7.21 (m, 3H), 6.94 (m, 1H), 3.68 (m, 1H), 2.45 (m, 2H), 2.21 (m, 1H), 1.83-1.51 (m, 12H), 1.32 (m, 2H).

Example 16

Synthesis of 3-(2-Cyclohexyl-4-hydroxy-6-oxo-piperidin-1-yl)-5-phenyl-thiophene-2-carboxylic acid methyl ester [Compound 12]

Step 1. 3-(1-Cyclohexyl-2-ethoxycarbonyl-ethylamino)-5-phenyl-thiophene-2-carboxylic acid methyl ester

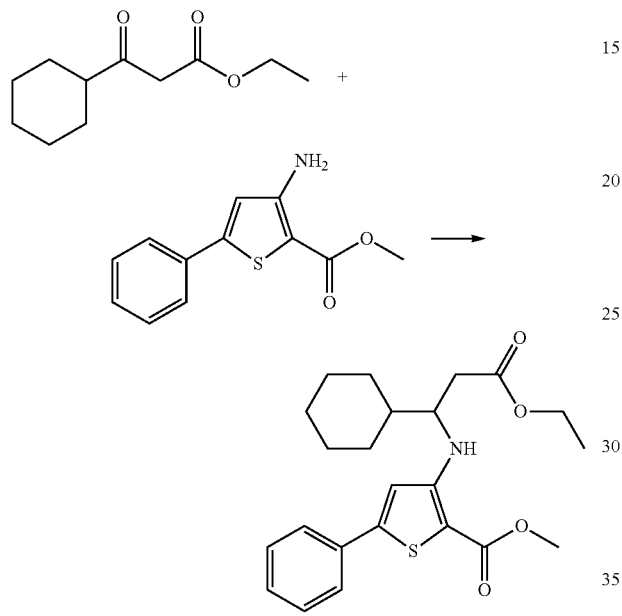

To a solution of 3-Cyclohexyl-3-oxo-propionic acid ethyl ester (1.0 g, 5.0 mmol, 1.0 equiv) in THF (5.0 mL) was added 3-Amino-5-phenyl-thiophene-2-carboxylic acid methyl ester (1.17 g, 5.0 mmol, 1.0 equiv) and $SnBu_2Cl_2$ (0.15 g, 0.50 mmol, 0.1 equiv) at room temperature. After stirred at room temperature for 5 minutes, the solution was added $PhSiH_3$. The resulting reaction mixture was stirred at 65° C. under $N_2$ for 18 hours, after which the solution was concentrated under vacuum and the residue was purified by silica gel column chromatography EtOAc/heptane, 10-60% to give product (0.7 g). MS: 416 [M+H$^+$].

Step 2. 3-(2-Carboxy-1-cyclohexyl-ethylamino)-5-phenyl-thiophene-2-carboxylic acid methyl ester

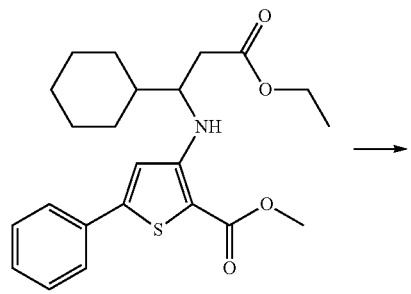

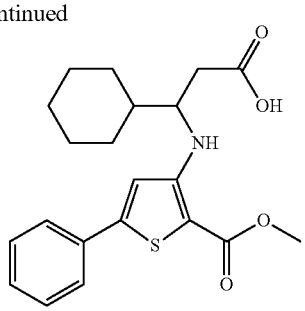

To a solution of 3-(1-cyclohexyl-2-ethoxycarbonyl-ethylamino)-5-phenyl-thiophene-2-carboxylic acid methyl ester (300 mg, 0.72 mmol, 1.0 equiv) in THF (2.0 mL), EtOH (1.0 mL) and water (2.0 mL) was added $LiOH \cdot H_2O$ (152 mg, 3.6 mmol, 5.0 equiv). The mixture was stirred at 55° C. for 20 minutes. The organic solvent was then evaporated. To the resulting solution was added 3.0 N HCl aq. solution until pH=5~6. The solid was then collected by filtration and washed with water. The filtrate was extracted with EtOAc and the organic layer was washed with sat. $NaHCO_3$ aq. solution, brine, dried over $Na_2SO_4$, and concentrated in vacuo. The crude material was continued to the next step with no further purification.

Step 3. Synthesis of 3-(2-Cyclohexyl-4,6-dioxo-piperidin-1-yl)-5-phenyl-thiophene-2-carboxylic acid methyl ester

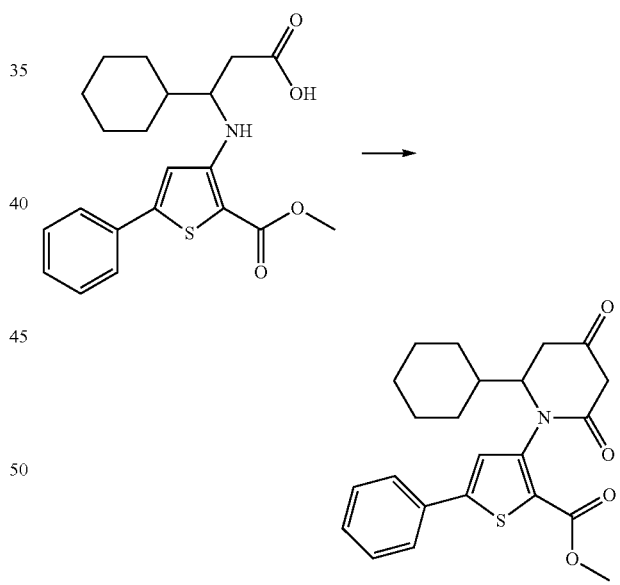

To a solution of 3-(2-carboxy-1-cyclohexyl-ethylamino)-5-phenyl-thiophene-2-carboxylic acid methyl ester (200 mg, 0.52 mmol, 1.0 equiv) in DCM (1.0 mL) was added EDC (148 mg, 0.77 mmol, 1.5 equiv), DMAP (95 mg, 0.77 mmol, 1.5 equiv), and Meldrum's acid (75 mg, 0.52 mmol, 1.0 equiv) at 0° C. The mixture was then warmed to room temperature and stirred at this temperature for 3 hours. To the reaction mixture was then added sat. $NaHSO_4$ aq. solution. The mixture was extracted with DCM and the organic phase was washed with brine, dried over $Na_2SO_4$ and concentrated in vacuo. The crude material was continued to the next step with no further purification.

The crude product from previous step (240 mg 0.47 mmol, 1.0 equiv) was dissolved in EtOAc (5.0 mL) and the resulting solution was heated to reflux for 2 hours. To the mixture was then added sat. aq. NaHSO$_4$ solution at room temperature. The mixture was extracted with DCM and the organic phase was washed with brine, dried over Na$_2$SO$_4$ and concentrated in vacuo. The residue was purified by silica gel column chromatography (EtOAc/Heptane 10%~60%) to give product (160 mg). MS: 412 [M+H$^+$]

Step 4. Synthesis of 3-(2-Cyclohexyl-4-hydroxy-6-oxo-piperidin-1-yl)-5-phenyl-thiophene-2-carboxylic acid methyl ester

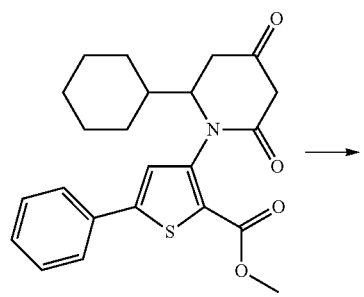

To a stirred solution of 3-(2-Cyclohexyl-4,6-dioxo-piperidin-1-yl)-5-phenyl-thiophene-2-carboxylic acid methyl ester (60 mg, 0.15 mmol, 1.0 equiv.) in anhydrous DCM (1.0 mL) was added NaBH$_4$ (11 mg, 0.29 mmol, 2 equiv) and AcOH (0.8 mg, 0.01 mmol, 0.1 equiv) at 0° C. The reaction mixture was then stirred at room temperature for 4 hours after which the reaction was quenched by addition of water. The mixture was extracted with DCM. The organic layer was washed with sat. aq. NaHCO$_3$ solution, dried over Na$_2$SO$_4$ and concentrated in vacuo. The residue was purified by silica gel column chromatography (EtOAc/heptane, 10%~60%) to give product 15 mg. The product was dissolved in THF (0.2 mL), EtOH (0.1 mL) and water (0.2 mL). To the solution was added LiOH.H$_2$O (7.6 mg, 0.18 mmol, 5 equiv) and the resulting mixture was stirred at 55° C. for 1 hour. The organic solvent was then evaporated and to the resulting solution was added 1.0 N HCl aq. solution until pH=4. The solution was extracted with EtOAc, and the organic layer was washed with sat. NaHCO$_3$ aqueous solution, brine, dried over Na$_2$SO$_4$, and concentrated in vacuo. The residue was purified by HPLC to give product 4 8 mg. MS: 400 [M+H$^+$].

Example 17

Synthesis of 3-(4-Benzoylamino-2-cyclohexyl-6-oxo-piperidin-1-yl)-5-phenyl-thiophene-2-carboxylic acid [Compound 21]

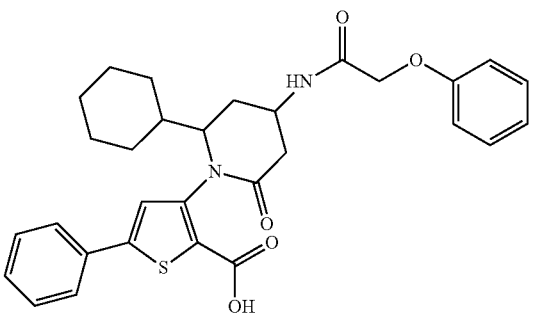 [SMILES: O=C(COc1ccccc1)NC1CC(=O)N(c2cc(-c3ccccc3)sc2C(=O)O)C(C2CCCCC2)C1]

Step 1. Synthesis of 3-(4-Amino-2-cyclohexyl-6-oxo-piperidin-1-yl)-5-phenyl-thiophene-2-carboxylic acid methyl ester

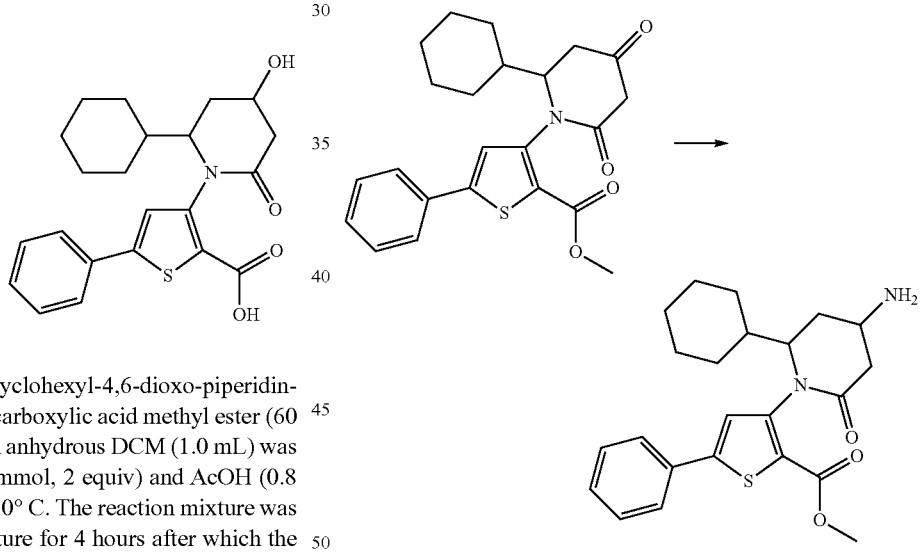

To a solution of 3-(2-cyclohexyl-4,6-dioxo-piperidin-1-yl)-5-phenyl-thiophene-2-carboxylic acid methyl ester (400 mg, 0.98 mmol, 1.0 equiv) in MeOH (2.0 mL) was added NH$_4$OAc (375 mg, 4.86 mmol, 5 equiv) and the resulting solution was stirred at room temperature for 18 hours. The reaction mixture was concentrated in vacuo and the residue was dissolved MeOH. To the solution was added NaCNBH$_3$ (247 mg, 1.16 mmol, 1.2 equiv) and HOAc (56 mg, 0.97 mmol, 1 equiv). The resulting mixture was stirred at room temperature for 18 hours. The solvent was then removed in vacuo. To the residue was added sat. aq. NaHCO$_3$ solution until pH>8. The mixture was extracted with DCM. The organic layer was dried over Na$_2$SO$_4$ and concentrated in vacuo. The crude material was continued to the next step with no further purification.

Step 2. Synthesis of 3-[2-Cyclohexyl-6-oxo-4-(2-phenoxy-acetylamino)-piperidin-1-yl]-5-phenyl-thiophene-2-carboxylic acid methyl ester

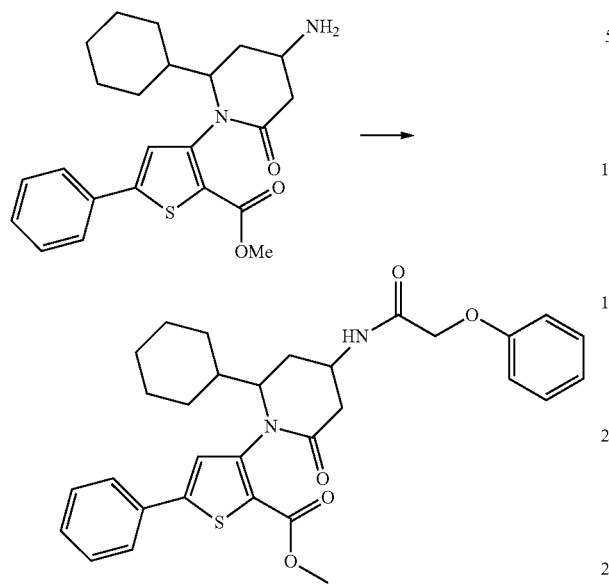

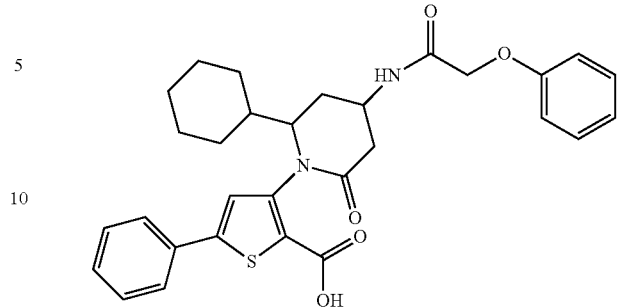

-continued

To a solution of 3-(4-amino-2-cyclohexyl-6-oxo-piperidin-1-yl)-5-phenyl-thiophene-2-carboxylic acid methyl ester (30 mg, 0.073 mmol, 1.0 equiv) in DCM (1.0 mL) at 0° C. was added phenoxyacetyl chloride (0.02 ml, 0.145 mmol, 2.0 equiv) and TEA (0.02 mL). The resulting mixture was then stirred at 0° C. for 20 minutes after which the solvent was removed under vacuum. The residue was purified by silica gel column chromatography (EtOAc/hepatane 10%~80%) to give product (20 mg). MS: 547 [M+H$^+$].)

Step 3. Synthesis of 3-[2-Cyclohexyl-6-oxo-4-(2-phenoxy-acetylamino)-piperidin-1-yl]-5-phenyl-thiophene-2-carboxylic acid

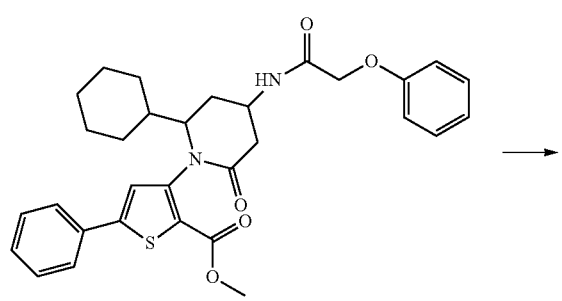

To a solution of methyl ester (10 mg, 0.018 mmol, 1.0 equiv) in THF (0.2 mL), EtOH (0.1 mL) and water (0.2 mL) was added LiOH.H$_2$O (8 mg, 0.18 mmol, 10 equiv). The mixture was stirred at 55° C. for 30 minutes, after which, the organic solvent was evaporated. To the resulting solution was added 3.0 N HCl aq. solution until pH=5. The solution was extracted with EtOAc, and the organic layer was washed with sat. NaHCO$_3$ aqueous solution, brine, dried over Na$_2$SO$_4$, and concentrated in vacuo. The residue was purified by prep-HPLC to give the product 6 mg. MS: 533[M+H$^+$]. $^1$H-NMR (400 MHz, DMSO): δ 10.31 (d, 1H), 7.63 (d, 2H), 7.42 (t, 2H), 7.31 (t, 2H), 7.23 (m, 2H), 7.14 (s, 1H), 6.98 (m, 3H), 4.61 (m, 2H), 4.45 (m, 1H), 4.10 (m, 1H), 3.32 (s, 2H), 2.20 (m, 1H), 1.88-1.76 (m, 4H), 1.65-1.58 (m, 2H), 1.41-1.05 (m, 6H).

Example 18

Synthesis of 3-[(2R,5R)-5-Cyclohexyl-2-(3-hydroxy-propyl)-3-oxo-morpholin-4-yl]-5-(3,3-dimethyl-but-1-ynyl)-thiophene-2-carboxylic acid and 3-[(2S,5R)-5-Cyclohexyl-2-(3-hydroxy-propyl)-3-oxo-morpholin-4-yl]-5-(3,3-dimethyl-but-1-ynyl)-thiophene-2-carboxylic acid [Compound 2] [Compound 3]

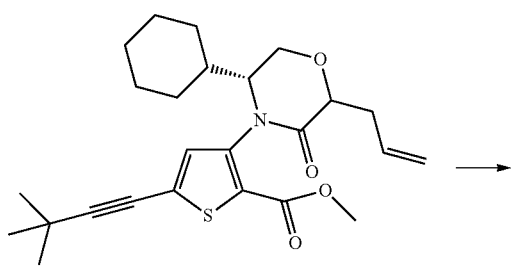

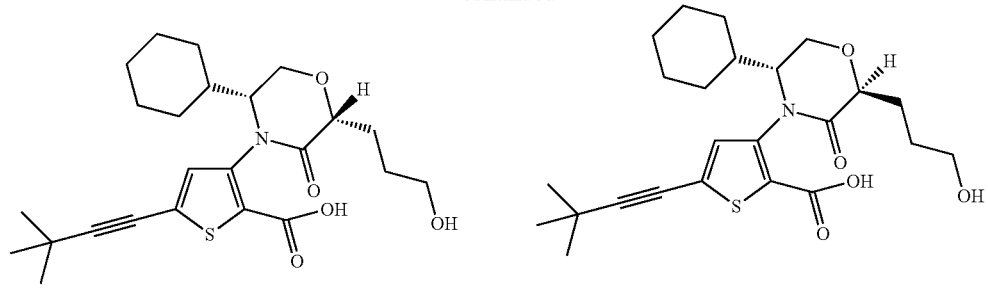

To a solution of 3-((R)-2-Allyl-5-cyclohexyl-3-oxo-morpholin-4-yl)-5-(3,3-dimethyl-but-1-ynyl)-thiophene-2-carboxylic acid methyl ester (200 mg, 0.45 mmol, 1.0 equiv) in THF (4.0 mL) at 0° C. was added 9-BBN (2.2 mL, 0.5 M in THF, 1.1 mmol, 2.5 equiv) over 10 minutes and the resulting solution was stirred at room temperature for 18 hours. The solution was then cooled to 0° C. and to the solution was added EtOH, aq. NaOH. solution, aq. $H_2O_2$ solution. The reaction mixture was heated to reflux for 90 minutes. After cooled to room temperature, the reaction mixture was extracted with EtOAc. The organic layer was dried over $Na_2SO_4$ and the residue was purified by prep-HPLC to give product 3-[(2R,5R)-5-Cyclohexyl-2-(3-hydroxy-propyl)-3-oxo-morpholin-4-yl]-5-(3,3-dimethyl-but-1-ynyl)-thiophene-2-carboxylic acid (20 mg) and 3-[(2S,5R)-5-Cyclohexyl-2-(3-hydroxy-propyl)-3-oxo-morpholin-4-yl]-5-(3,3-dimethyl-but-1-ynyl)-thiophene-2-carboxylic acid (20 mg). The stereochemistry at 2 position of morpholinone has not been established. Product 1: MW: 448.3 [M+H]$^+$. $^1$H-NMR (400 MHz, CD$_3$OD): δ 6.93 (s, 1H), 4.14 (m, 1H), 4.0 (m, 1H), 3.62 (m, 1H), 3.58 (m, 2H), 2.02-1.48 (m, 10H), 1.32 (s, 9H), 1.25-1.17 (m, 6H). Product 2: MW: 448.3 [M+H]$^+$. $^1$H-NMR (400 MHz, CD$_3$OD): δ 6.97 (s, 1H), 4.13 (m, 1H), 3.90 (m, 1H), 3.82 (m, 1H), 3.57 (m, 2H), 1.97-1.48 (m, 10H), 1.32 (s, 9H), 1.26-1.09 (m, 6H).

Example 19

Synthesis of 3-[(R)-2-Cyclohexyl-6-oxo-4-(6-pyrimidin-5-yl-pyridine-3-sulfonyl)-piperazin-1-yl]-5-phenyl-thiophene-2-carboxylic acid [Compound 206]

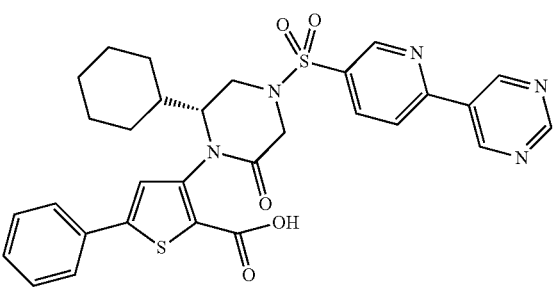

To a solution of 3-[(R)-4-(6-chloro-pyridine-3-sulfonyl)-2-cyclohexyl-6-oxo-piperazin-1-yl]-5-phenyl-thiophene-2-carboxylic acid (1.20 g, 2.14 mmol, 1.0 equiv) in acetonitrile (15.0 mL) was added potassium phosphate (8.58 ml, 1.0 M aqueous solution, 4.0 equiv) and chloro(2-dicyclohexyl phosphino-2',4',6'-tri-i-propyl-1,1'-biphenyl)[2-(2-amino ethyl) phenyl] Pd(II) Me-t-butyl ether adduct (0.32 g, 0.43 mmol, 0.2 equiv) at room temperature. The mixture was stirred at room temperature for 10 minutes to form a stock solution. To 0.8 mL of above solution was added 5-pyrimidinyl boronic acid (17.7 mg, 0.143 mmol, 2.0 equiv) and acetonitrile (0.5 mL) at room temperature. The mixture was stirred at 80° C. for 4 hours. The mixture was purified by HPLC (0.1% NH$_4$OH) to afford the product (15.9 mg, 36.9%). MS: 603.2 [M−H$^+$].

Example 20

3-[(R)-2-Cyclohexyl-4-(3-fluoro-2-morpholin-4-yl-benzyl)-6-oxo-piperazin-1-yl]-5-phenyl-thiophene-2-carboxylic acid [Compound 266]

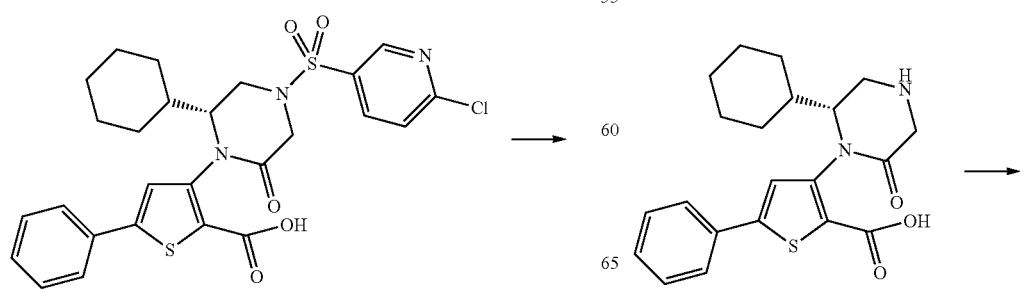 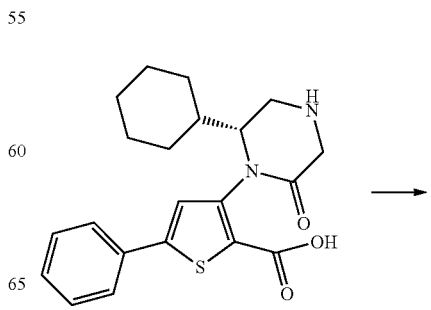

87
-continued

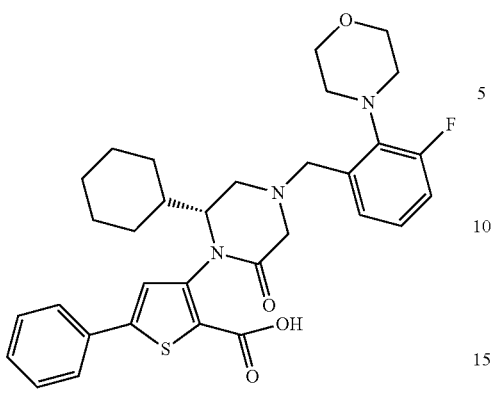

A solution of 3-((R)-2-cyclohexyl-6-oxo-piperazin-1-yl)-5-phenyl-thiophene-2-carboxylic acid (50.0 mg, 0.13 mmol, 1.0 equiv) and 3-fluoro-2-morpholinobenzaldehyde (108.8 mg, 0.52 mmol, 4.0 equiv) in acetic acid (0.2 mL) and methanol (0.5 mL) was stirred at room temperature for 60 minutes. Then sodium triacetoxyborohydride (110.2 mg, 0.52 mmol, 4.0 equiv) was added to the mixture and the resulting mixture was stirred at 75° C. for 3 hours. The solvent was removed by Genevac and the residue was dissolved in EtOAc (6 mL). The organic phase was washed by brine (3 mL), dried over $Na_2SO_4$ and concentrated. The residue was purified by HPLC (0.1% $NH_4OH$) to afford the product (9 mg, 12%). MS: 577.2 [M−H⁺].

Example 21

Synthesis of 3-((S)-3-Amino-6-cyclohexyl-2-oxo-piperidin-1-yl)-5-(3,3-dimethyl-but-1-ynyl)-thiophene-2-carboxylic acid [Compound 340]

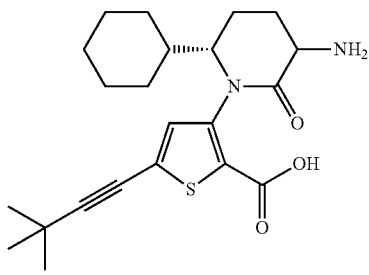 [SMILES: CC(C)(C)C#Cc1cc(N2C(=O)C(N)CC[C@H]2C2CCCCC2)c(C(=O)O)s1]

Step 1. Synthesis of 3-((S)-3-Bromo-6-cyclohexyl-2-oxo-piperidin-1-yl)-5-(3,3-dimethyl-but-1-ynyl)-thiophene-2-carboxylic acid methyl ester

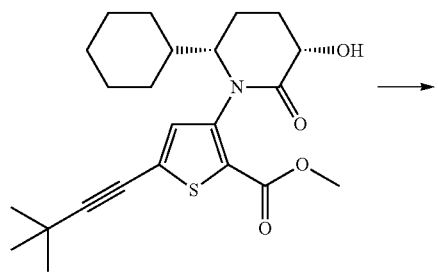

88
-continued

To a solution of 3-((3S,6S)-6-cyclohexyl-3-hydroxy-2-oxo-piperidin-1-yl)-5-(3,3-dimethyl-but-1-ynyl)-thiophene-2-carboxylic acid methyl ester (200 mg, 0.75 mmol, 1 equiv) in $CH_2Cl_2$ (1.0 mL) was added $PBr_3$ (1.0 M in $CH_2Cl_2$, 0.09 ml, 0.38 mmol, 0.8 equiv.) at room temperature and the resulting solution was stirred at room temperature for 18 hours. The reaction solution was then concentrated under vacuum and the residue was purified by silica gel column chromatography, (EtOAc/Heptane, 10%~60%) to give product 166 mg (yield 76%). MS: 481 [M+H⁺].

Step 2. Synthesis of 3-((S)-3-Azido-6-cyclohexyl-2-oxo-piperidin-1-yl)-5-(3,3-dimethyl-but-1-ynyl)-thiophene-2-carboxylic acid methyl ester

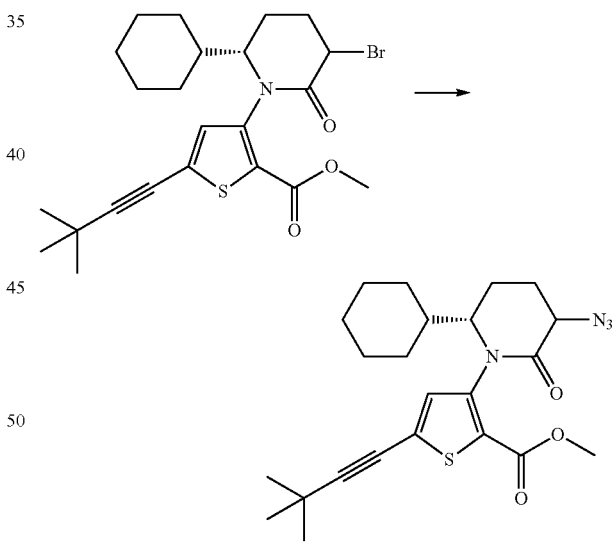

To the solution of 3-((S)-3-bromo-6-cyclohexyl-2-oxo-piperidin-1-yl)-5-(3,3-dimethyl-but-1-ynyl)-thiophene-2-carboxylic acid methyl ester (78 mg, 0.16 mmol, 1 equiv.) in DMF (1.0 mL) was added $NaN_3$ (12 mg, 0.19 mmol, 1.2 equiv) and the resulting mixture was stirred at 65° C. for 18 hours. The solvent was then removed under vacuum. The residue was purified by silica gel column chromatography (EtOAc/Heptane, 10%~60%) to give product 42 mg (yield 56%). MS: 442 [M+H⁺].

Step 3. Synthesis of 3-((S)-3-Amino-6-cyclohexyl-2-oxo-piperidin-1-yl)-5-(3,3-dimethyl-but-1-ynyl)-thiophene-2-carboxylic acid

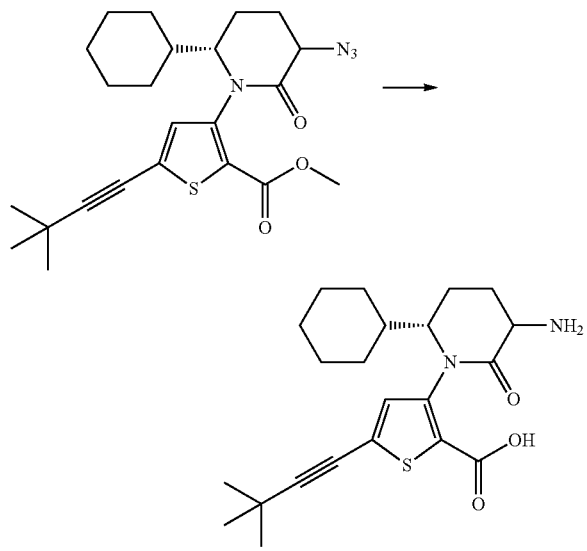

To the solution of 3-((S)-3-azido-6-cyclohexyl-2-oxo-piperidin-1-yl)-5-(3,3-dimethyl-but-1-ynyl)-thiophene-2-carboxylic acid methyl ester (40 mg, 0.09 mmol, 1 equiv) in MeOH (0.5 mL) was added SnCl$_2$ (17 mg, 0.09 mmol, 1 equiv) and the resulting solution was stirred at room temperature for 18 hours. The solvent was then removed under vacuum. The residue was dissolved in THF/H$_2$O/MeOH (0.5 mL/0.5 mL/1.0 mL) and to the solution was added LiOH.H$_2$O (21 mg, 0.48 mmol, 5 equiv). The reaction mixture was stirred at 50° C. for 20 minutes. The organic solvents were removed under vacuum and the residue was acidified to pH=5 by addition of 3.0 N HCl aq. solution. The mixture was extracted with EtOAc. The organic layer was dried over Na$_2$SO$_4$, and concentrated under vacuum. The residue was purified by prep-HPLC (XBridge Prep C 18 5 um, 30×50 mm) in basic condition (0.1% NH$_4$OH, 10%~45% CH$_3$CN/H$_2$O, 10 min run, 40 ml/min) to give product 12 mg. MS: 403 [M+H$^+$].
$^1$H-NMR (400 MHz, CD$_3$OD): δ 6.81 (s, 1H), 3.96 (br, 1H), 3.48 (m, 1H), 2.06 (m, 3H), 1.84 (m, 3H), 1.70 (br, 2H), 1.46 (m, 1H), 1.37 (m, 1H), 1.31 (s, 9H), 1.16 (m, 5H).

Example 22

Synthesis of 3-((S)-6-cyclohexyl-3-(3-hydroxy-propyl)-2-oxo-piperidin-1-yl)-5-(3,3-dimethyl-but-1-ynyl)-thiophene-2-carboxylic acid [Compound 341]

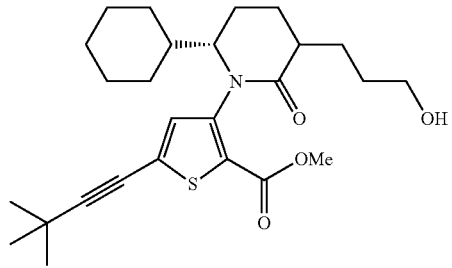 [SMILES: COC(=O)c1sc(C#CC(C)(C)C)cc1N1C(=O)C(CCCO)CC[C@H]1C1CCCCC1]

Step 1. Synthesis of 3-((S)-3-Allyl-6-cyclohexyl-2-oxo-piperidin-1-yl)-5-(3,3-dimethyl-but-1-ynyl)-thiophene-2-carboxylic acid methyl ester

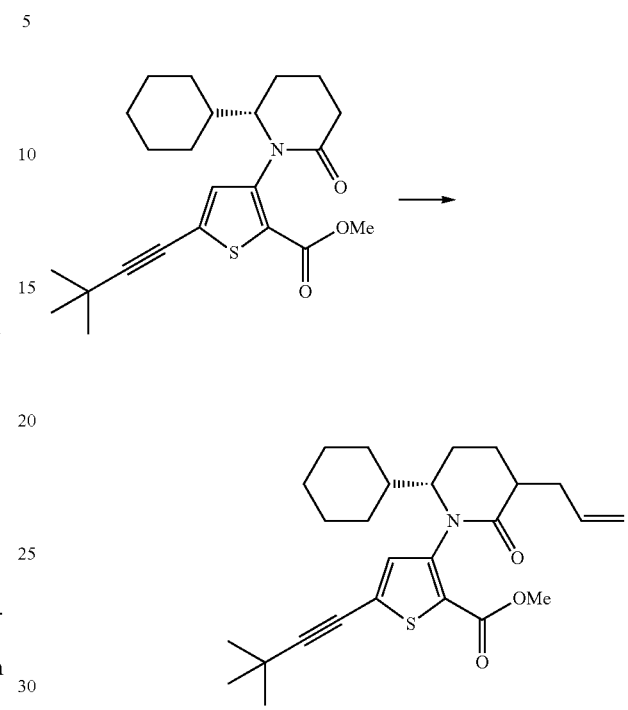

To a solution of 3-((S)-2-cyclohexyl-6-oxo-piperidin-1-yl)-5-(3,3-dimethyl-but-1-ynyl)-thiophene-2-carboxylic acid methyl ester (200 mg, 0.5 mmol, 1.0 equiv) in THF (2.0 mL) was added LDA (2.0 M in THF, 0.3 mL, 0.6 mmol, 1.2 equiv) at −78° C. and the resulting solution was stirred at −78° C. for 10 minutes. To the solution was then added 3-iodopropene (250 mg, 1.5 mmol, 3.0 equiv) and the reaction mixture was stirred at room temperature for 15 minutes. The reaction was quenched by addition of water. The mixture was extracted with EtOAc. The organic layer was washed with sat. NaHCO$_3$ aq. solution and brine, dried over Na$_2$SO$_4$, and concentrated under vacuum. The residue was purified by silica gel column chromatography, Heptane/DCM (contained 3% EtOAc) to give 60 mg of less polar diastereomer and 100 mg of more polar diastereomer. MS: 442 [M+H$^+$].

Step 2. Synthesis of 3-((S)-6-cyclohexyl-3-(3-hydroxy-propyl)-2-oxo-piperidin-1-yl)-5-(3,3-dimethyl-but-1-ynyl)-thiophene-2-carboxylic acid

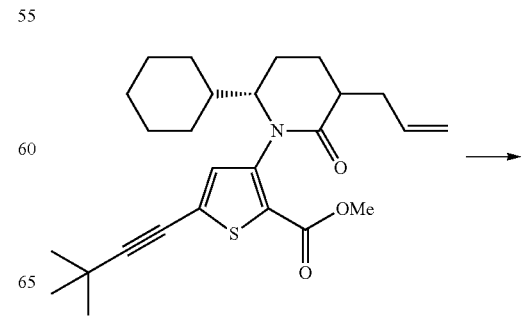

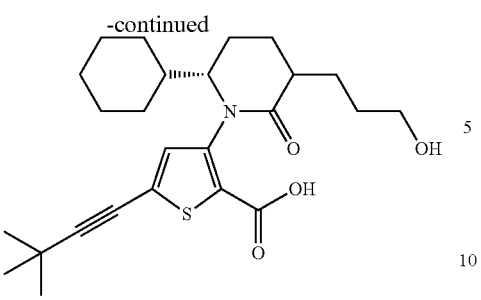
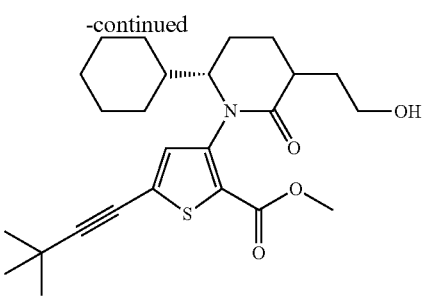

To a solution of 3-((S)-3-allyl-6-cyclohexyl-2-oxo-piperidin-1-yl)-5-(3,3-dimethyl-but-1-ynyl)-thiophene-2-carboxylic acid methyl ester (less polar diastereomer from previous step) (60 mg, 0.14 mmol, 1.0 equiv) in anhydrous THF (2.0 ml) was added 9-BBN (0.5 M in THF, 0.68 ml, 0.34 mmol, 2.5 equiv) at 0° C. and the resulting solution was stirred at room temperature for 2 hours. The solution was then cooled at 0° C. and to the solution was added EtOH, 1.0 M aq. NaOH solution and aqueous $H_2O_2$ solution. The reaction mixture was heated to reflux for 90 minutes and then cooled at room temperature. The mixture was extracted with EtOAc. The organic layer was dried over $Na_2SO_4$ and concentrated under vacuum. The residue was purified by prep-HPLC (0.1% $NH_4OH$) to give 20 mg of the desired product (yield 33%). MS: 446 [M+H$^+$]. $^1$H-NMR (400 MH$_z$, CD$_3$OD): 6.81 (s, 1H), 4.00 (br, 1H), 3.53 (t, 2H), 2.27 (br, 1H), 1.97 (m, 3H), 1.82~1.64 (m, 7H), 1.58 (m, 2H), 1.37 (m, 2H), 1.31 (s, 9H), 1.14 (m, 5H).

Example 23

Synthesis of 3-((S)-6-cyclohexyl-3-(2-hydroxy-ethyl)-2-oxo-piperidin-1-yl)-5-(3,3-dimethyl-but-1-ynyl)-thiophene-2-carboxylic acid [Compound 343]

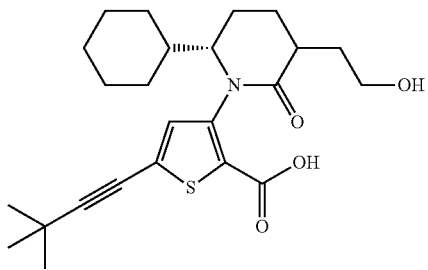 [SMILES: CC(C)(C)C#Cc1cc(N2C(=O)C(CCO)CC[C@H]2C2CCCCC2)c(C(=O)O)s1]

Step 1. Synthesis of 3-[(S)-6-Cyclohexyl-3-(2-hydroxy-ethyl)-2-oxo-piperidin-1-yl]-5-(3,3-dimethyl-but-1-ynyl)-thiophene-2-carboxylic acid methyl ester

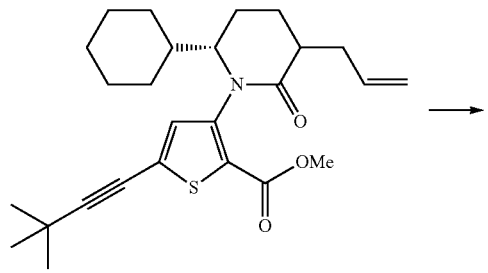

To a solution of 3-((S)-3-allyl-6-cyclohexyl-2-oxo-piperidin-1-yl)-5-(3,3-dimethyl-but-1-ynyl)-thiophene-2-carboxylic acid methyl ester (less polar diastereomer from previous step) (200 mg, 0.45 mmol, 1.0 equiv) in acetone (3.0 mL) at 0° C. was added N-methylmorpholine oxide (160 mg, 1.36 mmol, 3 equiv), water (1.0 mL) and $OsO_4$ (230 mg, 0.02 mmol, 0.05 equiv). The reaction mixture was stirred at room temperature for 1 hour. The solution was partitioned between brine and EtOAc. The phases were separated and the organic layer was dried over $Na_2SO_4$, and concentrated under vacuum. The residue was dissolved in THF/water (3.0 mL/1.0 mL). To the solution was added $NaIO_4$ (194 mg, 0.9 mmol, 2 equiv), and the resulting mixture was stirred at room temperature for 30 minutes, after which another portion of $NaIO_4$ (0.5 equiv) was added. After stirred at room temperature for 30 minutes, the mixture was partitioned between brine and EtOAc. The organic layer was separated, dried over $Na_2SO_4$, and concentrated. The residue was dissolved in EtOH (3.0 ml) and the solution was cooled at 0° C. To the solution was added $NaBH_4$ and the mixture was stirred at 0° C. for 15 minutes. The reaction was quenched by addition of water (2.0 mL) and EtOAc (10.0 mL). The organic layer was separated, dried over $Na_2SO_4$, and concentrated. The residue was purified by silica gel column chromatography, Heptane/EtOAc 1/1 to give 123 mg of the product (yield 60%). MS: 446 [M+H$^+$]

Step 2. Synthesis of 3-((S)-6-cyclohexyl-3-(2-hydroxy-ethyl)-2-oxo-piperidin-1-yl)-5-(3,3-dimethyl-but-1-ynyl)-thiophene-2-carboxylic acid

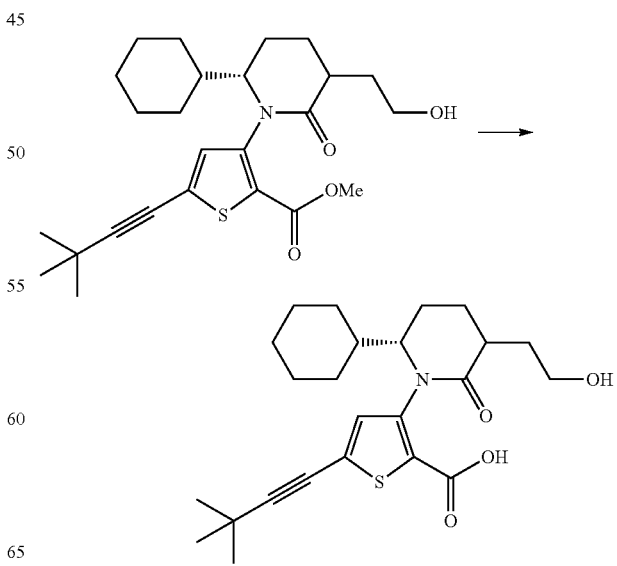

To a solution of 3-[(S)-6-cyclohexyl-3-(2-hydroxy-ethyl)-2-oxo-piperidin-1-yl]-5-(3,3-dimethyl-but-1-ynyl)-thiophene-2-carboxylic acid methyl ester (123 mg, 0.28 mmol, 1 equiv.) in THF/H₂O/MeOH (1.0 mL/1.0 mL/0.5 mL) was added LiOH.H₂O (60 mg, 1.38 mmol, 5 equiv) and the resulting solution was stirred at 50° C. for 20 minutes. The solution was then acidified to pH=5 by addition of 3.0 N HCl aq. solution. The solution was extracted with EtOAc. The organic layer was dried over Na₂SO₄, and concentrated. The residue was purified by prep-HPLC (XBridge Prep C 18 5 um, 30×50 mm) in basic condition (0.1% NH₄OH, 10%~45% CH₃CN/H₂O, 10 min run, 40 ml/min) to give product 28 mg (yield 23%). MS: 432 [M+H⁺]. ¹H-NMR (400 MHz, CD₃OD): 6.85 (s, 1H), 3.92 (br, 1H), 3.67 (m, 2H), 2.41 (br, 1H), 2.15 (m, 1H), 1.97 (m, 2H), 1.78 (m, 7H), 1.37 (m, 2H), 1.31 (s, 9H), 1.14 (m, 5H).

Example 24

Synthesis of 3-[(2R,5R)-5-Cyclohexyl-2-((R)-2-hydroxy-propyl)-3-oxo-morpholin-4-yl]-5-(3,3-dimethyl-but-1-ynyl)-thiophene-2-carboxylic acid [Compound 336]

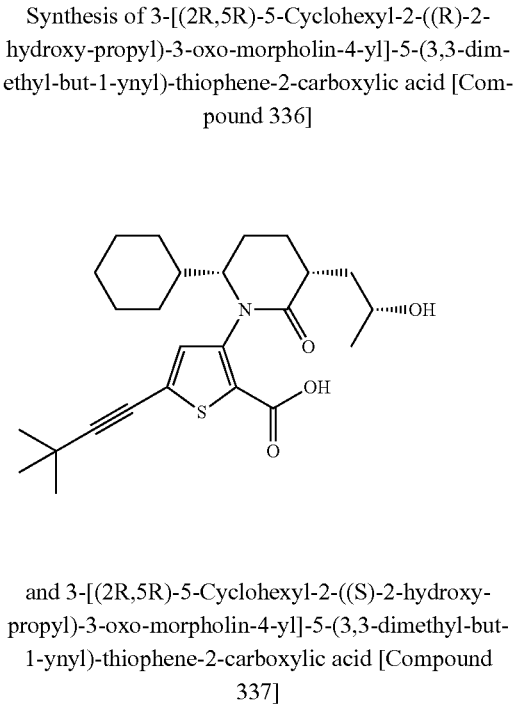

and 3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid [Compound 337]

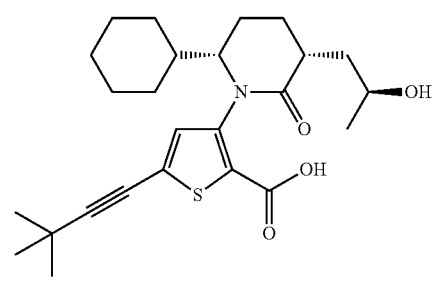 [SMILES: C[C@H](O)C[C@H]1CC[C@@H](C2CCCCC2)N(c2cc(C#CC(C)(C)C)sc2C(=O)O)C1=O]

Step 1. Synthesis of 3-[(2R,5R)-5-Cyclohexyl-3-oxo-2-(2-oxo-ethyl)-morpholin-4-yl]-5-(3,3-dimethyl-but-1-ynyl)-thiophene-2-carboxylic acid methyl ester

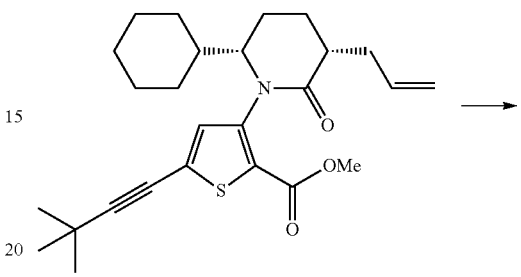

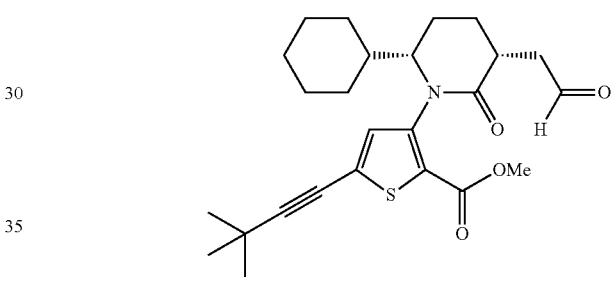

To a solution of 3-((2R,5R)-2-allyl-5-cyclohexyl-3-oxo-morpholin-4-yl)-5-(3,3-dimethyl-but-1-ynyl)-thiophene-2-carboxylic acid methyl ester (3.15 g, 7.10 mmol, 1.0 equiv) in acetone (40 mL) at 0° C. was added N-methylmorpholine oxide (2.51 g, 21.30 mmol, 3.0 equiv), water (14 mL) and osmium tetroxide (3.60 g, 2.5% wt in THF, 0.36 mmol, 0.05 equiv). The mixture was stirred at room temperature for 60 minutes. Acetone was removed under vacuum and the residue was partitioned between EtOAc (80 mL) and brine (15 mL). The phases were separated and the organic layer was dried (over Na₂SO₄) and concentrated. To the residue was added THF (40 mL) and water (14 mL). At 0° C., sodium periodate (2.28 g, 10.65 mmol, 1.5 equiv) was added to the mixture and the mixture was stirred at room temperature for 30 minutes. After cooled at 0° C., another portion of sodium periodate (0.76 g, 3.55 mmol, 0.5 equiv) was added. The mixture was stirred at room temperature for another 30 minutes. Volatile solvent was removed under vacuum and the residue was partitioned between EtOAc (100 mL) and brine (10 mL). The organic layer was separated, dried (over Na₂SO₄) and concentrated. The residue was purified by silica gel column chromatography (EtOAc/Heptane, 25% to 50%) to give product (2.1 g, 66%). MS: 446.3 [M−H⁺].

Step 2. Synthesis of 3-[(2R,5R)-5-Cyclohexyl-2-((R)-2-hydroxy-propyl)-3-oxo-morpholin-4-yl]-5-(3,3-dimethyl-but-1-ynyl)-thiophene-2-carboxylic acid methyl ester and 3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid methyl ester

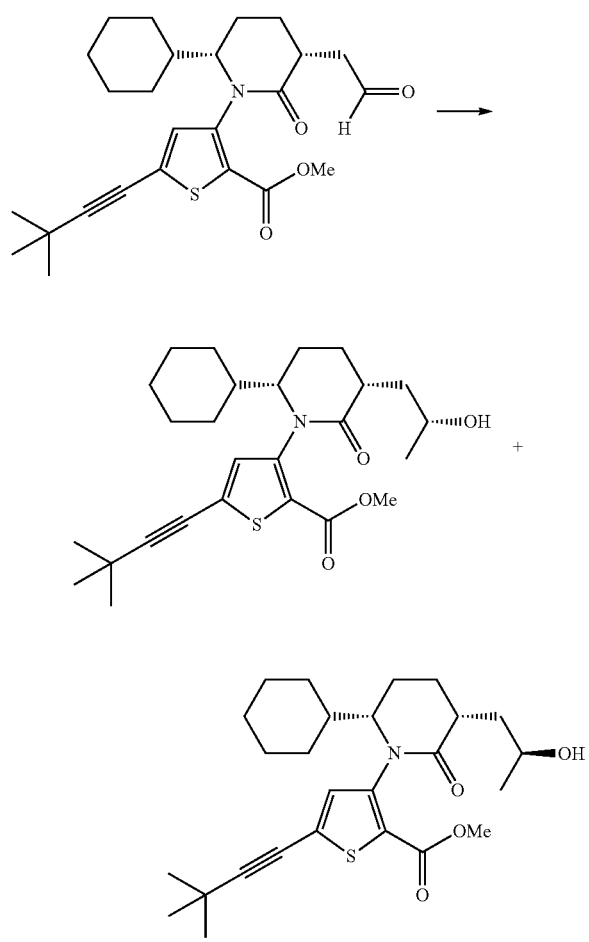

To a solution of 3-[(2R,5R)-5-cyclohexyl-3-oxo-2-(2-oxo-ethyl)-morpholin-4-yl]-5-(3,3-dimethyl-but-1-ynyl)-thiophene-2-carboxylic acid methyl ester (1.9 g, 4.26 mmol, 1.0 equiv) in THF (200 mL) at −10° C., was added MeMgBr (1.85 mL, 3.0 M solution in THF, 5.54 mmol, 1.3 equiv). The resulting solution was stirred at −10° C. for 20 minutes. The reaction was quenched by addition of 3.0 N HCl aqueous solution until pH=1. The volatile solvent was removed under vacuum and the residue was partitioned between EtOAc (100 mL) and brine (5 mL). The separated organic layer was dried over Na$_2$SO$_4$ and concentrated. The residue was purified by silica gel column chromatography [Et$_2$O (2% EtOAc)/Heptane, 25% to 50%] to give 3-[(2R,5R)-5-Cyclohexyl-2-((R)-2-hydroxy-propyl)-3-oxo-morpholin-4-yl]-5-(3,3-dimethyl-but-1-ynyl)-thiophene-2-carboxylic acid methyl ester (0.57 g, 29.0%) and 3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid methyl ester (0.80 g, 40.7%). MS: 462.4 [M−H$^+$].

Step 3. Synthesis of 3-[(2R,5R)-5-cyclohexyl-2-((R)-2-hydroxy-propyl)-3-oxo-morpholin-4-yl]-5-(3,3-dimethyl-but-1-ynyl)-thiophene-2-carboxylic acid

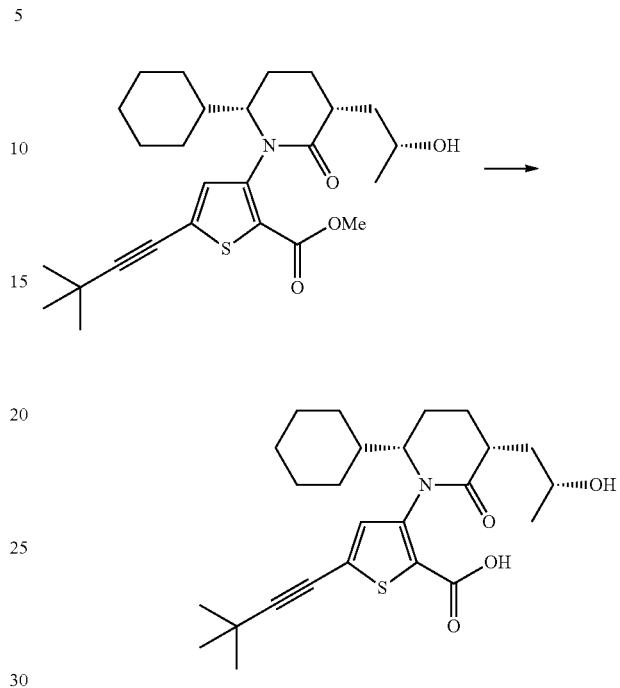

To a solution of 3-[(2R,5R)-5-cyclohexyl-2-((R)-2-hydroxy-propyl)-3-oxo-morpholin-4-yl]-5-(3,3-dimethyl-but-1-ynyl)-thiophene-2-carboxylic acid methyl ester (650 mg, 1.41 mmol, 1.0 equiv) in THF (10 mL), MeOH (5 mL) and water (5 mL) was added LiOH.H$_2$O (177 mg, 4.22 mmol, 3.0 equiv). The resulting solution was stirred at room temperature for 2 hours. The volatile solvent was removed under vacuum and to the residue was added water (15 mL). The mixture was cooled to 0° C. and acidified by addition of 3.0 N HCl aqueous solution until pH=1. The precipitate was isolated by filtration to give product (586 mg, 93%) as white solid. MS: 448.3 [M−H$^+$]. $^1$H NMR (400 MHz, CD$_3$OD): 1.09-1.31 (m, 8H) 1.32 (s, 9H) 1.45-1.85 (m, 5H) 1.89-2.10 (m, 3H) 3.56-3.61 (m, 1H) 3.93-4.00 (m, 1H) 4.00-4.10 (m, 1H) 4.12-4.22 (m, 2H) 6.99 (s, 1H).

Step 4. Synthesis of 3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid

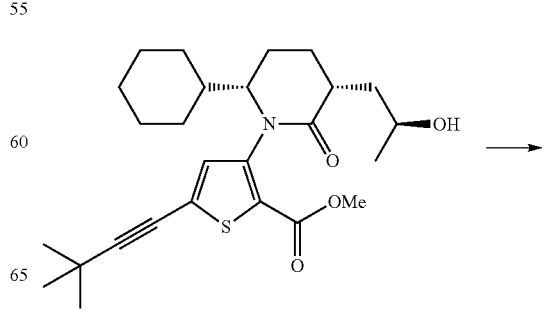

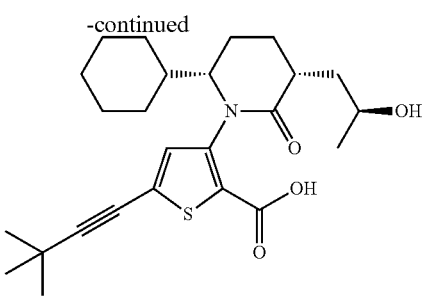

To a solution of 3-[(2R,5R)-5-cyclohexyl-2-(2-hydroxy-propyl)-3-oxo-morpholin-4-yl]-5-(3,3-dimethyl-but-1-ynyl)-thiophene-2-carboxylic acid methyl ester (420 mg, 0.91 mmol, 1.0 equiv) in THF (8 mL), MeOH (4 mL) and water (4 mL) was added LiOH.H$_2$O (115 mg, 2.73 mmol, 3.0 equiv). The resulting solution was stirred at room temperature for one hour. The volatile solvent was removed under vacuum and the residue was acidified by addition of 3.0 N HCl aqueous solution until pH=1. The mixture was extracted with EtOAc (50 mL). The separated organic layer was washed with brine (10 mL), dried (over Na$_2$SO$_4$) and concentrated. The residue was purified by HPLC (0.1% NH$_4$OH) to give product (68 mg, 16.7%). MS: 448.2 [M–H$^+$]. $^1$H NMR (400 MHz, CD$_3$OD) δ 1.07-1.31 (m, 8H) 1.32 (s, 9H) 1.45-1.60 (m, 2H) 1.63-1.85 (m, 4H) 1.87-1.98 (m, 1H) 2.02-2.11 (m, 1H) 3.60-3.66 (m, 1H) 3.93-4.03 (m, 2H) 4.15 (d, 1H) 4.26-4.35 (m, 1H) 6.94 (s, 1H).

Additional non-limiting exemplary compounds of the invention are provided in Table 1. The compounds of Table 1 may be prepared by analogy to the synthetic procedures provided in the general synthetic description, the procedures of Examples 1-20 and/or by synthetic methodology known to the skilled medicinal chemist.

TABLE 1

| Compound number | Name | Structure |
|---|---|---|
| 1 | 3-(2-Cyclohexyl-5-oxo-pyrrolidin-1-yl)-5-phenyl-thiophene-2-carboxylic acid | 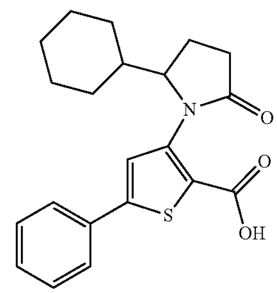 [SMILES: O=C(O)c1sc(-c2ccccc2)cc1N1C(=O)CCC1C1CCCCC1] |
| 2 | 3-[(2S,5R)-5-Cyclohexyl-2-(3-hydroxy-propyl)-3-oxo-morpholin-4-yl]-5-(3,3-dimethyl-but-1-ynyl)-thiophene-2-carboxylic acid | 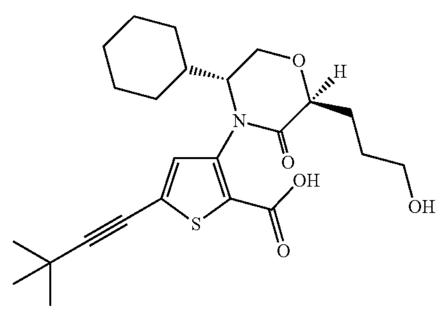 [SMILES: CC(C)(C)C#Cc1cc(N2C(=O)[C@H](CCCO)OC[C@H]2C2CCCCC2)c(C(=O)O)s1] |
| 3 | 3-[(2R,5R)-5-Cyclohexyl-2-(3-hydroxy-propyl)-3-oxo-morpholin-4-yl]-5-(3,3-dimethyl-but-1-ynyl)-thiophene-2-carboxylic acid | 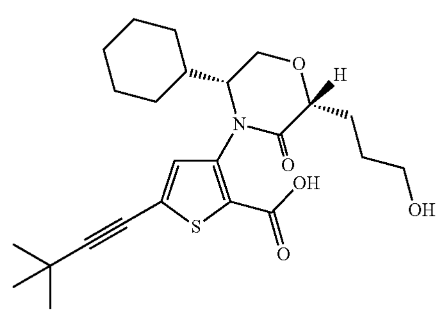 [SMILES: CC(C)(C)C#Cc1cc(N2C(=O)[C@@H](CCCO)OC[C@H]2C2CCCCC2)c(C(=O)O)s1] |

TABLE 1-continued

| Compound number | Name | Structure |
|---|---|---|
| 4 | 3-(2-Cyclohexyl-6-oxo-piperidin-1-yl)-5-phenyl-thiophene-2-carboxylic acid | 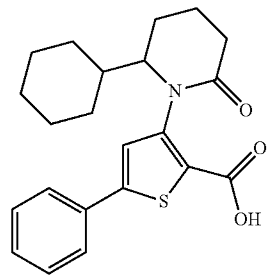 [SMILES: O=C(O)c1sc(-c2ccccc2)cc1N1C(=O)CCCC1C1CCCCC1] |
| 5 | 3-(6-Cyclohexyl-3-hydroxy-3-methyl-2-oxo-piperidin-1-yl)-5-p-tolyl-thiophene-2-carboxylic acid | 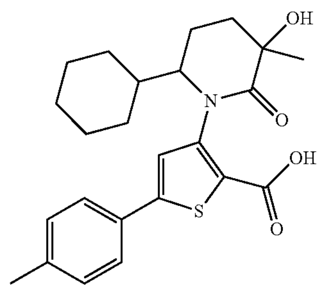 |
| 6 | 3-((S)-2-Cyclohexyl-5-oxo-pyrrolidin-1-yl)-5-phenyl-thiophene-2-carboxylic acid | 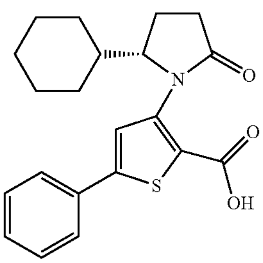 [SMILES: O=C(O)c1sc(-c2ccccc2)cc1N1C(=O)CC[C@H]1C1CCCCC1] |
| 7 | 3-[(2S,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid | 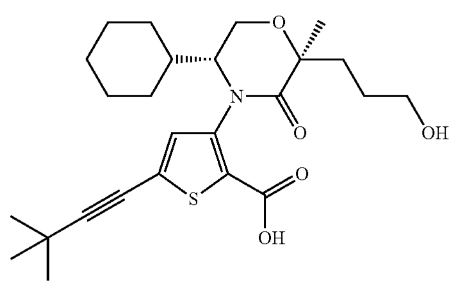 [SMILES: CC(C)(C)C#Cc1cc(N2C(=O)[C@](C)(CCCO)OC[C@H]2C2CCCCC2)c(C(=O)O)s1] |
| 8 | 3-[(2R,5R)-5-Cyclohexyl-2-(2-hydroxy-ethyl)-3-oxo-morpholin-4-yl]-5-(3,3-dimethyl-but-1-ynyl)-thiophene-2-carboxylic acid | 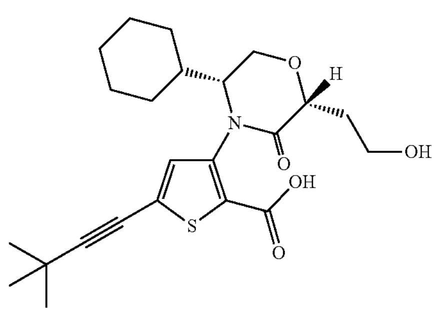 [SMILES: CC(C)(C)C#Cc1cc(N2C(=O)[C@@H](CCO)OC[C@H]2C2CCCCC2)c(C(=O)O)s1] |

TABLE 1-continued

| Compound number | Name | Structure |
|---|---|---|
| 9 | 3-(2-Cyclohexyl-4,6-dioxo-piperidin-1-yl)-5-phenyl-thiophene-2-carboxylic acid | 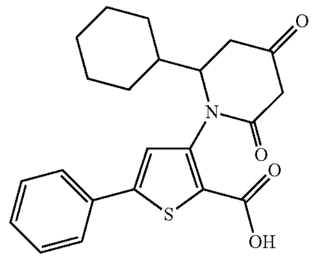 [SMILES: O=C1CC(=O)N(c2cc(-c3ccccc3)sc2C(=O)O)C(C2CCCCC2)C1] |
| 10 | 3-[(2R,5R)-5-Cyclohexyl-2-(2,3-dihydroxy-propyl)-3-oxo-morpholin-4-yl)-5-(3,3-dimethyl-but-1-ynyl)-thiophene-2-carboxylic acid | 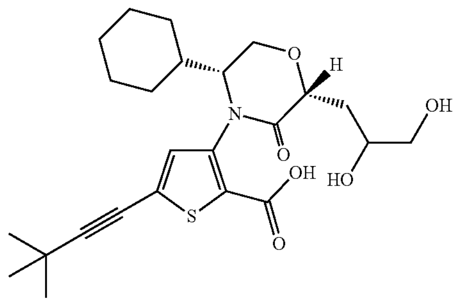 [SMILES: CC(C)(C)C#Cc1cc(N2C(=O)[C@@H](CC(O)CO)OC[C@H]2C2CCCCC2)c(C(=O)O)s1] |
| 11 | 3-[6-Cyclohexyl-3-hydroxy-3-(3-hydroxy-propyl)-2-oxo-piperidin-1-yl]-5-(3,3-dimethyl-but-1-ynyl)-thiophene-2-carboxylic acid | 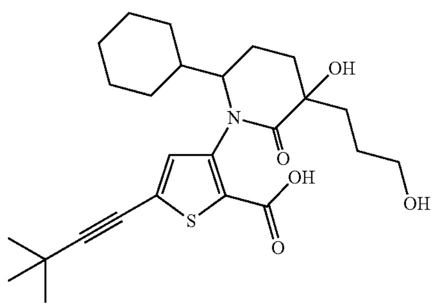 [SMILES: CC(C)(C)C#Cc1cc(N2C(=O)C(O)(CCCO)CCC2C2CCCCC2)c(C(=O)O)s1] |
| 12 | 3-(2-Cyclohexyl-4-hydroxy-6-oxo-piperidin-1-yl)-5-phenyl-thiophene-2-carboxylic acid | 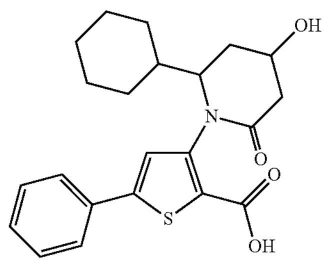 [SMILES: O=C(O)c1sc(-c2ccccc2)cc1N1C(=O)CC(O)CC1C1CCCCC1] |
| 13 | 3-(3-Cyclohexyl-5-oxo-morpholin-4-yl)-5-phenyl-thiophene-2-carboxylic acid | 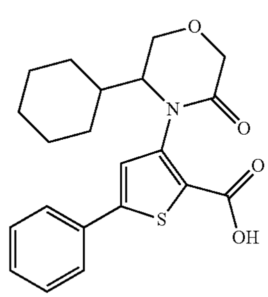 [SMILES: O=C(O)c1sc(-c2ccccc2)cc1N1C(=O)COCC1C1CCCCC1] |

TABLE 1-continued

| Compound number | Name | Structure |
|---|---|---|
| 14 | (R)-4-(2-Carboxy-5-phenyl-thiophen-3-yl)-3-cyclohexyl-5-oxo-piperazine-1-carboxylic acid tert-butyl ester | 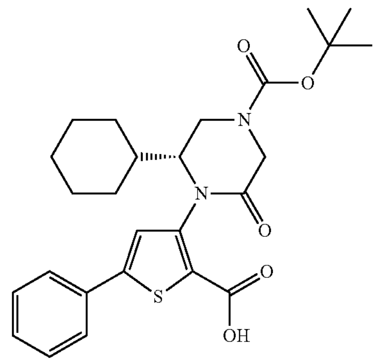 [SMILES: CC(C)(C)OC(=O)N1CC(=O)N(c2cc(-c3ccccc3)sc2C(=O)O)[C@H](C2CCCCC2)C1] |
| 15 | 3-((R)-2-Cyclohexyl-6-oxo-piperazin-1-yl]-5-phenyl-thiophene-2-carboxylic acid | 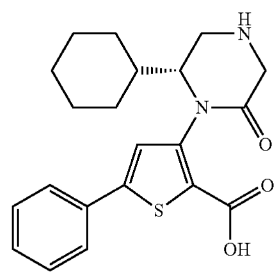 [SMILES: O=C(O)c1sc(-c2ccccc2)cc1N1C(=O)CNC[C@H]1C1CCCCC1] |
| 16 | 3-((R)-4-Benzoyl-2-cyclohexyl-6-oxo-piperazin-1-yl)-5-phenyl-thiophene-2-carboxylic acid | 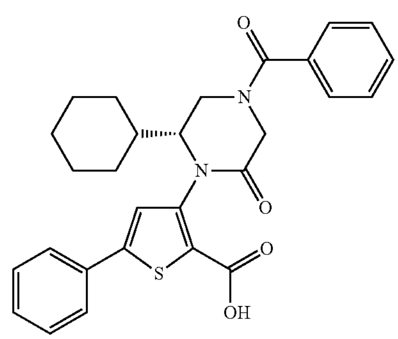 [SMILES: O=C(O)c1sc(-c2ccccc2)cc1N1C(=O)CN(C(=O)c2ccccc2)C[C@H]1C1CCCCC1] |
| 17 | 3-((R)-4-Benzyl-2-cyclohexyl-6-oxo-piperazin-1-yl)-5-phenyl-thiophene-2-carboxylic acid | 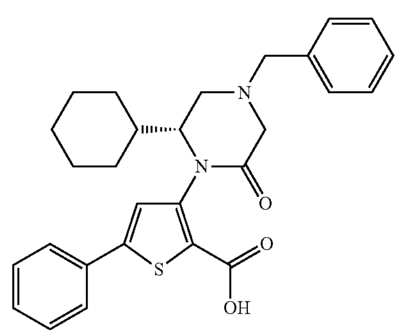 [SMILES: O=C(O)c1sc(-c2ccccc2)cc1N1C(=O)CN(Cc2ccccc2)C[C@H]1C1CCCCC1] |

TABLE 1-continued

| Compound number | Name | Structure |
|---|---|---|
| 18 | 3-[(R)-2-Cyclohexyl-6-oxo-4-(toluene-4-sulfonyl)-piperazin-1-yl]-5-phenyl-thiophene-2-carboxylic acid | 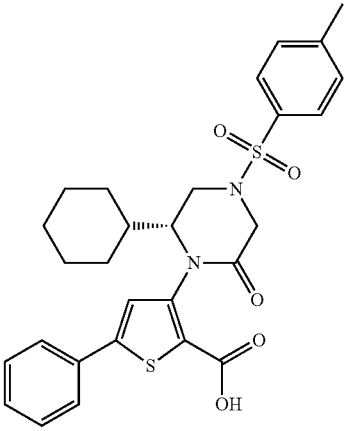 [SMILES: Cc1ccc(S(=O)(=O)N2CC(=O)N(c3cc(-c4ccccc4)sc3C(=O)O)[C@H](C3CCCCC3)C2)cc1] |
| 19 | 3-(2-Cyclohexyl-6-oxo-piperidin-1-yl)-5-(3,3-dimethyl-but-1-ynyl)-thiophene-2-carboxylic acid | 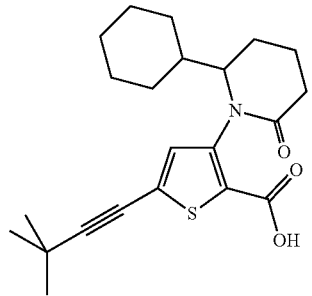 |
| 20 | 3-(2-Cyclohexyl-6-oxo-4-phenylacetylamino-piperidin-1-yl)-5-phenyl-thiophene-2-carboxylic acid | 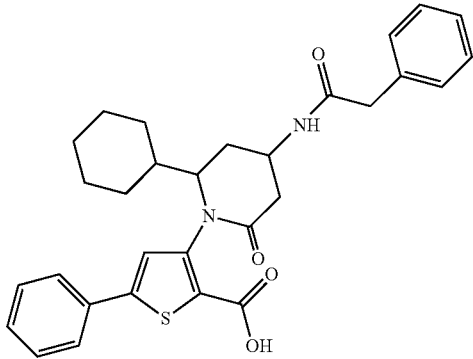 [SMILES: O=C(Cc1ccccc1)NC1CC(=O)N(c2cc(-c3ccccc3)sc2C(=O)O)C(C2CCCCC2)C1] |
| 21 | 3-[2-Cyclohexyl-6-oxo-4-(2-phenoxy-acetylamino)-piperidin-1-yl]-5-phenyl-thiophene-2-carboxylic acid | 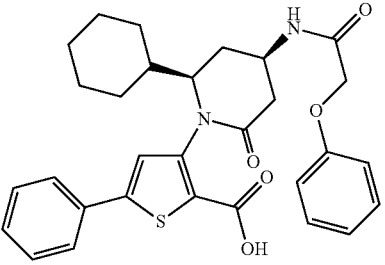 [SMILES: O=C(COc1ccccc1)N[C@H]1CC(=O)N(c2cc(-c3ccccc3)sc2C(=O)O)[C@@H](C2CCCCC2)C1] |

TABLE 1-continued

| Compound number | Name | Structure |
|---|---|---|
| 22 | 3-[(2R,4S)-2-Cyclohexyl-6-oxo-4-(2-phenoxy-acetylamino)-piperidin-1-yl]-5-phenyl-thiophene-2-carboxylic acid | 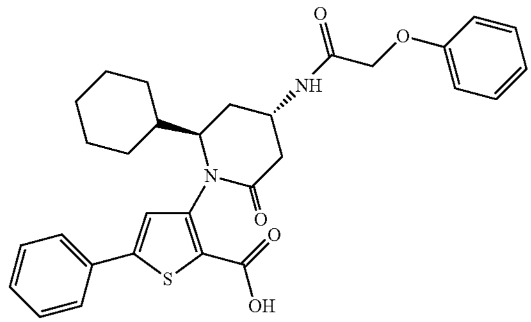 [SMILES: O=C(COc1ccccc1)N[C@@H]1CC(=O)N(c2cc(-c3ccccc3)sc2C(=O)O)[C@@H](C2CCCCC2)C1] |
| 23 | 3-((2R,4R)-4-Amino-2-cyclohexyl-6-oxo-piperidin-1-yl)-5-phenyl-thiophene-2-carboxylic acid | 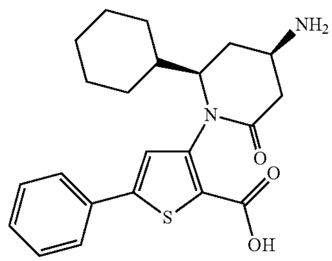 [SMILES: N[C@H]1CC(=O)N(c2cc(-c3ccccc3)sc2C(=O)O)[C@@H](C2CCCCC2)C1] |
| 24 | 3-((2S,4R)-4-Benzoylamino-2-cyclohexyl-6-oxo-piperidin-1-yl)-5-phenyl-thiophene-2-carboxylic acid | 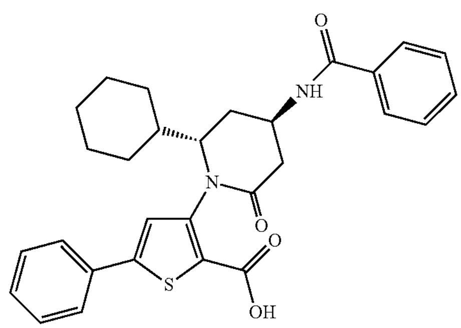 [SMILES: O=C(N[C@H]1CC(=O)N(c2cc(-c3ccccc3)sc2C(=O)O)[C@H](C2CCCCC2)C1)c1ccccc1] |
| 25 | 3-((2R,4R)-4-Benzoylamino-2-cyclohexyl-6-oxo-piperidin-1-yl)-5-phenyl-thiophene-2-carboxylic acid | 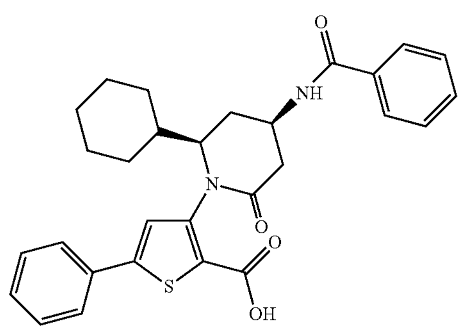 [SMILES: O=C(N[C@H]1CC(=O)N(c2cc(-c3ccccc3)sc2C(=O)O)[C@@H](C2CCCCC2)C1)c1ccccc1] |
| 26 | 3-(2-Cyclohexyl-4-methanesulfonyl-6-oxo-piperazin-1-yl)-5-phenyl-thiophene-2-carboxylic acid | 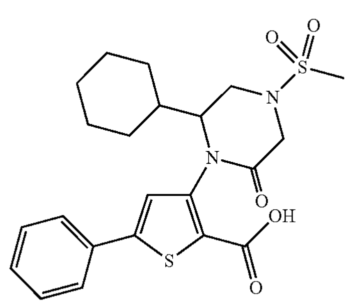 [SMILES: CS(=O)(=O)N1CC(=O)N(c2cc(-c3ccccc3)sc2C(=O)O)C(C2CCCCC2)C1] |

TABLE 1-continued

| Compound number | Name | Structure |
|---|---|---|
| 27 | 3-(2-Cyclohexyl-6-oxo-4-phenylmethanesulfonyl-piperazin-1-yl)-5-phenyl-thiophene-2-carboxylic acid | 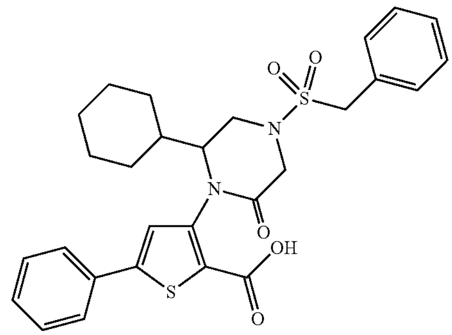 [SMILES: O=C(O)c1sc(-c2ccccc2)cc1N1C(=O)CN(S(=O)(=O)Cc2ccccc2)CC1C1CCCCC1] |
| 28 | 3-((2S,4R)-4-Amino-2-cyclohexyl-6-oxo-piperidin-1-yl)-5-phenyl-thiophene-2-carboxylic acid | 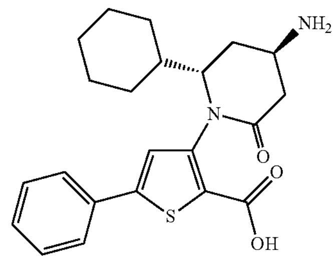 [SMILES: N[C@H]1CC(=O)N(c2cc(-c3ccccc3)sc2C(=O)O)[C@H](C2CCCCC2)C1] |
| 29 | 3-[4-(3-Carboxy-4-methoxy-benzenesulfonyl)-2-cyclohexyl-6-oxo-piperazin-1-yl]-5-phenyl-thiophene-2-carboxylic acid | 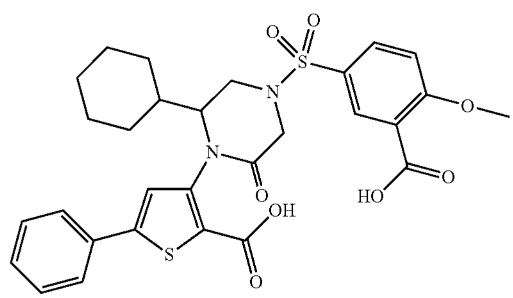 [SMILES: COc1ccc(S(=O)(=O)N2CC(=O)N(c3cc(-c4ccccc4)sc3C(=O)O)C(C3CCCCC3)C2)cc1C(=O)O] |
| 30 | 3-[4-(4-Carboxy-benzenesulfonyl)-2-cyclohexyl-6-oxo-piperazin-1-yl]-5-phenyl-thiophene-2-carboxylic acid | Chiral |
| 31 | 3-[2-Cyclohexyl-6-oxo-4-(pentane-1-sulfonyl)-piperazin-1-yl]-5-phenyl-thiophene-2-carboxylic acid | 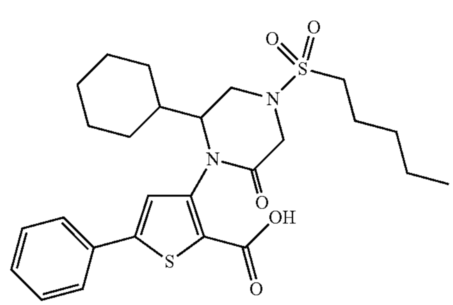 [SMILES: CCCCCS(=O)(=O)N1CC(=O)N(c2cc(-c3ccccc3)sc2C(=O)O)C(C2CCCCC2)C1] |

TABLE 1-continued

| Compound number | Name | Structure |
|---|---|---|
| 32 | 3-[2-Cyclohexyl-4-(3,5-dimethyl-isoxazole-4-sulfonyl)-6-oxo-piperazin-1-yl]-5-phenyl-thiophene-2-carboxylic acid | 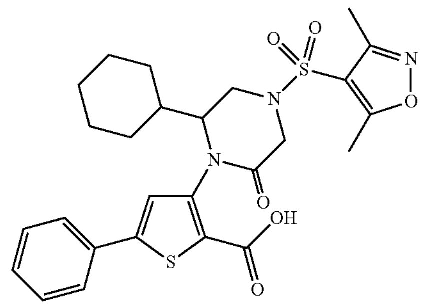 [SMILES: Cc1noc(C)c1S(=O)(=O)N1CC(=O)N(c2cc(-c3ccccc3)sc2C(=O)O)C(C2CCCCC2)C1] |
| 33 | 4-[4-(2-Carboxy-5-phenyl-thiophen-3-yl)-3-cyclohexyl-5-oxo-piperazine-1-sulfonyl]-2,5-dimethyl-furan-3-carboxylic acid | 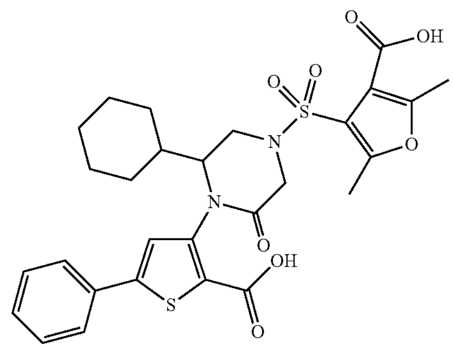 [SMILES: Cc1oc(C)c(S(=O)(=O)N2CC(=O)N(c3cc(-c4ccccc4)sc3C(=O)O)C(C3CCCCC3)C2)c1C(=O)O] |
| 34 | 3-((R)-2-Cyclohexyl-6-oxo-piperidin-1-yl)-5-(3,3-dimethyl-but-1-ynyl)-thiophene-2-carboxylic acid | 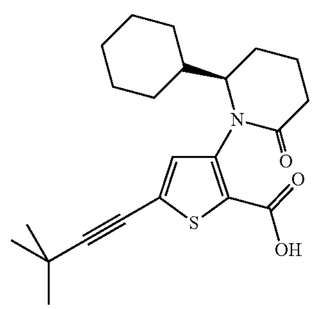 [SMILES: CC(C)(C)C#Cc1cc(N2C(=O)CCC[C@@H]2C2CCCCC2)c(C(=O)O)s1] |
| 35 | 3-((S)-2-Cyclohexyl-6-oxo-piperidin-1-yl)-5-(3,3-dimethyl-but-1-ynyl)-thiophene-2-carboxylic acid | 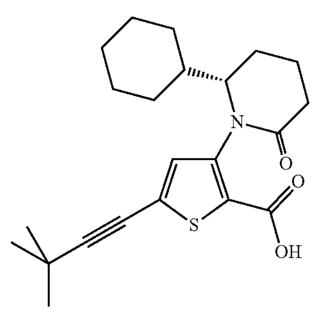 [SMILES: CC(C)(C)C#Cc1cc(N2C(=O)CCC[C@H]2C2CCCCC2)c(C(=O)O)s1] |
| 36 | 3-[2-Cyclohexyl-4-(4-methyl-piperidine-1-sulfonyl)-6-oxo-piperazin-1-yl]-5-phenyl-thiophene-2-carboxylic acid | 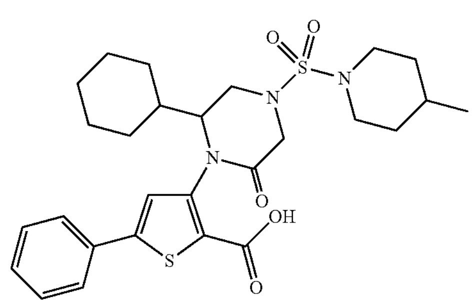 [SMILES: CC1CCN(S(=O)(=O)N2CC(=O)N(c3cc(-c4ccccc4)sc3C(=O)O)C(C3CCCCC3)C2)CC1] |

TABLE 1-continued

| Compound number | Name | Structure |
|---|---|---|
| 37 | 3-[2-Cyclohexyl-6-oxo-4-(propane-2-sulfonyl)-piperazin-1-yl]-5-phenyl-thiophene-2-carboxylic acid | 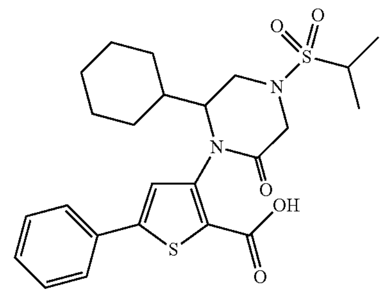 [SMILES: CC(C)S(=O)(=O)N1CC(=O)N(c2cc(-c3ccccc3)sc2C(=O)O)C(C2CCCCC2)C1] |
| 38 | 3-[2-Cyclohexyl-4-(2-methyl-propane-1-sulfonyl)-6-oxo-piperazin-1-yl]-5-phenyl-thiophene-2-carboxylic acid | 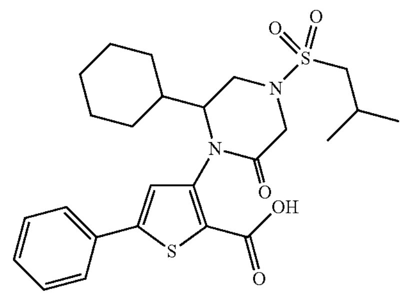 [SMILES: CC(C)CS(=O)(=O)N1CC(=O)N(c2cc(-c3ccccc3)sc2C(=O)O)C(C2CCCCC2)C1] |
| 39 | 3-[2-Cyclohexyl-6-oxo-4-(2-phenyl-ethanesulfonyl)-piperazin-1-yl]-5-phenyl-thiophene-2-carboxylic acid | 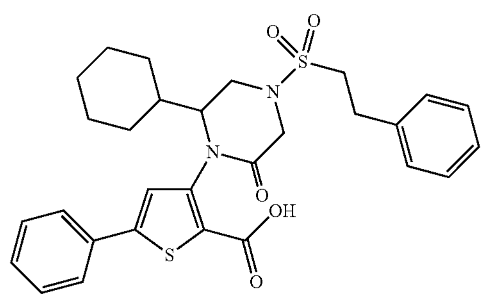 [SMILES: O=C(O)c1sc(-c2ccccc2)cc1N1C(=O)CN(S(=O)(=O)CCc2ccccc2)CC1C1CCCCC1] |
| 40 | 3-[2-Cyclohexyl-4-(2-fluoro-benzenesulfonyl)-6-oxo-piperazin-1-yl]-5-phenyl-thiophene-2-carboxylic acid | Chiral |
| 41 | 3-[4-(2-Carboxy-ethanesulfonyl)-2-cyclohexyl-6-oxo-piperazin-1-yl]-5-phenyl-thiophene-2-carboxylic acid | 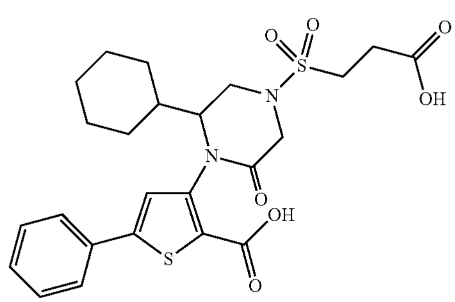 [SMILES: O=C(O)CCS(=O)(=O)N1CC(=O)N(c2cc(-c3ccccc3)sc2C(=O)O)C(C2CCCCC2)C1] |

TABLE 1-continued

| Compound number | Name | Structure |
|---|---|---|
| 42 | 3-(2-Cyclohexyl-4-cyclopentanesulfonyl-6-oxo-piperazin-1-yl)-5-phenyl-thiophene-2-carboxylic acid | 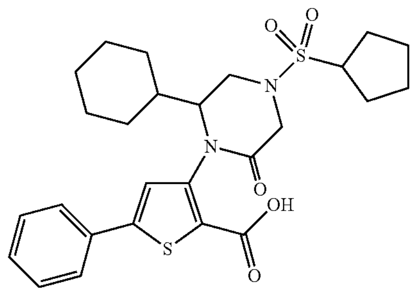 [SMILES: O=C(O)c1sc(-c2ccccc2)cc1N1C(=O)CN(S(=O)(=O)C2CCCC2)CC1C1CCCCC1] |
| 43 | 3-[(2S,4R)-2-Cyclohexyl-6-oxo-4-(toluene-4-sulfonylamino)-piperidin-1-yl]-5-phenyl-thiophene-2-carboxylic acid | 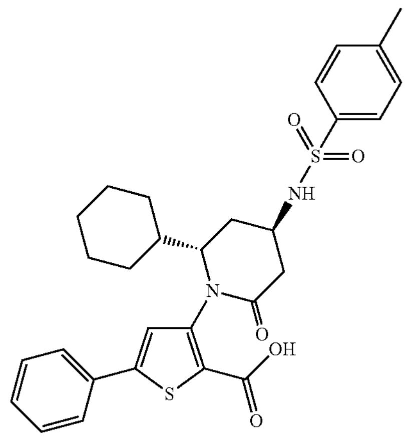 [SMILES: Cc1ccc(S(=O)(=O)N[C@H]2CC(=O)N(c3cc(-c4ccccc4)sc3C(=O)O)[C@H](C3CCCCC3)C2)cc1] |
| 44 | 3-[(2R,4R)-2-Cyclohexyl-6-oxo-4-(toluene-4-sulfonylamino)-piperidin-1-yl]-5-phenyl-thiophene-2-carboxylic acid | 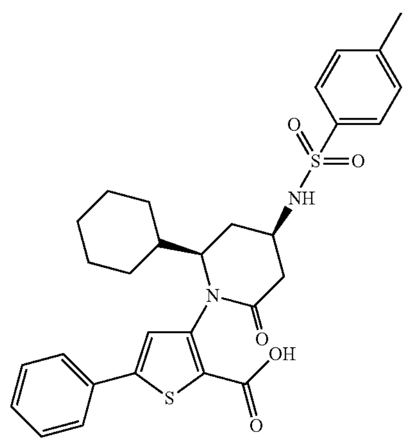 [SMILES: Cc1ccc(S(=O)(=O)N[C@H]2CC(=O)N(c3cc(-c4ccccc4)sc3C(=O)O)[C@@H](C3CCCCC3)C2)cc1] |
| 45 | 3-[4-(Butane-2-sulfonyl)-2-cyclohexyl-6-oxo-piperazin-1-yl]-5-phenyl-thiophene-2-carboxylic acid | 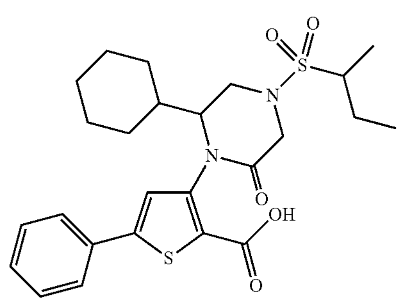 [SMILES: CCC(C)S(=O)(=O)N1CC(=O)N(c2cc(-c3ccccc3)sc2C(=O)O)C(C2CCCCC2)C1] |

TABLE 1-continued

| Compound number | Name | Structure |
|---|---|---|
| 46 | 3-(4-Cyclohexanesulfonyl-2-cyclohexyl-6-oxo-piperazin-1-yl)-5-phenyl-thiophene-2-carboxylic acid | 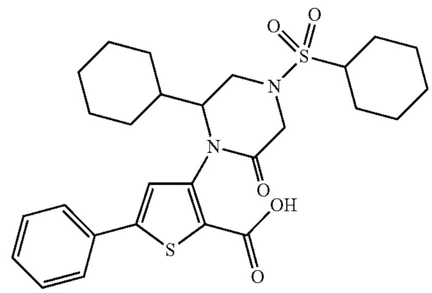 [SMILES: O=C(O)c1sc(-c2ccccc2)cc1N1C(=O)CN(S(=O)(=O)C2CCCCC2)CC1C1CCCCC1] |
| 47 | 3-[4-(2-Amino-ethanesulfonyl)-2-cyclohexyl-6-oxo-piperazin-1-yl]-5-phenyl-thiophene-2-carboxylic acid | 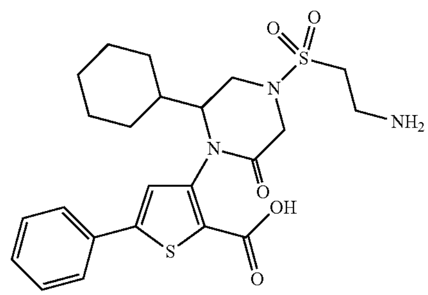 [SMILES: NCCS(=O)(=O)N1CC(=O)N(c2cc(-c3ccccc3)sc2C(=O)O)C(C2CCCCC2)C1] |
| 48 | 3-(2-Cyclohexyl-6-oxo-piperidin-1-yl)-5-(3-fluoro-phenyl)-thiophene-2-carboxylic acid | 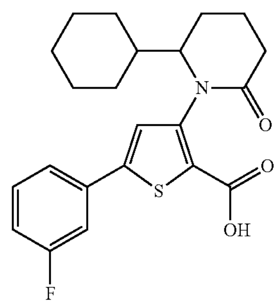 |
| 49 | 3-[2-Cyclohexyl-6-oxo-4-(toluene-3-sulfonyl)-piperazin-1-yl]-5-phenyl-thiophene-2-carboxylic acid | 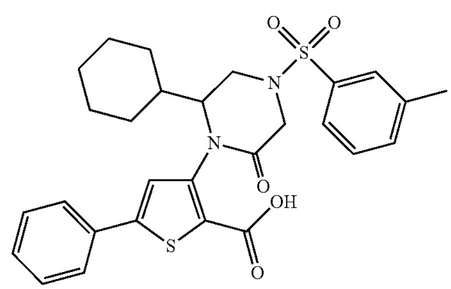 [SMILES: Cc1cccc(S(=O)(=O)N2CC(=O)N(c3cc(-c4ccccc4)sc3C(=O)O)C(C3CCCCC3)C2)c1] |
| 50 | 3-[4-(4-Acetylamino-benzenesulfonyl)-2-cyclohexyl-6-oxo-piperazin-1-yl]-5-phenyl-thiophene-2-carboxylic acid | 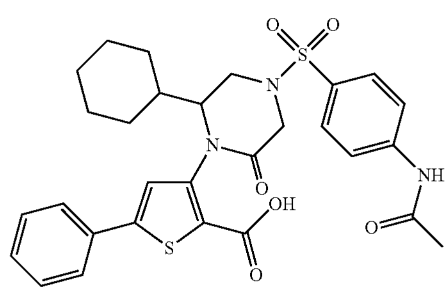 [SMILES: CC(=O)Nc1ccc(S(=O)(=O)N2CC(=O)N(c3cc(-c4ccccc4)sc3C(=O)O)C(C3CCCCC3)C2)cc1] |

TABLE 1-continued

| Compound number | Name | Structure |
|---|---|---|
| 51 | 3-[2-Cyclohexyl-6-oxo-4-(4-phenoxy-benzenesulfonyl)-piperazin-1-yl]-5-phenyl-thiophene-2-carboxylic acid | 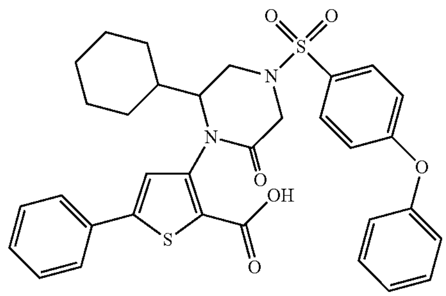 [SMILES: O=C(O)c1sc(-c2ccccc2)cc1N1C(=O)CN(S(=O)(=O)c2ccc(Oc3ccccc3)cc2)CC1C1CCCCC1] |
| 52 | 3-(4-Benzenesulfonyl-2-cyclohexyl-6-oxo-piperazin-1-yl)-5-phenyl-thiophene-2-carboxylic acid | 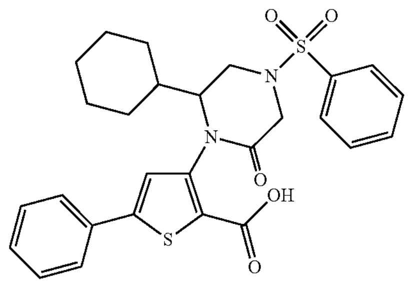 [SMILES: O=C(O)c1sc(-c2ccccc2)cc1N1C(=O)CN(S(=O)(=O)c2ccccc2)CC1C1CCCCC1] |
| 53 | 3-[2-Cyclohexyl-6-oxo-4-(4-trifluoromethoxy-benzenesulfonyl)-piperazin-1-yl]-5-[(Z)-1-eth-(E)-ylidene-but-2-enyl]-thiophene-2-carboxylic acid | 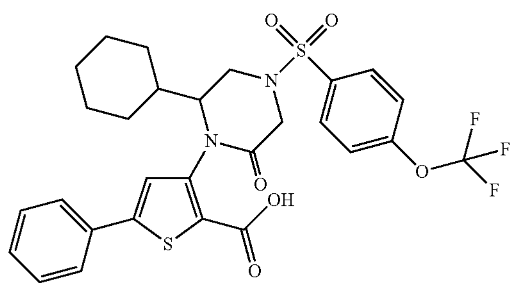 [SMILES: O=C(O)c1sc(-c2ccccc2)cc1N1C(=O)CN(S(=O)(=O)c2ccc(OC(F)(F)F)cc2)CC1C1CCCCC1] |
| 54 | 3-[2-Cyclohexyl-6-oxo-4-(4-trifluoromethyl-benzenesulfonyl)-piperazin-1-yl]-5-phenyl-thiophene-2-carboxylic acid | 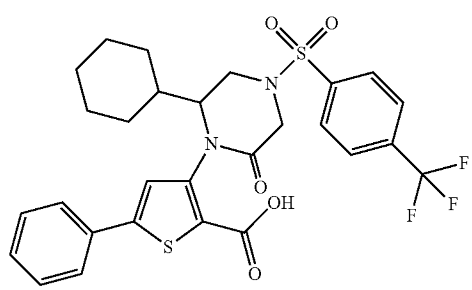 [SMILES: O=C(O)c1sc(-c2ccccc2)cc1N1C(=O)CN(S(=O)(=O)c2ccc(C(F)(F)F)cc2)CC1C1CCCCC1] |
| 55 | 3-[2-Cyclohexyl-4-(4-ethyl-benzenesulfonyl)-6-oxo-piperazin-1-yl]-5-phenyl-thiophene-2-carboxylic acid | 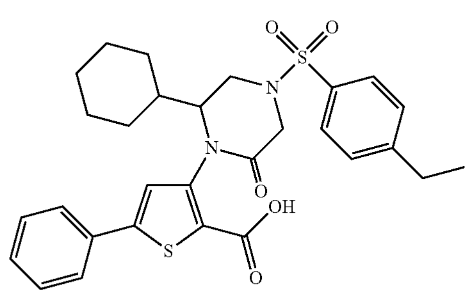 [SMILES: CCc1ccc(S(=O)(=O)N2CC(=O)N(c3cc(-c4ccccc4)sc3C(=O)O)C(C3CCCCC3)C2)cc1] |

TABLE 1-continued

| Compound number | Name | Structure |
|---|---|---|
| 56 | 3-[2-Cyclohexyl-4-(4-ethyl-benzenesulfonyl)-6-oxo-piperazin-1-yl]-5-phenyl-thiophene-2-carboxylic acid | 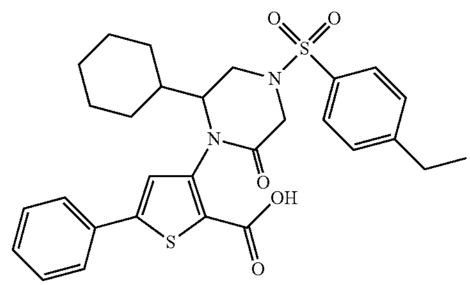 [SMILES: CCc1ccc(S(=O)(=O)N2CC(=O)N(c3cc(-c4ccccc4)sc3C(=O)O)C(C3CCCCC3)C2)cc1] |
| 57 | 3-[2-Cyclohexyl-4-(1-methyl-1H-indole-7-sulfonyl)-6-oxo-piperazin-1-yl]-5-phenyl-thiophene-2-carboxylic acid | 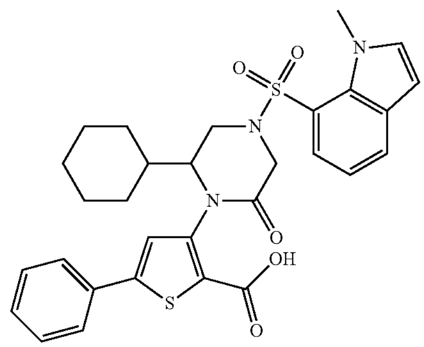 [SMILES: Cn1ccc2cccc(S(=O)(=O)N3CC(=O)N(c4cc(-c5ccccc5)sc4C(=O)O)C(C4CCCCC4)C3)c21] |
| 58 | 3-[2-Cyclohexyl-6-oxo-4-(toluene-2-sulfonyl)-piperazin-1-yl]-5-phenyl-thiophene-2-carboxylic acid | 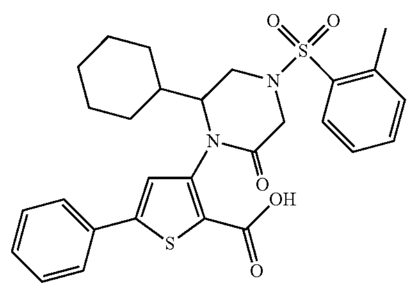 [SMILES: Cc1ccccc1S(=O)(=O)N1CC(=O)N(c2cc(-c3ccccc3)sc2C(=O)O)C(C2CCCCC2)C1] |
| 59 | 3-[2-Cyclohexyl-6-oxo-4-(3-trifluoromethoxy-benzenesulfonyl)-piperazin-1-yl]-5-[(E)-((Z)-1-propenyl)-buta-1,3-dienyl]-thiophene-2-carboxylic acid | 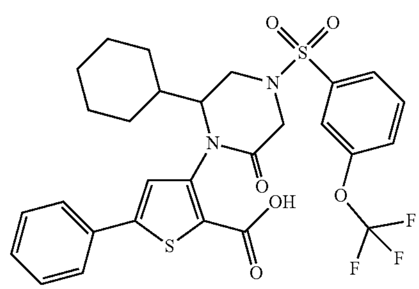 [SMILES: O=C(O)c1sc(-c2ccccc2)cc1N1C(=O)CN(S(=O)(=O)c2cccc(OC(F)(F)F)c2)CC1C1CCCCC1] |
| 60 | 3-[4-(Biphenyl-4-sulfonyl)-2-cyclohexyl-6-oxo-piperazin-1-yl]-5-phenyl-thiophene-2-carboxylic acid | 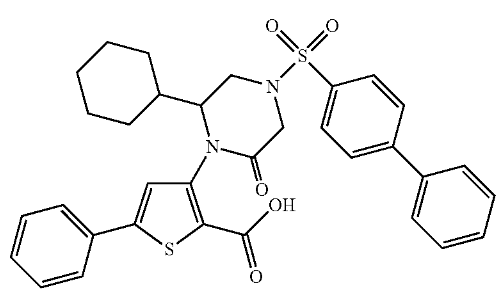 [SMILES: O=C(O)c1sc(-c2ccccc2)cc1N1C(=O)CN(S(=O)(=O)c2ccc(-c3ccccc3)cc2)CC1C1CCCCC1] |

TABLE 1-continued

| Compound number | Name | Structure |
|---|---|---|
| 61 | 3-[2-Cyclohexyl-4-(1-methyl-1H-indole-5-sulfonyl)-6-oxo-piperazin-1-yl)-5-phenyl-thiophene-2-carboxylic acid | 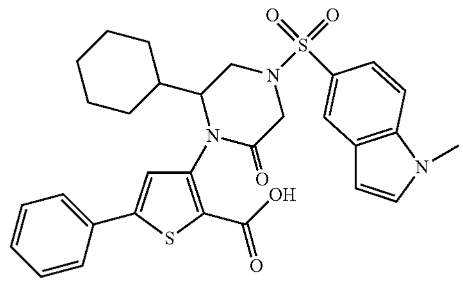 [SMILES: Cn1ccc2cc(S(=O)(=O)N3CC(=O)N(c4cc(-c5ccccc5)sc4C(=O)O)C(C4CCCCC4)C3)ccc21] |
| 62 | 3-[2-Cyclohexyl-4-(1-methyl-1H-pyrazole-3-sulfonyl)-6-oxo-piperazin-1-yl]-5-phenyl-thiophene-2-carboxylic acid | 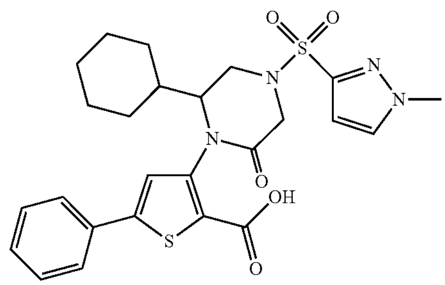 [SMILES: Cn1ccc(S(=O)(=O)N2CC(=O)N(c3cc(-c4ccccc4)sc3C(=O)O)C(C3CCCCC3)C2)n1] |
| 63 | 3-{2-Cyclohexyl-4-[3-(2-methyl-pyrimidin-4-yl)-benzenesulfonyl]-6-oxo-piperazin-1-yl}-5-phenyl-thiophene-2-carboxylic acid | 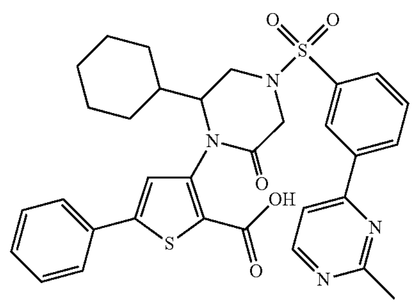 [SMILES: Cc1nccc(-c2cccc(S(=O)(=O)N3CC(=O)N(c4cc(-c5ccccc5)sc4C(=O)O)C(C4CCCCC4)C3)c2)n1] |
| 64 | 3-[2-Cyclohexyl-4-(1-methyl-1H-indole-4-sulfonyl)-6-oxo-piperazin-1-yl]-5-phenyl-thiophene-2-carboxylic acid | 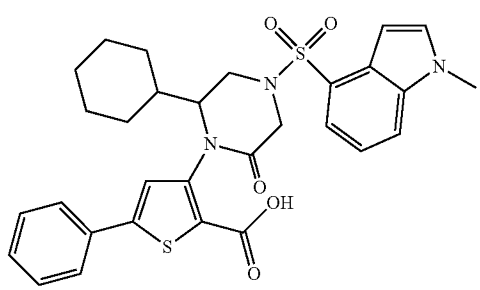 [SMILES: Cn1ccc2c(S(=O)(=O)N3CC(=O)N(c4cc(-c5ccccc5)sc4C(=O)O)C(C4CCCCC4)C3)cccc21] |
| 65 | 3-[4-(Biphenyl-3-sulfonyl)-2-cyclohexyl-6-oxo-piperazin-1-yl]-5-phenyl-thiophene-2-carboxylic acid | 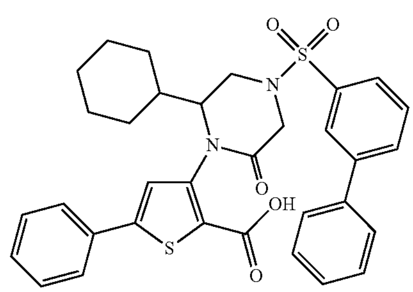 [SMILES: O=C(O)c1sc(-c2ccccc2)cc1N1C(=O)CN(S(=O)(=O)c2cccc(-c3ccccc3)c2)CC1C1CCCCC1] |

TABLE 1-continued

| Compound number | Name | Structure |
|---|---|---|
| 66 | 3-[2-Cyclohexyl-4-(4-fluoro-3-trifluoromethyl-benzenesulfonyl)-6-oxo-piperazin-1-yl]-5-phenyl-thiophene-2-carboxylic acid | 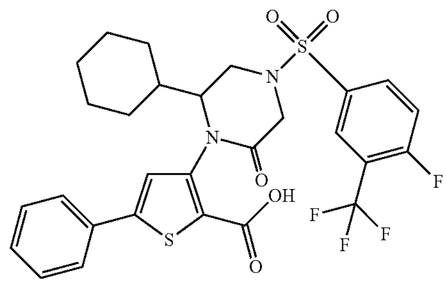 [SMILES: O=C(O)c1sc(-c2ccccc2)cc1N1C(=O)CN(S(=O)(=O)c2ccc(F)c(C(F)(F)F)c2)CC1C1CCCCC1] |
| 67 | 3-(2-Cyclohexyl-6-oxo-piperidin-1-yl)-5-(2-fluoro-phenyl)-thiophene-2-carboxylic acid | 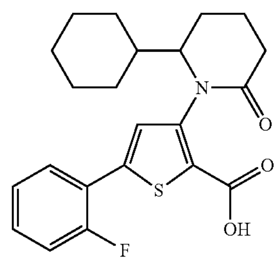 |
| 68 | 3-[2-Cyclohexyl-6-oxo-4-(2-trifluoromethyl-benzenesulfonyl)-piperazin-1-yl]-5-phenyl-thiophene-2-carboxylic acid | 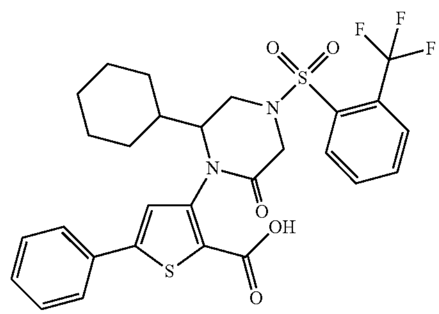 [SMILES: O=C(O)c1sc(-c2ccccc2)cc1N1C(=O)CN(S(=O)(=O)c2ccccc2C(F)(F)F)CC1C1CCCCC1] |
| 69 | 3-[2-Cyclohexyl-4-(6-diethylamino-pyridine-3-sulfonyl)-6-oxo-piperazin-1-yl]-5-phenyl-thiophene-2-carboxylic acid | 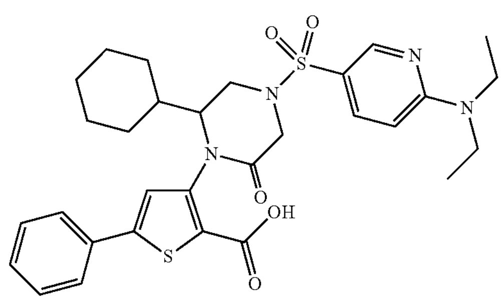 [SMILES: CCN(CC)c1ccc(S(=O)(=O)N2CC(=O)N(c3cc(-c4ccccc4)sc3C(=O)O)C(C3CCCCC3)C2)cn1] |
| 70 | 3-(2-Cyclohexyl-6-oxo-piperidin-1-yl)-5-(4-fluoro-phenyl)-thiophene-2-carboxylic acid | 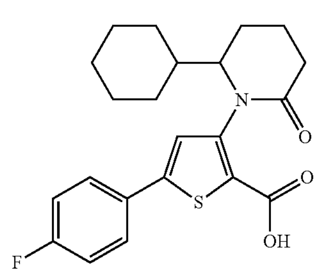 |

TABLE 1-continued

| Compound number | Name | Structure |
|---|---|---|
| 71 | 3-(2-Cyclohexyl-6-oxo-piperidin-1-yl)-5-p-tolyl-thiophene-2-carboxylic acid | 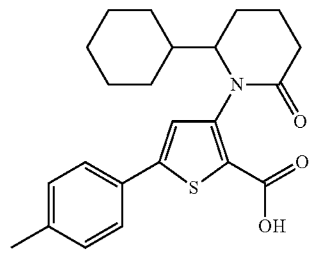 |
| 72 | 3-(2-Cyclohexyl-6-oxo-piperidin-1-yl)-5-(4-ethyl-phenyl)-thiophene-2-carboxylic acid | 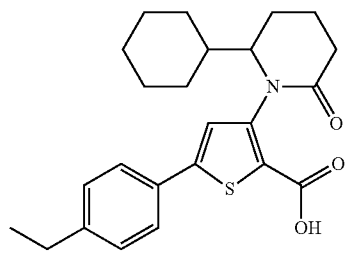 |
| 73 | 5-(4-Chloro-phenyl)-3-(2-cyclohexyl-6-oxo-piperidin-1-yl)-thiophene-2-carboxylic acid | 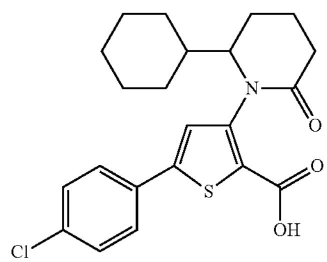 |
| 74 | 3-[4-(6-Azetidin-1-yl-pyridine-3-sulfonyl)-2-cyclohexyl-6-oxo-piperazin-1-yl]-5-phenyl-thiophene-2-carboxylic acid | 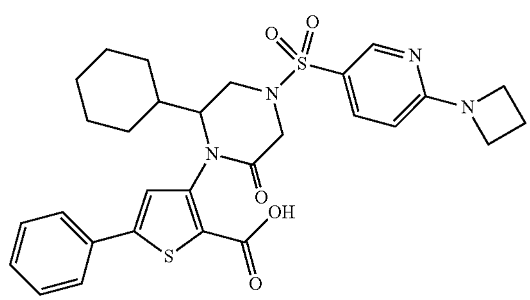 [SMILES: O=C(O)c1sc(-c2ccccc2)cc1N1C(=O)CN(S(=O)(=O)c2ccc(N3CCC3)nc2)CC1C1CCCCC1] |
| 75 | 3-[2-Cyclohexyl-4-(6-cyclohexylamino-pyridine-3-sulfonyl)-6-oxo-piperazin-1-yl]-5-phenyl-thiophene-2-carboxylic acid | 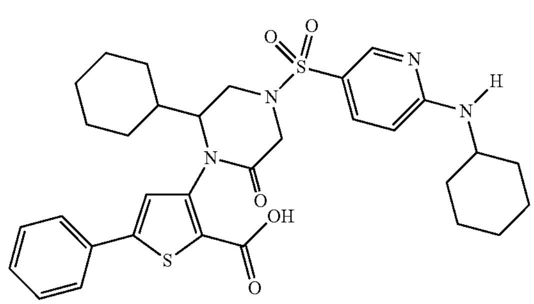 [SMILES: O=C(O)c1sc(-c2ccccc2)cc1N1C(=O)CN(S(=O)(=O)c2ccc(NC3CCCCC3)nc2)CC1C1CCCCC1] |

TABLE 1-continued

| Compound number | Name | Structure |
|---|---|---|
| 76 | 3-[2-Cyclohexyl-6-oxo-4-(6-pyrrolidin-1-yl-pyridine-3-sulfonyl)-piperazin-1-yl]-5-phenyl-thiophene-2-carboxylic acid | 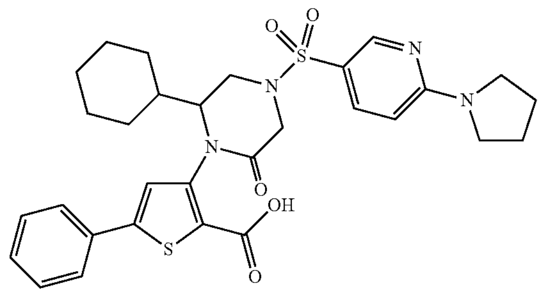 [SMILES: O=C(O)c1sc(-c2ccccc2)cc1N1C(=O)CN(S(=O)(=O)c2ccc(N3CCCC3)nc2)CC1C1CCCCC1] |
| 77 | 3-[2-Cyclohexyl-4-(6-dipropylamino-pyridine-3-sulfonyl)-6-oxo-piperazin-1-yl]-5-phenyl-thiophene-2-carboxylic acid | 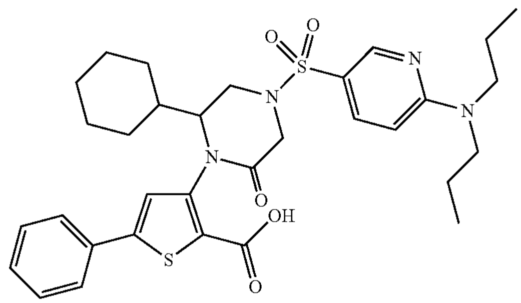 [SMILES: CCCN(CCC)c1ccc(S(=O)(=O)N2CC(=O)N(c3cc(-c4ccccc4)sc3C(=O)O)C(C3CCCCC3)C2)cn1] |
| 78 | 3-{2-Cyclohexyl-4-[6-(2-methoxy-ethylamino)-pyridine-3-sulfonyl]-6-oxo-piperazin-1-yl}-5-phenyl-thiophene-2-carboxylic acid | 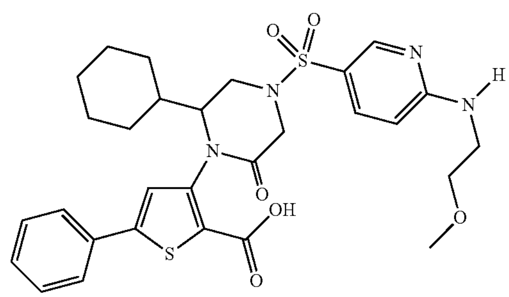 [SMILES: COCCNc1ccc(S(=O)(=O)N2CC(=O)N(c3cc(-c4ccccc4)sc3C(=O)O)C(C3CCCCC3)C2)cn1] |
| 79 | 3-[2-Cyclohexyl-6-oxo-4-(6-thiomorpholin-4-yl-pyridine-3-sulfonyl)-piperazin-1-yl]-5-phenyl-thiophene-2-carboxylic acid | 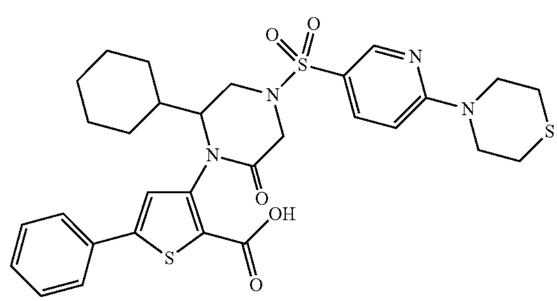 [SMILES: O=C(O)c1sc(-c2ccccc2)cc1N1C(=O)CN(S(=O)(=O)c2ccc(N3CCSCC3)nc2)CC1C1CCCCC1] |
| 80 | 3-(4-{6-[Bis-(2-methoxy-ethyl)-amino]-pyridine-3-sulfonyl}-2-cyclohexyl-6-oxo-piperazin-1-yl)-5-phenyl-thiophene-2-carboxylic acid | 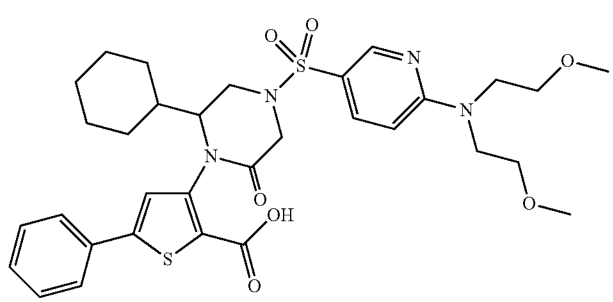 [SMILES: COCCN(CCOC)c1ccc(S(=O)(=O)N2CC(=O)N(c3cc(-c4ccccc4)sc3C(=O)O)C(C3CCCCC3)C2)cn1] |

TABLE 1-continued

| Compound number | Name | Structure |
|---|---|---|
| 81 | 3-{2-Cyclohexyl-4-[6-(2-dimethylamino-ethylamino)-pyridine-3-sulfonyl]-6-oxo-piperazin-1-yl}-5-phenyl-thiophene-2-carboxylic acid | 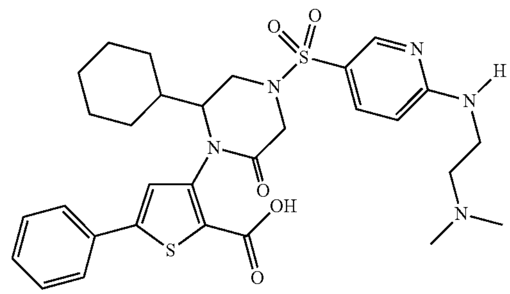 [SMILES: CN(C)CCNc1ccc(S(=O)(=O)N2CC(=O)N(c3cc(-c4ccccc4)sc3C(=O)O)C(C3CCCCC3)C2)cn1] |
| 82 | 3-[2-Cyclohexyl-4-(6-cyclopentylamino-pyridine-3-sulfonyl)-6-oxo-piperazin-1-yl]-5-phenyl-thiophene-2-carboxylic acid | 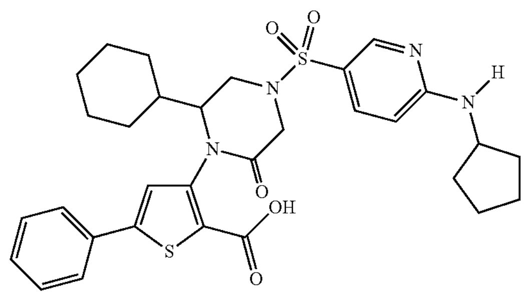 [SMILES: O=C(O)c1sc(-c2ccccc2)cc1N1C(=O)CN(S(=O)(=O)c2ccc(NC3CCCC3)nc2)CC1C1CCCCC1] |
| 83 | 3-(4-{6-[Bis-(2-hydroxy-ethyl)-amino]-pyridine-3-sulfonyl}-2-cyclohexyl-6-oxo-piperazin-1-yl)-5-phenyl-thiophene-2-carboxylic acid | 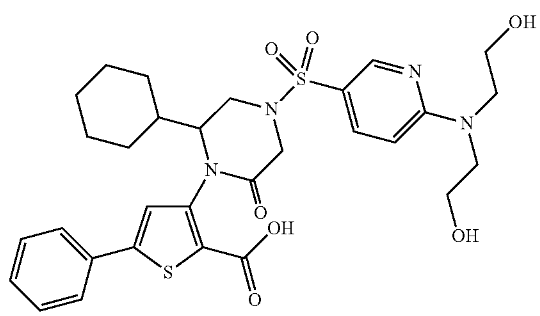 [SMILES: O=C(O)c1sc(-c2ccccc2)cc1N1C(=O)CN(S(=O)(=O)c2ccc(N(CCO)CCO)nc2)CC1C1CCCCC1] |
| 84 | 3-[2-Cyclohexyl-6-oxo-4-(3,4,5,6-tetrahydro-2H-[1,2']bipyridinyl-5'-sulfonyl)-piperazin-1-yl]-5-phenyl-thiophene-2-carboxylic acid | 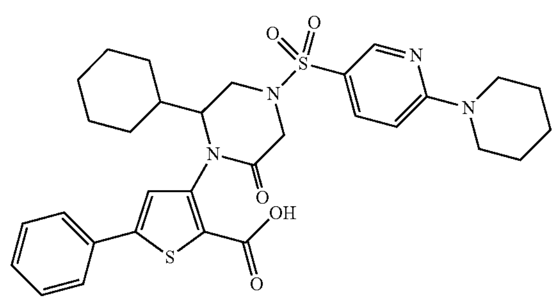 [SMILES: O=C(O)c1sc(-c2ccccc2)cc1N1C(=O)CN(S(=O)(=O)c2ccc(N3CCCCC3)nc2)CC1C1CCCCC1] |
| 85 | 3-[2-Cyclohexyl-4-(6-isopropylamino-pyridine-3-sulfonyl)-6-oxo-piperazin-1-yl]-5-phenyl-thiophene-2-carboxylic acid | 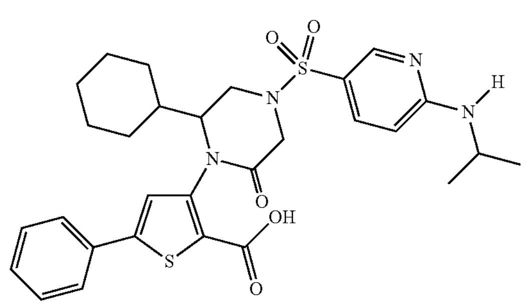 [SMILES: CC(C)Nc1ccc(S(=O)(=O)N2CC(=O)N(c3cc(-c4ccccc4)sc3C(=O)O)C(C3CCCCC3)C2)cn1] |

TABLE 1-continued

| Compound number | Name | Structure |
|---|---|---|
| 86 | 3-{2-Cyclohexyl-4-[6-(2-hydroxy-ethylamino)-pyridine-3-sulfonyl]-6-oxo-piperazin-1-yl}-5-phenyl-thiophene-2-carboxylic acid | 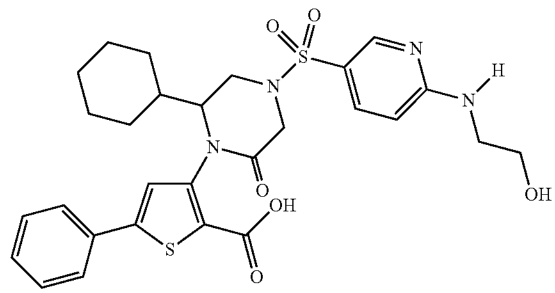 [SMILES: O=C(O)c1sc(-c2ccccc2)cc1N1C(=O)CN(S(=O)(=O)c2ccc(NCCO)nc2)CC1C1CCCCC1] |
| 87 | 3-{2-Cyclohexyl-4-[6-(2,6-dimethyl-morpholin-4-yl)-pyridine-3-sulfonyl]-6-oxo-piperazin-1-yl}-5-phenyl-thiophene-2-carboxylic acid | 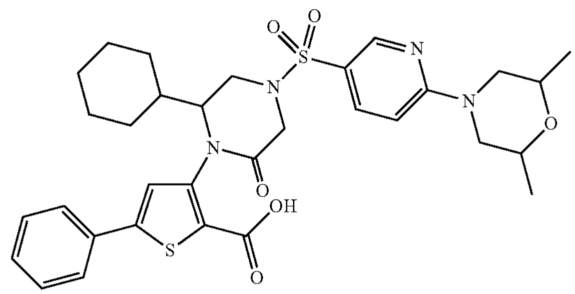 [SMILES: CC1CN(c2ccc(S(=O)(=O)N3CC(=O)N(c4cc(-c5ccccc5)sc4C(=O)O)C(C4CCCCC4)C3)cn2)CC(C)O1] |
| 88 | 3-[2-Cyclohexyl-6-oxo-4-(6-piperazin-1-yl-pyridine-3-sulfonyl)-piperazin-1-yl]-5-phenyl-thiophene-2-carboxylic acid | 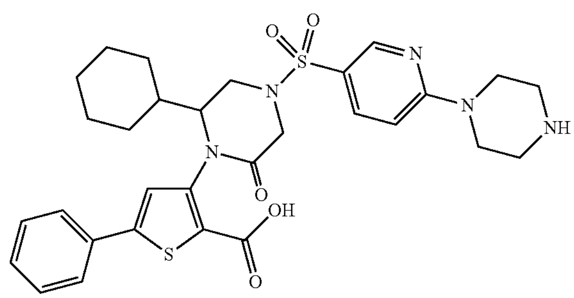 [SMILES: O=C(O)c1sc(-c2ccccc2)cc1N1C(=O)CN(S(=O)(=O)c2ccc(N3CCNCC3)nc2)CC1C1CCCCC1] |
| 89 | 3-{4-[6-(4-Acetyl-piperazin-1-yl)-pyridine-3-sulfonyl]-2-cyclohexyl-6-oxo-piperazin-1-yl}-5-phenyl-thiophene-2-carboxylic acid | 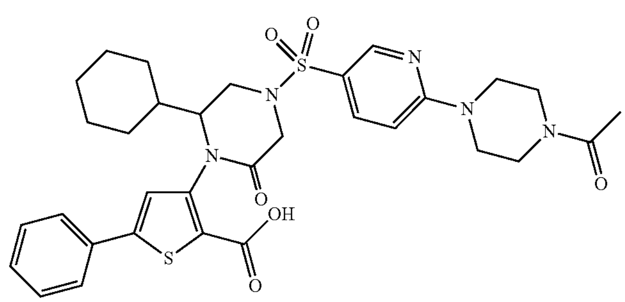 [SMILES: CC(=O)N1CCN(c2ccc(S(=O)(=O)N3CC(=O)N(c4cc(-c5ccccc5)sc4C(=O)O)C(C4CCCCC4)C3)cn2)CC1] |
| 90 | 3-{2-Cyclohexyl-6-oxo-4-[6-(tetrahydro-pyran-4-ylamino)-pyridine-3-sulfonyl]-piperazin-1-yl}-5-phenyl-thiophene-2-carboxylic acid | 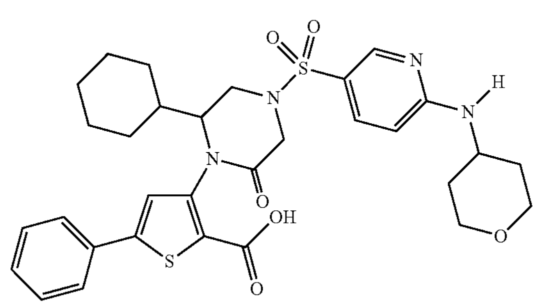 |

TABLE 1-continued

| Compound number | Name | Structure |
|---|---|---|
| 91 | 3-{2-Cyclohexyl-4-[6-(cyclohexyl-methyl-amino)-pyridine-3-sulfonyl]-6-oxo-piperazin-1-yl}-5-phenyl-thiophene-2-carboxylic acid | 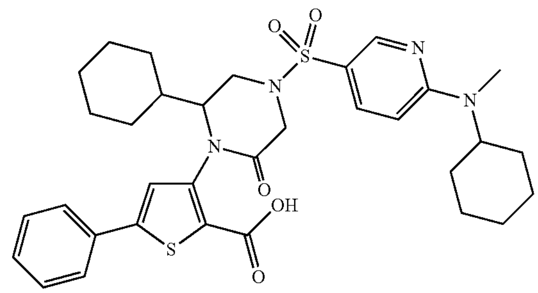 [SMILES: CN(c1ccc(S(=O)(=O)N2CC(=O)N(c3cc(-c4ccccc4)sc3C(=O)O)C(C3CCCCC3)C2)cn1)C1CCCCC1] |
| 92 | 3-{2-Cyclohexyl-4-[6-(2,5-dimethyl-pyrrolidin-1-yl)-pyridine-3-sulfonyl]-6-oxo-piperazin-1-yl}-5-phenyl-thiophene-2-carboxylic acid | 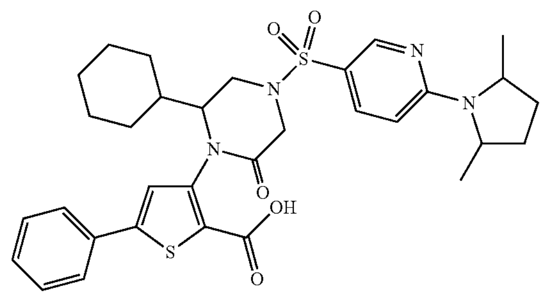 [SMILES: CC1CCC(C)N1c1ccc(S(=O)(=O)N2CC(=O)N(c3cc(-c4ccccc4)sc3C(=O)O)C(C3CCCCC3)C2)cn1] |
| 93 | 3-[2-Cyclohexyl-4-(4-hydroxy-3,4,5,6-tetrahydro-2H-[1,2']bipyridinyl-5'-sulfonyl)-6-oxo-piperazin-1-yl]-5-phenyl-thiophene-2-carboxylic acid | 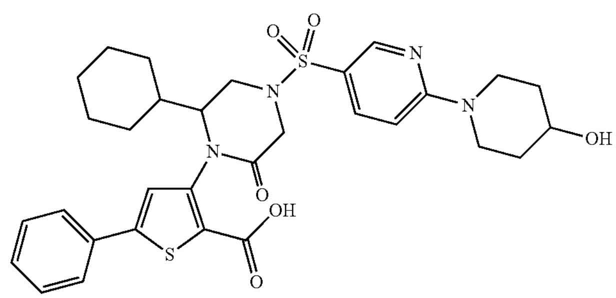 [SMILES: O=C(O)c1sc(-c2ccccc2)cc1N1C(=O)CN(S(=O)(=O)c2ccc(N3CCC(O)CC3)nc2)CC1C1CCCCC1] |
| 94 | 3-[2-Cyclohexyl-4-(4-methoxy-3,4,5,6-tetrahydro-2H-[1,2']bipyridinyl-5'-sulfonyl)-6-oxo-piperazin-1-yl]-5-phenyl-thiophene-2-carboxylic acid | 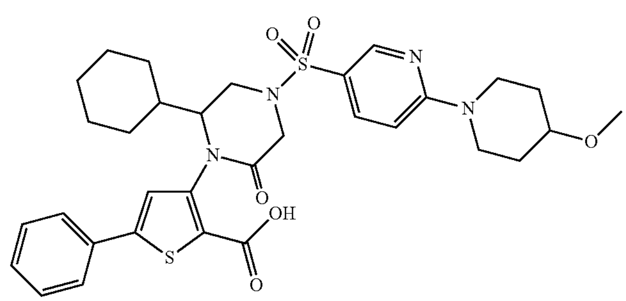 [SMILES: COC1CCN(c2ccc(S(=O)(=O)N3CC(=O)N(c4cc(-c5ccccc5)sc4C(=O)O)C(C4CCCCC4)C3)cn2)CC1] |
| 95 | 3-[2-Cyclohexyl-4-(4,4-difluoro-3,4,5,6-tetrahydro-2H-[1,2']bipyridinyl-5'-sulfonyl)-6-oxo-piperazin-1-yl]-5-phenyl-thiophene-2-carboxylic acid | 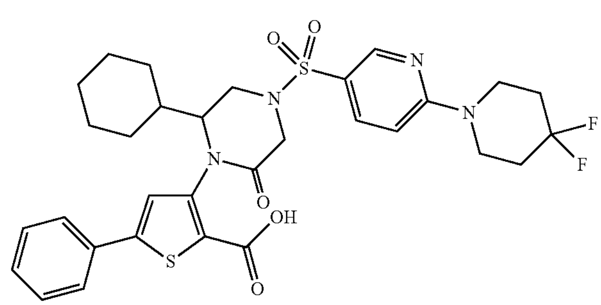 [SMILES: O=C(O)c1sc(-c2ccccc2)cc1N1C(=O)CN(S(=O)(=O)c2ccc(N3CCC(F)(F)CC3)nc2)CC1C1CCCCC1] |

TABLE 1-continued

| Compound number | Name | Structure |
|---|---|---|
| 96 | 3-[2-Cyclohexyl-4-(4-methyl-3,4,5,6-tetrahydro-2H-[1,2']bipyridinyl-5'-sulfonyl)-6-oxo-piperazin-1-yl]-5-phenyl-thiophene-2-carboxylic acid | 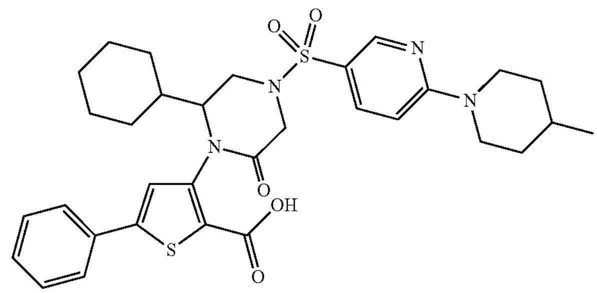 [SMILES: CC1CCN(c2ccc(S(=O)(=O)N3CC(=O)N(c4cc(-c5ccccc5)sc4C(=O)O)C(C4CCCCC4)C3)cn2)CC1] |
| 97 | 3-[(R)-4-(3-Cyano-benzenesulfonyl)-2-cyclohexyl-6-oxo-piperazin-1-yl]-5-phenyl-thiophene-2-carboxylic acid | 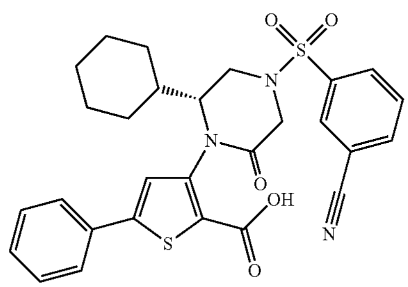 [SMILES: N#Cc1cccc(S(=O)(=O)N2CC(=O)N(c3cc(-c4ccccc4)sc3C(=O)O)[C@H](C3CCCCC3)C2)c1] |
| 98 | 3-[2-Cyclohexyl-4-(4-methylcarbamoyl-benzenesulfonyl)-6-oxo-piperazin-1-yl]-5-phenyl-thiophene-2-carboxylic acid | 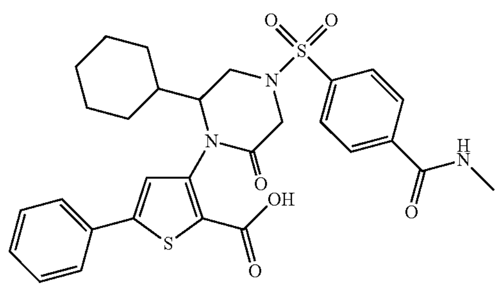 [SMILES: CNC(=O)c1ccc(S(=O)(=O)N2CC(=O)N(c3cc(-c4ccccc4)sc3C(=O)O)C(C3CCCCC3)C2)cc1] |
| 99 | 3-[2-Cyclohexyl-4-(4-methyl-3,4-dihydro-2H-pyrido[3,2-b][1,4]oxazine-7-sulfonyl)-6-oxo-piperazin-1-yl]-5-phenyl-thiophene-2-carboxylic acid | 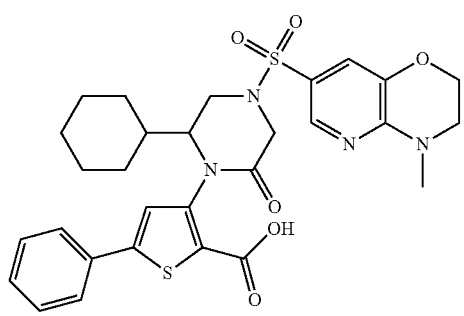 [SMILES: CN1CCOc2cc(S(=O)(=O)N3CC(=O)N(c4cc(-c5ccccc5)sc4C(=O)O)C(C4CCCCC4)C3)cnc21] |
| 100 | 3-[2-Cyclohexyl-4-(4-isopropyl-benzenesulfonyl)-6-oxo-piperazin-1-yl]-5-phenyl-thiophene-2-carboxylic acid | 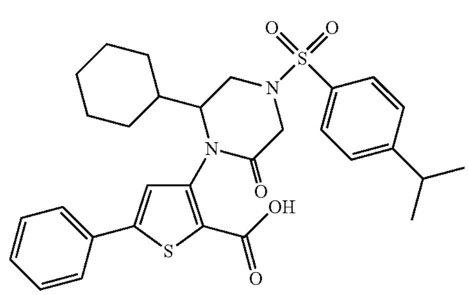 [SMILES: CC(C)c1ccc(S(=O)(=O)N2CC(=O)N(c3cc(-c4ccccc4)sc3C(=O)O)C(C3CCCCC3)C2)cc1] |

TABLE 1-continued

| Compound number | Name | Structure |
|---|---|---|
| 101 | 3-[2-Cyclohexyl-6-oxo-4-(4-pyrazol-1-yl-benzenesulfonyl)-piperazin-1-yl]-5-phenyl-thiophene-2-carboxylic acid | 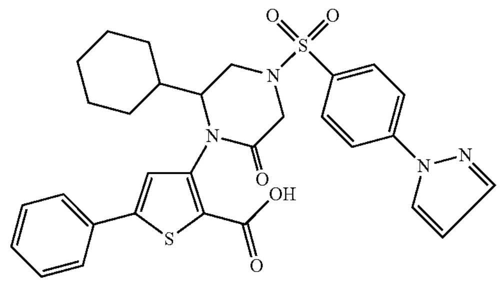 [SMILES: O=C(O)c1sc(-c2ccccc2)cc1N1C(=O)CN(S(=O)(=O)c2ccc(-n3cccn3)cc2)CC1C1CCCCC1] |
| 102 | 3-[2-Cyclohexyl-4-(3,4-dimethoxy-benzenesulfonyl)-6-oxo-piperazin-1-yl]-5-phenyl-thiophene-2-carboxylic acid | 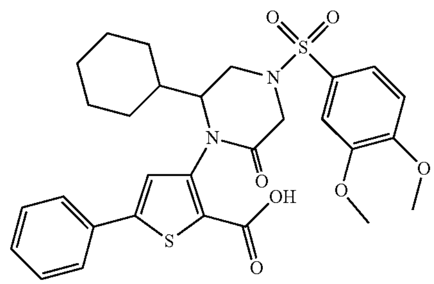 [SMILES: COc1ccc(S(=O)(=O)N2CC(=O)N(c3cc(-c4ccccc4)sc3C(=O)O)C(C3CCCCC3)C2)cc1OC] |
| 103 | 3-[2-Cyclohexyl-4-(4-methoxy-benzenesulfonyl)-6-oxo-piperazin-1-yl]-5-phenyl-thiophene-2-carboxylic acid | 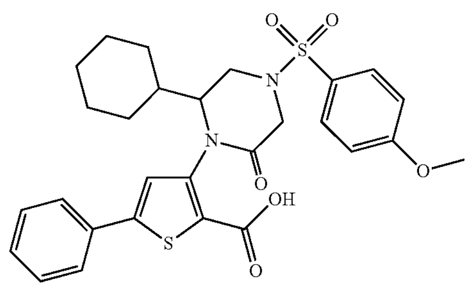 [SMILES: COc1ccc(S(=O)(=O)N2CC(=O)N(c3cc(-c4ccccc4)sc3C(=O)O)C(C3CCCCC3)C2)cc1] |
| 104 | 3-[2-Cyclohexyl-4-(3-fluoro-benzenesulfonyl)-6-oxo-piperazin-1-yl]-5-phenyl-thiophene-2-carboxylic acid | 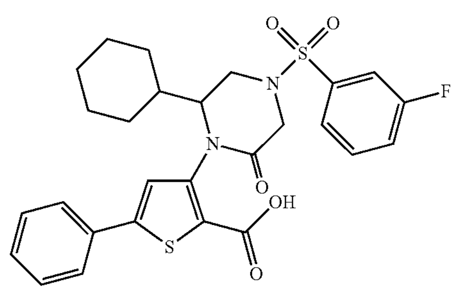 [SMILES: O=C(O)c1sc(-c2ccccc2)cc1N1C(=O)CN(S(=O)(=O)c2cccc(F)c2)CC1C1CCCCC1] |
| 105 | 3-[4-(4-tert-Butyl-benzenesulfonyl)-2-cyclohexyl-6-oxo-piperazin-1-yl]-5-phenyl-thiophene-2-carboxylic acid | 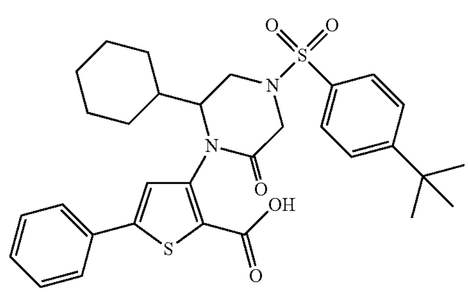 [SMILES: CC(C)(C)c1ccc(S(=O)(=O)N2CC(=O)N(c3cc(-c4ccccc4)sc3C(=O)O)C(C3CCCCC3)C2)cc1] |

TABLE 1-continued

| Compound number | Name | Structure |
|---|---|---|
| 106 | 3-[2-Cyclohexyl-4-(4-difluoromethoxy-benzenesulfonyl)-6-oxo-piperazin-1-yl]-5-phenyl-thiophene-2-carboxylic acid | 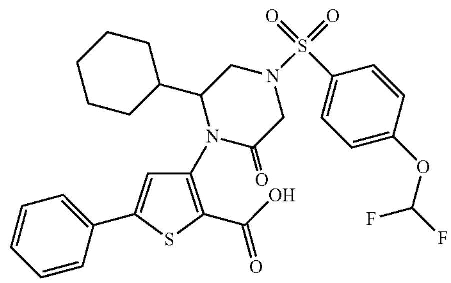 [SMILES: O=C(O)c1sc(-c2ccccc2)cc1N1C(=O)CN(S(=O)(=O)c2ccc(OC(F)F)cc2)CC1C1CCCCC1] |
| 107 | 3-[(R)-2-Cyclohexyl-4-(3-methoxy-benzenesulfonyl)-6-oxo-piperazin-1-yl]-5-phenyl-thiophene-2-carboxylic acid | 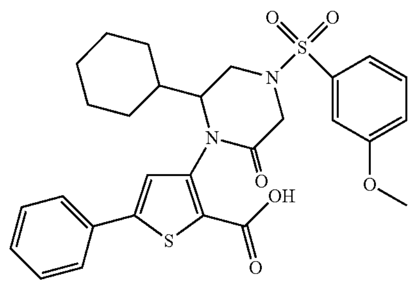 [SMILES: COc1cccc(S(=O)(=O)N2CC(=O)N(c3cc(-c4ccccc4)sc3C(=O)O)C(C3CCCCC3)C2)c1] |
| 108 | 3-[2-Cyclohexyl-6-oxo-4-(pyridine-3-sulfonyl)-piperazin-1-yl]-5-phenyl-thiophene-2-carboxylic acid | 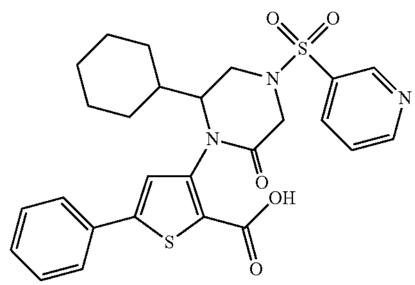 [SMILES: O=C(O)c1sc(-c2ccccc2)cc1N1C(=O)CN(S(=O)(=O)c2cccnc2)CC1C1CCCCC1] |
| 109 | 3-[2-Cyclohexyl-4-(4-fluoro-benzenesulfonyl)-6-oxo-piperazin-1-yl]-5-phenyl-thiophene-2-carboxylic acid | 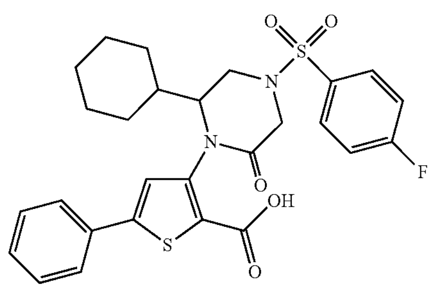 [SMILES: O=C(O)c1sc(-c2ccccc2)cc1N1C(=O)CN(S(=O)(=O)c2ccc(F)cc2)CC1C1CCCCC1] |
| 110 | 3-[2-Cyclohexyl-4-(naphthalene-1-sulfonyl)-6-oxo-piperazin-1-yl]-5-phenyl-thiophene-2-carboxylic acid | 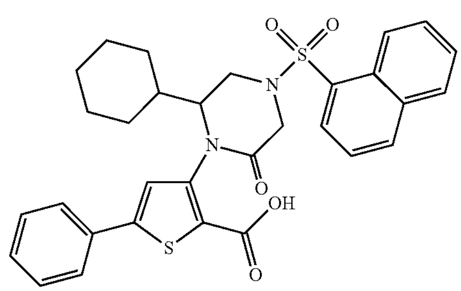 [SMILES: O=C(O)c1sc(-c2ccccc2)cc1N1C(=O)CN(S(=O)(=O)c2cccc3ccccc23)CC1C1CCCCC1] |

TABLE 1-continued

| Compound number | Name | Structure |
|---|---|---|
| 111 | 3-[2-Cyclohexyl-4-(2,3-dichloro-benzenesulfonyl)-6-oxo-piperazin-1-yl]-5-phenyl-thiophene-2-carboxylic acid | 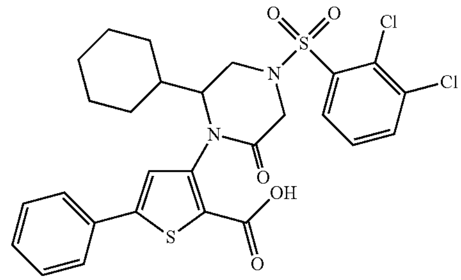 [SMILES: O=C(O)c1sc(-c2ccccc2)cc1N1C(=O)CN(S(=O)(=O)c2cccc(Cl)c2Cl)CC1C1CCCCC1] |
| 112 | 4-[4-(2-Carboxy-5-phenyl-thiophen-3-yl)-3-cyclohexyl-5-oxo-piperazine-1-sulfonyl]-piperidine-1-carboxylic acid benzyl ester | 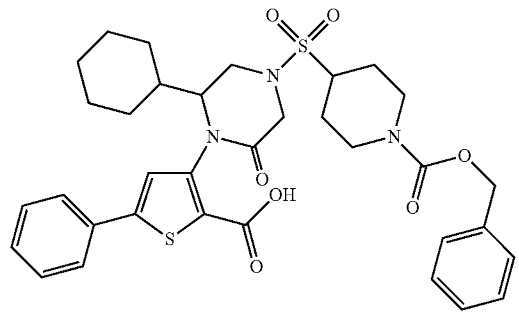 [SMILES: O=C(O)c1sc(-c2ccccc2)cc1N1C(=O)CN(S(=O)(=O)C2CCN(C(=O)OCc3ccccc3)CC2)CC1C1CCCCC1] |
| 113 | 5-(4-tert-Butyl-phenyl)-3-(2-cyclohexyl-6-oxo-piperidin-1-yl)-thiophene-2-carboxylic acid | 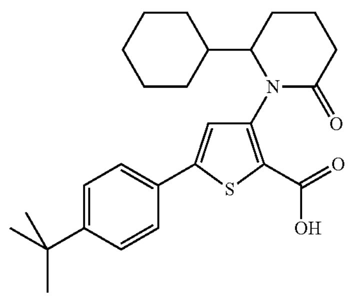 [SMILES: CC(C)(C)c1ccc(-c2cc(N3C(=O)CCCC3C3CCCCC3)c(C(=O)O)s2)cc1] |
| 114 | 3-(2-Cyclohexyl-6-oxo-piperidin-1-yl)-5-(4-methoxy-phenyl)-thiophene-2-carboxylic acid | 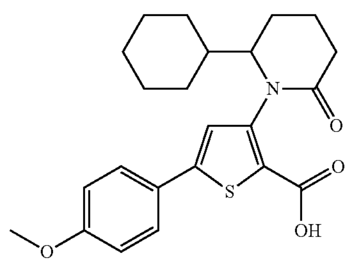 [SMILES: COc1ccc(-c2cc(N3C(=O)CCCC3C3CCCCC3)c(C(=O)O)s2)cc1] |
| 115 | 3-[(R)-5-Cyclohexyl-2,2-bis-(3-hydroxy-propyl)-3-oxo-morpholin-4-yl]-5-(3,3-dimethyl-but-1-ynyl)-thiophene-2-carboxylic acid | 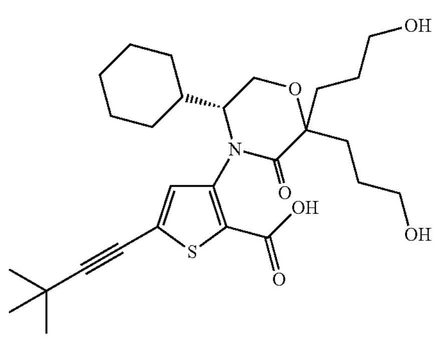 [SMILES: CC(C)(C)C#Cc1cc(N2C(=O)C(CCCO)(CCCO)OC[C@H]2C2CCCCC2)c(C(=O)O)s1] |

TABLE 1-continued

| Compound number | Name | Structure |
|---|---|---|
| 116 | 3-(2-Cyclohexyl-6-oxo-piperidin-1-yl)-5-(4-ethoxy-phenyl)-thiophene-2-carboxylic acid | 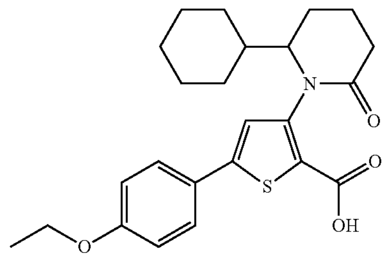 [SMILES: CCOc1ccc(-c2cc(N3C(=O)CCCC3C3CCCCC3)c(C(=O)O)s2)cc1] |
| 117 | 3-(2-Cyclohexyl-6-oxo-piperidin-1-yl)-5-(4-trifluoromethyl-phenyl)-thiophene-2-carboxylic acid | 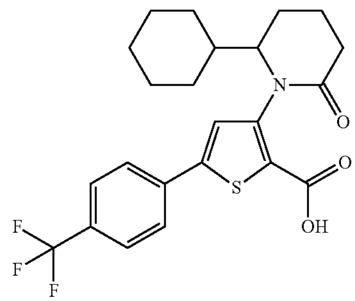 [SMILES: O=C(O)c1sc(-c2ccc(C(F)(F)F)cc2)cc1N1C(=O)CCCC1C1CCCCC1] |
| 118 | 3-{2-Cyclohexyl-4-[6-((R)-2-methyl-pyrrolidin-1-yl)-pyridine-3-sulfonyl]-6-oxo-piperazin-1-yl}-5-phenyl-thiophene-2-carboxylic acid | 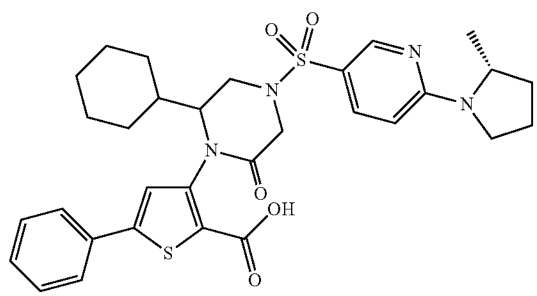 |
| 119 | 3-{2-Cyclohexyl-4-[6-((S)-2-methyl-pyrrolidin-1-yl)-pyridine-3-sulfonyl]-6-oxo-piperazin-1-yl}-5-phenyl-thiophene-2-carboxylic acid | 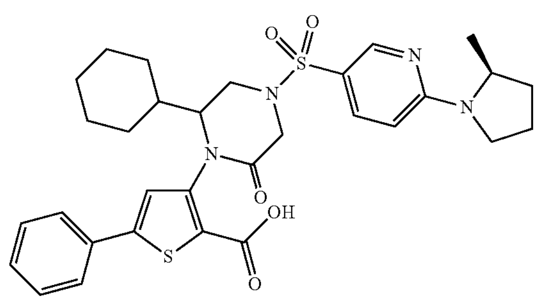 [SMILES: C[C@H]1CCCN1c1ccc(S(=O)(=O)N2CC(=O)N(c3cc(-c4ccccc4)sc3C(=O)O)C(C3CCCCC3)C2)cn1] |
| 120 | 3-{2-Cyclohexyl-4-[6-((R)-3-fluoro-pyrrolidin-1-yl)-pyridine-3-sulfonyl]-6-oxo-piperazin-1-yl}-5-phenyl-thiophene-2-carboxylic acid | 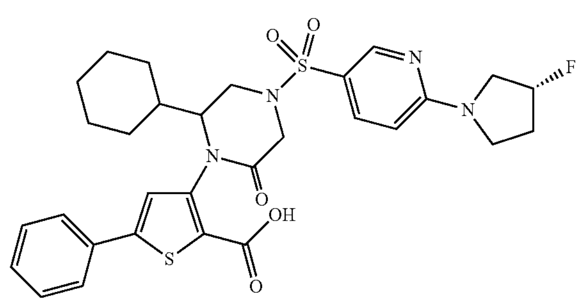 [SMILES: O=C(O)c1sc(-c2ccccc2)cc1N1C(=O)CN(S(=O)(=O)c2ccc(N3CC[C@@H](F)C3)nc2)CC1C1CCCCC1] |

TABLE 1-continued

| Compound number | Name | Structure |
|---|---|---|
| 121 | 3-{2-Cyclohexyl-4-[6-((S)-3-fluoro-pyrrolidin-1-yl)-pyridine-3-sulfonyl]-6-oxo-piperazin-1-yl}-5-phenyl-thiophene-2-carboxylic acid | 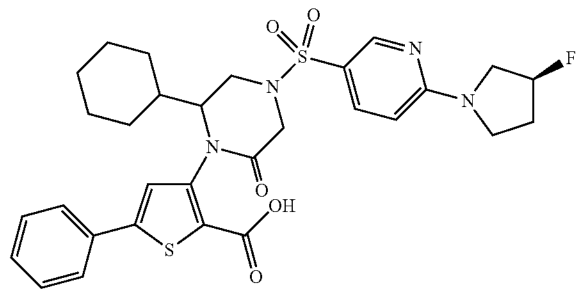 [SMILES: O=C(O)c1sc(-c2ccccc2)cc1N1C(=O)CN(S(=O)(=O)c2ccc(N3CC[C@H](F)C3)nc2)CC1C1CCCCC1] |
| 122 | 3-{2-Cyclohexyl-4-[6-((2R,4R)-4-hydroxy-2-methyl-pyrrolidin-1-yl)-pyridine-3-sulfonyl]-6-oxo-piperazin-1-yl}-5-phenyl-thiophene-2-carboxylic acid | 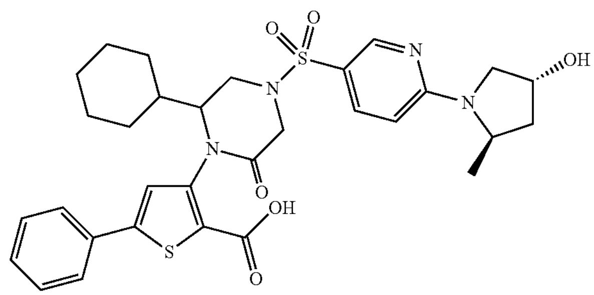 [SMILES: C[C@@H]1C[C@@H](O)CN1c1ccc(S(=O)(=O)N2CC(=O)N(c3cc(-c4ccccc4)sc3C(=O)O)C(C3CCCCC3)C2)cn1] |
| 123 | 3-{2-Cyclohexyl-4-[6-((R)-3-hydroxy-pyrrolidin-1-yl)-pyridine-3-sulfonyl]-6-oxo-piperazin-1-yl}-5-phenyl-thiophene-2-carboxylic acid | 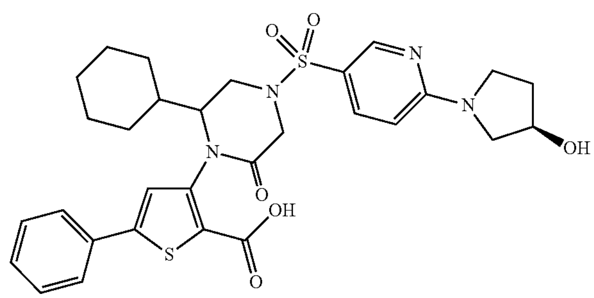 [SMILES: O=C(O)c1sc(-c2ccccc2)cc1N1C(=O)CN(S(=O)(=O)c2ccc(N3CC[C@@H](O)C3)nc2)CC1C1CCCCC1] |
| 124 | 3-{2-Cyclohexyl-4-[6-((S)-3-hydroxy-pyrrolidin-1-yl)-pyridine-3-sulfonyl]-6-oxo-piperazin-1-yl}-5-phenyl-thiophene-2-carboxylic acid | 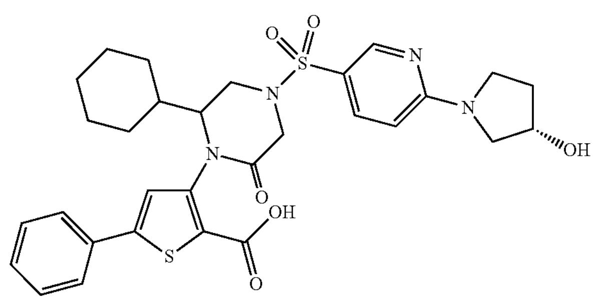 [SMILES: O=C(O)c1sc(-c2ccccc2)cc1N1C(=O)CN(S(=O)(=O)c2ccc(N3CC[C@H](O)C3)nc2)CC1C1CCCCC1] |
| 125 | 3-{4-[6-(7-Aza-bicyclo[2.2.1]hept-7-yl)-pyridine-3-sulfonyl]-2-cyclohexyl-6-oxo-piperazin-1-yl}-5-phenyl-thiophene-2-carboxylic acid | 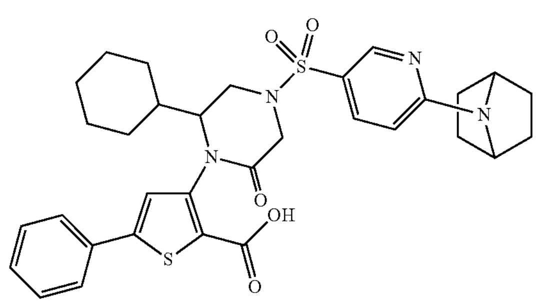 [SMILES: O=C(O)c1sc(-c2ccccc2)cc1N1C(=O)CN(S(=O)(=O)c2ccc(N3C4CCC3CC4)nc2)CC1C1CCCCC1] |

TABLE 1-continued

| Compound number | Name | Structure |
|---|---|---|
| 126 | 3-[2-Cyclohexyl-4-((2S,6R)-2,6-dimethyl-3,4,5,6-tetrahydro-2H-[1,2']bipyridinyl-5'-sulfonyl)-6-oxo-piperazin-1-yl]-5-phenyl-thiophene-2-carboxylic acid | 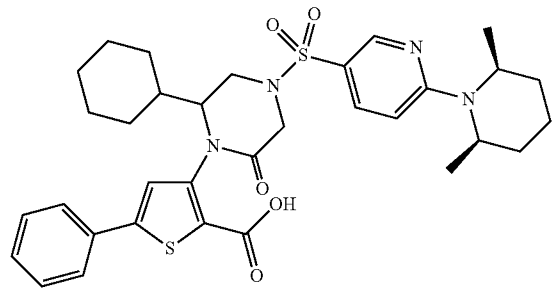 [SMILES: C[C@@H]1CCC[C@H](C)N1c1ccc(S(=O)(=O)N2CC(=O)N(c3cc(-c4ccccc4)sc3C(=O)O)C(C3CCCCC3)C2)cn1] |
| 127 | 3-{2-Cyclohexyl-4-[4-((R)-2-methyl-pyrrolidin-1-yl)-benzenesulfonyl]-6-oxo-piperazin-1-yl}-5-phenyl-thiophene-2-carboxylic acid | 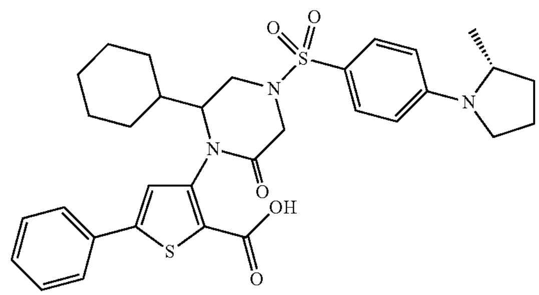 [SMILES: C[C@@H]1CCCN1c1ccc(S(=O)(=O)N2CC(=O)N(c3cc(-c4ccccc4)sc3C(=O)O)C(C3CCCCC3)C2)cc1] |
| 128 | 3-[6-Cyclohexyl-3-methyl-4-(6-morpholin-4-yl-pyridine-3-sulfonyl)-2-oxo-piperazin-1-yl]-5-phenyl-thiophene-2-carboxylic acid | 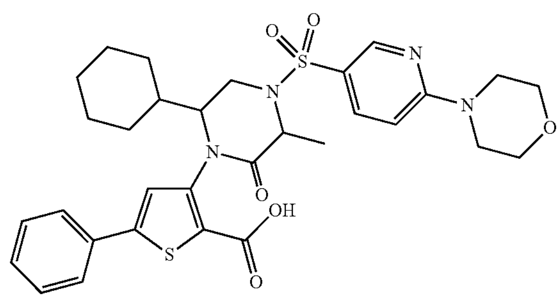 [SMILES: CC1C(=O)N(c2cc(-c3ccccc3)sc2C(=O)O)C(C2CCCCC2)CN1S(=O)(=O)c1ccc(N2CCOCC2)nc1] |
| 129 | 5-(4-Cyano-phenyl)-3-(2-cyclohexyl-6-oxo-piperidin-1-yl)-thiophene-2-carboxylic acid | 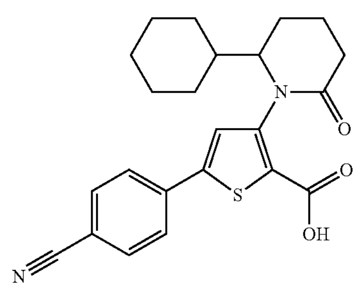 [SMILES: N#Cc1ccc(-c2cc(N3C(=O)CCCC3C3CCCCC3)c(C(=O)O)s2)cc1] |
| 130 | 3-{(R)-2-Cyclohexyl-4-[6-((R)-2-methyl-pyrrolidin-1-yl)-pyridine-3-sulfonyl]-6-oxo-piperazin-1-yl}-5-phenyl-thiophene-2-carboxylic acid | 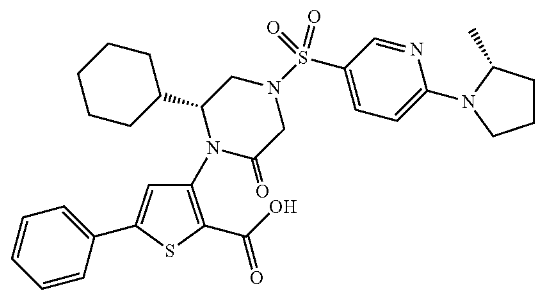 [SMILES: C[C@@H]1CCCN1c1ccc(S(=O)(=O)N2CC(=O)N(c3cc(-c4ccccc4)sc3C(=O)O)[C@H](C3CCCCC3)C2)cn1] |

TABLE 1-continued

| Compound number | Name | Structure |
|---|---|---|
| 131 | 3-{(S)-2-Cyclohexyl-4-[6-((R)-2-methyl-pyrrolidin-1-yl)-pyridine-3-sulfonyl]-6-oxo-piperazin-1-yl}-5-phenyl-thiophene-2-carboxylic acid | 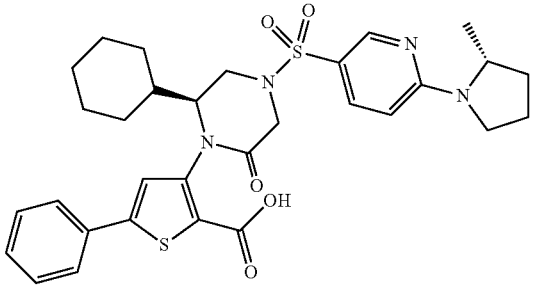 [SMILES: C[C@@H]1CCCN1c1ccc(S(=O)(=O)N2CC(=O)N(c3cc(-c4ccccc4)sc3C(=O)O)[C@@H](C3CCCCC3)C2)cn1] |
| 132 | 3-[(S)-2-Cyclohexyl-6-oxo-4-(6-piperazin-1-yl-pyridine-3-sulfonyl)-piperazin-1-yl]-5-phenyl-thiophene-2-carboxylic acid | 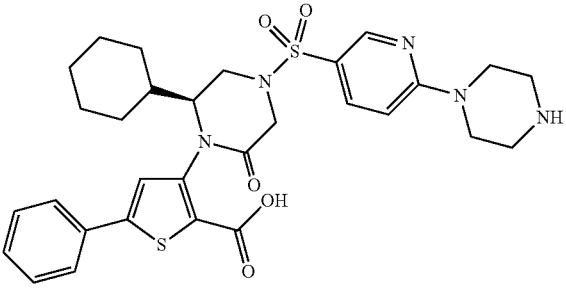 [SMILES: O=C(O)c1sc(-c2ccccc2)cc1N1C(=O)CN(S(=O)(=O)c2ccc(N3CCNCC3)nc2)C[C@@H]1C1CCCCC1] |
| 133 | 5-(3-Chloro-phenyl)-3-(2-cyclohexyl-6-oxo-piperidin-1-yl)-thiophene-2-carboxylic acid | 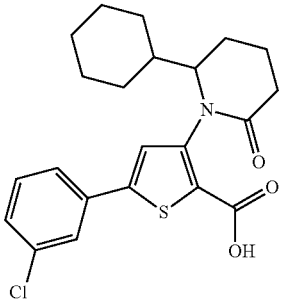 [SMILES: O=C(O)c1sc(-c2cccc(Cl)c2)cc1N1C(=O)CCCC1C1CCCCC1] |
| 134 | 3-(2-Cyclohexyl-6-oxo-piperidin-1-yl)-5-m-tolyl-thiophene-2-carboxylic acid | 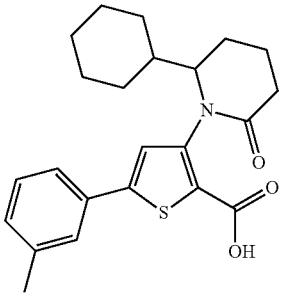 [SMILES: Cc1cccc(-c2cc(N3C(=O)CCCC3C3CCCCC3)c(C(=O)O)s2)c1] |
| 135 | 3-[(R)-2-Cyclohexyl-6-oxo-4-(6-pyrrolidin-1-yl-pyridine-3-sulfonyl)-piperazin-1-yl]-5-phenyl-thiophene-2-carboxylic acid | 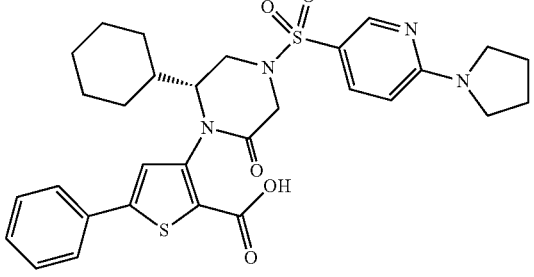 |

TABLE 1-continued

| Compound number | Name | Structure |
|---|---|---|
| 136 | 3-[(S)-2-Cyclohexyl-6-oxo-4-(6-pyrrolidin-1-yl-pyridine-3-sulfonyl)-piperazin-1-yl]-5-phenyl-thiophene-2-carboxylic acid | 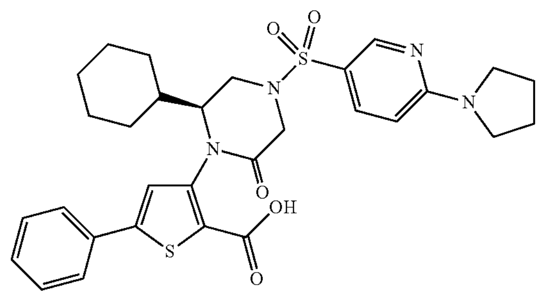 [SMILES: O=C(O)c1sc(-c2ccccc2)cc1N1C(=O)CN(S(=O)(=O)c2ccc(N3CCCC3)nc2)C[C@@H]1C1CCCCC1] |
| 137 | 3-{(R)-2-Cyclohexyl-4-[6-(4-methyl-piperazin-1-yl)-pyridine-3-sulfonyl]-6-oxo-piperazin-1-yl}-5-phenyl-thiophene-2-carboxylic acid | 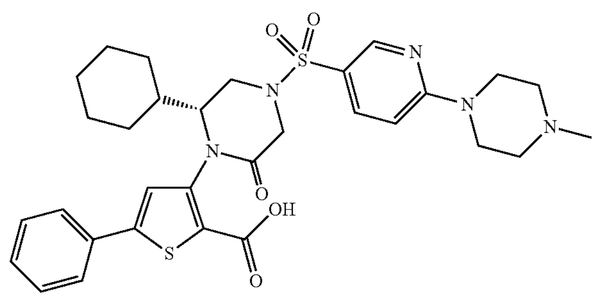 [SMILES: CN1CCN(c2ccc(S(=O)(=O)N3CC(=O)N(c4cc(-c5ccccc5)sc4C(=O)O)[C@H](C4CCCCC4)C3)cn2)CC1] |
| 138 | 3-[(R)-4-(4-Amino-4-methyl-3,4,5,6-tetrahydro-2H-[1,2']bipyridinyl-5'-sulfonyl)-2-cyclohexyl-6-oxo-piperazin-1-yl]-5-phenyl-thiophene-2-carboxylic acid | 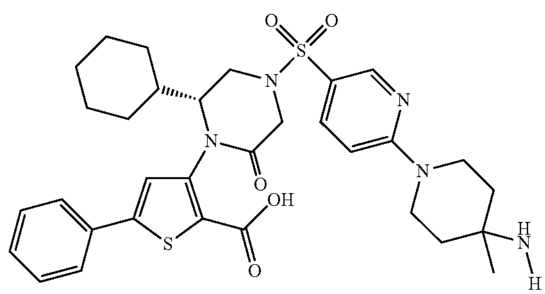 [SMILES: CC1(N)CCN(c2ccc(S(=O)(=O)N3CC(=O)N(c4cc(-c5ccccc5)sc4C(=O)O)[C@H](C4CCCCC4)C3)cn2)CC1] |
| 139 | 3-{(R)-2-Cyclohexyl-4-[6-((S)-3-hydroxymethyl-piperazin-1-yl)-pyridine-3-sulfonyl]-6-oxo-piperazin-1-yl}-5-phenyl-thiophene-2-carboxylic acid | 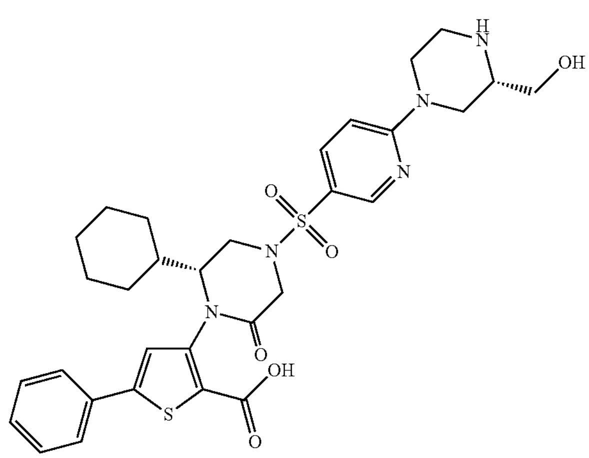 [SMILES: O=C(O)c1sc(-c2ccccc2)cc1N1C(=O)CN(S(=O)(=O)c2ccc(N3CCN[C@H](CO)C3)nc2)C[C@H]1C1CCCCC1] |

TABLE 1-continued

| Compound number | Name | Structure |
|---|---|---|
| 140 | 3-{(R)-2-Cyclohexyl-4-[6-((R)-3-methyl-piperazin-1-yl)-pyridine-3-sulfonyl]-6-oxo-piperazin-1-yl}-5-phenyl-thiophene-2-carboxylic acid | 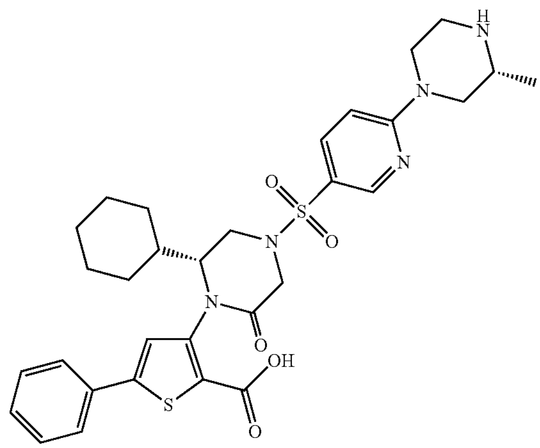 [SMILES: C[C@@H]1CN(c2ccc(S(=O)(=O)N3CC(=O)N(c4cc(-c5ccccc5)sc4C(=O)O)[C@H](C4CCCCC4)C3)cn2)CCN1] |
| 141 | 3-{(R)-4-[6-((R)-3-Amino-pyrrolidin-1-yl)-pyridine-3-sulfonyl)-2-cyclohexyl-6-oxo-piperazin-1-yl}-5-phenyl-thiophene-2-carboxylic acid | 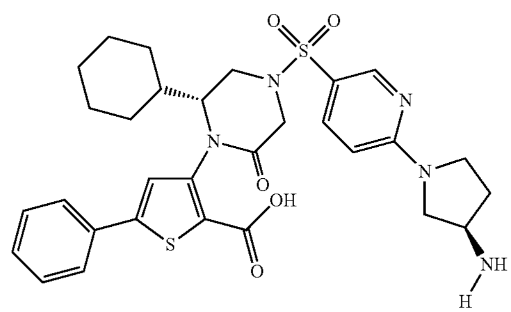 [SMILES: N[C@@H]1CCN(c2ccc(S(=O)(=O)N3CC(=O)N(c4cc(-c5ccccc5)sc4C(=O)O)[C@H](C4CCCCC4)C3)cn2)C1] |
| 142 | 3-[(R)-4-((S)-3-Amino-3,4,5,6-tetrahydro-2H-[1,2']bipyridinyl-5'-sulfonyl)-2-cyclohexyl-6-oxo-piperazin-1-yl]-5-phenyl-thiophene-2-carboxylic acid | 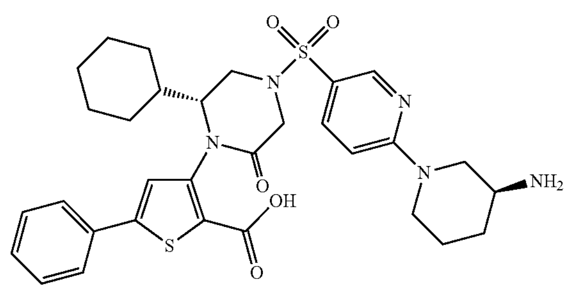 [SMILES: N[C@H]1CCCN(c2ccc(S(=O)(=O)N3CC(=O)N(c4cc(-c5ccccc5)sc4C(=O)O)[C@H](C4CCCCC4)C3)cn2)C1] |
| 143 | 3-[(R)-4-(4-Aminomethyl-3,4,5,6-tetrahydro-2H-[1,2']bipyridinyl-5'-sulfonyl)-2-cyclohexyl-6-oxo-piperazin-1-yl]-5-phenyl-thiophene-2-carboxylic acid | 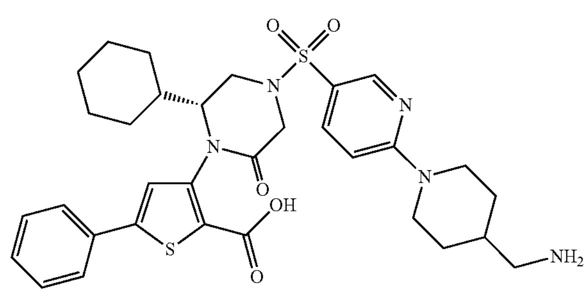 [SMILES: NCC1CCN(c2ccc(S(=O)(=O)N3CC(=O)N(c4cc(-c5ccccc5)sc4C(=O)O)[C@H](C4CCCCC4)C3)cn2)CC1] |

TABLE 1-continued

| Compound number | Name | Structure |
|---|---|---|
| 144 | 3-{(R)-4-[6-((S)-3-Amino-pyrrolidin-1-yl)-pyridine-3-sulfonyl]-2-cyclohexyl-6-oxo-piperazin-1-yl}-5-phenyl-thiophene-2-carboxylic acid | 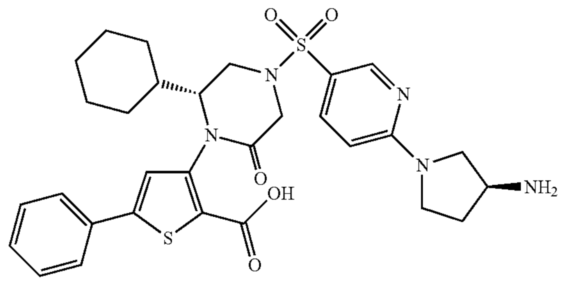 [SMILES: N[C@H]1CCN(c2ccc(S(=O)(=O)N3CC(=O)N(c4cc(-c5ccccc5)sc4C(=O)O)[C@H](C4CCCCC4)C3)cn2)C1] |
| 145 | 3-{(R)-2-Cyclohexyl-4-[6-((S)-3-methyl-piperazin-1-yl)-pyridine-3-sulfonyl]-6-oxo-piperazin-1-yl}-5-phenyl-thiophene-2-carboxylic acid | 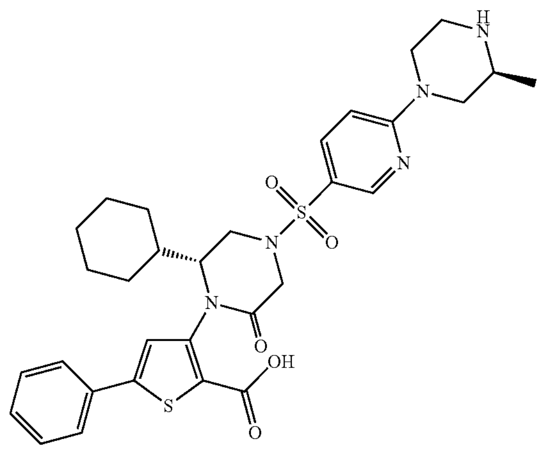 [SMILES: C[C@H]1CN(c2ccc(S(=O)(=O)N3CC(=O)N(c4cc(-c5ccccc5)sc4C(=O)O)[C@H](C4CCCCC4)C3)cn2)CCN1] |
| 146 | 3-{(R)-4-[6-((R)-3-tert-Butoxycarbonylamino-pyrrolidin-1-yl)-pyridine-3-sulfonyl]-2-cyclohexyl-6-oxo-piperazin-1-yl}-5-phenyl-thiophene-2-carboxylic acid | 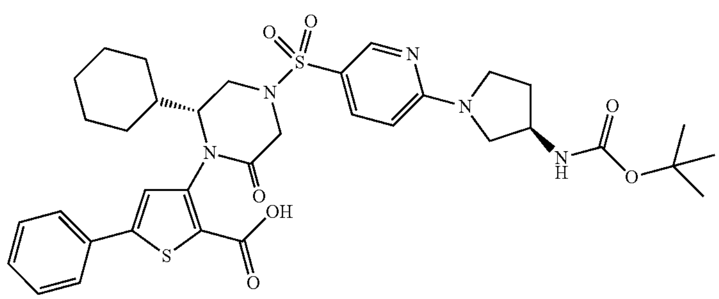 [SMILES: CC(C)(C)OC(=O)N[C@@H]1CCN(c2ccc(S(=O)(=O)N3CC(=O)N(c4cc(-c5ccccc5)sc4C(=O)O)[C@H](C4CCCCC4)C3)cn2)C1] |
| 147 | 3-[(R)-2-Cyclohexyl-4-(4-dimethylamino-3,4,5,6-tetrahydro-2H-[1,2']bipyridinyl-5'-sulfonyl)-6-oxo-piperazin-1-yl]-5-phenyl-thiophene-2-carboxylic acid | 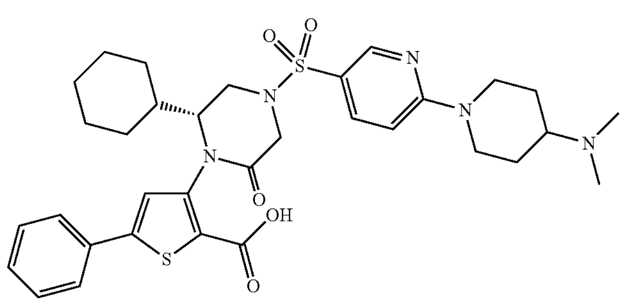 [SMILES: CN(C)C1CCN(c2ccc(S(=O)(=O)N3CC(=O)N(c4cc(-c5ccccc5)sc4C(=O)O)[C@H](C4CCCCC4)C3)cn2)CC1] |

TABLE 1-continued

| Compound number | Name |
|---|---|
| 148 | 3-{(R)-2-Cyclohexyl-4-[6-(4-ethyl-piperazin-1-yl)-pyridine-3-sulfonyl]-6-oxo-piperazin-1-yl}-5-phenyl-thiophene-2-carboxylic acid |
| 149 | 3-{(R)-4-[4-(tert-Butoxycarbonylamino-methyl)-3,4,5,6-tetrahydro-2H-[1,2']bipyridinyl-5'-sulfonyl]-2-cyclohexyl-6-oxo-piperazin-1-yl}-5-phenyl-thiophene-2-carboxylic acid |
| 150 | 3-{(R)-2-Cyclohexyl-4-[6-((3R,5S)-3,5-dimethyl-piperazin-1-yl)-pyridine-3-sulfonyl]-6-oxo-piperazin-1-yl}-5-phenyl-thiophene-2-carboxylic acid |
| 151 | (R)-4-{5-[(R)-4-(2-Carboxy-5-phenyl-thiophen-3-yl)-3-cyclohexyl-5-oxo-piperazine-1-sulfonyl]-pyridin-2-yl}-2-methyl-piperazine-1-carboxylic acid tert-butyl ester |
| 152 | 3-{(R)-4-[6-(4-tert-Butyl-piperazin-1-yl)-pyridine-3-sulfonyl]-2-cyclohexyl-6-oxo-piperazin-1-yl}-5-phenyl-thiophene-2-carboxylic acid |

TABLE 1-continued

| Compound number | Name | Structure |
|---|---|---|
| 153 | 3-[(R)-4-(4-tert-Butoxycarbonylamino-4-methyl-3,4,5,6-tetrahydro-2H-[1,2']bipyridinyl-5'-sulfonyl)-2-cyclohexyl-6-oxo-piperazin-1-yl]-5-phenyl-thiophene-2-carboxylic acid | 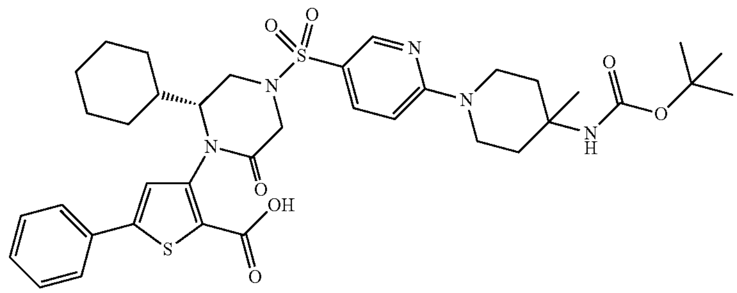 [SMILES: CC1(NC(=O)OC(C)(C)C)CCN(c2ccc(S(=O)(=O)N3CC(=O)N(c4cc(-c5ccccc5)sc4C(=O)O)[C@H](C4CCCCC4)C3)cn2)CC1] |
| 154 | 3-{(R)-2-Cyclohexyl-4-[6-(2-ethyl-pyrrolidin-1-yl)-pyridine-3-sulfonyl]-6-oxo-piperazin-1-yl}-5-phenyl-thiophene-2-carboxylic acid | 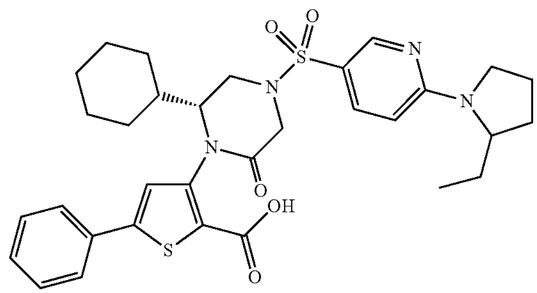 [SMILES: CCC1CCCN1c1ccc(S(=O)(=O)N2CC(=O)N(c3cc(-c4ccccc4)sc3C(=O)O)[C@H](C3CCCCC3)C2)cn1] |
| 155 | 3-[(R)-2-Cyclohexyl-4-(3-dimethylamino-3,4,5,6-tetrahydro-2H-[1,2']bipyridinyl-5'-sulfonyl)-6-oxo-piperazin-1-yl]-5-phenyl-thiophene-2-carboxylic acid | 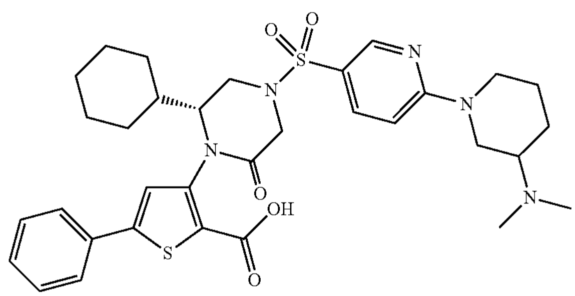 [SMILES: CN(C)C1CCCN(c2ccc(S(=O)(=O)N3CC(=O)N(c4cc(-c5ccccc5)sc4C(=O)O)[C@H](C4CCCCC4)C3)cn2)C1] |
| 156 | 3-{(R)-2-Cyclohexyl-4-[6-((S)-3-dimethylamino-pyrrolidin-1-yl)-pyridine-3-sulfonyl]-6-oxo-piperazin-1-yl}-5-phenyl-thiophene-2-carboxylic acid | 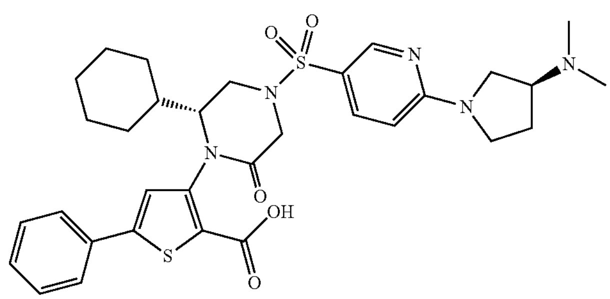 [SMILES: CN(C)[C@H]1CCN(c2ccc(S(=O)(=O)N3CC(=O)N(c4cc(-c5ccccc5)sc4C(=O)O)[C@H](C4CCCCC4)C3)cn2)C1] |
| 157 | 3-{(R)-2-Cyclohexyl-4-[6-(hexahydro-pyrrolo[1,2-a]pyrazin-2-yl)-pyridine-3-sulfonyl]-6-oxo-piperazin-1-yl}-5-phenyl-thiophene-2-carboxylic acid | 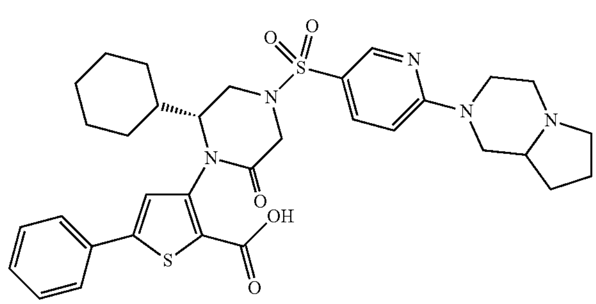 [SMILES: O=C(O)c1sc(-c2ccccc2)cc1N1C(=O)CN(S(=O)(=O)c2ccc(N3CCN4CCCC4C3)nc2)C[C@H]1C1CCCCC1] |

TABLE 1-continued

| Compound number | Name | Structure |
|---|---|---|
| 158 | 3-[(R)-4-((S)-3-tert-Butoxycarbonylamino-3,4,5,6-tetrahydro-2H-[1,2']bipyridinyl-5'-sulfonyl)-2-cyclohexyl-6-oxo-piperazin-1-yl]-5-phenyl-thiophene-2-carboxylic acid | 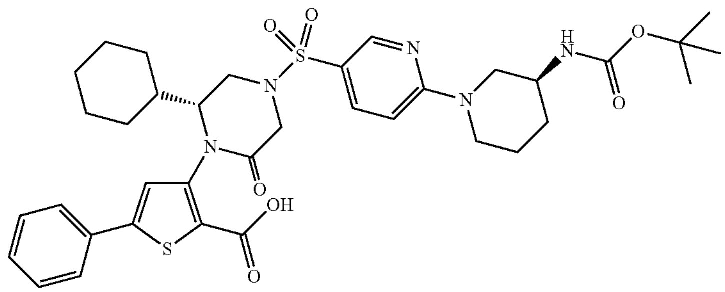 [SMILES: CC(C)(C)OC(=O)N[C@H]1CCCN(c2ccc(S(=O)(=O)N3CC(=O)N(c4cc(-c5ccccc5)sc4C(=O)O)[C@H](C4CCCCC4)C3)cn2)C1] |
| 159 | 3-[(R)-4-((S)-3-tert-Butoxycarbonylamino-3,4,5,6-tetrahydro-2H-[1,2']bipyridinyl-5'-sulfonyl)-2-cyclohexyl-6-oxo-piperazin-1-yl]-5-phenyl-thiophene-2-carboxylic acid | 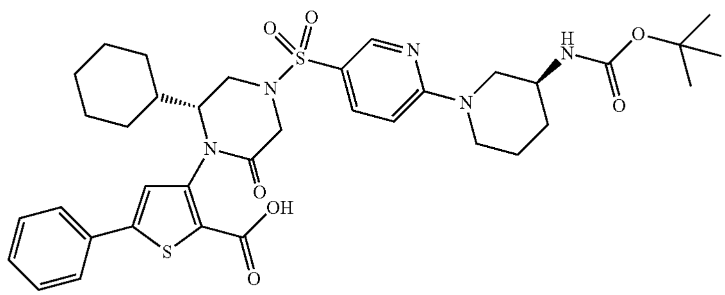 [SMILES: CC(C)(C)OC(=O)N[C@H]1CCCN(c2ccc(S(=O)(=O)N3CC(=O)N(c4cc(-c5ccccc5)sc4C(=O)O)[C@H](C4CCCCC4)C3)cn2)C1] |
| 160 | 3-{(R)-2-Cyclohexyl-4-[6-(4-isopropyl-piperazin-1-yl)-pyridine-3-sulfonyl]-6-oxo-piperazin-1-yl}-5-phenyl-thiophene-2-carboxylic acid | 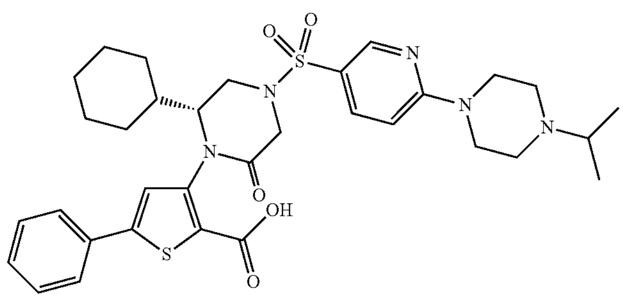 |
| 161 | (R)-4-{5-[(R)-4-(2-Carboxy-5-phenyl-thiophen-3-yl)-3-cyclohexyl-5-oxo-piperazine-1-sulfonyl]-pyridin-2-yl}-2-hydroxymethyl-piperazine-1-carboxylic acid tert-butyl ester | 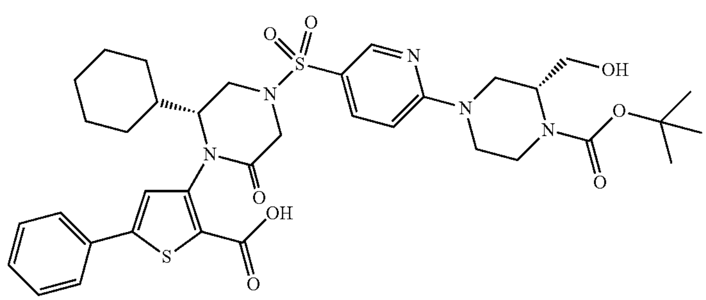 [SMILES: CC(C)(C)OC(=O)N1CCN(c2ccc(S(=O)(=O)N3CC(=O)N(c4cc(-c5ccccc5)sc4C(=O)O)[C@H](C4CCCCC4)C3)cn2)C[C@@H]1CO] |
| 162 | (S)-4-{5-[(R)-4-(2-Carboxy-5-phenyl-thiophen-3-yl)-3-cyclohexyl-5-oxo-piperazine-1-sulfonyl]-pyridin-2-yl}-2-methyl-piperazine-1-carboxylic acid tert-butyl ester | 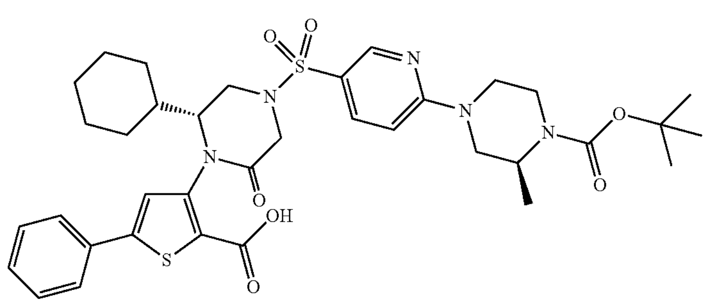 [SMILES: C[C@H]1CN(c2ccc(S(=O)(=O)N3CC(=O)N(c4cc(-c5ccccc5)sc4C(=O)O)[C@H](C4CCCCC4)C3)cn2)CCN1C(=O)OC(C)(C)C] |

TABLE 1-continued

| Compound number | Name | Structure |
|---|---|---|
| 163 | 3-{(R)-2-Cyclohexyl-4-[6-((R)-3-dimethylamino-pyrrolidin-1-yl)-pyridine-3-sulfonyl]-6-oxo-piperazin-1-yl}-5-phenyl-thiophene-2-carboxylic acid | 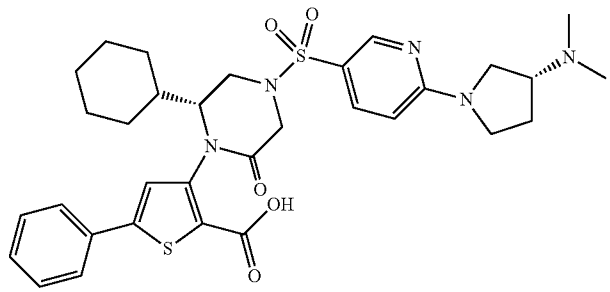 [SMILES: CN(C)[C@@H]1CCN(c2ccc(S(=O)(=O)N3CC(=O)N(c4cc(-c5ccccc5)sc4C(=O)O)[C@H](C4CCCCC4)C3)cn2)C1] |
| 164 | 3-{(R)-2-Cyclohexyl-4-[6-((2S,5R)-2,5-dimethyl-pyrrolidin-1-yl)-pyridine-3-sulfonyl]-6-oxo-piperazin-1-yl}-5-phenyl-thiophene-2-carboxylic acid | 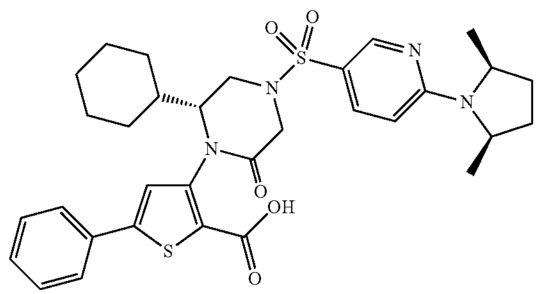 [SMILES: C[C@@H]1CC[C@H](C)N1c1ccc(S(=O)(=O)N2CC(=O)N(c3cc(-c4ccccc4)sc3C(=O)O)[C@H](C3CCCCC3)C2)cn1] |
| 165 | 3-{(R)-4-[6-((S)-3-tert-Butoxycarbonylamino-pyrrolidin-1-yl)-pyridine-3-sulfonyl]-2-cyclohexyl-6-oxo-piperazin-1-yl}-5-phenyl-thiophene-2-carboxylic acid | 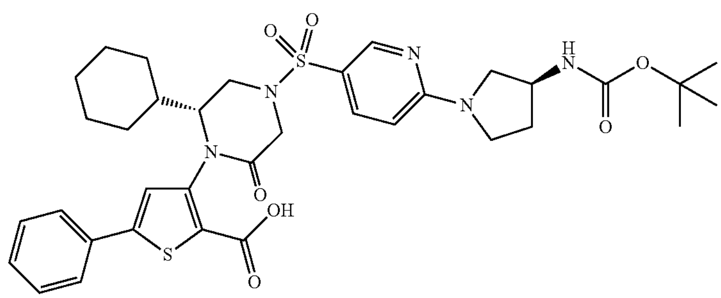 [SMILES: CC(C)(C)OC(=O)N[C@H]1CCN(c2ccc(S(=O)(=O)N3CC(=O)N(c4cc(-c5ccccc5)sc4C(=O)O)[C@H](C4CCCCC4)C3)cn2)C1] |
| 166 | 3-[2-Cyclohexyl-6-oxo-4-(toluene-4-sulfonyl)-piperazin-1-yl]-5-(3,3-dimethyl-but-1-ynyl)-thiophene-2-carboxylic acid | 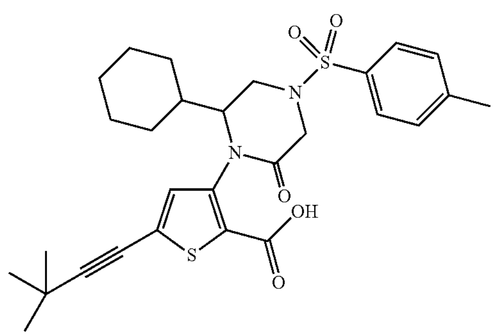 [SMILES: Cc1ccc(S(=O)(=O)N2CC(=O)N(c3cc(C#CC(C)(C)C)sc3C(=O)O)C(C3CCCCC3)C2)cc1] |
| 167 | 3-{(R)-2-Cyclohexyl-4-[6-((2R,6S)-2,6-dimethyl-morpholin-4-yl)-pyridine-3-sulfonyl]-6-oxo-piperazin-1-yl}-5-phenyl-thiophene-2-carboxylic acid | 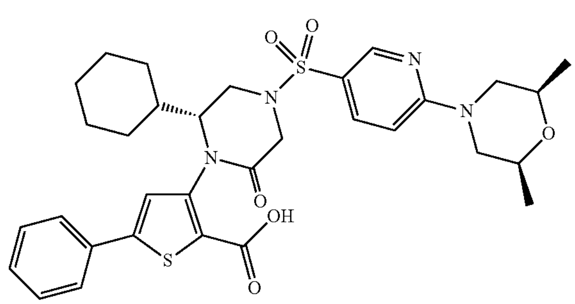 [SMILES: C[C@@H]1CN(c2ccc(S(=O)(=O)N3CC(=O)N(c4cc(-c5ccccc5)sc4C(=O)O)[C@H](C4CCCCC4)C3)cn2)C[C@H](C)O1] |

TABLE 1-continued

| Compound number | Name | Structure |
|---|---|---|
| 168 | 3-[2-Cyclohexyl-4-(6-morpholin-4-yl-pyridine-3-sulfonyl)-6-oxo-piperazin-1-yl]-5-(3,3-dimethyl-but-1-ynyl)-thiophene-2-carboxylic acid | 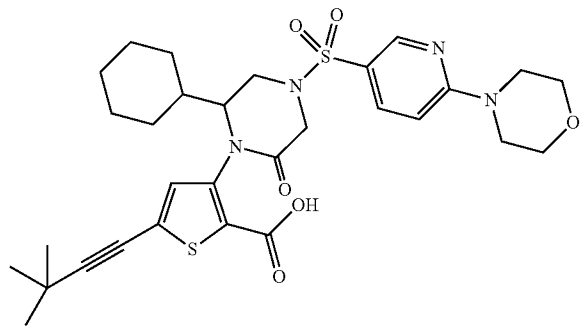 [SMILES: CC(C)(C)C#Cc1cc(N2C(=O)CN(S(=O)(=O)c3ccc(N4CCOCC4)nc3)CC2C2CCCCC2)c(C(=O)O)s1] |
| 169 | | 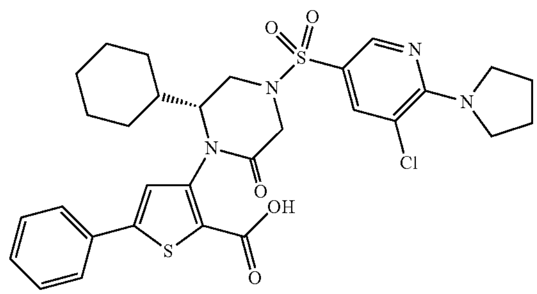 [SMILES: O=C(O)c1sc(-c2ccccc2)cc1N1C(=O)CN(S(=O)(=O)c2cnc(N3CCCC3)c(Cl)c2)C[C@H]1C1CCCCC1] |
| 170 | 3-{(R)-4-[5-Chloro-6-((R)-2-methyl-pyrrolidin-1-yl)-pyridine-3-sulfonyl]-2-cyclohexyl-6-oxo-piperazin-1-yl}-5-phenyl-thiophene-2-carboxylic acid | 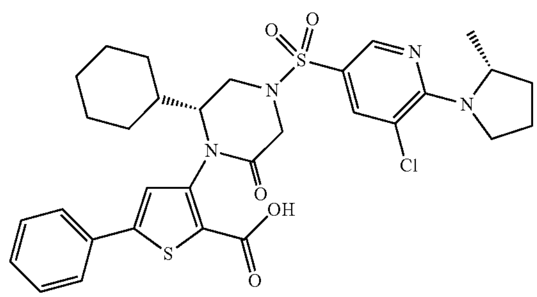 [SMILES: C[C@@H]1CCCN1c1ncc(S(=O)(=O)N2CC(=O)N(c3cc(-c4ccccc4)sc3C(=O)O)[C@H](C3CCCCC3)C2)cc1Cl] |
| 171 | 3-{(R)-2-Cyclohexyl-4-[6-((S)-2-methoxymethyl-pyrrolidin-1-yl)-pyridine-3-sulfonyl]-6-oxo-piperazin-1-yl}-5-phenyl-thiophene-2-carboxylic acid | 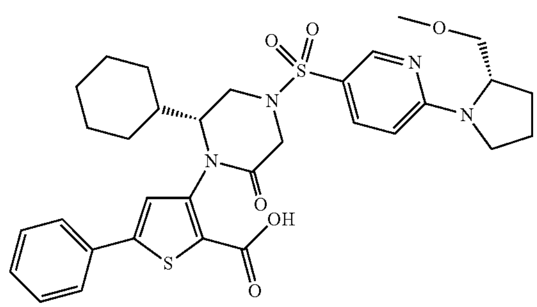 [SMILES: COC[C@@H]1CCCN1c1ccc(S(=O)(=O)N2CC(=O)N(c3cc(-c4ccccc4)sc3C(=O)O)[C@H](C3CCCCC3)C2)cn1] |
| 172 | 3-[(R)-2-Cyclohexyl-4-(5-methyl-6-pyrrolidin-1-yl-pyridine-3-sulfonyl)-6-oxo-piperazin-1-yl]-5-phenyl-thiophene-2-carboxylic acid | 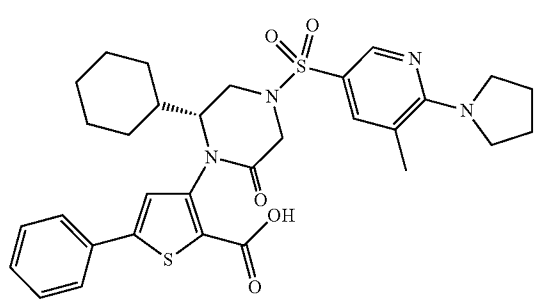 [SMILES: Cc1cc(S(=O)(=O)N2CC(=O)N(c3cc(-c4ccccc4)sc3C(=O)O)[C@H](C3CCCCC3)C2)cnc1N1CCCC1] |

TABLE 1-continued

| Compound number | Name | Structure |
|---|---|---|
| 173 | 3-{(R)-2-Cyclohexyl-4-[5-methyl-6-((R)-2-methyl-pyrrolidin-1-yl)-pyridine-3-sulfonyl]-6-oxo-piperazin-1-yl}-5-phenyl-thiophene-2-carboxylic acid | 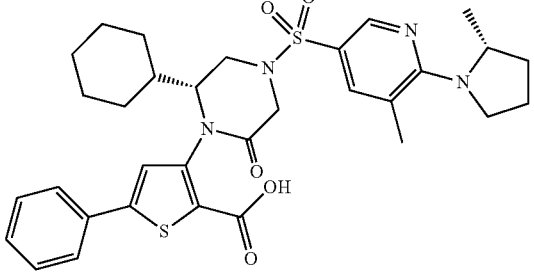 |
| 174 | 3-[2-Cyclohexyl-4-(4-methyl-benzyl)-6-oxo-piperazin-1-yl]-5-(3,3-dimethyl-but-1-ynyl)-thiophene-2-carboxylic acid | 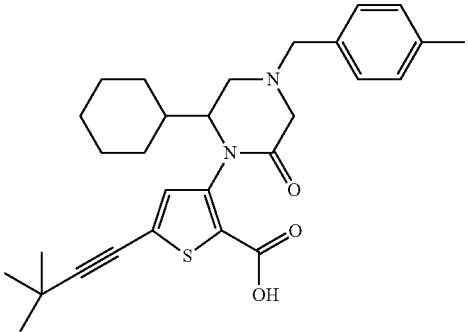 [SMILES: Cc1ccc(CN2CC(=O)N(c3cc(C#CC(C)(C)C)sc3C(=O)O)C(C3CCCCC3)C2)cc1] |
| 175 | 3-(2-Cyclohexyl-6-oxo-piperazin-1-yl)-5-(3,3-dimethyl-but-1-ynyl)-thiophene-2-carboxylic acid | 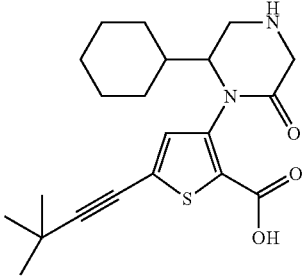 [SMILES: CC(C)(C)C#Cc1cc(N2C(=O)CNCC2C2CCCCC2)c(C(=O)O)s1] |
| 176 | 3-[(R)-2-Cyclohexyl-4-(4-isopropyl-benzenesulfonyl)-6-oxo-piperazin-1-yl]-5-(3,3-dimethyl-but-1-ynyl)-thiophene-2-carboxylic acid | 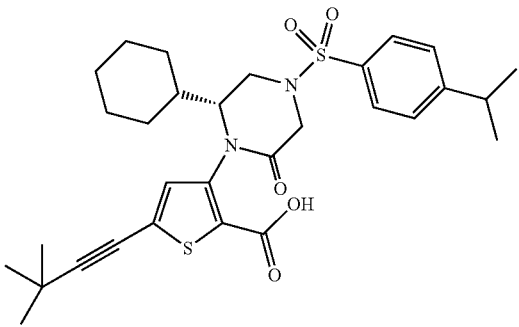 [SMILES: CC(C)c1ccc(S(=O)(=O)N2CC(=O)N(c3cc(C#CC(C)(C)C)sc3C(=O)O)[C@H](C3CCCCC3)C2)cc1] |
| 177 | 3-[(R)-2-Cyclohexyl-4-(6-diethylamino-pyridine-3-sulfonyl)-6-oxo-piperazin-1-yl]-5-phenyl-thiophene-2-carboxylic acid | 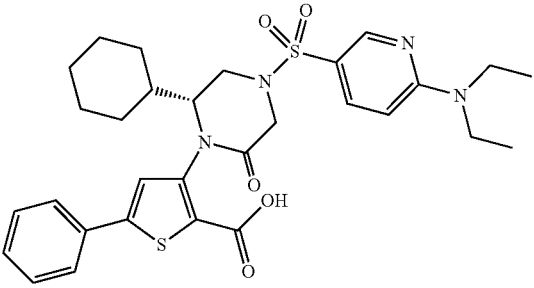 [SMILES: CCN(CC)c1ccc(S(=O)(=O)N2CC(=O)N(c3cc(-c4ccccc4)sc3C(=O)O)[C@H](C3CCCCC3)C2)cn1] |

TABLE 1-continued

| Compound number | Name | Structure |
|---|---|---|
| 178 | 3-[(R)-2-Cyclohexyl-6-oxo-4-(6-phenyl-pyridine-3-sulfonyl)-piperazin-1-yl]-5-phenyl-thiophene-2-carboxylic acid | 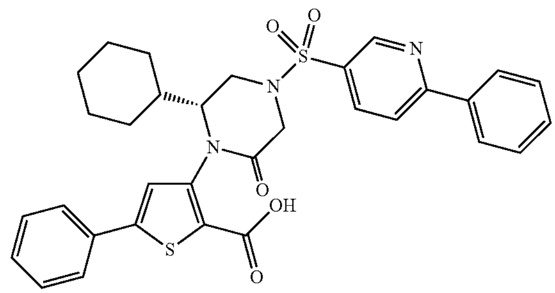 [SMILES: O=C(O)c1sc(-c2ccccc2)cc1N1C(=O)CN(S(=O)(=O)c2ccc(-c3ccccc3)nc2)C[C@H]1C1CCCCC1] |
| 179 | 3-[(R)-2-Cyclohexyl-6-oxo-4-(3,4,5,6-tetrahydro-2H-[1,2']bipyridinyl-5'-sulfonyl)-piperazin-1-yl]-5-phenyl-thiophene-2-carboxylic acid | 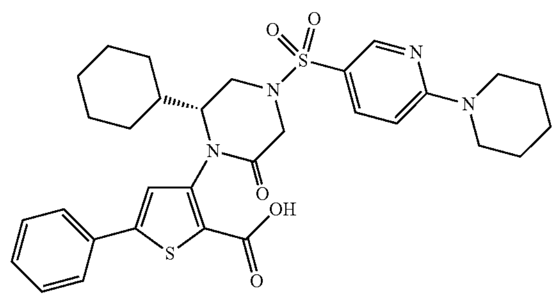 [SMILES: O=C(O)c1sc(-c2ccccc2)cc1N1C(=O)CN(S(=O)(=O)c2ccc(N3CCCCC3)nc2)C[C@H]1C1CCCCC1] |
| 180 | 3-{(R)-2-Cyclohexyl-4-[6-((R)-2-methyl-pyrrolidin-1-yl)-pyridine-3-sulfonyl]-6-oxo-piperazin-1-yl}-5-p-tolyl-thiophene-2-carboxylic acid | 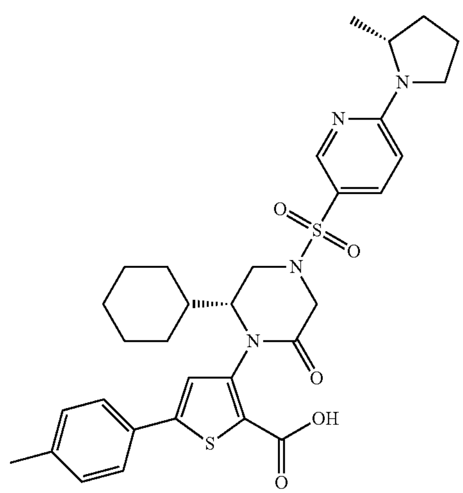 [SMILES: Cc1ccc(-c2cc(N3C(=O)CN(S(=O)(=O)c4ccc(N5CCC[C@H]5C)nc4)C[C@H]3C3CCCCC3)c(C(=O)O)s2)cc1] |
| 181 | 3-((R)-4-Cyclohexyl-2-oxo-oxazolidin-3-yl)-5-(3,3-dimethyl-but-1-ynyl)-thiophene-2-carboxylic acid | 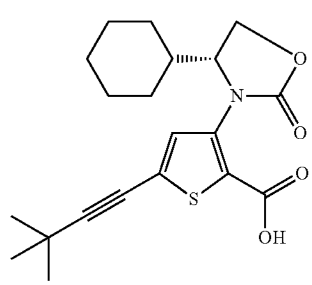 [SMILES: CC(C)(C)C#Cc1cc(N2C(=O)OC[C@H]2C2CCCCC2)c(C(=O)O)s1] |

TABLE 1-continued

| Compound number | Name | Structure |
|---|---|---|
| 182 | 3-[(R)-2-Cyclohexyl-6-oxo-4-(6-pyrrolidin-1-yl-pyridin-3-ylmethyl)-piperazin-1-yl]-5-phenyl-thiophene-2-carboxylic acid | 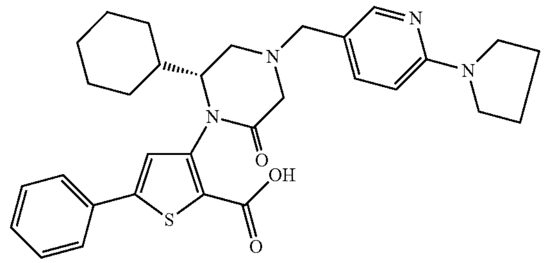 [SMILES: O=C(O)c1sc(-c2ccccc2)cc1N1C(=O)CN(Cc2ccc(N3CCCC3)nc2)C[C@H]1C1CCCCC1] |
| 183 | 3-[(R)-2-Cyclohexyl-4-((R)-2-methyl-3,4,5,6-tetrahydro-2H-[1,2']bipyridinyl-5'-sulfonyl)-6-oxo-piperazin-1-yl]-5-phenyl-thiophene-2-carboxylic acid | 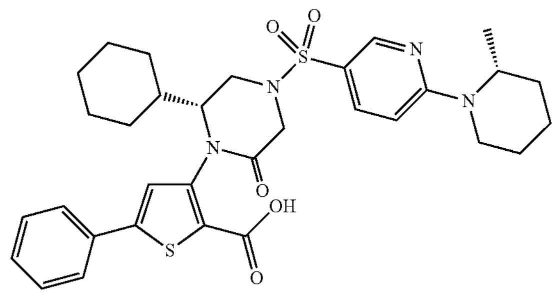 [SMILES: C[C@@H]1CCCCN1c1ccc(S(=O)(=O)N2CC(=O)N(c3cc(-c4ccccc4)sc3C(=O)O)[C@H](C3CCCCC3)C2)cn1] |
| 184 | 3-[(R)-2-Cyclohexyl-4-(6-morpholin-4-yl-pyridine-3-sulfonyl)-6-oxo-piperazin-1-yl]-5-phenyl-thiophene-2-carboxylic acid | 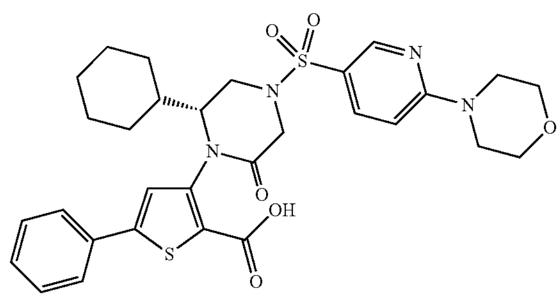 [SMILES: O=C(O)c1sc(-c2ccccc2)cc1N1C(=O)CN(S(=O)(=O)c2ccc(N3CCOCC3)nc2)C[C@H]1C1CCCCC1] |
| 185 | 3-{(R)-2-Cyclohexyl-4-[6-((R)-2-methyl-pyrrolidin-1-yl)-pyridine-3-sulfonyl]-6-oxo-piperazin-1-yl}-5-(4-fluoro-phenyl)-thiophene-2-carboxylic acid | 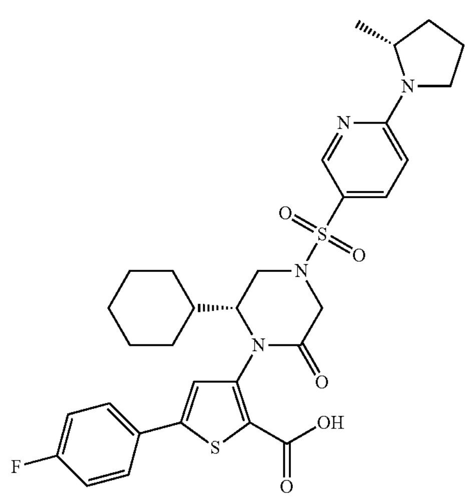 [SMILES: C[C@@H]1CCCN1c1ccc(S(=O)(=O)N2CC(=O)N(c3cc(-c4ccc(F)cc4)sc3C(=O)O)[C@H](C3CCCCC3)C2)cn1] |

| Compound number | Name | Structure |
|---|---|---|
| 186 | 3-[(R)-2-Cyclohexyl-4-(6-[1,4]oxazepan-4-yl-pyridine-3-sulfonyl)-6-oxo-piperazin-1-yl]-5-(4-fluoro-phenyl)-thiophene-2-carboxylic acid | 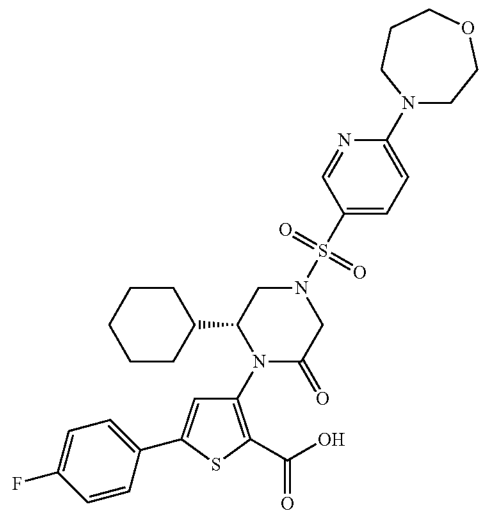 [SMILES: O=C(O)c1sc(-c2ccc(F)cc2)cc1N1C(=O)CN(S(=O)(=O)c2ccc(N3CCCOCC3)nc2)C[C@H]1C1CCCCC1] |
| 187 | 3-[(R)-2-Cyclohexyl-4-(6-morpholin-4-yl-pyridine-3-sulfonyl)-6-oxo-piperazin-1-yl]-5-p-tolyl-thiophene-2-carboxylic acid | 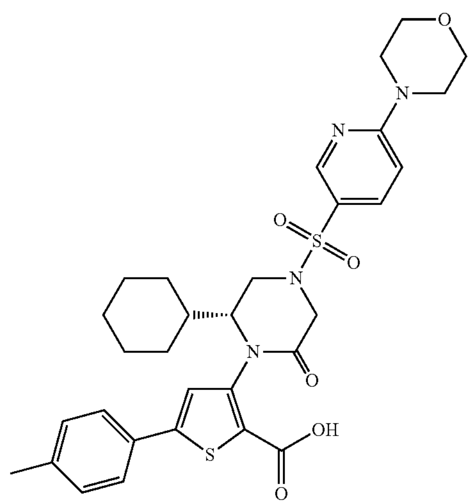 |
| 188 | 3-[(R)-2-Cyclohexyl-4-(6-[1,4]oxazepan-4-yl-pyridine-3-sulfonyl)-6-oxo-piperazin-1-yl]-5-p-tolyl-thiophene-2-carboxylic acid | 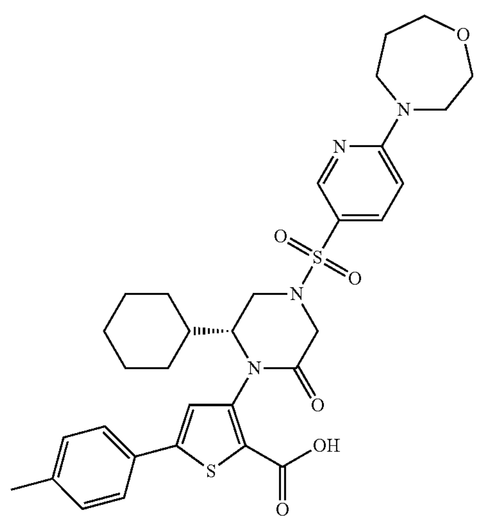 [SMILES: Cc1ccc(-c2cc(N3C(=O)CN(S(=O)(=O)c4ccc(N5CCCOCC5)nc4)C[C@H]3C3CCCCC3)c(C(=O)O)s2)cc1] |

TABLE 1-continued

| Compound number | Name | Structure |
|---|---|---|
| 189 | 3-[(R)-2-Cyclohexyl-4-(6-morpholin-4-yl-pyridine-3-sulfonyl)-6-oxo-piperazin-1-yl]-5-4-fluoro-phenyl)-thiophene-2-carboxylic acid | 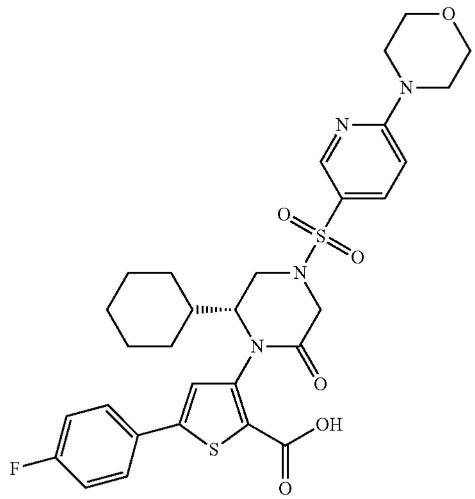 [SMILES: O=C(O)c1sc(-c2ccc(F)cc2)cc1N1C(=O)CN(S(=O)(=O)c2ccc(N3CCOCC3)nc2)C[C@H]1C1CCCCC1] |
| 190 | 3-[(R)-2-Cyclohexyl-4-(4-methoxy-benzenesulfonyl)-6-oxo-piperazin-1-yl]-5-(3,3-dimethyl-but-1-ynyl)-thiophene-2-carboxylic acid | 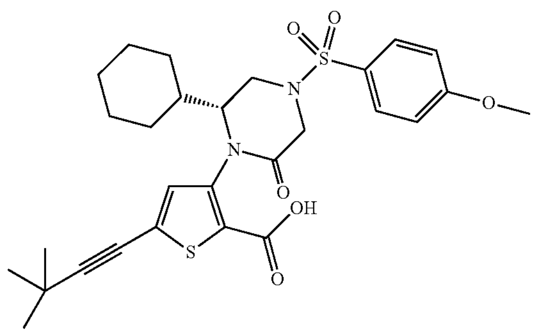 [SMILES: COc1ccc(S(=O)(=O)N2CC(=O)N(c3cc(C#CC(C)(C)C)sc3C(=O)O)[C@H](C3CCCCC3)C2)cc1] |
| 191 | 3-[(R)-2-Cyclohexyl-4-(6-methoxy-pyridine-3-sulfonyl)-6-oxo-piperazin-1-yl]-5-(3,3-dimethyl-but-1-ynyl)-thiophene-2-carboxylic acid | 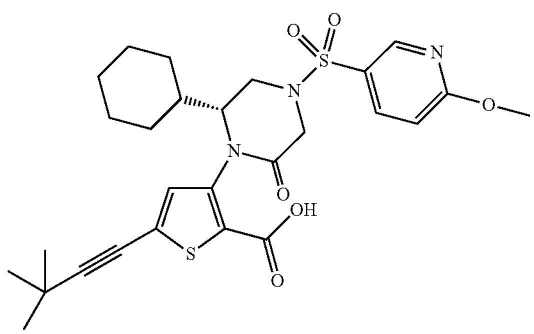 [SMILES: COc1ccc(S(=O)(=O)N2CC(=O)N(c3cc(C#CC(C)(C)C)sc3C(=O)O)[C@H](C3CCCCC3)C2)cn1] |
| 192 | 3-[(R)-2-Cyclohexyl-6-oxo-4-(pyridine-3-sulfonyl)-piperazin-1-yl]-5-(3,3-dimethyl-but-1-ynyl)-thiophene-2-carboxylic acid | 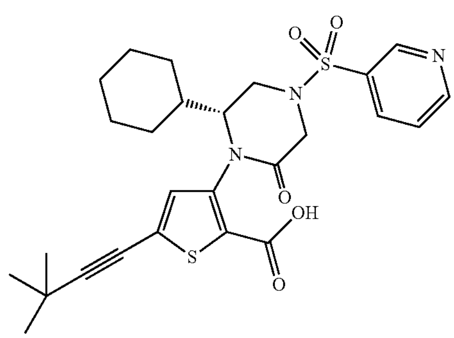 [SMILES: CC(C)(C)C#Cc1cc(N2C(=O)CN(S(=O)(=O)c3cccnc3)C[C@H]2C2CCCCC2)c(C(=O)O)s1] |

TABLE 1-continued

| Compound number | Name | Structure |
|---|---|---|
| 193 | 3-[(R)-2-Cyclohexyl-4-(1-methyl-1H-pyrazole-3-sulfonyl)-6-oxo-piperazin-1-yl]-5-(3,3-dimethyl-but-1-ynyl)-thiophene-2-carboxylic acid | 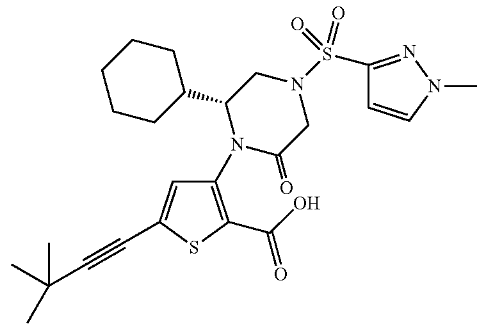 [SMILES: Cn1ccc(S(=O)(=O)N2CC(=O)N(c3cc(C#CC(C)(C)C)sc3C(=O)O)[C@H](C3CCCCC3)C2)n1] |
| 194 | 3-{(R)-2-Cyclohexyl-6-oxo-4-[6-(tetrahydro-pyran-4-ylamino)-pyridine-3-sulfonyl]-piperazin-1-yl}-5-phenyl-thiophene-2-carboxylic acid | 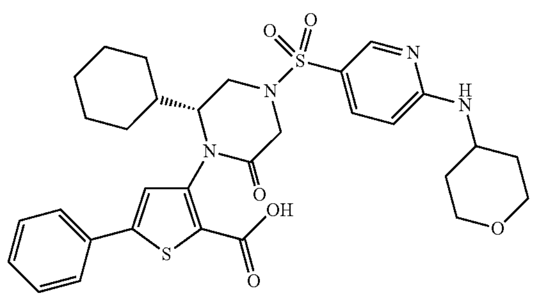 [SMILES: O=C(O)c1sc(-c2ccccc2)cc1N1C(=O)CN(S(=O)(=O)c2ccc(NC3CCOCC3)nc2)C[C@H]1C1CCCCC1] |
| 195 | 3-{(R)-2-Cyclohexyl-4-[6-((R)-3-methyl-morpholin-4-yl)-pyridine-3-sulfonyl]-6-oxo-piperazin-1-yl}-5-(4-fluoro-phenyl)-thiophene-2-carboxylic acid | 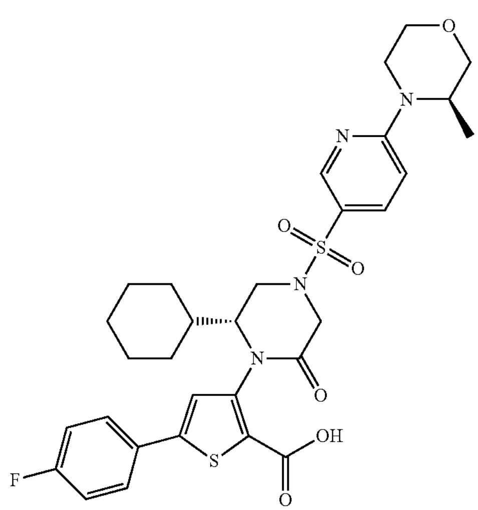 |

TABLE 1-continued

| Compound number | Name | Structure |
|---|---|---|
| 196 | 3-{(R)-2-Cyclohexyl-4-[6-(8-oxa-3-aza-bicyclo[3.2.1]oct-3-yl)-pyridine-3-sulfonyl]-6-oxo-piperazin-1-yl}-5-(4-fluoro-phenyl)-thiophene-2-carboxylic acid | 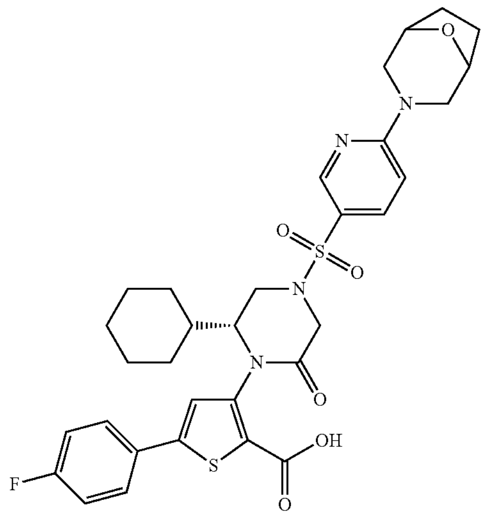 [SMILES: O=C(O)c1sc(-c2ccc(F)cc2)cc1N1C(=O)CN(S(=O)(=O)c2ccc(N3CC4CCC(C3)O4)nc2)C[C@H]1C1CCCCC1] |
| 197 | 3-{(R)-2-Cyclohexyl-4-[6-((R)-3-methyl-morpholin-4-yl)-pyridine-3-sulfonyl]-6-oxo-piperazin-1-yl}-5-p-tolyl-thiophene-2-carboxylic acid | 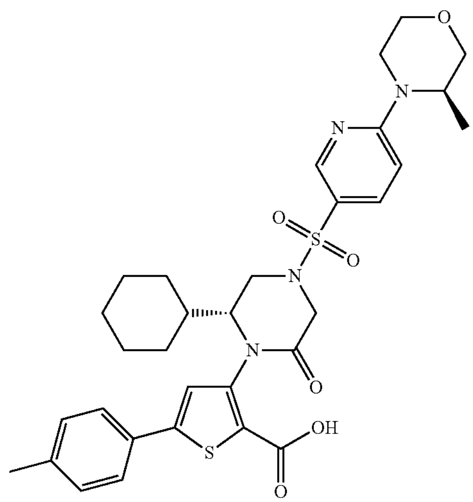 |
| 198 | 3-{(R)-2-Cyclohexyl-4-[6-(8-oxa-3-aza-bicyclo[3.2.1]oct-3-yl)-pyridine-3-sulfonyl]-6-oxo-piperazin-1-yl}-5-p-tolyl-thiophene-2-carboxylic acid | 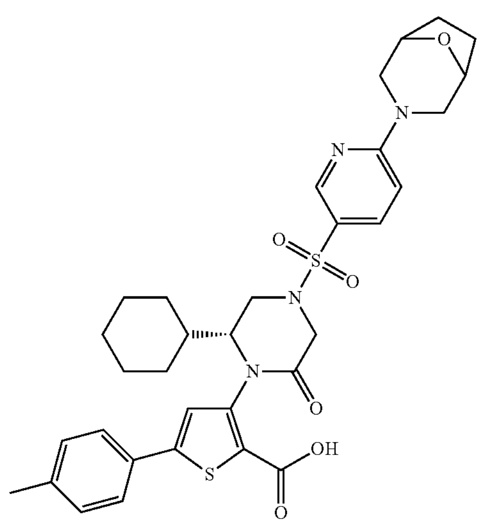 [SMILES: Cc1ccc(-c2cc(N3C(=O)CN(S(=O)(=O)c4ccc(N5CC6CCC(C5)O6)nc4)C[C@H]3C3CCCCC3)c(C(=O)O)s2)cc1] |

TABLE 1-continued

| Compound number | Name | Structure |
|---|---|---|
| 199 | 5-(4-Chlorophenyl)-3-[(R)-2-cyclohexyl-4-(6-morpholin-4-yl-pyridine-3-sulfonyl)-6-oxo-piperazin-1-yl]-thiophene-2-carboxylic acid | 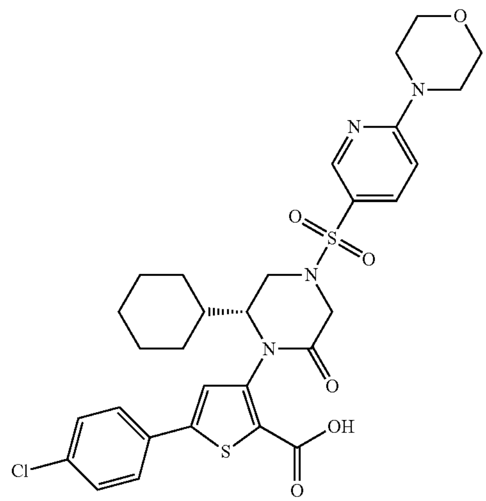 [SMILES: O=C(O)c1sc(-c2ccc(Cl)cc2)cc1N1C(=O)CN(S(=O)(=O)c2ccc(N3CCOCC3)nc2)C[C@H]1C1CCCCC1] |
| 200 | 5-(4-Chlorophenyl)-3-[(R)-2-cyclohexyl-4-(6-[1,4]oxazepan-4-yl-pyridine-3-sulfonyl)-6-oxo-piperazin-1-yl]-thiophene-2-carboxylic acid | 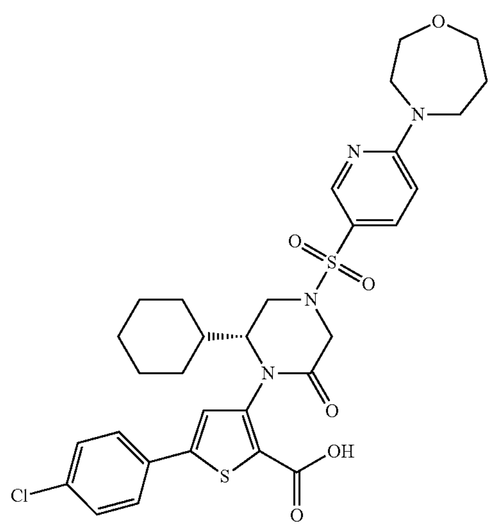 [SMILES: O=C(O)c1sc(-c2ccc(Cl)cc2)cc1N1C(=O)CN(S(=O)(=O)c2ccc(N3CCCOCC3)nc2)C[C@H]1C1CCCCC1] |
| 201 | 5-(4-Chlorophenyl)-3-{(R)-2-((R)-2-methyl-pyrrolidin-1-yl)-pyridine-3-sulfonyl]-6-oxo-piperazin-1-yl}-thiophene-2-carboxylic acid | 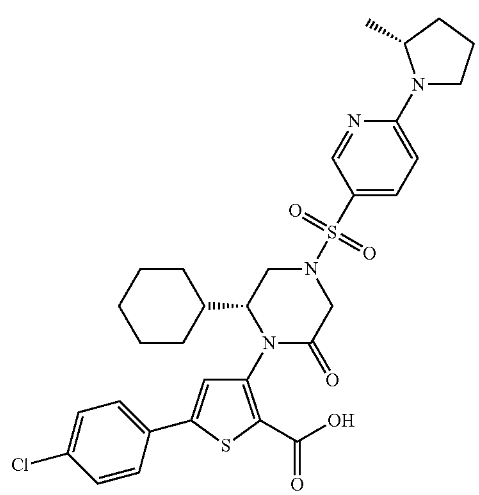 [SMILES: C[C@@H]1CCCN1c1ccc(S(=O)(=O)N2CC(=O)N(c3cc(-c4ccc(Cl)cc4)sc3C(=O)O)[C@H](C3CCCCC3)C2)cn1] |

TABLE 1-continued

| Compound number | Name | Structure |
|---|---|---|
| 202 | 3-((R)-2-Cyclohexyl-4-{6-[4-(4-methyl-piperazine-1-carbonyl)-phenyl]-pyridine-3-sulfonyl}-6-oxo-piperazin-1-yl)-5-phenyl-thiophene-2-carboxylic acid | Chiral |
| 203 | 3-{(R)-2-Cyclohexyl-4-[6-(4-dimethylamino-phenyl)-pyridine-3-sulfonyl]-6-oxo-piperazin-1-yl}-5-phenyl-thiophene-2-carboxylic acid | 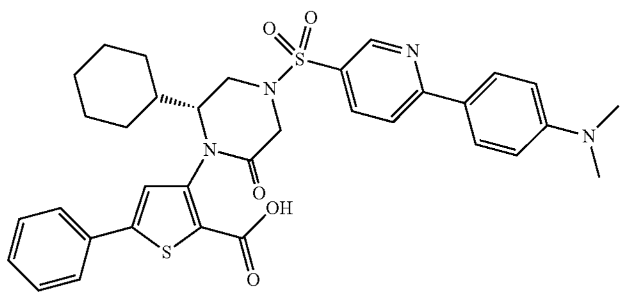 [SMILES: CN(C)c1ccc(-c2ccc(S(=O)(=O)N3CC(=O)N(c4cc(-c5ccccc5)sc4C(=O)O)[C@H](C4CCCCC4)C3)cn2)cc1] |
| 204 | 3-[(R)-2-Cyclohexyl-4-(4'-methoxy-[2,3']bipyridinyl-5-sulfonyl)-6-oxo-piperazin-1-yl]-5-phenyl-thiophene-2-carboxylic acid | 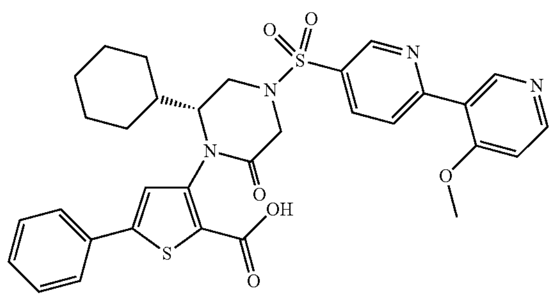 [SMILES: COc1ccncc1-c1ccc(S(=O)(=O)N2CC(=O)N(c3cc(-c4ccccc4)sc3C(=O)O)[C@H](C3CCCCC3)C2)cn1] |
| 205 | 3-{(R)-2-Cyclohexyl-4-[6-(2,4-difluoro-phenyl)-pyridine-3-sulfonyl]-6-oxo-piperazin-1-yl}-5-phenyl-thiophene-2-carboxylic acid | 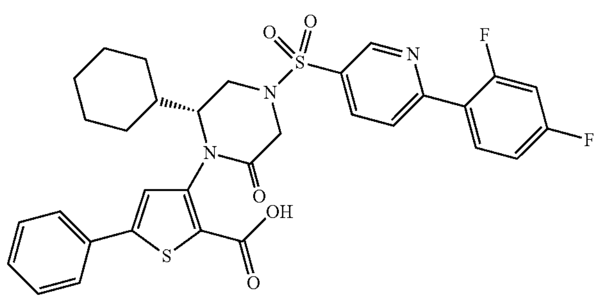 [SMILES: O=C(O)c1sc(-c2ccccc2)cc1N1C(=O)CN(S(=O)(=O)c2ccc(-c3ccc(F)cc3F)nc2)C[C@H]1C1CCCCC1] |
| 206 | 3-[(R)-2-Cyclohexyl-6-oxo-4-(6-pyrimidin-5-yl-pyridine-3-sulfonyl)-piperazin-1-yl]-5-phenyl-thiophene-2-carboxylic acid | Chiral |

TABLE 1-continued

| Compound number | Name | Structure |
|---|---|---|
| 207 | 3-[(R)-4-([2,4']Bipyridinyl-5-sulfonyl)-2-cyclohexyl-6-oxo-piperazin-1-yl]-5-[(E)-((Z)-1-propenyl)-buta-1,3-dienyl]-thiophene-2-carboxylic acid | 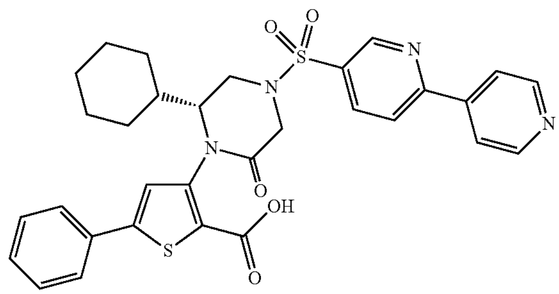 [SMILES: O=C(O)c1sc(-c2ccccc2)cc1N1C(=O)CN(S(=O)(=O)c2ccc(-c3ccncc3)nc2)C[C@H]1C1CCCCC1] |
| 208 | 3-{(R)-2-Cyclohexyl-4-[6-(4-morpholin-4-ylmethyl-phenyl)-pyridine-3-sulfonyl]-6-oxo-piperazin-1-yl}-5-phenyl-thiophene-2-carboxylic acid | 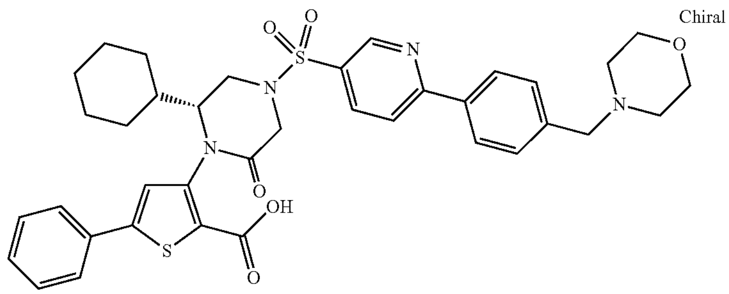 |
| 209 | 3-{(R)-2-Cyclohexyl-6-oxo-4-[6-(2H-pyrazol-3-yl)-pyridine-3-sulfonyl]-piperazin-1-yl}-5-phenyl-thiophene-2-carboxylic acid | 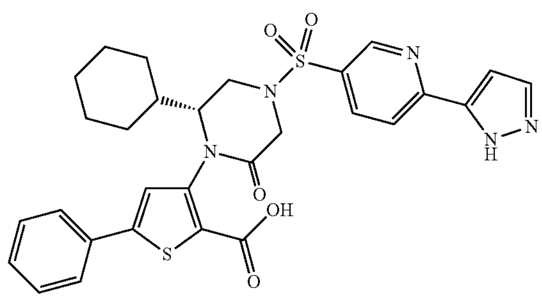 [SMILES: O=C(O)c1sc(-c2ccccc2)cc1N1C(=O)CN(S(=O)(=O)c2ccc(-c3ccn[nH]3)nc2)C[C@H]1C1CCCCC1] |
| 210 | 3-{(R)-4-[6-(5-Carboxy-thiophen-2-yl)-pyridine-3-sulfonyl]-2-cyclohexyl-6-oxo-piperazin-1-yl}-5-phenyl-thiophene-2-carboxylic acid | 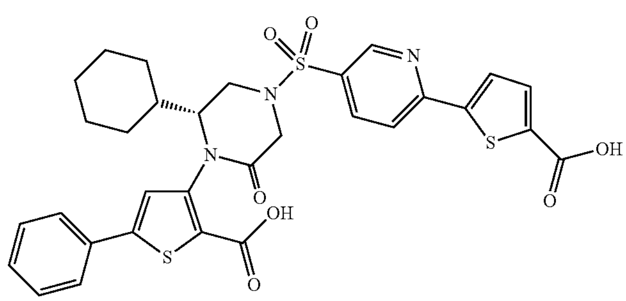 [SMILES: O=C(O)c1ccc(-c2ccc(S(=O)(=O)N3CC(=O)N(c4cc(-c5ccccc5)sc4C(=O)O)[C@H](C4CCCCC4)C3)cn2)s1] |
| 211 | 3-{(R)-2-Cyclohexyl-4-[6-(2-methyl-furan-3-yl)-pyridine-3-sulfonyl]-6-oxo-piperazin-1-yl}-5-phenyl-thiophene-2-carboxylic acid | 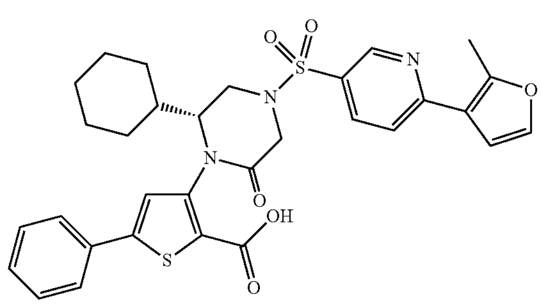 [SMILES: Cc1occc1-c1ccc(S(=O)(=O)N2CC(=O)N(c3cc(-c4ccccc4)sc3C(=O)O)[C@H](C3CCCCC3)C2)cn1] |

TABLE 1-continued

| Compound number | Name | Structure |
|---|---|---|
| 212 | 3-{(R)-2-Cyclohexyl-4-[6-(3,4-dihydro-2H-benzo[b][1,4]dioxepin-7-yl)-pyridine-3-sulfonyl]-6-oxo-piperazin-1-yl}-5-phenyl-thiophene-2-carboxylic acid | 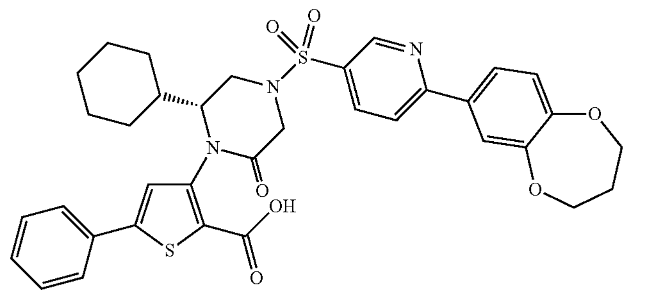 [SMILES: O=C(O)c1sc(-c2ccccc2)cc1N1C(=O)CN(S(=O)(=O)c2ccc(-c3ccc4c(c3)OCCCO4)nc2)C[C@H]1C1CCCCC1] |
| 213 | 3-{(R)-4-[6-(2-Cyano-phenyl)-pyridine-3-sulfonyl]-2-cyclohexyl-6-oxo-piperazin-1-yl}-5-phenyl-thiophene-2-carboxylic acid | 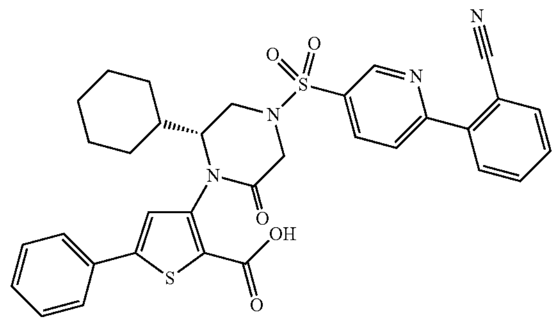 [SMILES: N#Cc1ccccc1-c1ccc(S(=O)(=O)N2CC(=O)N(c3cc(-c4ccccc4)sc3C(=O)O)[C@H](C3CCCCC3)C2)cn1] |
| 214 | 3-[(R)-4-([2,3']Bipyridinyl-5-sulfonyl)-2-cyclohexyl-6-oxo-piperazin-1-yl]-5-phenyl-thiophene-2-carboxylic acid | 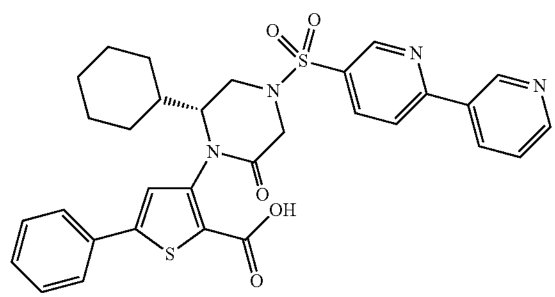 |
| 215 | 3-[(R)-2-Cyclohexyl-4-(6-cyclopent-1-enyl-pyridine-3-sulfonyl)-6-oxo-piperazin-1-yl]-5-phenyl-thiophene-2-carboxylic acid | 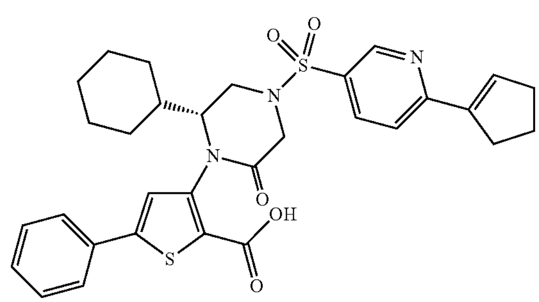 [SMILES: O=C(O)c1sc(-c2ccccc2)cc1N1C(=O)CN(S(=O)(=O)c2ccc(C3=CCCC3)nc2)C[C@H]1C1CCCCC1] |
| 216 | 3-{(R)-2-Cyclohexyl-4-[6-(8-oxa-3-aza-bicyclo[3.2.1]oct-3-yl)-pyridine-3-sulfonyl]-6-oxo-piperazin-1-yl}-5-phenyl-thiophene-2-carboxylic acid | 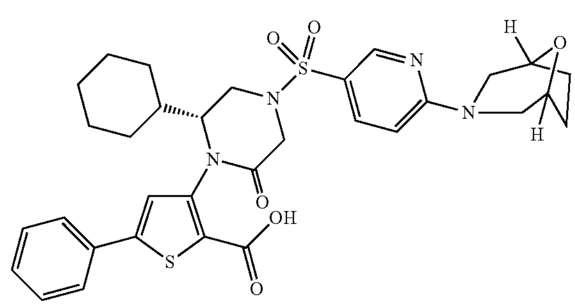 [SMILES: O=C(O)c1sc(-c2ccccc2)cc1N1C(=O)CN(S(=O)(=O)c2ccc(N3CC4CCC(C3)O4)nc2)C[C@H]1C1CCCCC1] |

TABLE 1-continued

| Compound number | Name | Structure |
|---|---|---|
| 217 | 3-{(R)-2-Cyclohexyl-4-[6-(2-oxa-5-azabicyclo[2.2.1]hept-5-yl)-pyridine-3-sulfonyl]-6-oxo-piperazin-1-yl}-5-phenyl-thiophene-2-carboxylic acid | 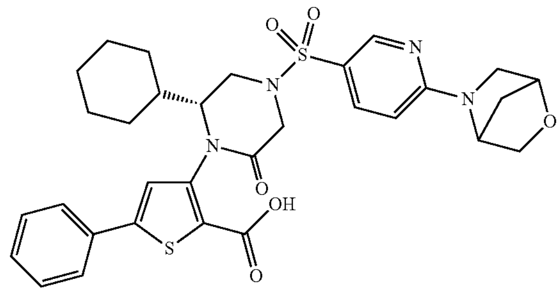 [SMILES: O=C(O)c1sc(-c2ccccc2)cc1N1C(=O)CN(S(=O)(=O)c2ccc(N3CC4CC3CO4)nc2)C[C@H]1C1CCCCC1] |
| 218 | 3-{(R)-2-Cyclohexyl-4-[6-(2,2-diethyl-morpholin-4-yl)-pyridine-3-sulfonyl]-6-oxo-piperazin-1-yl}-5-phenyl-thiophene-2-carboxylic acid | 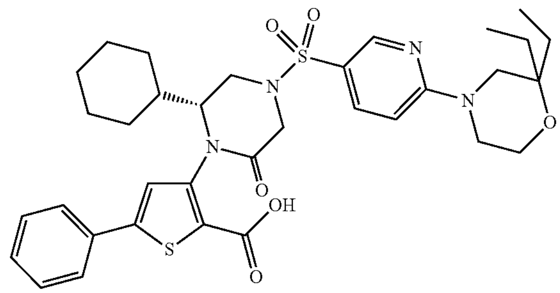 [SMILES: CCC1(CC)CN(c2ccc(S(=O)(=O)N3CC(=O)N(c4cc(-c5ccccc5)sc4C(=O)O)[C@H](C4CCCCC4)C3)cn2)CCO1] |
| 219 | 3-{(R)-2-Cyclohexyl-4-[6-(3,3-dimethyl-pyrrolidin-1-yl)-pyridine-3-sulfonyl]-6-oxo-piperazin-1-yl}-5-phenyl-thiophene-2-carboxylic acid | 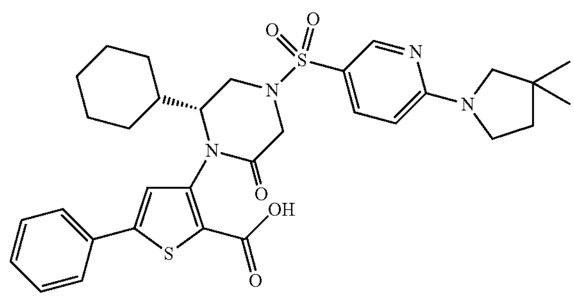 [SMILES: CC1(C)CCN(c2ccc(S(=O)(=O)N3CC(=O)N(c4cc(-c5ccccc5)sc4C(=O)O)[C@H](C4CCCCC4)C3)cn2)C1] |
| 220 | 3-(2-Cyclohexyl-5-oxo-pyrrolidin-1-yl)-5-(3,3-dimethyl-but-1-ynyl)-thiophene-2-carboxylic acid | 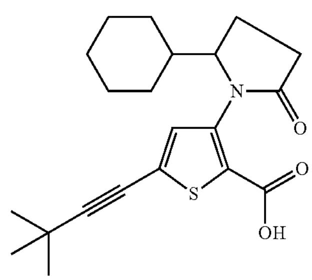 |
| 221 | 3-[(R)-2-Cyclohexyl-6-oxo-4-(propane-2-sulfonyl)-piperazin-1-yl]-5-(3,3-dimethyl-but-1-ynyl)-thiophene-2-carboxylic acid | 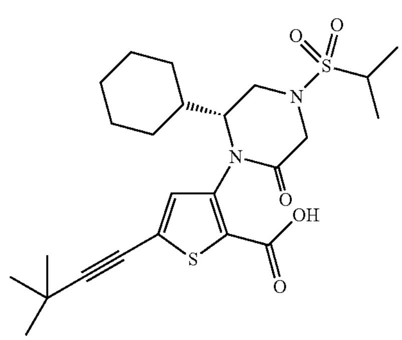 [SMILES: CC(C)S(=O)(=O)N1CC(=O)N(c2cc(C#CC(C)(C)C)sc2C(=O)O)[C@H](C2CCCCC2)C1] |

TABLE 1-continued

| Compound number | Name | Structure |
|---|---|---|
| 222 | 3-{(R)-2-Cyclohexyl-4-[6-(1-methyl-1H-pyrazol-4-yl)-pyridine-3-sulfonyl]-6-oxo-piperazin-1-yl}-5-phenyl-thiophene-2-carboxylic acid | 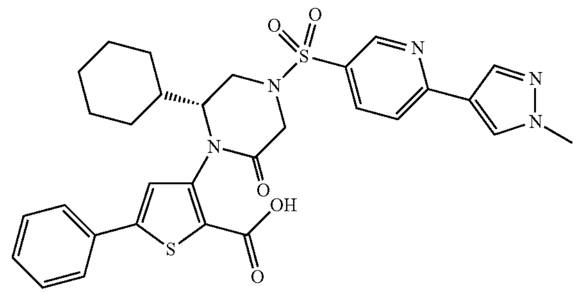 [SMILES: Cn1cc(-c2ccc(S(=O)(=O)N3CC(=O)N(c4cc(-c5ccccc5)sc4C(=O)O)[C@H](C4CCCCC4)C3)cn2)cn1] |
| 223 | 3-[(R)-2-Cyclohexyl-6-oxo-4-(4-trifluoromethoxy-benzenesulfonyl)-piperazin-1-yl]-5-(3,3-dimethyl-but-1-ynyl)-thiophene-2-carboxylic acid | 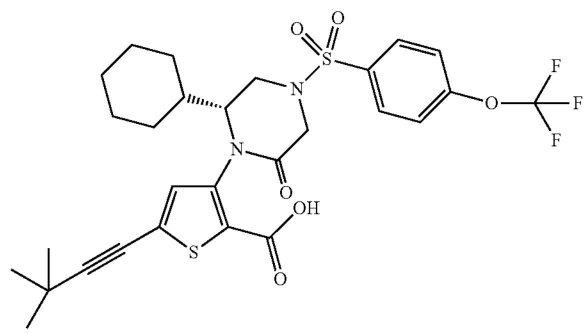 [SMILES: CC(C)(C)C#Cc1cc(N2C(=O)CN(S(=O)(=O)c3ccc(OC(F)(F)F)cc3)C[C@H]2C2CCCCC2)c(C(=O)O)s1] |
| 224 | 3-{(R)-2-Cyclohexyl-4-[6'-(4-methyl-piperazin-1-yl)-[2,3']bipyridinyl-5-sulfonyl]-6-oxo-piperazin-1-yl}-5-phenyl-thiophene-2-carboxylic acid | 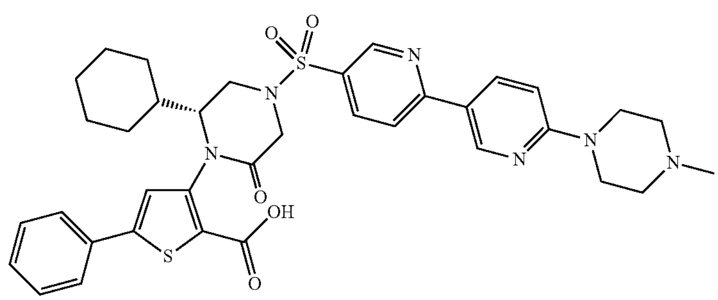 [SMILES: CN1CCN(c2ccc(-c3ccc(S(=O)(=O)N4CC(=O)N(c5cc(-c6ccccc6)sc5C(=O)O)[C@H](C5CCCCC5)C4)cn3)cn2)CC1] |
| 225 | 3-{(R)-2-Cyclohexyl-4-[6-((R)-3-methyl-morpholin-4-yl)-pyridine-3-sulfonyl]-6-oxo-piperazin-1-yl}-5-phenyl-thiophene-2-carboxylic acid | 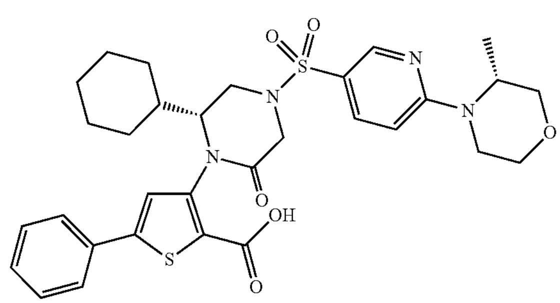 [SMILES: C[C@@H]1COCCN1c1ccc(S(=O)(=O)N2CC(=O)N(c3cc(-c4ccccc4)sc3C(=O)O)[C@H](C3CCCCC3)C2)cn1] |

TABLE 1-continued

| Compound number | Name | Structure |
|---|---|---|
| 226 | 5-(4-Chloro-phenyl)-3-{(R)-2-cyclohexyl-4-[6-((R)-3-methyl-morpholin-4-yl)-pyridine-3-sulfonyl]-6-oxo-piperazin-1-yl}-thiophene-2-carboxylic acid | 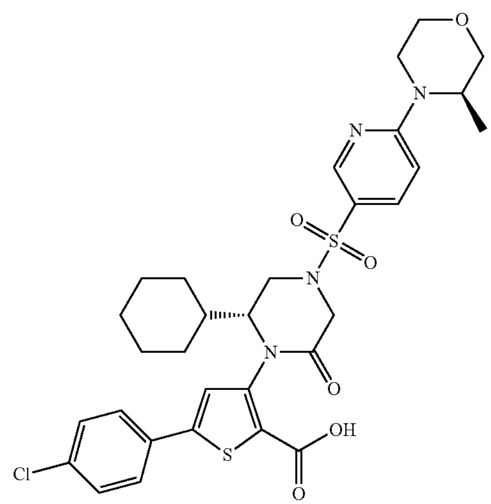 [SMILES: C[C@@H]1COCCN1c1ccc(S(=O)(=O)N2CC(=O)N(c3cc(-c4ccc(Cl)cc4)sc3C(=O)O)[C@H](C3CCCCC3)C2)cn1] |
| 227 | 5-(4-Chloro-phenyl)-3-{(R)-2-cyclohexyl-4-[6-(8-oxa-3-aza-bicyclo[3.2.1]oct-3-yl)-pyridine-3-sulfonyl]-6-oxo-piperazin-1-yl}-thiophene-2-carboxylic acid | 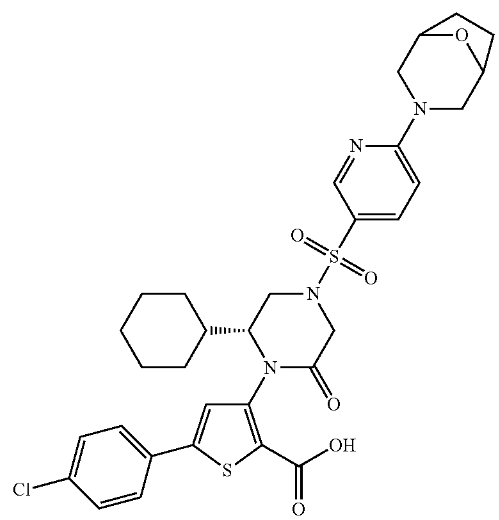 [SMILES: O=C(O)c1sc(-c2ccc(Cl)cc2)cc1N1C(=O)CN(S(=O)(=O)c2ccc(N3CC4CCC(C3)O4)nc2)C[C@H]1C1CCCCC1] |
| 228 | 3-{(R)-2-Cyclohexyl-4-[6-(2-oxa-5-aza-bicyclo[2.2.1]hept-5-yl)-pyridine-3-sulfonyl]-6-oxo-piperazin-1-yl}-5-(4-fluoro-phenyl)-thiophene-2-carboxylic acid | 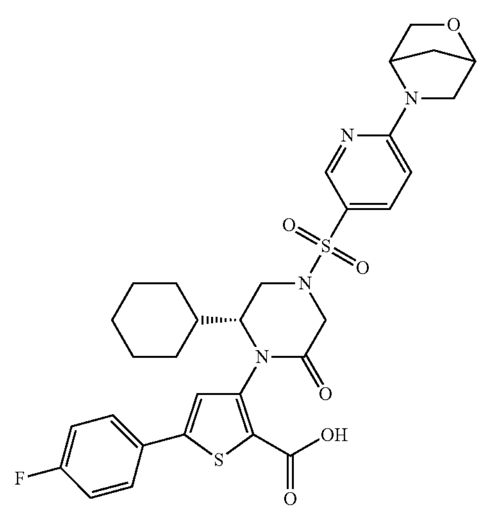 [SMILES: O=C(O)c1sc(-c2ccc(F)cc2)cc1N1C(=O)CN(S(=O)(=O)c2ccc(N3CC4CC3CO4)nc2)C[C@H]1C1CCCCC1] |

| Compound number | Name | Structure |
|---|---|---|
| 229 | 5-(4-Chloro-phenyl)-3-{(R)-2-cyclohexyl-4-[6-(2-oxa-5-aza-bicyclo[2.2.1]hept-5-yl)-pyridine-3-sulfonyl]-6-oxo-piperazin-1-yl}-thiophene-2-carboxylic acid | 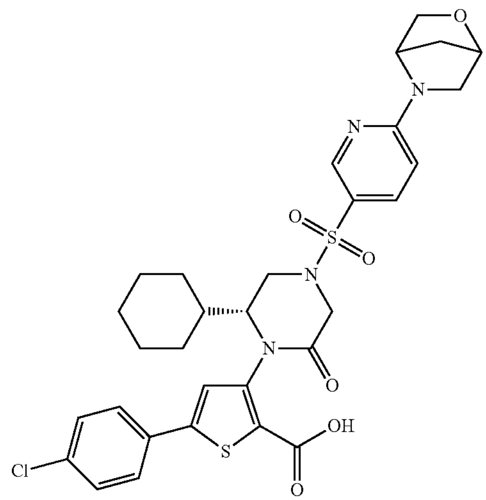 [SMILES: O=C(O)c1sc(-c2ccc(Cl)cc2)cc1N1C(=O)CN(S(=O)(=O)c2ccc(N3CC4CC3CO4)nc2)C[C@H]1C1CCCCC1] |
| 230 | 3-[(R)-2-Cyclohexyl-6-oxo-4-(6-trifluoromethyl-pyridine-3-sulfonyl)-piperazin-1-yl]-5-(3,3-dimethyl-but-1-ynyl)-thiophene-2-carboxylic acid | 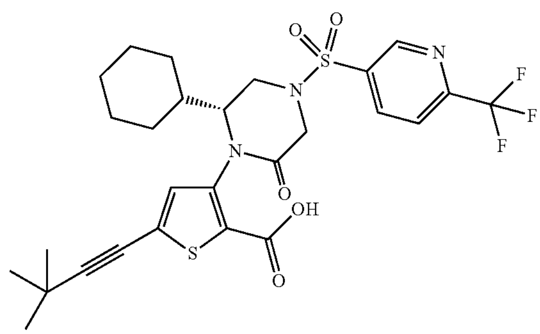 [SMILES: CC(C)(C)C#Cc1cc(N2C(=O)CN(S(=O)(=O)c3ccc(C(F)(F)F)nc3)C[C@H]2C2CCCCC2)c(C(=O)O)s1] |
| 231 | 5-(4-Chloro-phenyl)-3-[(R)-2-cyclohexyl-6-oxo-4-(4-pyrrolidin-1-yl-benzenesulfonyl)-piperazin-1-yl]-thiophene-2-carboxylic acid | 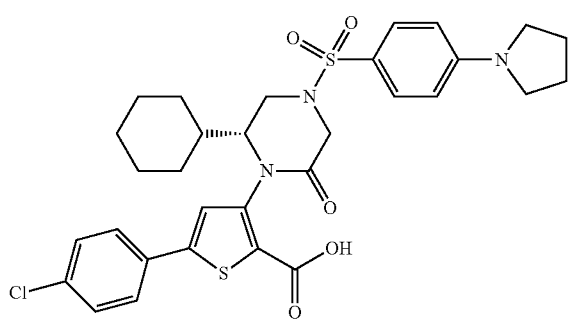 [SMILES: O=C(O)c1sc(-c2ccc(Cl)cc2)cc1N1C(=O)CN(S(=O)(=O)c2ccc(N3CCCC3)cc2)C[C@H]1C1CCCCC1] |
| 232 | 3-[(R)-2-Cyclohexyl-6-oxo-4-(6-pyrrolidin-1-yl-pyridine-3-sulfonyl)-piperazin-1-yl]-5-(4-fluoro-phenyl)-thiophene-2-carboxylic acid | 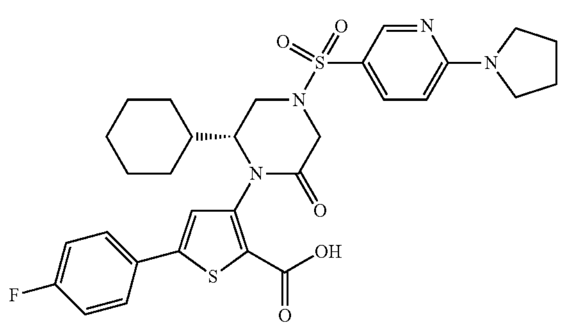 [SMILES: O=C(O)c1sc(-c2ccc(F)cc2)cc1N1C(=O)CN(S(=O)(=O)c2ccc(N3CCCC3)nc2)C[C@H]1C1CCCCC1] |

TABLE 1-continued

| Compound number | Name | Structure |
|---|---|---|
| 233 | 5-(4-Chloro-phenyl)-3-[(R)-2-cyclohexyl-6-oxo-4-(4-piperidin-1-yl-benzenesulfonyl)-piperazin-1-yl]-thiophene-2-carboxylic acid | 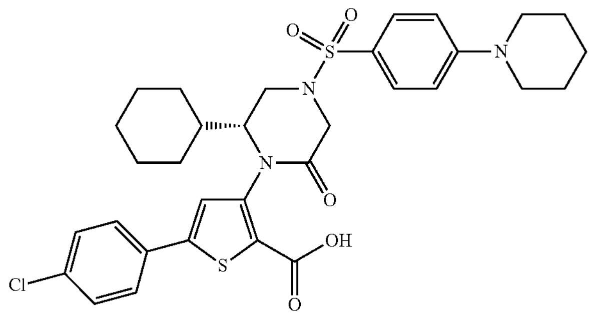 [SMILES: O=C(O)c1sc(-c2ccc(Cl)cc2)cc1N1C(=O)CN(S(=O)(=O)c2ccc(N3CCCCC3)cc2)C[C@H]1C1CCCCC1] |
| 234 | 5-(4-Chloro-phenyl)-3-{(R)-2-cyclohexyl-4-[4-((R)-2-methyl-pyrrolidin-1-yl)-benzenesulfonyl]-6-oxo-piperazin-1-yl}-thiophene-2-carboxylic acid | 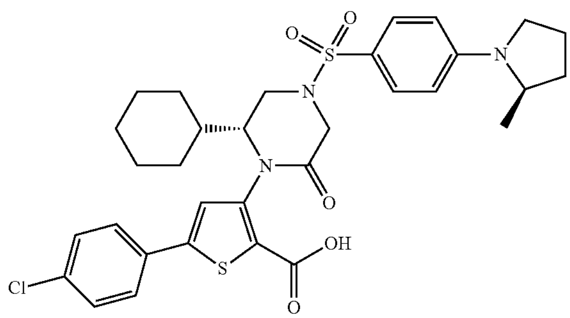 [SMILES: C[C@@H]1CCCN1c1ccc(S(=O)(=O)N2CC(=O)N(c3cc(-c4ccc(Cl)cc4)sc3C(=O)O)[C@H](C3CCCCC3)C2)cc1] |
| 235 | 3-[(R)-2-Cyclohexyl-6-oxo-4-(3,4,5,6-tetrahydro-2H-[1,2']bipyridinyl-5'-sulfonyl)-piperazin-1-yl]-5-(4-fluoro-phenyl)-thiophene-2-carboxylic acid | 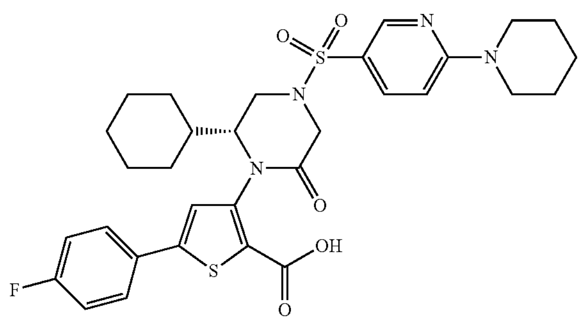 [SMILES: O=C(O)c1sc(-c2ccc(F)cc2)cc1N1C(=O)CN(S(=O)(=O)c2ccc(N3CCCCC3)nc2)C[C@H]1C1CCCCC1] |
| 236 | 3-((R)-3-Cyclohexyl-5-oxo-morpholin-4-yl)-5-(3,3-dimethyl-but-1-ynyl)-thiophene-2-carboxylic acid | 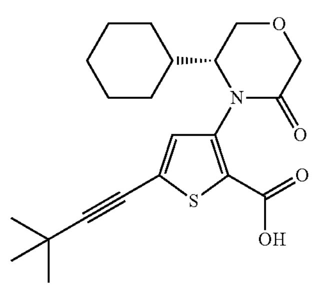 [SMILES: CC(C)(C)C#Cc1cc(N2C(=O)COC[C@H]2C2CCCCC2)c(C(=O)O)s1] |
| 237 | 3-((4S,5R)-5-Cyclohexyl-3,4-dimethyl-2-oxo-imidazolidin-1-yl)-5-(3,3-dimethyl-but-1-ynyl)-thiophene-2-carboxylic acid | 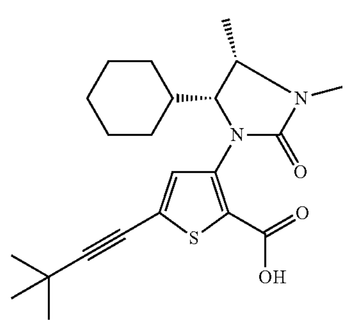 [SMILES: C[C@H]1[C@@H](C2CCCCC2)N(c2cc(C#CC(C)(C)C)sc2C(=O)O)C(=O)N1C] |

TABLE 1-continued

| Compound number | Name | Structure |
|---|---|---|
| 238 | 3-[(R)-4-(4-Cyano-benzenesulfonyl)-2-cyclohexyl-6-oxo-piperazin-1-yl]-5-(3,3-dimethyl-but-1-ynyl)-thiophene-2-carboxylic acid | 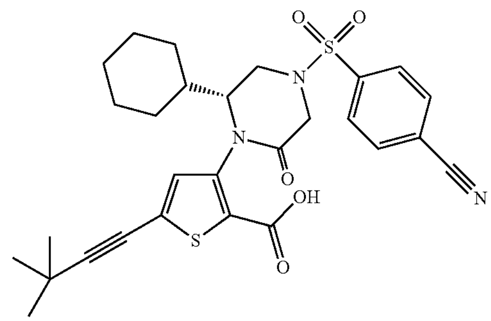 [SMILES: CC(C)(C)C#Cc1cc(N2C(=O)CN(S(=O)(=O)c3ccc(C#N)cc3)C[C@H]2C2CCCCC2)c(C(=O)O)s1] |
| 239 | 3-[(R)-2-Cyclohexyl-4-(3-fluoro-benzenesulfonyl)-6-oxo-piperazin-1-yl]-5-(3,3-dimethyl-but-1-ynyl)-thiophene-2-carboxylic acid | 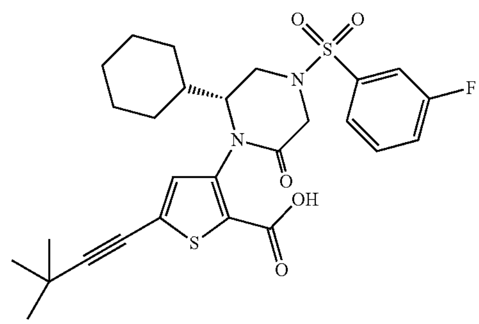 [SMILES: CC(C)(C)C#Cc1cc(N2C(=O)CN(S(=O)(=O)c3cccc(F)c3)C[C@H]2C2CCCCC2)c(C(=O)O)s1] |
| 240 | 3-[(R)-2-Cyclohexyl-4-(5-methyl-isoxazole-4-sulfonyl)-6-oxo-piperazin-1-yl]-5-(3,3-dimethyl-but-1-ynyl)-thiophene-2-carboxylic acid | 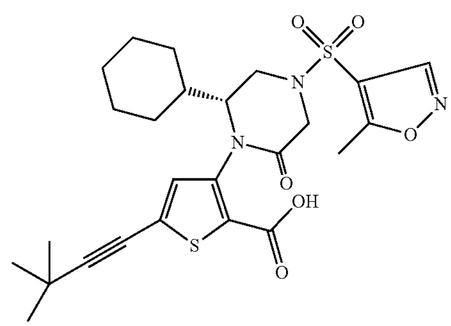 [SMILES: Cc1oncc1S(=O)(=O)N1CC(=O)N(c2cc(C#CC(C)(C)C)sc2C(=O)O)[C@H](C2CCCCC2)C1] |
| 241 | 3-[(R)-2-Cyclohexyl-6-oxo-4-(1H-pyrazole-4-sulfonyl)-piperazin-1-yl]-5-(3,3-dimethyl-but-1-ynyl)-thiophene-2-carboxylic acid | 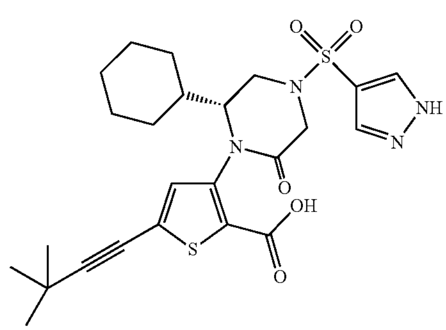 [SMILES: CC(C)(C)C#Cc1cc(N2C(=O)CN(S(=O)(=O)c3cn[nH]c3)C[C@H]2C2CCCCC2)c(C(=O)O)s1] |

TABLE 1-continued

| Compound number | Name | Structure |
|---|---|---|
| 242 | 3-[(R)-4-(3-Chloro-benzenesulfonyl)-2-cyclohexyl-6-oxo-piperazin-1-yl]-5-(3,3-dimethyl-but-1-ynyl)-thiophene-2-carboxylic acid | 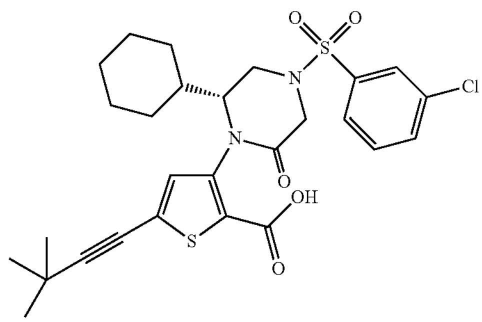 [SMILES: CC(C)(C)C#Cc1cc(N2C(=O)CN(S(=O)(=O)c3cccc(Cl)c3)C[C@H]2C2CCCCC2)c(C(=O)O)s1] |
| 243 | 3-[(R)-2-Cyclohexyl-4-(4-fluoro-benzenesulfonyl)-6-oxo-piperazin-1-yl]-5-(3,3-dimethyl-but-1-ynyl)-thiophene-2-carboxylic acid | 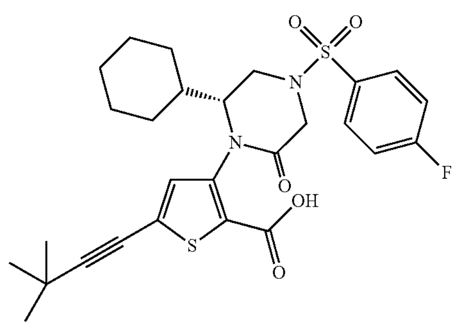 [SMILES: CC(C)(C)C#Cc1cc(N2C(=O)CN(S(=O)(=O)c3ccc(F)cc3)C[C@H]2C2CCCCC2)c(C(=O)O)s1] |
| 244 | 3-[(R)-2-Cyclohexyl-4-(2,4-dimethyl-thiazole-5-sulfonyl)-6-oxo-piperazin-1-yl]-5-(3,3-dimethyl-but-1-ynyl)-thiophene-2-carboxylic acid | 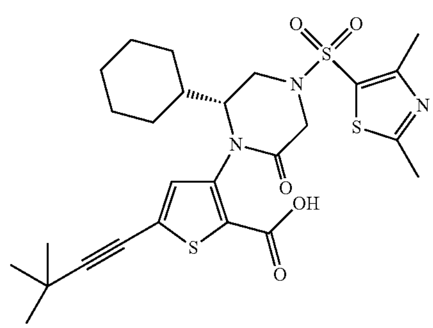 [SMILES: Cc1nc(C)c(S(=O)(=O)N2CC(=O)N(c3cc(C#CC(C)(C)C)sc3C(=O)O)[C@H](C3CCCCC3)C2)s1] |
| 245 | 3-((R)-2-Cyclohexyl-4-cyclopropanesulfonyl-6-oxo-piperazin-1-yl)-5-(3,3-dimethyl-but-1-ynyl)-thiophene-2-carboxylic acid | 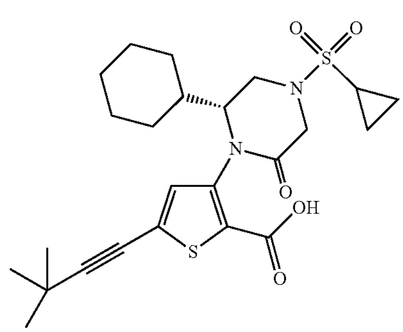 [SMILES: CC(C)(C)C#Cc1cc(N2C(=O)CN(S(=O)(=O)C3CC3)C[C@H]2C2CCCCC2)c(C(=O)O)s1] |

TABLE 1-continued

| Compound number | Name | Structure |
|---|---|---|
| 246 | 3-[(R)-2-Cyclohexyl-4-(3-fluoro-4-methoxy-benzenesulfonyl)-6-oxo-piperazin-1-yl]-5-(3,3-dimethyl-but-1-ynyl)-thiophene-2-carboxylic acid | 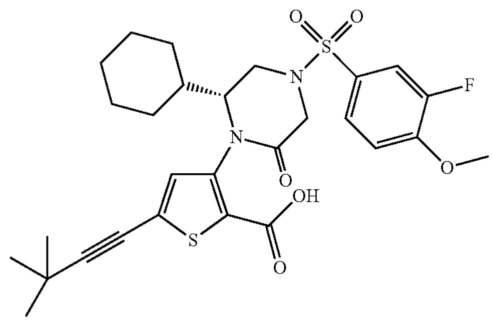 [SMILES: COc1ccc(S(=O)(=O)N2CC(=O)N(c3cc(C#CC(C)(C)C)sc3C(=O)O)[C@H](C3CCCCC3)C2)cc1F] |
| 247 | 3-[(R)-2-Cyclohexyl-4-(1H-imidazole-4-sulfonyl)-6-oxo-piperazin-1-yl]-5-(3,3-dimethyl-but-1-ynyl)-thiophene-2-carboxylic acid | 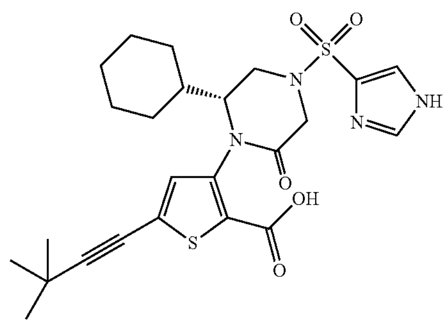 [SMILES: CC(C)(C)C#Cc1cc(N2C(=O)CN(S(=O)(=O)c3c[nH]cn3)C[C@H]2C2CCCCC2)c(C(=O)O)s1] |
| 248 | 3-[(R)-2-Cyclohexyl-4-(1,2-dimethyl-1H-imidazole-4-sulfonyl)-6-oxo-piperazin-1-yl]-5-(3,3-dimethyl-but-1-ynyl)-thiophene-2-carboxylic acid | 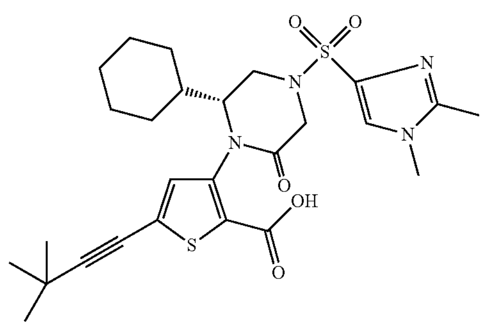 [SMILES: Cc1nc(S(=O)(=O)N2CC(=O)N(c3cc(C#CC(C)(C)C)sc3C(=O)O)[C@H](C3CCCCC3)C2)cn1C] |
| 249 | 3-[(R)-2-Cyclohexyl-6-oxo-4-(2-trifluoromethoxy-benzenesulfonyl)-piperazin-1-yl]-5-(3,3-dimethyl-but-1-ynyl)-thiophene-2-carboxylic acid | 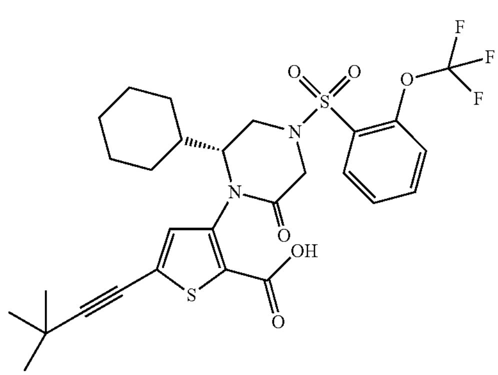 [SMILES: CC(C)(C)C#Cc1cc(N2C(=O)CN(S(=O)(=O)c3ccccc3OC(F)(F)F)C[C@H]2C2CCCCC2)c(C(=O)O)s1] |

TABLE 1-continued

| Compound number | Name | Structure |
|---|---|---|
| 250 | 3-[(R)-2-Cyclohexyl-6-oxo-4-(4-trifluoromethyl-benzenesulfonyl)-piperazin-1-yl]-5-(3,3-dimethyl-but-1-ynyl)-thiophene-2-carboxylic acid | 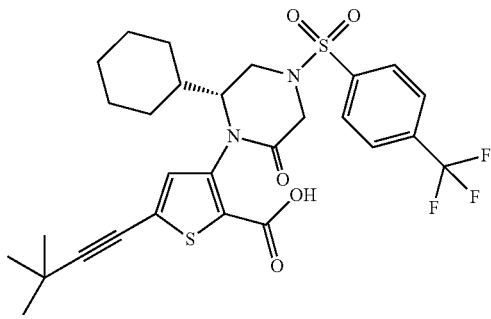 [SMILES: CC(C)(C)C#Cc1cc(N2C(=O)CN(S(=O)(=O)c3ccc(C(F)(F)F)cc3)C[C@H]2C2CCCCC2)c(C(=O)O)s1] |
| 251 | 3-[(R)-2-Cyclohexyl-4-(2,6-difluoro-benzenesulfonyl)-6-oxo-piperazin-1-yl]-5-(3,3-dimethyl-but-1-ynyl)-thiophene-2-carboxylic acid | 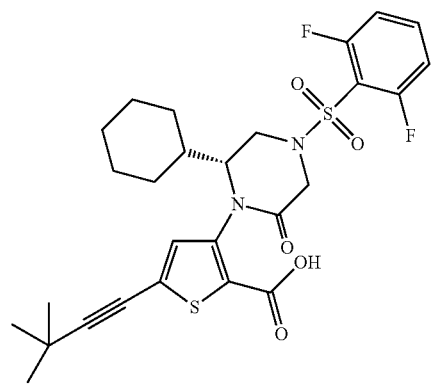 [SMILES: CC(C)(C)C#Cc1cc(N2C(=O)CN(S(=O)(=O)c3c(F)cccc3F)C[C@H]2C2CCCCC2)c(C(=O)O)s1] |
| 252 | 3-[(R)-2-Cyclohexyl-6-oxo-4-(2-oxo-2,3-dihydro-benzooxazole-5-sulfonyl)-piperazin-1-yl]-5-(3,3-dimethyl-but-1-ynyl)-thiophene-2-carboxylic acid | 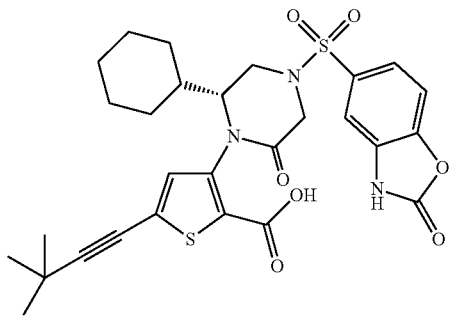 [SMILES: CC(C)(C)C#Cc1cc(N2C(=O)CN(S(=O)(=O)c3ccc4oc(=O)[nH]c4c3)C[C@H]2C2CCCCC2)c(C(=O)O)s1] |
| 253 | 3-[(R)-2-Cyclohexyl-4-(4-methylcarbamoyl-benzenesulfonyl)-6-oxo-piperazin-1-yl]-5-(3,3-dimethyl-but-1-ynyl)-thiophene-2-carboxylic acid | 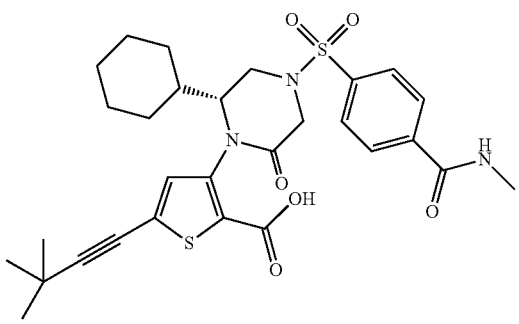 [SMILES: CNC(=O)c1ccc(S(=O)(=O)N2CC(=O)N(c3cc(C#CC(C)(C)C)sc3C(=O)O)[C@H](C3CCCCC3)C2)cc1] |

TABLE 1-continued

| Compound number | Name | Structure |
|---|---|---|
| 254 | 3-[(R)-2-Cyclohexyl-4-(2-methyl-2H-pyrazole-3-sulfonyl)-6-oxo-piperazin-1-yl]-5-(3,3-dimethyl-but-1-ynyl)-thiophene-2-carboxylic acid | 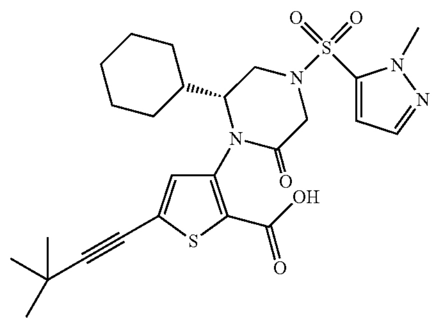 [SMILES: Cn1nccc1S(=O)(=O)N1CC(=O)N(c2cc(C#CC(C)(C)C)sc2C(=O)O)[C@H](C2CCCCC2)C1] |
| 255 | 3-[(R)-2-Cyclohexyl-4-(2,3-dimethyl-3H-imidazole-4-sulfonyl)-6-oxo-piperazin-1-yl]-5-(3,3-dimethyl-but-1-ynyl)-thiophene-2-carboxylic acid | 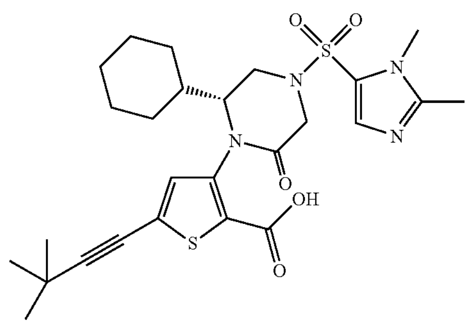 [SMILES: Cc1ncc(S(=O)(=O)N2CC(=O)N(c3cc(C#CC(C)(C)C)sc3C(=O)O)[C@H](C3CCCCC3)C2)n1C] |
| 256 | 3-[(R)-2-Cyclohexyl-4-(4-ethyl-benzenesulfonyl)-6-oxo-piperazin-1-yl]-5-(3,3-dimethyl-but-1-ynyl)-thiophene-2-carboxylic acid | 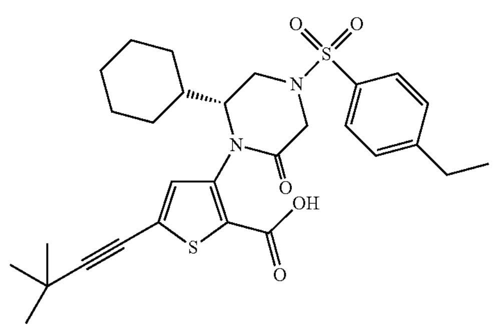 [SMILES: CCc1ccc(S(=O)(=O)N2CC(=O)N(c3cc(C#CC(C)(C)C)sc3C(=O)O)[C@H](C3CCCCC3)C2)cc1] |
| 257 | 3-[(R)-2-Cyclohexyl-4-(3-methoxy-benzenesulfonyl)-6-oxo-piperazin-1-yl]-5-(3,3-dimethyl-but-1-ynyl)-thiophene-2-carboxylic acid | 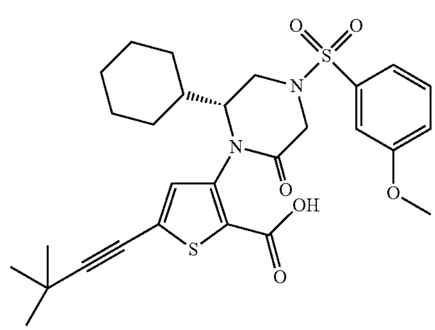 [SMILES: COc1cccc(S(=O)(=O)N2CC(=O)N(c3cc(C#CC(C)(C)C)sc3C(=O)O)[C@H](C3CCCCC3)C2)c1] |

TABLE 1-continued

| Compound number | Name | Structure |
|---|---|---|
| 258 | 3-[(R)-2-Cyclohexyl-4-(2-methoxy-benzenesulfonyl)-6-oxo-piperazin-1-yl]-5-(3,3-dimethyl-but-1-ynyl)-thiophene-2-carboxylic acid | 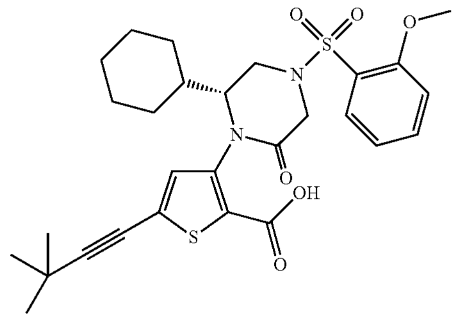 [SMILES: COc1ccccc1S(=O)(=O)N1CC(=O)N(c2cc(C#CC(C)(C)C)sc2C(=O)O)[C@H](C2CCCCC2)C1] |
| 259 | 3-[(R)-4-(3-Cyano-benzenesulfonyl)-2-cyclohexyl-6-oxo-piperazin-1-yl]-5-(3,3-dimethyl-but-1-ynyl)-thiophene-2-carboxylic acid | 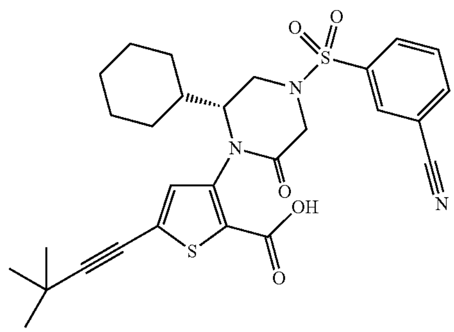 [SMILES: CC(C)(C)C#Cc1cc(N2C(=O)CN(S(=O)(=O)c3cccc(C#N)c3)C[C@H]2C2CCCCC2)c(C(=O)O)s1] |
| 260 | 3-[(R)-2-Cyclohexyl-4-(1,3-dimethyl-1H-pyrazole-4-sulfonyl)-6-oxo-piperazin-1-yl]-5-(3,3-dimethyl-but-1-ynyl)-thiophene-2-carboxylic acid | 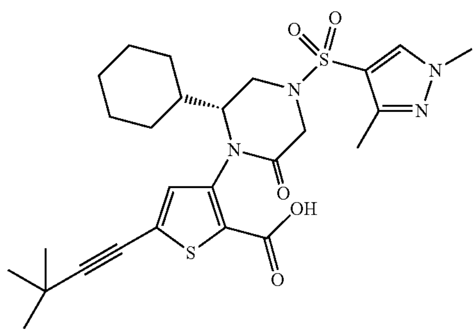 [SMILES: Cc1nn(C)cc1S(=O)(=O)N1CC(=O)N(c2cc(C#CC(C)(C)C)sc2C(=O)O)[C@H](C2CCCCC2)C1] |
| 261 | 3-[(R)-2-Cyclohexyl-6-oxo-4-(3-pyrrol-1-yl-benzyl)-piperazin-1-yl]-5-phenyl-thiophene-2-carboxylic acid | 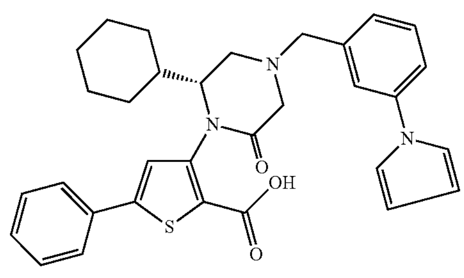 [SMILES: O=C(O)c1sc(-c2ccccc2)cc1N1C(=O)CN(Cc2cccc(-n3cccc3)c2)C[C@H]1C1CCCCC1] |
| 262 | 3-{(R)-2-Cyclohexyl-6-oxo-4-[4-(2-oxo-pyrrolidin-1-yl)-benzyl]-piperazin-1-yl}-5-phenyl-thiophene-2-carboxylic acid | 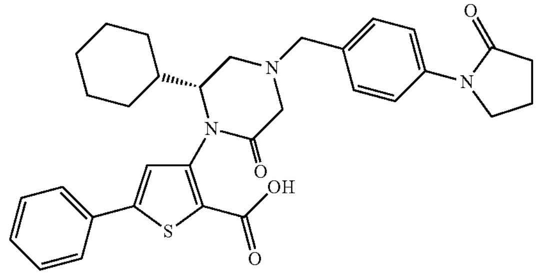 [SMILES: O=C(O)c1sc(-c2ccccc2)cc1N1C(=O)CN(Cc2ccc(N3CCCC3=O)cc2)C[C@H]1C1CCCCC1] |

TABLE 1-continued

| Compound number | Name | Structure |
|---|---|---|
| 263 | 3-[(R)-2-Cyclohexyl-4-(3-methyl-benzyl)-6-oxo-piperazin-1-yl]-5-phenyl-thiophene-2-carboxylic acid | 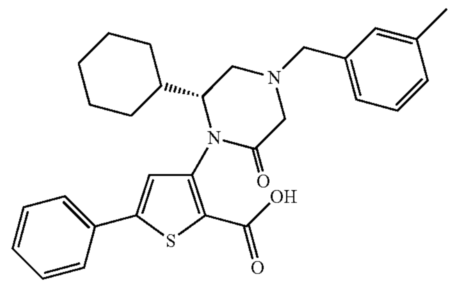 [SMILES: Cc1cccc(CN2CC(=O)N(c3cc(-c4ccccc4)sc3C(=O)O)[C@H](C3CCCCC3)C2)c1] |
| 264 | 3-[(R)-2-Cyclohexyl-4-(2,6-dimethyl-benzyl)-6-oxo-piperazin-1-yl]-5-phenyl-thiophene-2-carboxylic acid | 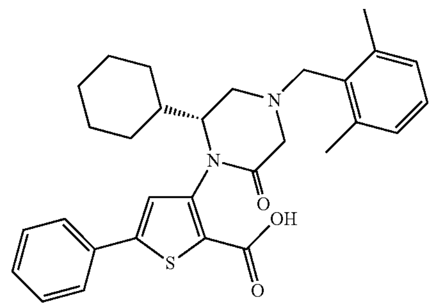 [SMILES: Cc1cccc(C)c1CN1CC(=O)N(c2cc(-c3ccccc3)sc2C(=O)O)[C@H](C2CCCCC2)C1] |
| 265 | 3-((R)-2-Cyclohexyl-4-cyclohexylmethyl-6-oxo-piperazin-1-yl)-5-phenyl-thiophene-2-carboxylic acid | 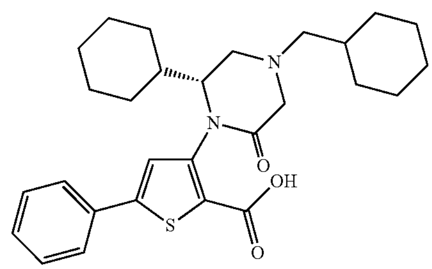 [SMILES: O=C(O)c1sc(-c2ccccc2)cc1N1C(=O)CN(CC2CCCCC2)C[C@H]1C1CCCCC1] |
| 266 | 3-[(R)-2-Cyclohexyl-4-(3-fluoro-2-morpholin-4-yl-benzyl)-6-oxo-piperazin-1-yl]-5-phenyl-thiophene-2-carboxylic acid | 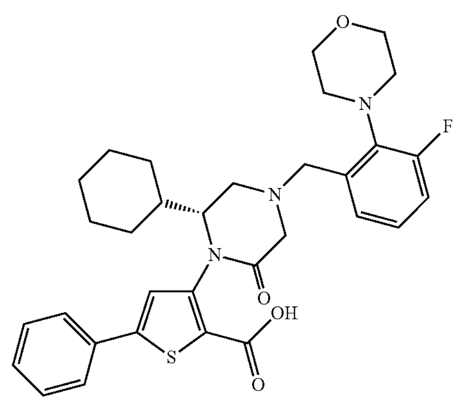 [SMILES: O=C(O)c1sc(-c2ccccc2)cc1N1C(=O)CN(Cc2cccc(F)c2N2CCOCC2)C[C@H]1C1CCCCC1] |
| 267 | 3-[(R)-4-(6-Chloro-pyridin-3-ylmethyl)-2-cyclohexyl-6-oxo-piperazin-1-yl]-5-phenyl-thiophene-2-carboxylic acid | 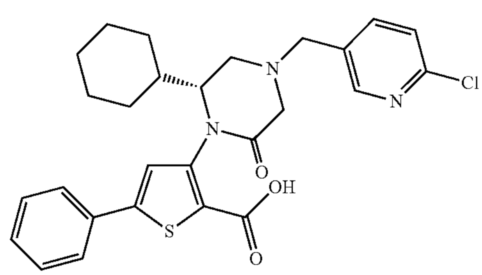 [SMILES: O=C(O)c1sc(-c2ccccc2)cc1N1C(=O)CN(Cc2ccc(Cl)nc2)C[C@H]1C1CCCCC1] |

TABLE 1-continued

| Compound number | Name | Structure |
|---|---|---|
| 268 | 3-((R)-2-Cyclohexyl-6-oxo-4-phenethyl-piperazin-1-yl)-5-phenyl-thiophene-2-carboxylic acid | 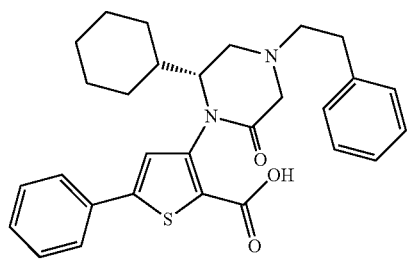 [SMILES: O=C(O)c1sc(-c2ccccc2)cc1N1C(=O)CN(CCc2ccccc2)C[C@H]1C1CCCCC1] |
| 269 | 3-[(R)-2-Cyclohexyl-4-(2-methyl-benzyl)-6-oxo-piperazin-1-yl]-5-phenyl-thiophene-2-carboxylic acid | 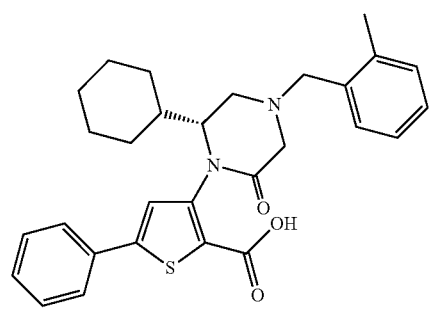 [SMILES: Cc1ccccc1CN1CC(=O)N(c2cc(-c3ccccc3)sc2C(=O)O)[C@H](C2CCCCC2)C1] |
| 270 | 3-[(R)-2-Cyclohexyl-4-(4-dimethylamino-benzyl)-6-oxo-piperazin-1-yl]-5-phenyl-thiophene-2-carboxylic acid | 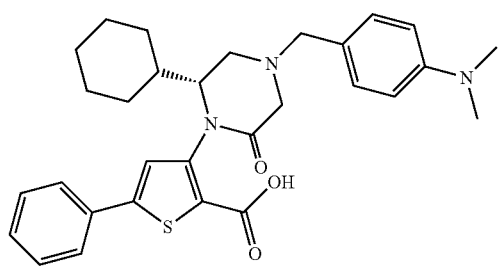 [SMILES: CN(C)c1ccc(CN2CC(=O)N(c3cc(-c4ccccc4)sc3C(=O)O)[C@H](C3CCCCC3)C2)cc1] |
| 271 | 3-[(R)-2-Cyclohexyl-4-(1-methyl-piperidin-4-yl)-6-oxo-piperazin-1-yl]-5-phenyl-thiophene-2-carboxylic acid | 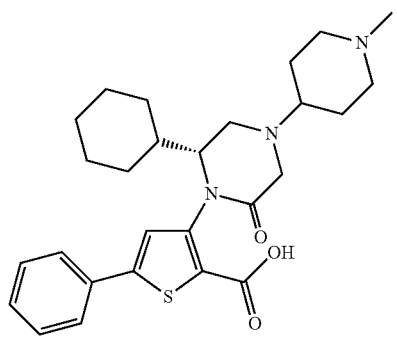 [SMILES: CN1CCC(N2CC(=O)N(c3cc(-c4ccccc4)sc3C(=O)O)[C@H](C3CCCCC3)C2)CC1] |

| Compound number | Name | Structure |
|---|---|---|
| 272 | 3-[(R)-2-Cyclohexyl-6-oxo-4-(6-pyrrolidin-1-yl-pyridine-3-sulfonyl)-piperazin-1-yl]-5-p-tolyl-thiophene-2-carboxylic acid | 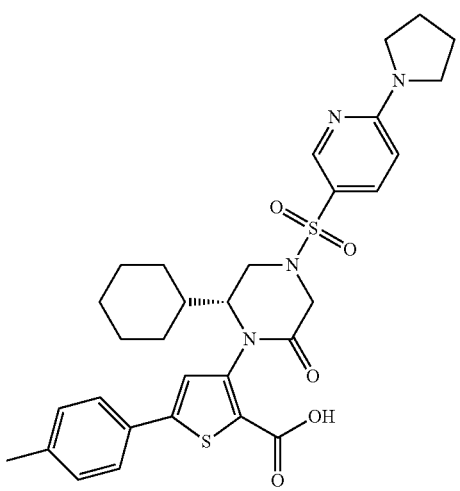 [SMILES: Cc1ccc(-c2cc(N3C(=O)CN(S(=O)(=O)c4ccc(N5CCCC5)nc4)C[C@H]3C3CCCCC3)c(C(=O)O)s2)cc1] |
| 273 | 3-{(R)-2-Cyclohexyl-4-[(1R,4R)-6-(2-oxa-5-aza-bicyclo[2.2.1]hept-5-yl)-pyridine-3-sulfonyl]-6-oxo-piperazin-1-yl}-5-(4-fluoro-phenyl)-thiophene-2-carboxylic acid | 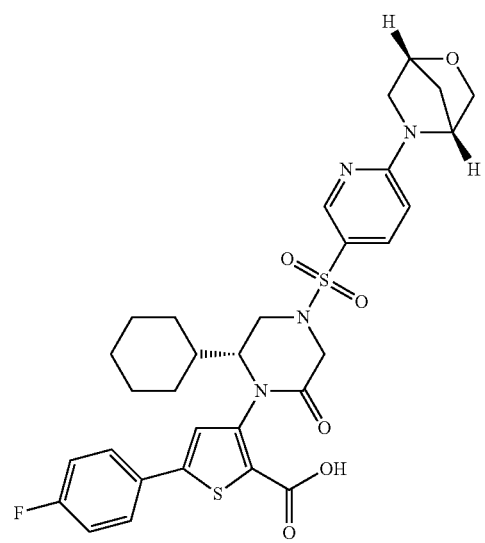 [SMILES: O=C(O)c1sc(-c2ccc(F)cc2)cc1N1C(=O)CN(S(=O)(=O)c2ccc(N3C[C@H]4C[C@@H]3CO4)nc2)C[C@H]1C1CCCCC1] |
| 274 | 5-(4-Chloro-phenyl)-3-{(R)-2-cyclohexyl-4-[(1R,4R)-6-(2-oxa-5-aza-bicyclo[2.2.1]hept-5-yl)-pyridine-3-sulfonyl]-6-oxo-piperazin-1-yl}-thiophene-2-carboxylic acid | 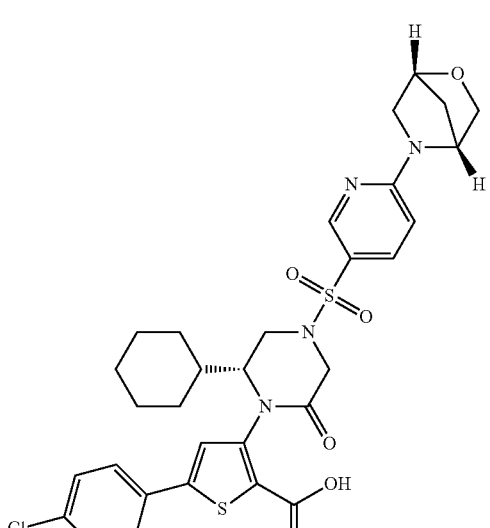 |

TABLE 1-continued

| Compound number | Name | Structure |
|---|---|---|
| 275 | 3-[(R)-2-Cyclohexyl-4-(1-ethyl-1H-pyrazole-4-sulfonyl)-6-oxo-piperazin-1-yl]-5-(3,3-dimethyl-but-1-ynyl)-thiophene-2-carboxylic acid | 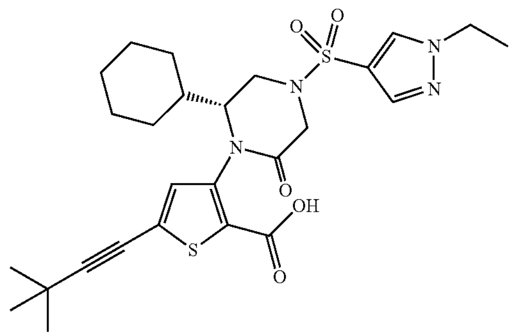 [SMILES: CCn1cc(S(=O)(=O)N2CC(=O)N(c3cc(C#CC(C)(C)C)sc3C(=O)O)[C@H](C3CCCCC3)C2)cn1] |
| 276 | 3-[(R)-2-Cyclohexyl-4-(2-fluoro-4,5-dimethoxy-benzenesulfonyl)-6-oxo-piperazin-1-yl]-5-(3,3-dimethyl-but-1-ynyl)-thiophene-2-carboxylic acid | 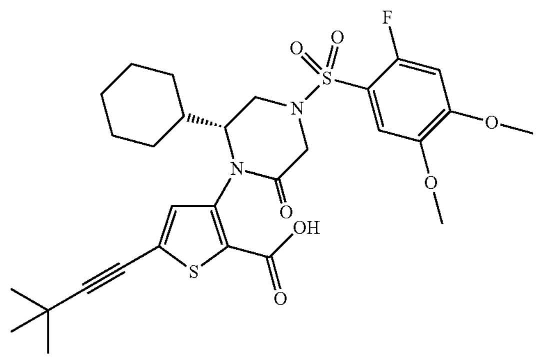 [SMILES: COc1cc(F)c(S(=O)(=O)N2CC(=O)N(c3cc(C#CC(C)(C)C)sc3C(=O)O)[C@H](C3CCCCC3)C2)cc1OC] |
| 277 | 3-[(R)-2-Cyclohexyl-4-(3,4-dimethoxy-benzenesulfonyl)-6-oxo-piperazin-1-yl]-5-(3,3-dimethyl-but-1-ynyl)-thiophene-2-carboxylic acid | 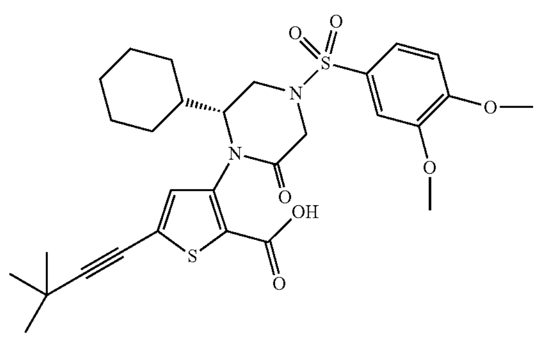 [SMILES: COc1ccc(S(=O)(=O)N2CC(=O)N(c3cc(C#CC(C)(C)C)sc3C(=O)O)[C@H](C3CCCCC3)C2)cc1OC] |
| 278 | 3-{(R)-2-Cyclohexyl-4-[6-((2R,6S)-2,6-dimethyl-morpholin-4-yl)-pyridine-3-sulfonyl]-6-oxo-piperazin-1-yl}-5-(4-fluoro-phenyl)-thiophene-2-carboxylic acid | 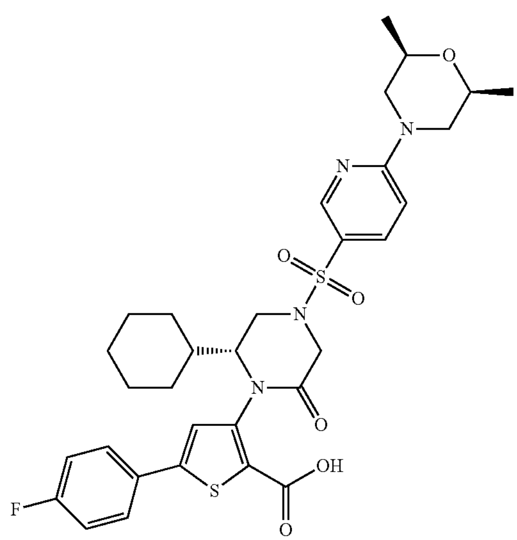 [SMILES: C[C@@H]1CN(c2ccc(S(=O)(=O)N3CC(=O)N(c4cc(-c5ccc(F)cc5)sc4C(=O)O)[C@H](C4CCCCC4)C3)cn2)C[C@H](C)O1] |

TABLE 1-continued

| Compound number | Name | Structure |
|---|---|---|
| 279 | 3-{(R)-2-Cyclohexyl-4-[6-((S)-2-methoxymethyl-pyrrolidin-1-yl)-pyridine-3-sulfonyl]-6-oxo-piperazin-1-yl}-5-(4-fluoro-phenyl)-thiophene-2-carboxylic acid | 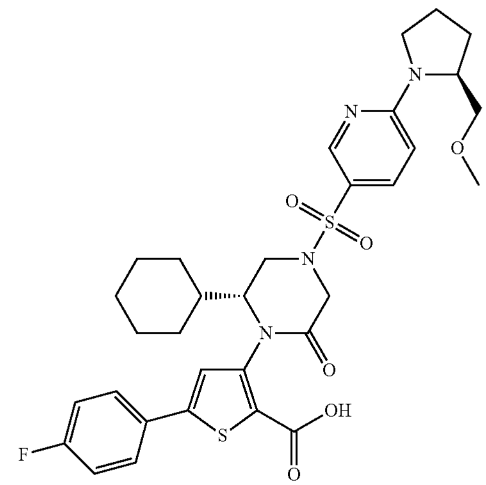 [SMILES: COC[C@@H]1CCCN1c1ccc(S(=O)(=O)N2CC(=O)N(c3cc(-c4ccc(F)cc4)sc3C(=O)O)[C@H](C3CCCCC3)C2)cn1] |
| 280 | 3-{(R)-2-Cyclohexyl-4-[6-((R)-3-fluoro-pyrrolidin-1-yl)-pyridine-3-sulfonyl]-6-oxo-piperazin-1-yl}-5-(4-fluoro-phenyl)-thiophene-2-carboxylic acid | 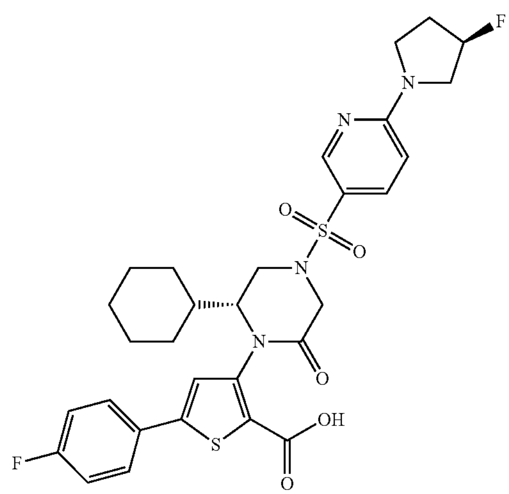 [SMILES: O=C(O)c1sc(-c2ccc(F)cc2)cc1N1C(=O)CN(S(=O)(=O)c2ccc(N3CC[C@@H](F)C3)nc2)C[C@H]1C1CCCCC1] |
| 281 | 3-[(R)-2-Cyclohexyl-4-(2,4-difluoro-benzenesulfonyl)-6-oxo-piperazin-1-dimethyl-but-1-ynyl)-thiophene-2-carboxylic acid | 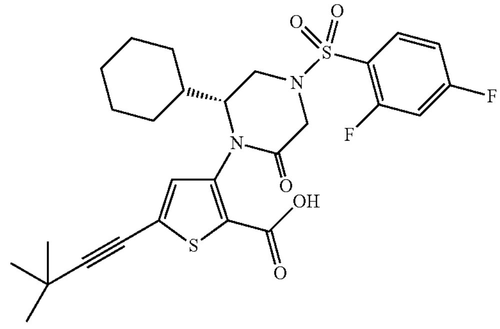 [SMILES: CC(C)(C)C#Cc1cc(N2C(=O)CN(S(=O)(=O)c3ccc(F)cc3F)C[C@H]2C2CCCCC2)c(C(=O)O)s1] |

TABLE 1-continued

| Compound number | Name | Structure |
|---|---|---|
| 282 | 3-[(R)-2-Cyclohexyl-4-(2,6-dichloro-benzenesulfonyl)-6-oxo-piperazin-1-yl]-5-(3,3-dimethyl-but-1-ynyl)-thiophene-2-carboxylic acid | 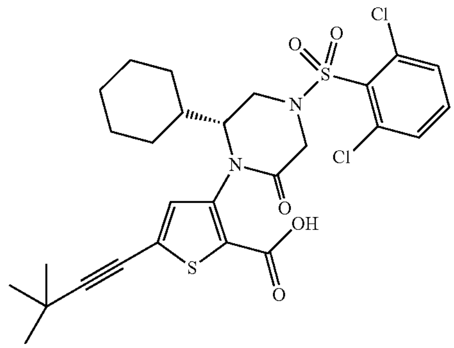 [SMILES: CC(C)(C)C#Cc1cc(N2C(=O)CN(S(=O)(=O)c3c(Cl)cccc3Cl)C[C@H]2C2CCCCC2)c(C(=O)O)s1] |
| 283 | 3-[(R)-2-Cyclohexyl-4-(4-fluoro-3-methoxy-benzenesulfonyl)-6-oxo-piperazin-1-yl]-5-(3,3-dimethyl-but-1-ynyl)-thiophene-2-carboxylic acid | 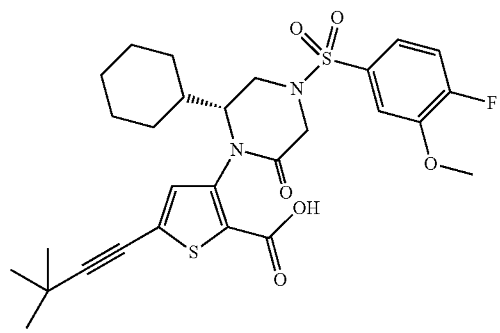 [SMILES: COc1cc(S(=O)(=O)N2CC(=O)N(c3cc(C#CC(C)(C)C)sc3C(=O)O)[C@H](C3CCCCC3)C2)ccc1F] |
| 284 | 5-(4-Chloro-phenyl)-3-[(R)-2-cyclohexyl-4-(1-methyl-1H-pyrazole-3-sulfonyl)-6-oxo-piperazin-1-yl]-thiophene-2-carboxylic acid | 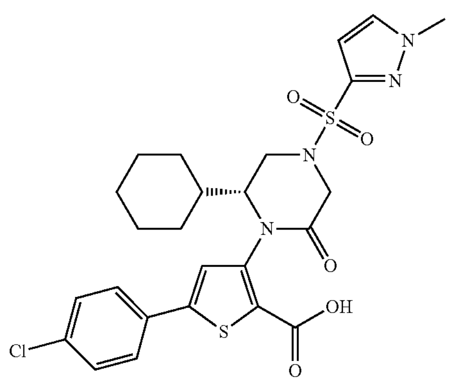 [SMILES: Cn1ccc(S(=O)(=O)N2CC(=O)N(c3cc(-c4ccc(Cl)cc4)sc3C(=O)O)[C@H](C3CCCCC3)C2)n1] |
| 285 | 3-[(R)-4-(6-Azepan-1-yl-pyridine-3-sulfonyl)-2-cyclohexyl-6-oxo-piperazin-1-yl]-5-(4-fluoro-phenyl)-thiophene-2-carboxylic acid | 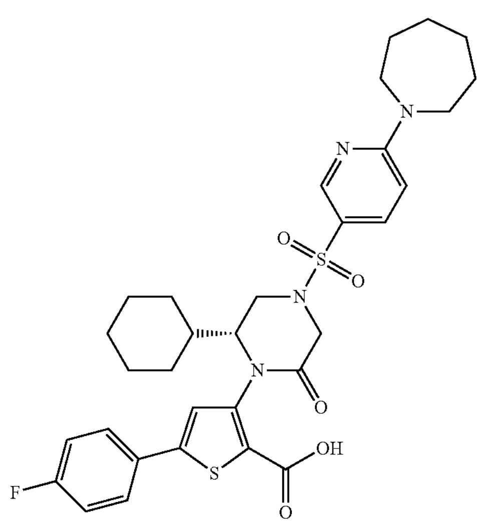 |

TABLE 1-continued

| Compound number | Name | Structure |
|---|---|---|
| 286 | 3-{(R)-2-Cyclohexyl-4-[6-(3,3-difluoro-pyrrolidin-1-yl)-pyridine-3-sulfonyl]-6-oxo-piperazin-1-yl}-5-(4-fluoro-phenyl)-thiophene-2-carboxylic acid | 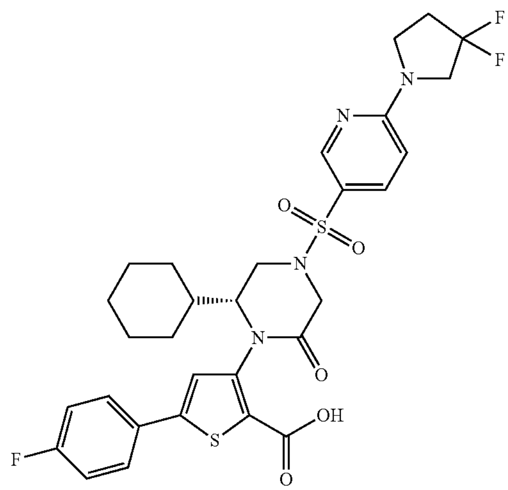 [SMILES: O=C(O)c1sc(-c2ccc(F)cc2)cc1N1C(=O)CN(S(=O)(=O)c2ccc(N3CCC(F)(F)C3)nc2)C[C@H]1C1CCCCC1] |
| 287 | 3-{(R)-2-Cyclohexyl-4-[6-((S)-3-fluoro-pyrrolidin-1-yl)-pyridine-3-sulfonyl]-6-oxo-piperazin-1-yl}-5-(4-fluoro-phenyl)-thiophene-2-carboxylic acid | 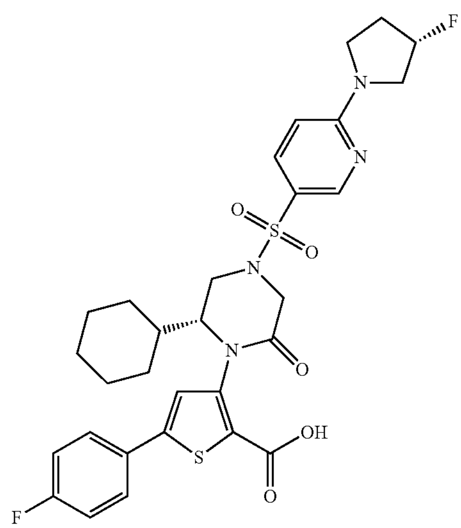 [SMILES: O=C(O)c1sc(-c2ccc(F)cc2)cc1N1C(=O)CN(S(=O)(=O)c2ccc(N3CC[C@H](F)C3)nc2)C[C@H]1C1CCCCC1] |
| 288 | 3-{(R)-2-Cyclohexyl-4-[6-(3-hydroxy-3-methyl-pyrrolidin-1-yl)-pyridine-3-sulfonyl]-6-oxo-piperazin-1-yl}-5-(4-fluoro-phenyl)-thiophene-2-carboxylic acid | 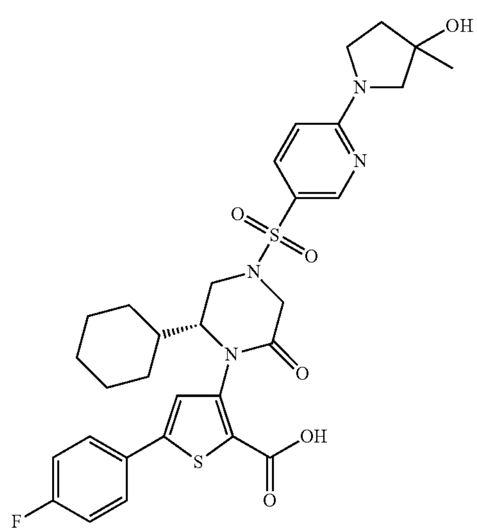 [SMILES: CC1(O)CCN(c2ccc(S(=O)(=O)N3CC(=O)N(c4cc(-c5ccc(F)cc5)sc4C(=O)O)[C@H](C4CCCCC4)C3)cn2)C1] |

TABLE 1-continued

| Compound number | Name | Structure |
|---|---|---|
| 289 | 3-{(R)-2-Cyclohexyl-4-[(1R,4R)-6-(2-oxa-5-aza-bicyclo[2.2.1]hept-5-yl)-pyridine-3-sulfonyl]-6-oxo-piperazin-1-yl}-5-p-tolyl-thiophene-2-carboxylic acid | 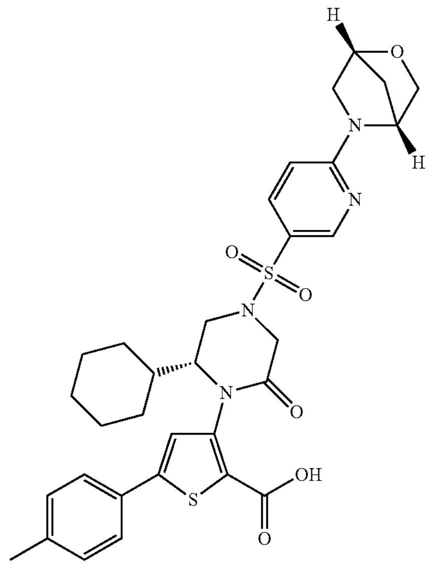 [SMILES: Cc1ccc(-c2cc(N3C(=O)CN(S(=O)(=O)c4ccc(N5C[C@H]6C[C@@H]5CO6)nc4)C[C@H]3C3CCCCC3)c(C(=O)O)s2)cc1] |
| 290 | 3-((R)-5-Cyclohexyl-2,2-dimethyl-3-oxo-morpholin-4-yl)-5-(3,3-dimethyl-but-1-ynyl)-thiophene-2-carboxylic acid | 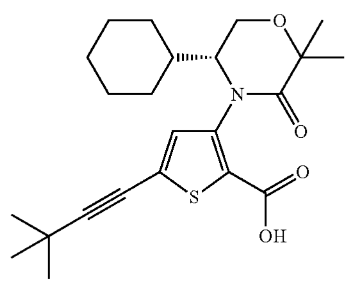 [SMILES: CC(C)(C)C#Cc1cc(N2C(=O)C(C)(C)OC[C@H]2C2CCCCC2)c(C(=O)O)s1] |
| 291 | 3-((2R,3R)-3-Cyclohexyl-2-methyl-5-oxo-morpholin-4-yl)-5-(3,3-dimethyl-but-1-ynyl)-thiophene-2-carboxylic acid | 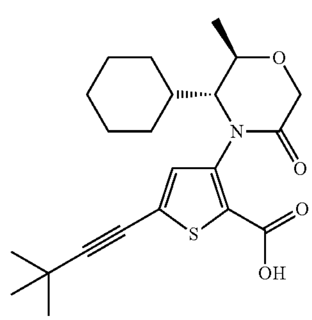 [SMILES: C[C@H]1OCC(=O)N(c2cc(C#CC(C)(C)C)sc2C(=O)O)[C@@H]1C1CCCCC1] |

TABLE 1-continued

| Compound number | Name | Structure |
|---|---|---|
| 292 | 5-(4-Chloro-phenyl)-3-{(R)-2-cyclohexyl-4-[6-(3,3-dimethyl-pyrrolidin-1-yl)-pyridine-3-sulfonyl]-6-oxo-piperazin-1-yl}-thiophene-2-carboxylic acid | 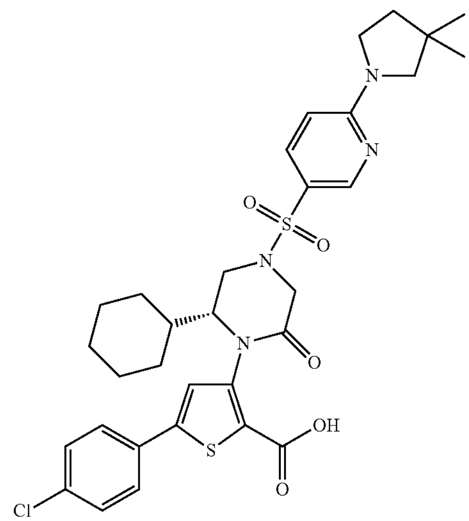 [SMILES: CC1(C)CCN(c2ccc(S(=O)(=O)N3CC(=O)N(c4cc(-c5ccc(Cl)cc5)sc4C(=O)O)[C@H](C4CCCCC4)C3)cn2)C1] |
| 293 | 5-(4-Chloro-phenyl)-3-((R)-3-cyclohexyl-5-oxo-morpholin-4-yl)-thiophene-2-carboxylic acid | 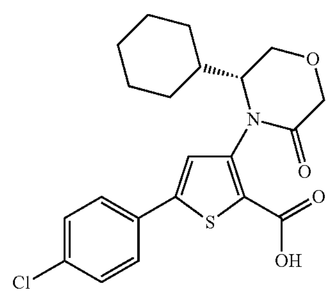 [SMILES: O=C(O)c1sc(-c2ccc(Cl)cc2)cc1N1C(=O)COC[C@H]1C1CCCCC1] |
| 294 | 3-[(R)-5-Cyclohexyl-2-(2-morpholin-4-yl-2-oxo-ethyl)-3-oxo-morpholin-4-yl]-5-(3,3-dimethyl-but-1-ynyl)-thiophene-2-carboxylic acid | 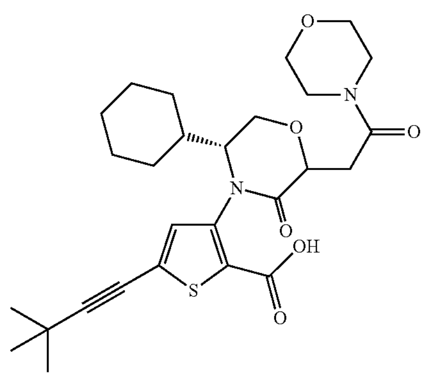 [SMILES: CC(C)(C)C#Cc1cc(N2C(=O)C(CC(=O)N3CCOCC3)OC[C@H]2C2CCCCC2)c(C(=O)O)s1] |

TABLE 1-continued
| Compound number | Name | Structure |
|---|---|---|
| 295 | 3-[(R)-2-Cyclohexyl-4-(1-methyl-1H-pyrazole-4-sulfonyl)-6-oxo-piperazin-1-yl]-5-p-tolyl-thiophene-2-carboxylic acid | 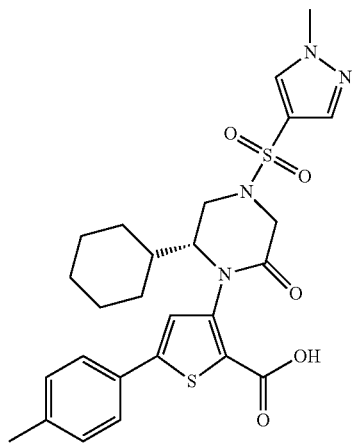 [SMILES: Cc1ccc(-c2cc(N3C(=O)CN(S(=O)(=O)c4cnn(C)c4)C[C@H]3C3CCCCC3)c(C(=O)O)s2)cc1] |
| 296 | 3-[(R)-2-Cyclohexyl-4-(1-ethyl-1H-pyrazole-4-sulfonyl)-6-oxo-piperazin-1-yl]-5-p-tolyl-thiophene-2-carboxylic acid | 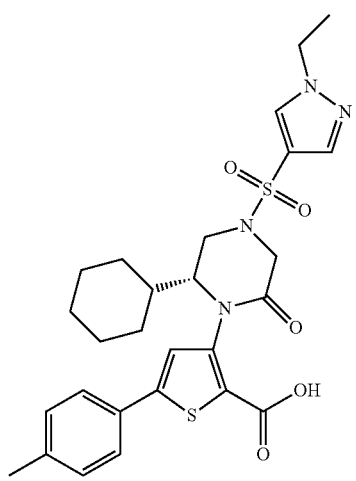 [SMILES: CCn1cc(S(=O)(=O)N2CC(=O)N(c3cc(-c4ccc(C)cc4)sc3C(=O)O)[C@H](C3CCCCC3)C2)cn1] |
| 297 | 3-[(R)-2-Cyclohexyl-4-(1-methyl-1H-imidazole-4-sulfonyl)-6-oxo-piperazin-1-yl]-5-p-tolyl-thiophene-2-carboxylic acid | 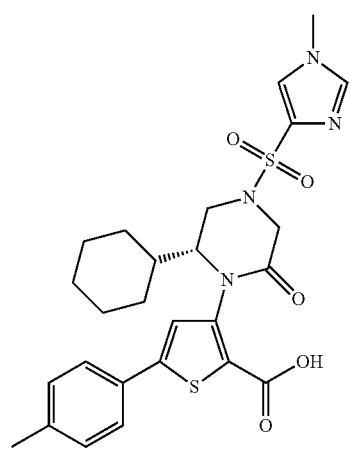 [SMILES: Cc1ccc(-c2cc(N3C(=O)CN(S(=O)(=O)c4cn(C)cn4)C[C@H]3C3CCCCC3)c(C(=O)O)s2)cc1] |

TABLE 1-continued

| Compound number | Name | Structure |
|---|---|---|
| 298 | 3-[(R)-2-Cyclohexyl-4-(1,2-dimethyl-1H-imidazole-4-sulfonyl)-6-oxo-piperazin-1-yl]-5-p-tolyl-thiophene-2-carboxylic acid | 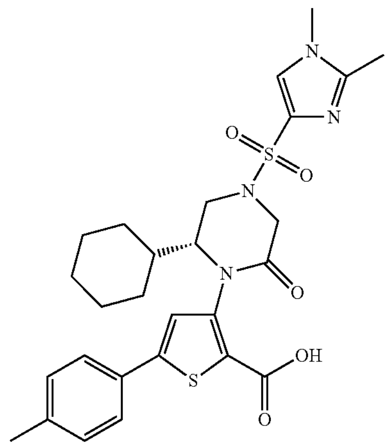 |
| 299 | 3-[(R)-5-Cyclohexyl-2-(3-hydroxy-propyl)-3-oxo-morpholin-4-yl]-5-(3,3-dimethyl-but-1-ynyl)-thiophene-2-carboxylic acid | 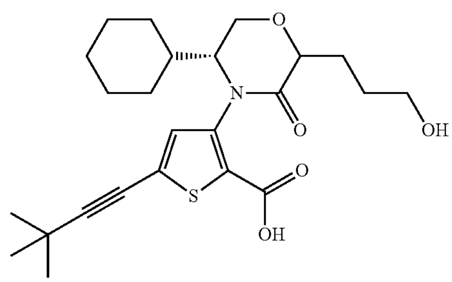 [SMILES: CC(C)(C)C#Cc1cc(N2C(=O)C(CCCO)OC[C@H]2C2CCCCC2)c(C(=O)O)s1] |
| 300 | 3-[(R)-2-Cyclohexyl-6-oxo-4-(6-trifluoromethyl-pyridine-3-sulfonyl)-piperazin-1-yl]-5-p-tolyl-thiophene-2-carboxylic acid | 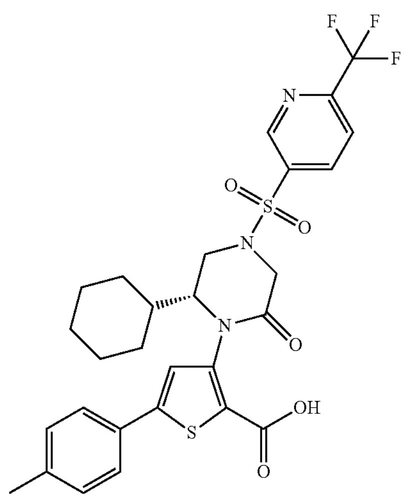 [SMILES: Cc1ccc(-c2cc(N3C(=O)CN(S(=O)(=O)c4ccc(C(F)(F)F)nc4)C[C@H]3C3CCCCC3)c(C(=O)O)s2)cc1] |

TABLE 1-continued

| Compound number | Name | Structure |
|---|---|---|
| 301 | 3-[(R)-2-Cyclohexyl-4-(1-isobutyl-1H-pyrazole-4-sulfonyl)-6-oxo-piperazin-1-yl]-5-p-tolyl-thiophene-2-carboxylic acid | 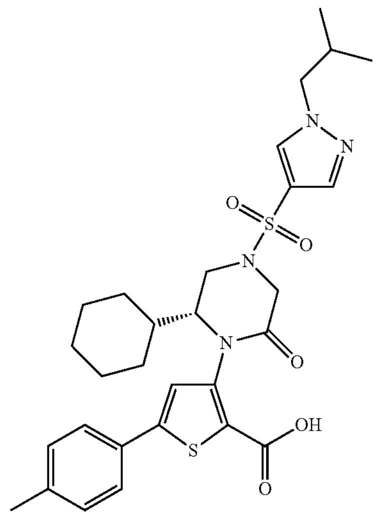 [SMILES: Cc1ccc(-c2cc(N3C(=O)CN(S(=O)(=O)c4cnn(CC(C)C)c4)C[C@H]3C3CCCCC3)c(C(=O)O)s2)cc1] |
| 302 | 3-[(R)-2-Cyclohexyl-4-(6-methyl-pyridine-3-sulfonyl)-6-oxo-piperazin-1-yl]-5-p-tolyl-thiophene-2-carboxylic acid | 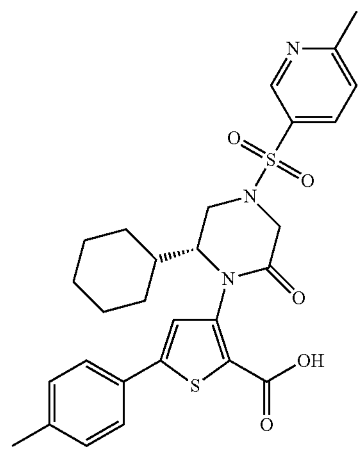 [SMILES: Cc1ccc(-c2cc(N3C(=O)CN(S(=O)(=O)c4ccc(C)nc4)C[C@H]3C3CCCCC3)c(C(=O)O)s2)cc1] |
| 303 | 3-[(R)-4-(6-tert-Butyl-pyridine-3-sulfonyl)-2-cyclohexyl-6-oxo-piperazin-1-yl]-5-p-tolyl-thiophene-2-carboxylic acid | 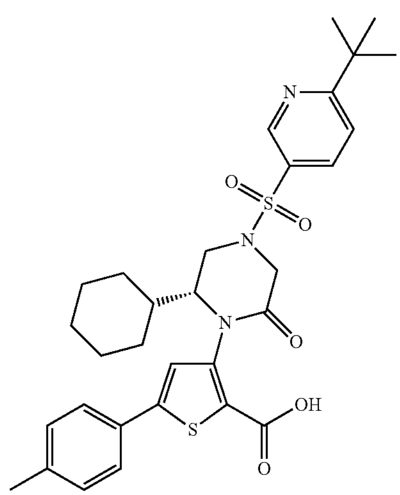 [SMILES: Cc1ccc(-c2cc(N3C(=O)CN(S(=O)(=O)c4ccc(C(C)(C)C)nc4)C[C@H]3C3CCCCC3)c(C(=O)O)s2)cc1] |

TABLE 1-continued

| Compound number | Name | Structure |
|---|---|---|
| 304 | 3-[(R)-2-Cyclohexyl-4-(6-ethyl-pyridine-3-sulfonyl)-6-oxo-piperazin-1-yl]-5-p-tolyl-thiophene-2-carboxylic acid | 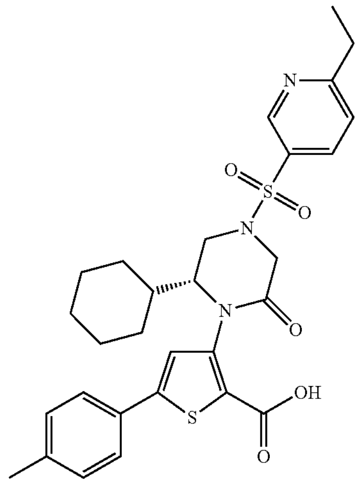 [SMILES: CCc1ccc(S(=O)(=O)N2CC(=O)N(c3cc(-c4ccc(C)cc4)sc3C(=O)O)[C@H](C3CCCCC3)C2)cn1] |
| 305 | 3-[(R)-2-Cyclohexyl-4-(5,6-dimethyl-pyridine-3-sulfonyl)-6-oxo-piperazin-1-yl]-5-p-tolyl-thiophene-2-carboxylic acid | 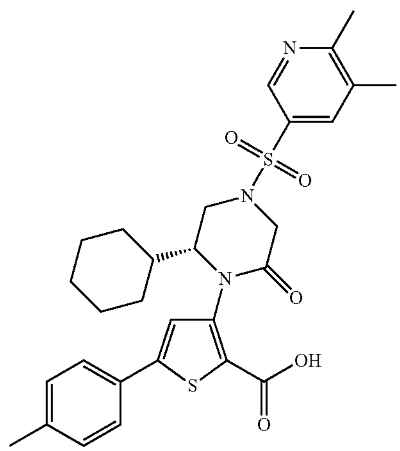 |
| 306 | 3-[(R)-5-Cyclohexyl-2-(3-methanesulfonyl-propyl)-3-oxo-morpholin-4-yl]-5-(3,3-dimethyl-but-1-ynyl)-thiophene-2-carboxylic acid | 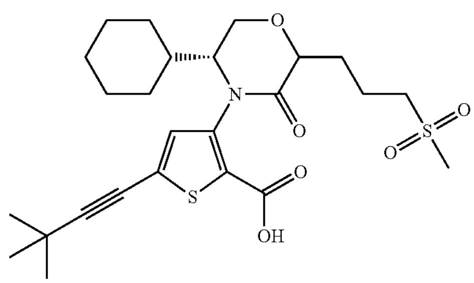 [SMILES: CC(C)(C)C#Cc1cc(N2C(=O)C(CCCS(C)(=O)=O)OC[C@H]2C2CCCCC2)c(C(=O)O)s1] |
| 307 | 3-{(R)-5-Cyclohexyl-2-[(2-methoxy-ethylamino)-methyl]-3-oxo-morpholin-4-yl}-5-(3,3-dimethyl-but-1-ynyl)-thiophene-2-carboxylic acid | 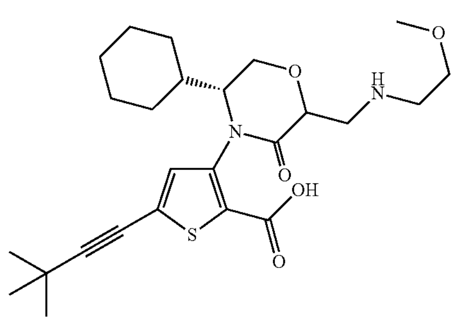 [SMILES: COCCNCC1OC[C@@H](C2CCCCC2)N(c2cc(C#CC(C)(C)C)sc2C(=O)O)C1=O] |

TABLE 1-continued

| Compound number | Name | Structure |
|---|---|---|
| 308 | 3-(4-Cyclohexyl-2-oxo-[1,3]oxazinan-3-yl)-5-(3,3-dimethyl-but-1-ynyl)-thiophene-2-carboxylic acid | 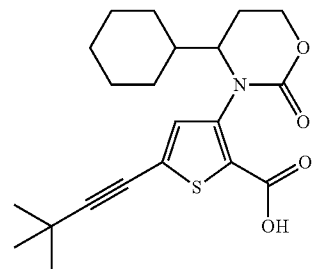 [SMILES: CC(C)(C)C#Cc1cc(N2C(=O)OCCC2C2CCCCC2)c(C(=O)O)s1] |
| 309 | N-[3-((R)-3-Cyclohexyl-5-oxo-morpholin-4-yl)-5-(3,3-dimethyl-but-1-ynyl)-thiophene-2-carbonyl]-methanesulfonamide | 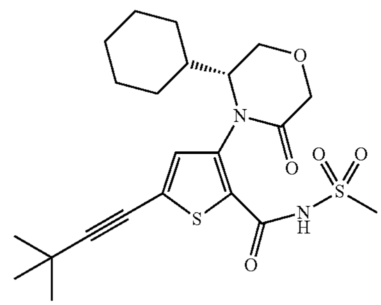 [SMILES: CC(C)(C)C#Cc1cc(N2C(=O)COC[C@H]2C2CCCCC2)c(C(=O)NS(C)(=O)=O)s1] |
| 310 | 3-((R)-5-Cyclohexyl-2-morpholin-4-ylmethyl-3-oxo-morpholin-4-yl)-5-(3,3-dimethyl-but-1-ynyl)-thiophene-2-carboxylic acid | 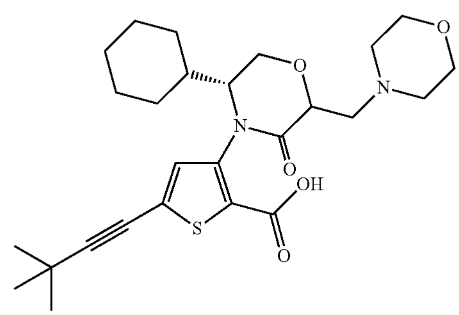 [SMILES: CC(C)(C)C#Cc1cc(N2C(=O)C(CN3CCOCC3)OC[C@H]2C2CCCCC2)c(C(=O)O)s1] |
| 311 | 3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid | 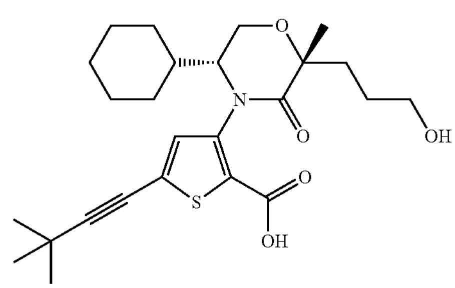 [SMILES: CC(C)(C)C#Cc1cc(N2C(=O)[C@@](C)(CCCO)OC[C@H]2C2CCCCC2)c(C(=O)O)s1] |
| 312 | 3-((2S,5R)-2-Cyanomethyl-5-cyclohexyl-2-methyl-3-oxo-morpholin-4-yl)-5-(3,3-dimethyl-but-1-ynyl)-thiophene-2-carboxylic acid | 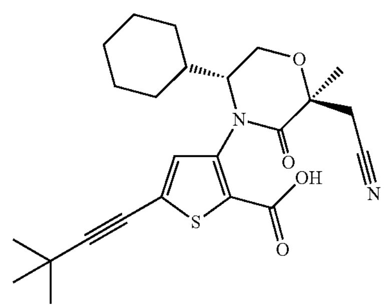 [SMILES: CC(C)(C)C#Cc1cc(N2C(=O)[C@](C)(CC#N)OC[C@H]2C2CCCCC2)c(C(=O)O)s1] |

TABLE 1-continued

| Compound number | Name | Structure |
|---|---|---|
| 313 | 3-(6-Cyclohexyl-3-hydroxy-2-oxo-piperidin-1-yl)-5-(3,3-dimethyl-but-1-ynyl)-thiophene-2-carboxylic acid | 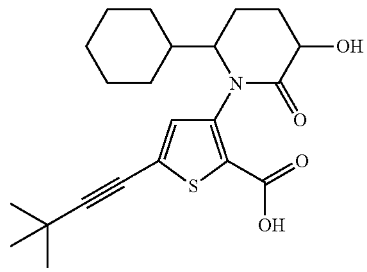 [SMILES: CC(C)(C)C#Cc1cc(N2C(=O)C(O)CCC2C2CCCCC2)c(C(=O)O)s1] |
| 314 | 3-((R)-5-Cyclohexyl-2,2-dimethyl-3-oxo-morpholin-4-yl)-5-p-tolyl-thiophene-2-carboxylic acid | 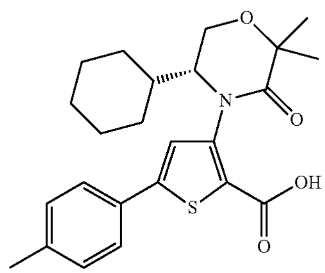 |
| 315 | 5-(4-Chloro-phenyl)-3-((R)-5-cyclohexyl-2,2-dimethyl-3-oxo-morpholin-4-yl)-thiophene-2-carboxylic acid | 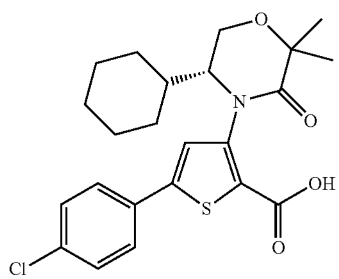 [SMILES: CC1(C)OC[C@@H](C2CCCCC2)N(c2cc(-c3ccc(Cl)cc3)sc2C(=O)O)C1=O] |
| 316 | 3-[6-Cyclohexyl-3-(1-hydroxy-ethyl)-2-oxo-piperidin-1-yl]-5-(3,3-dimethyl-but-1-ynyl)-thiophene-2-carboxylic acid | 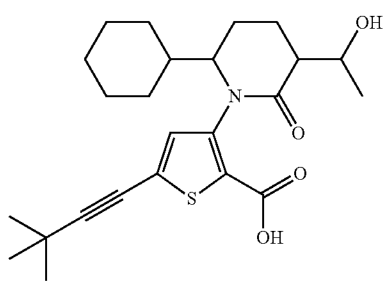 [SMILES: CC(O)C1CCC(C2CCCCC2)N(c2cc(C#CC(C)(C)C)sc2C(=O)O)C1=O] |
| 317 | 3-(6-Cyclohexyl-3-hydroxy-2-oxo-piperidin-1-yl)-5-p-tolyl-thiophene-2-carboxylic acid | 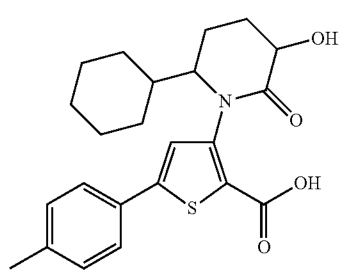 [SMILES: Cc1ccc(-c2cc(N3C(=O)C(O)CCC3C3CCCCC3)c(C(=O)O)s2)cc1] |

TABLE 1-continued

| Compound number | Name | Structure |
|---|---|---|
| 318 | 3-[(2S,5R)-5-Cyclohexyl-2-(3-hydroxy-3-methyl-butyl)-2-methyl-3-oxo-morpholin-4-yl]-5-(3,3-dimethyl-but-1-ynyl)-thiophene-2-carboxylic acid | 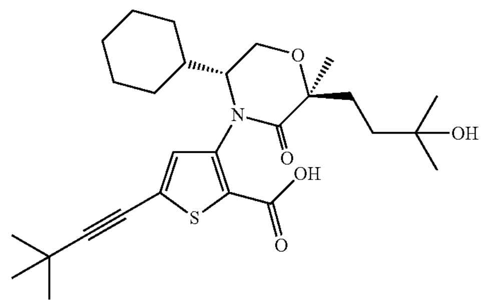 [SMILES: CC(C)(C)C#Cc1cc(N2C(=O)[C@](C)(CCC(C)(C)O)OC[C@H]2C2CCCCC2)c(C(=O)O)s1] |
| 319 | 3-[(2R,5R)-5-Cyclohexyl-2-(3-hydroxy-3-methyl-butyl)-2-methyl-3-oxo-morpholin-4-yl]-5-(3,3-dimethyl-but-1-ynyl)-thiophene-2-carboxylic acid | 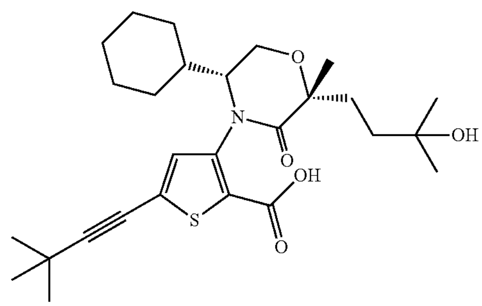 [SMILES: CC(C)(C)C#Cc1cc(N2C(=O)[C@@](C)(CCC(C)(C)O)OC[C@H]2C2CCCCC2)c(C(=O)O)s1] |
| 320 | 3-[(2S,5R)-5-Cyclohexyl-2-((R)-3-hydroxy-butyl)-2-methyl-3-oxo-morpholin-4-yl]-5-(3,3-dimethyl-but-1-ynyl)-thiophene-2-carboxylic acid | 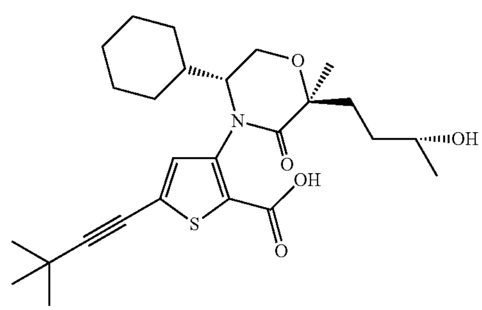 [SMILES: C[C@@H](O)CC[C@]1(C)OC[C@@H](C2CCCCC2)N(c2cc(C#CC(C)(C)C)sc2C(=O)O)C1=O] |
| 321 | 3-[(2R,5R)-5-Cyclohexyl-2-((R)-3-hydroxy-butyl)-2-methyl-3-oxo-morpholin-4-yl]-5-(3,3-dimethyl-but-1-ynyl)-thiophene-2-carboxylic acid | 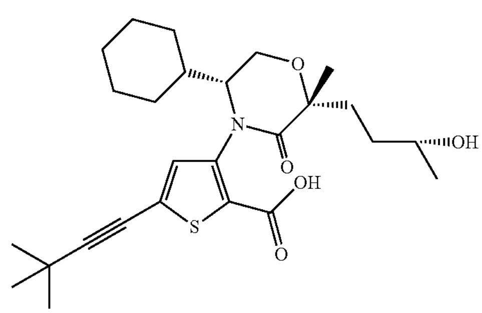 [SMILES: C[C@@H](O)CC[C@@]1(C)OC[C@@H](C2CCCCC2)N(c2cc(C#CC(C)(C)C)sc2C(=O)O)C1=O] |
| 322 | 3-((3S,6S)-6-Cyclohexyl-3-hydroxy-2-oxo-piperidin-1-yl)-5-(3,3-dimethyl-but-1-ynyl)-thiophene-2-carboxylic acid | 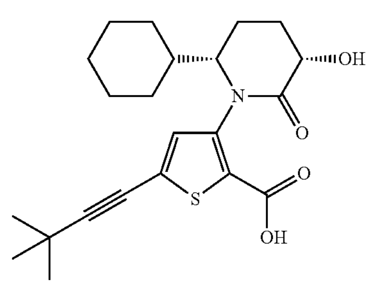 |

TABLE 1-continued

| Compound number | Name | Structure |
|---|---|---|
| 323 | 3-[(2R,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid | 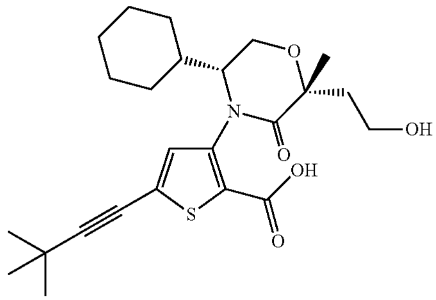 [SMILES: CC(C)(C)C#Cc1cc(N2C(=O)[C@@](C)(CCO)OC[C@H]2C2CCCCC2)c(C(=O)O)s1] |
| 324 | 3-(6-Cyclohexyl-3-hydroxy-3-methyl-2-oxo-piperidin-1-yl)-5-p-tolyl-thiophene-2-carboxylic acid | 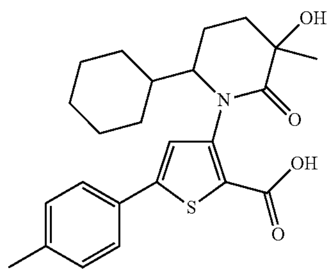 |
| 325 | 3-((R)-3-Cyclohexyl-5-oxo-1,9-dioxa-4-aza-spiro[5.5]undec-4-yl)-5-(3,3-dimethyl-but-1-ynyl)-thiophene-2-carboxylic acid | 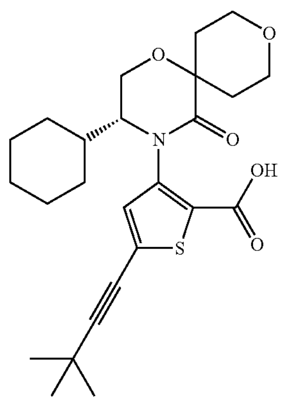 [SMILES: CC(C)(C)C#Cc1cc(N2C(=O)C3(CCOCC3)OC[C@H]2C2CCCCC2)c(C(=O)O)s1] |
| 326 | 3-[(2S,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid | 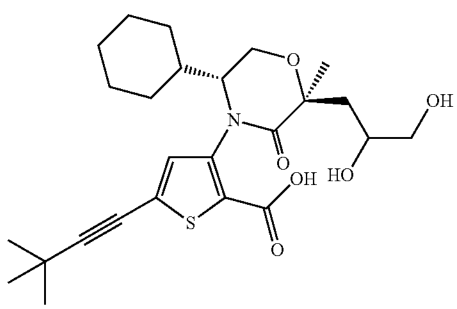 [SMILES: CC(C)(C)C#Cc1cc(N2C(=O)[C@](C)(CC(O)CO)OC[C@H]2C2CCCCC2)c(C(=O)O)s1] |
| 327 | 3-[(2S,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid | 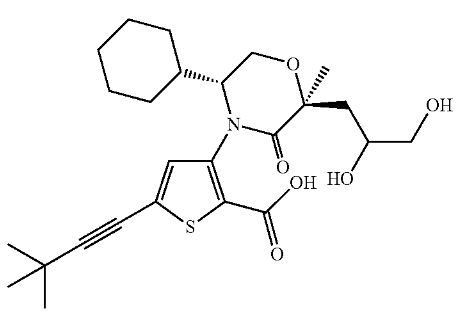 [SMILES: CC(C)(C)C#Cc1cc(N2C(=O)[C@](C)(CC(O)CO)OC[C@H]2C2CCCCC2)c(C(=O)O)s1] |

TABLE 1-continued

| Compound number | Name | Structure |
|---|---|---|
| 328 | 3-[(2S,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid | 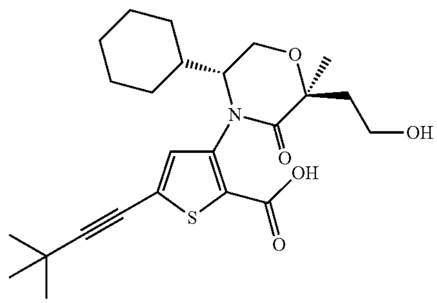 [SMILES: CC(C)(C)C#Cc1cc(N2C(=O)[C@](C)(CCO)OC[C@H]2C2CCCCC2)c(C(=O)O)s1] |
| 329 | 3-((R)-5-Cyclohexyl-2-hydroxymethyl-3-oxo-morpholin-4-yl)-5-(3,3-dimethyl-but-1-ynyl)-thiophene-2-carboxylic acid | 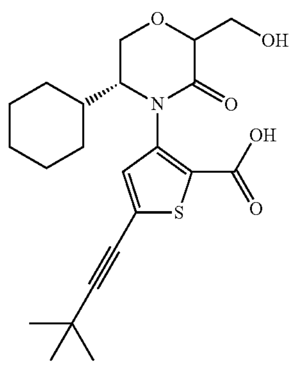 [SMILES: CC(C)(C)C#Cc1cc(N2C(=O)C(CO)OC[C@H]2C2CCCCC2)c(C(=O)O)s1] |
| 330 | 3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid | 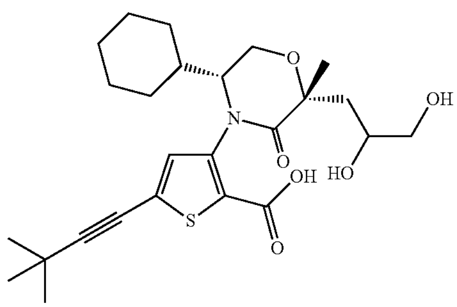 [SMILES: CC(C)(C)C#Cc1cc(N2C(=O)[C@@](C)(CC(O)CO)OC[C@H]2C2CCCCC2)c(C(=O)O)s1] |
| 331 | 3-[(2S,5R)-5-Cyclohexyl-2-(2,3-dihydroxy-propyl)-3-oxo-morpholin-4-yl]-5-(3,3-dimethyl-but-1-ynyl)-thiophene-2-carboxylic acid | 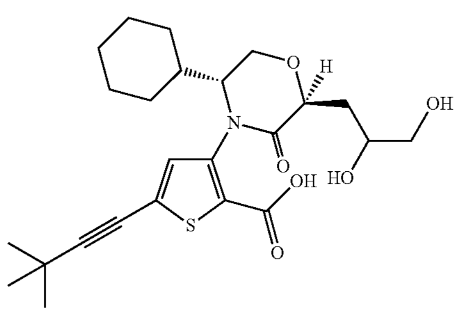 [SMILES: CC(C)(C)C#Cc1cc(N2C(=O)[C@H](CC(O)CO)OC[C@H]2C2CCCCC2)c(C(=O)O)s1] |

TABLE 1-continued

| Compound number | Name | Structure |
|---|---|---|
| 332 | 3-[(2S,5R)-5-Cyclohexyl-2-(2-hydroxy-ethyl)-3-oxo-morpholin-4-yl]-5-(3,3-dimethyl-but-1-ynyl)-thiophene-2-carboxylic acid | 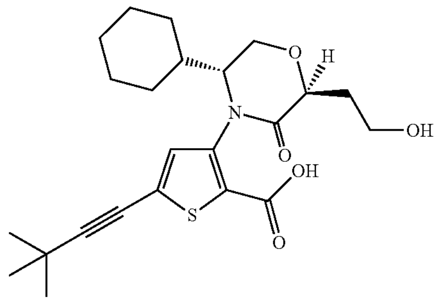 [SMILES: CC(C)(C)C#Cc1cc(N2C(=O)[C@H](CCO)OC[C@H]2C2CCCCC2)c(C(=O)O)s1] |
| 333 | 3-[(R)-5-Cyclohexyl-2,2-bis-(2-hydroxy-ethyl)-3-oxo-morpholin-4-yl]-5-(3,3-dimethyl-but-1-ynyl)-thiophene-2-carboxylic acid | 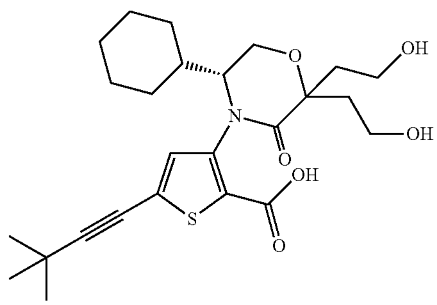 [SMILES: CC(C)(C)C#Cc1cc(N2C(=O)C(CCO)(CCO)OC[C@H]2C2CCCCC2)c(C(=O)O)s1] |
| 334 | 3-((3R,6S)-6-Cyclohexyl-3-hydroxy-2-oxo-piperidin-1-yl)-5-(3,3-dimethyl-but-1-ynyl)-thiophene-2-carboxylic acid | 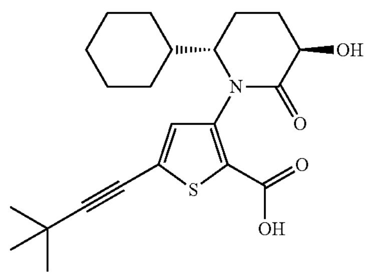 [SMILES: CC(C)(C)C#Cc1cc(N2C(=O)[C@H](O)CC[C@H]2C2CCCCC2)c(C(=O)O)s1] |
| 335 | 3-((S)-2-Cyclohexyl-7-oxo-azepan-1-yl)-5-(3,3-dimethyl-but-1-ynyl)-thiophene-2-carboxylic acid | 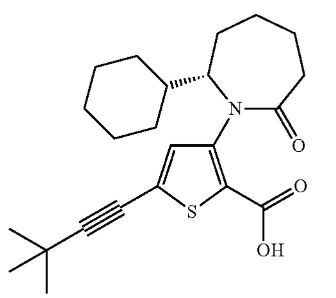 [SMILES: CC(C)(C)CCc1cc(N2C(=O)CCCC[C@H]2C2CCCCC2)c(C(=O)O)s1] |
| 336 | 3-[(2R,5R)-5-Cyclohexyl-2-((R)-2-hydroxy-propyl)-3-oxo-morpholin-4-yl]-5-(3,3-dimethyl-but-1-ynyl)-thiophene-2-carboxylic acid | 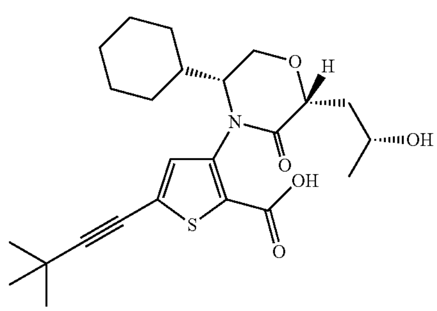 [SMILES: C[C@@H](O)C[C@H]1OC[C@@H](C2CCCCC2)N(c2cc(C#CC(C)(C)C)sc2C(=O)O)C1=O] |

TABLE 1-continued

| Compound number | Name | Structure |
|---|---|---|
| 337 | 3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid | 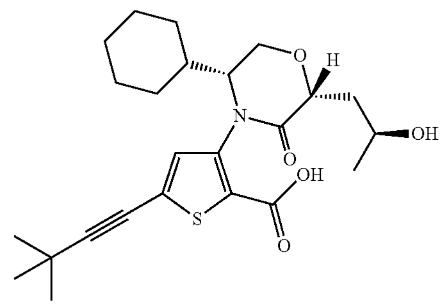 [SMILES: C[C@H](O)C[C@H]1OC[C@@H](C2CCCCC2)N(c2cc(C#CC(C)(C)C)sc2C(=O)O)C1=O] |
| 338 | 3-[(2S,5R)-5-Cyclohexyl-2-(4-hydroxy-butyl)-3-oxo-morpholin-4-yl]-5-(3,3-dimethyl-but-1-ynyl)-thiophene-2-carboxylic acid | 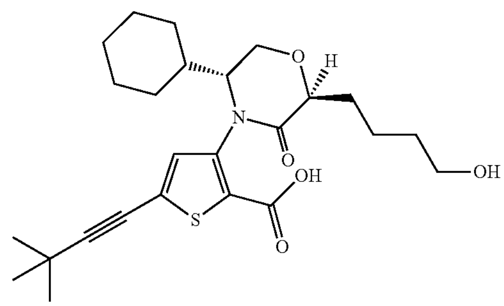 [SMILES: CC(C)(C)C#Cc1cc(N2C(=O)[C@H](CCCCO)OC[C@H]2C2CCCCC2)c(C(=O)O)s1] |
| 339 | 3-[(S)-6-Cyclohexyl-3-(3-hydroxy-propyl)-2-oxo-piperidin-1-yl]-5-(3,3-dimethyl-but-1-ynyl)-thiophene-2-carboxylic acid | 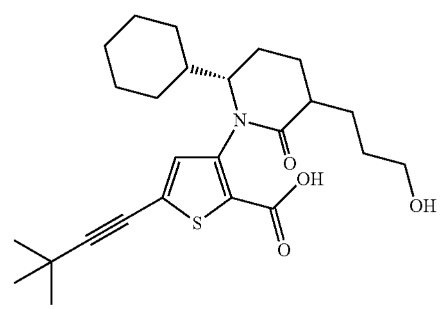 [SMILES: CC(C)(C)C#Cc1cc(N2C(=O)C(CCCO)CC[C@H]2C2CCCCC2)c(C(=O)O)s1] |
| 340 | 3-((S)-3-Amino-6-cyclohexyl-2-oxo-piperidin-1-yl)-5-(3,3-dimethyl-but-1-ynyl)-thiophene-2-carboxylic acid | 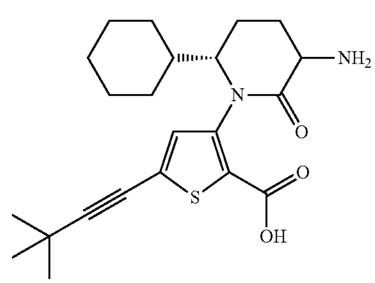 [SMILES: CC(C)(C)C#Cc1cc(N2C(=O)C(N)CC[C@H]2C2CCCCC2)c(C(=O)O)s1] |
| 341 | 3-[(S)-6-Cyclohexyl-3-(3-hydroxy-propyl)-2-oxo-piperidin-1-yl]-5-(3,3-dimethyl-but-1-ynyl)-thiophene-2-carboxylic acid | 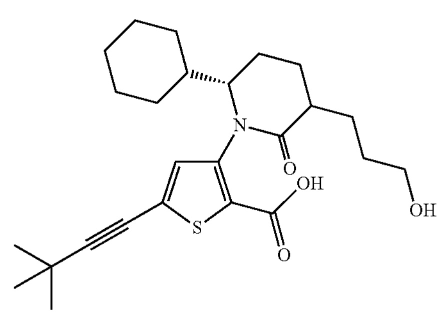 [SMILES: CC(C)(C)C#Cc1cc(N2C(=O)C(CCCO)CC[C@H]2C2CCCCC2)c(C(=O)O)s1] |

TABLE 1-continued

| Compound number | Name | Structure |
|---|---|---|
| 342 | 3-[(S)-6-Cyclohexyl-3-(2-hydroxy-ethyl)-2-oxo-piperidin-1-yl]-5-(3,3-dimethyl-but-1-ynyl)-thiophene-2-carboxylic acid | 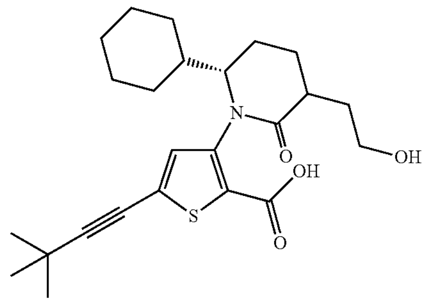 [SMILES: CC(C)(C)C#Cc1cc(N2C(=O)C(CCO)CC[C@H]2C2CCCCC2)c(C(=O)O)s1] |
| 343 | 3-[(S)-6-Cyclohexyl-3-(2-hydroxy-ethyl)-2-oxo-piperidin-1-yl]-5-(3,3-dimethyl-but-1-ynyl)-thiophene-2-carboxylic acid | 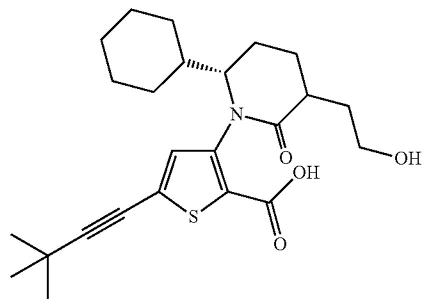 [SMILES: CC(C)(C)C#Cc1cc(N2C(=O)C(CCO)CC[C@H]2C2CCCCC2)c(C(=O)O)s1] |

NMR data for certain compounds of the invention are provided in Table 2.

TABLE 2

| Compound number | NMR data |
|---|---|
| 1 | $^1$H-NMR (400 MHz, CD$_3$OD): 7.80(d, 2H), 7.40(t, 2H), 7.29(t, 1H), 7.18(s, 1H), 4.62(m, 1H), 2.30(m, 2H), 2.03(m, 1H), 1.80-1.10 (m, 12H) |
| 2 | $^1$H-NMR (400 MHz, CD$_3$OD): δ 6.97(s, 1H), 4.13(m, 1H), 3.90(m, 1H), 3,82(m, 1H), 3.57(m, 2H), 1.97-1.48(m, 10H), 1.32(s, 9H), 1.26-1.09(m, 6H). |
| 3 | $^1$H-NMR (400 MHz, CD$_3$OD): δ 6.93(s, 1H), 4.14(m, 1H), 4.0(m, 1H), 3.62(m, 1H), 3.58(m, 2H), 2.02-1.48(m, 10H), 1.32(s, 9H), 1.25-1.17(m, 6H). |
| 4 | $^1$H-NMR (400 MHz, CDCl$_3$): δ 7.43(m, 2H), 7.21(m, 3H), 6.94(m, 1H), 3.68(m, 1H), 2.45(m, 2H), 2.21(m, 1H), 1.83-1.51 (m, 12H), 1.32(m, 2H). |
| 5 | 1H NMR (400 MHz, CDCl$_3$): δ 0.88-1.12(m, 5H), 1.29(m, 2H), 1.37(s, 3H), 1.48-1.60(m, 2H), 1.71(m, 2H), 1.84(m, 2H), 1.96(m, 1H), 2.12(m, 1H), 2.29(s, 3H), 3.72(m, 1H), 6.93(s, 1H), 7.11(d, 2H), 7.39(d, 2H) |
| 6 | $^1$H-NMR (400 MHz, DMSO-d$_6$): δ 13.1(s, 1H), 7.75(d, 2H), 7.58(s, 1H), 7.37-7.52(m, 3H), 4.21(m, 1H), 2.34(m, 2H), 2.09(m, 1H), 1.91(m, 1H), 1.36-1.79(m, 5H), 0.91-1.31(m, 6H). |
| 7 | $^1$H-NMR (400 MHz, CD$_3$OD): δ 6.93(s, 1H), 4.12(d, 1H), 3.91(d, 1H), 3.66(s, 1H), 3.54(t, 2H), 2.14(m, 1H), 1.91(m, 1H), 1.44-1.85(m, 8H), 1.41(s, 3H), 1.06-1.37(m, 14H) |
| 8 | $^1$H-NMR (400 MHz, CD$_3$OD): δ 6.90(s, 1H), 4.24(tert, 1H), 4.13(d, 1H), 4.01(tert, 1H), 3.73(d, 1H), 3.71(d, 1H), 3.66(t, 1H), 2.21(m, 1H), 1.41-1.98(m, 8H), 1.05-1.37(m, 15H). |
| 10 | $^1$H-NMR (400 MHz, DMSO-d$_6$): δ 7.57(s, 1H), 7.32-7.45(m, 6H), 7.28(t, 3H), 7.20(t, 1H), 5.45(m, 1H), 2.52-2.63(m, 3H), 1.89(m, 1H). |
| 11 | $^1$H-NMR (400 MHz, CD$_3$OD): δ 6.89(s, 1H), 3.94(m, 1H), 3.58(m, 2H), 2.05(m, 1H), 1.92-1.39(m, 13H), 1.32(s, 9H), 1.25-1.13 (m, 5H) |
| 13 | $^1$H-NMR (400 MHz, CDCl$_3$): δ 7.56(d, 2H), 7.35(m, 3H), 7.12(s, 1H), 4.26(tert, 2H), 3.98(m, 2H), 3.60(s, 1H), 0.94-1.93(m, 11H) |
| 18 | $^1$H-NMR (400 MHz, CD$_3$OD): δ 7.74(d, 2H), 7.65(d, 2H), 7.49(d, 2H), 7.41(t, 2H), 7.33(t, 1H), 7.21(s, 1H), 4.12(d, 1H), 3.95(d, 1H), 3.93(s, 1H), 3.37(d, 1H), 3.02(tert, 1H), 2.47(s, 3H), 1.41-1.99(m, 7H), 1.05-1.32(m, 4H) |
| 22 | $^1$H-NMR (400 MHz, DMSO): δ 10.31(d, 1H), 7.63(d, 2H), 7.42(t, 2H), 7.31(t, 2H), 7.23(m, 2H), 7.14(s, 1H), 6.98(m, 3H), 4.61(m, 2H), 4.45(m, 1H), 4.10(m, 1H), 3.32(s, 2H), 2.20(m, 1H), 1.88-1.76(m, 4H), 1.65-1.58(m, 2H), 1.41-1.05(m, 6H) |
| 23 | $^1$H-NMR (400 MHz, DMSO): δ 8.55(m, 2H), 7.63(d, 2H), 7.48(t, 2H), 7.32(t, 2H), 7.15(s, 1H), 5.76(s, 1H), 3.98(m, 1H), 3.82(m, 1H), 2.33(m, 2H), 2.07(m, 1H), 1.80(m, 2H), 1.61(m, 3H), 1.38(m, 2H), 1.03(m, 5H) |

TABLE 2-continued

| Compound number | NMR data |
|---|---|
| 35 | $^1$H-NMR (400 MHz, CD$_3$OD): δ 7.03(s, 1H), 3.81(m, 1H), 2.25(m, 1H), 1.88-1.38(m, 6H), 1.29(s, 9H), 1.18(m, 4H), 1.06 (m, 4H) |
| 62 | $^1$H-NMR (400 MHz, CD$_3$OD): δ 7.82(d, 1H), 7.68(d, 2H), 7.44(m, 3H), 7.36(s, 1H), 6.78(d, 1H), 4.16(d, 1H), 4.02(s, 3H), 3.94(d, 1H), 3.81(s, 1H), 3.65(d, 1H), 3.18(tert, 1H), 2.00(d, 1H), 1.36-1.87(m, 6H), 1.05-1.29(m, 4H) |
| 135 | $^1$H-NMR (400 MHz, CD$_3$OD): δ 8.47(d, 1H), 7.85(tert, 1H), 7.64(d, 2H), 7.43(t, 2H), 7.30(m, 2H), 6.61(d, 1H), 3.94(s, 1H), 3.88(d, 1H), 3.74(d, 1H), 2.81-3.24(m, 6H), 1.49-2.06(m, 8H), 0.98-1.35(m, 7H) |
| 184 | $^1$H-NMR (400 MHz, CD$_3$OD): δ 8.51(d, 1H), 7.86(tert, 1H), 7.64(d, 2H), 7.41(t, 2H), 7.32(t, 1H), 7.19(s, 1H), 7.91(d, 1H), 4.10(d, 1H), 3.96(s, 1H), 3.89(d, 1H), 3.65-3.81(m, 8H), 3.41(d, 1H), 3.06(d, 1H), 1.37-1.98(m, 8H), 1.03-1.26(m, 3H) |
| 185 | 1H NMR (400 MHz, CDCl$_3$): δ 1.03(m, 3H), 1.15(d, 3H), 1.30(m, 1H), 1.43(m, 2H), 1.58(m, 2H), 1.63(m, 1H), 1.7-1.8(m, 2H), 1.9(d, 1H), 1.95-2.10(m, 3H), 2.96(d, 1H), 3.33(d, 2H), 3.60(s, 1H), 3.75(s, 1H), 3.81(d, 1H), 4.05(s, 1H), 4.20(d, 1H), 6.37(d, 1H), 7.02-7.05(m, 3H), 7.50-7.54(m, 2H), 7.66(m, 1H), 8.38(s, 1H) |
| 193 | $^1$H-NMR (400 MHz, CD$_3$OD): δ 7.80(d, 1H), 6.95(s, 1H), 6.75(d, 1H), 4.14(d, 1H), 3.93(d, 1H), 3.64(d, 1H), 3.16(m, 1H), 2.30(m, 2H), 1.90(m, 1H), 1.83(m, 3H), 1.69 (m, 2H), 1.58(t, 3H), 1.47 (m, 2H), 1.31(s, 9H), 1.18 (m, 4H) |
| 196 | 1H NMR (400 MHz, CDCl$_3$): δ 0.95-1.15(m, 4H), 1.20(m, 1H), 1.30-1.40(m, 1H), 1.47(m, 1H), 1.57(m, 2H), 1.66(s, 1H), 1.70-1.85(m, 3H), 1.85-1.95(m, 2H), 3.03(m, 1H), 3.18(d, 2H), 3.43(d, 1H), 3.69(s, 1H), 3.75-3.90(m, 3H), 4.10(d, 1H), 4.45(s, 2H), 6.51(d, 1H), 7.00-7.10(m, 3H), 7.49(m, 2H), 7.70(m, 1H), 8.46(s, 1H) |
| 200 | 1H NMR (400 MHz, CDCl$_3$): δ 0.90-1.15(m, 5H), 1.40-1.60(m, 3H), 1.60-1.85(m, 3H), 1.95(m, 2H), 3.20(d, 1H), 3.55(d, 2H), 3.68(m, 2H), 3.70-3.85(m, 6H), 3.85-3.95(m, 2H), 6.48(d, 1H), 7.02(s, 1H), 7.27(d, 2H), 7.42(d, 2H), 7.67(d, 1H), 8.43(d, 1H) |
| 236 | $^1$H-NMR (400 MHz, CD$_3$OD): δ 6.87(s, 1H), 4.19(s, 2H), 4.05(m, 2H), 3.82(s, 1H), 1.43-1.90(m, 6H), 1.06-1.39(m, 14H) |
| 279 | 1H NMR (400 MHz, CDCl$_3$): δ 0.93-1.15(m, 4H), 1.29-1.39(m, 1H), 1.45(m, 1H), 1.50-1.60(m, 2H), 1.65(m, 1H), 1.70-1.80(m, 1H), 1.80-1.90(d, 1H), 1.90-2.10(m, 4H), 3.05(d, 1H), 3.20(m, 1H), 3.27(s, 3H), 3.30(m, 1H), 3.36-3.53(m, 3H), 3.61-3.74(m, 2H), 4.06(d, 1H), 6.42(s, 1H), 6.99-7.07(m, 3H), 7.48(m, 2H), 7.64(d, 1H), 8.42(s, 1H) |
| 295 | 1H NMR (400 MHz, CDCl$_3$): δ 0.96-1.14(m, 4H), 1.32-1.44(m, 1H), 1.48(m, 1H), 1.57(m, 2H), 1.67(m, 1H), 1.76(d, 1H), 1.83(d, 1H), 2.30(s, 3H), 2.98(d, 1H), 3.40(d, 1H), 3.67(m, 1H), 3.79(d, 1H), 3.91(s, 3H), 4.10(d, 1H), 7.06(s, 1H), 7.15(d, 2H), 7.42(d, 2H), 7.71(d, 1H), 7.75(s, 1H) |
| 302 | 1H NMR (400 MHz, CDCl$_3$): δ 0.97-1.15(m, 4H), 1.27(m, 1H), 1.47-1.64(m, 3H), 1.68(m, 1H), 1.76(d, 1H), 1.84(d, 1H), 2.28(s, 3H), 2.73(s, 3H), 3.31(d, 1H), 3.52(d, 1H), 3.71(m, 1H), 3.85(d, 1H), 4.14(d, 1H), 7.06(s, 1H), 7.12(d, 1H), 7.40(d, 2H), 7.45(d, 1H), 8.13(d, 1H), 8.98(s, 1H) |
| 311 | $^1$H-NMR (400 MHz, CD$_3$OD): δ 6.91(s, 1H), 4.23(d, 1H), 3.94(d, 1H), 3.62(m, 1H), 3.55(m, 2H), 1.96-1.52(m, 10H), 1.45(s, 3H), 1.32(s, 9H), 1.21 (m, 4H), 1.05(m, 1H) |
| 314 | 1H NMR (400 MHz, CDCl$_3$): δ 0.94-1.13(m, 4H), 1.26(m, 1H), 1.38(m, 1H), 1.43(s, 3H), 1.45(s, 3H), 1.47-1.59(m, 2H), 1.62(m, 1H), 1.74(d, 1H), 1.87(d, 1H), 2.29(s, 3H), 3.45(m, 1H), 3.84(d, 1H), 4.09(d, 1H), 7.02(s, 1H), 7.12(d, 2H), 7.42(d, 2H) |
| 316 | $^1$H-NMR (400 MHz, CD$_3$OD): δ 6.93(s, 1H), 4.23(d, 1H), 3.80(m, 1H), 2.49(m, 1H), 2.06-1.42(m, 10H), 1.32(s, 9H), 1.22(d, 3H), 1.12 (m, 5H). |
| 318 | $^1$H-NMR (400 MHz, CD$_3$OD): δ 6.97(s, 1H), 4.11(d, 1H), 3.92(d, 1H), 3.62(m, 1H), 2.17(m, 1H), 1.93(m, 1H), 1.62-1.85(m, 4H), 1.45-1.62(m, 4H), 1.37-1.44(m, 3H), 1.27-1.37(m, 10H), 1.11-1.27(m, 10H) |
| 319 | $^1$H-NMR (400 MHz, CD$_3$OD): δ 6.97(s, 1H), 4.18(d, 1H), 3.94(d, 1H), 3.53(m, 1H), 2.17(t, 1H), 1.95(m, 2H), 1.70-1.86(m, 4H), 1.58-1.69(m, 2H), 1.46-1.58(m, 2H), 1.39-1.46(m, 3H), 1.29-1.39(m, 10H), 1.10-1.29(m, 10H) |
| 322 | $^1$H-NMR (400 MHz, CD$_3$OD): δ 6.95(s, 1H), 4.09(m, 1H), 3.74(m, 1H), 2.09(m, 1H), 1.94-1.67(m, 8H), 1.38(m, 1H), 1.33(s, 9H), 1.17(m, 5H) |
| 323 | $^1$H-NMR (400 MHz, CD$_3$OD): δ 6.87(s, 1H), 4.24(tert, 1H), 3.93(d, 1H), 3.62-3.82(m, 3H), 2.08-2.21(m, 1H), 1.88-2.04(m, 2H), 1.56-1.87(m, 4H), 1.43-1.56(m, 4H), 0.98-1.35(m, 14H) |
| 324 | 1H NMR (400 MHz, CDCl$_3$): δ 0.88-1.13(m, 4H), 1.32(m, 2H), 1.43(s, 3H), 1.48-1.67(m, 3H), 1.69-1.87(m, 4H), 1.96(m, 1H), 2.06(m, 1H), 2.31(s, 3H), 3.67(m, 1H), 7.08(s, 1H), 7.15(d, 2H), 7.44(d, 2H) |
| 325 | 1H NMR (400 MHz, CDCl$_3$): δ 0.96-1.19(m, 5H), 1.23(s, 9H), 1.37(m, 1H), 1.45(m, 1H), 1.61(m, 2H), 1.64-1.81(m, 4H), 1.83(m, 1H), 2.22(m, 1H), 3.37(m, 1H), 3.57-3.78(m, 4H), 3.89(d, 1H), 3.98(d, 1H), 6.79(s, 1H) |
| 326 | $^1$H-NMR (400 MHz, CD$_3$OD): δ 6.78(s, 1H), 4.07(m, 1H), 3.53(m, 2H), 2.26(m, 1H), 1.96-1.38(m, 14H), 1.30(s, 9H), 1.14 (m, 5H). |
| 328 | $^1$H-NMR (400 MHz, CD$_3$OD): δ 6.87(s, 1H), 4.14(tert, 1H), 3.92(tert, 1H), 3.77(d, 1H), 3.70(t, 2H), 2.32(m, 1H), 1.82-1.99(m, 2H), 1.71-1.82(m, 2H), 1.66(m, 1H), 1.41-1.59(m, 5H), 1.03-1.34(m, 14H) |
| 334 | $^1$H-NMR (400 MHz, CD$_3$OD): δ 6.95(s, 1H), 4.08(m, 1H), 3.74(m, 1H), 2.18(m, 1H), 1.94-1.67(m, 8H), 1.42(m, 1H), 1.33(s, 9H), 1.17(m, 5H) |

TABLE 2-continued

| Compound number | NMR data |
|---|---|
| 336 | $^1$H NMR (400 MHz, CD$_3$OD): δ 1.09-1.31 (m, 8H), 1.32 (s, 9H), 1.45-1.85 (m, 5H), 1.89-2.10 (m, 3H), 3.56-3.61 (m, 1H), 3.93-4.00 (m, 1H), 4.00-4.10 (m, 1H), 4.12-4.22 (m, 2H), 6.99 (s, 1H) |
| 337 | $^1$H NMR (400 MHz, CD$_3$OD): δ 1.07-1.31 (m, 8H), 1.32 (s, 9H), 1.45-1.60 (m, 2H), 1.63-1.85 (m, 4H), 1.87-1.98 (m, 1H), 2.02-2.11 (m, 1H), 3.60-3.66 (m, 1H), 3.93-4.03 (m, 2H), 4.15 (d, 1H), 4.26-4.35 (m, 1H), 6.94 (s, 1H) |
| 340 | $^1$H-NMR (400 MH$_z$, CD$_3$OD): δ 6.81 (s, 1H), 3.96 (br, 1H), 3.48 (m, 1H), 2.06(m, 3H), 1.84(m, 3H), 1.70(br, 2H), 1.46 (m, 1H), 1.37(m, 1H), 1.31(s, 9H), 1.16(m, 5H) |
| 341 | $^1$H-NMR (400 MH$_z$, CD$_3$OD): δ 6.81 (s, 1H), 4.00 (br, 1H), 3.53 (t, 2H), 2.27(br, 1H), 1.97(m, 3H), 1.82-1.64(m, 7H), 1.58 (m, 2H), 1.37(m, 2H), 1.31(s, 9H), 1.14(m, 5H) |
| 343 | $^1$H-NMR (400 MH$_z$, CD$_3$OD): δ 6.85(s, 1H), 3.92 (br, 1H), 3.67 (m, 2H), 2.41(br, 1H), 2.15(m, 1H), 1.97(m, 2H), 1.78 (m, 7H), 1.37(m, 2H), 1.31(s, 9H), 1.14(m, 5H). |

Biological Examples

Biological Example 1

Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture was disclosed in U.S. Pat. No. 5,738,985 to Miles et al. In vitro assays have been reported in Ferrari et al. *Jnl. of Vir.*, 73:1649-1654, 1999; Ishii et al., *Hepatology*, 29:1227-1235, 1999; Lohmann et al., *Jnl of Bio. Chem.*, 274:10807-10815, 1999; and Yamashita et al., *Jnl. of Bio. Chem.*, 273:15479-15486, 1998.

WO 97/12033, filed on Sep. 27, 1996, by Emory University, listing C. Hagedorn and A. Reinoldus as inventors, which claims priority to U.S. Provisional Patent Application Ser. No. 60/004,383, filed on September 1995, described an HCV polymerase assay that can be used to evaluate the activity of the of the compounds described herein. Another HCV polymerase assay has been reported by Bartholomeusz, et al., Hepatitis C Virus (HCV) RNA polymerase assay using cloned HCV non-structural proteins; Antiviral Therapy 1996: 1(Supp 4) 18-24.

Screens that measure reductions in kinase activity from HCV drugs were disclosed in U.S. Pat. No. 6,030,785, to Katze et al., U.S. Pat. No. 6,228,576, Delvecchio, and U.S. Pat. No. 5,759,795 to Jubin et al. Screens that measure the protease inhibiting activity of proposed HCV drugs were disclosed in U.S. Pat. No. 5,861,267 to Su et al., U.S. Pat. No. 5,739,002 to De Francesco et al., and U.S. Pat. No. 5,597,691 to Houghton et al.

Biological Example 2

Replicon Assay

A cell line, ET (Huh-lucubineo-ET) was used for screening of compounds for inhibiting HCV RNA dependent RNA polymerase. The ET cell line was stably transfected with RNA transcripts harboring a I$_{389}$luc-ubi-neo/NS3-3'/ET; replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The ET cells were grown in DMEM (Dulbeco's Modified Eagle's Medium), supplemented with 10% fetal calf serum, 2 mM Glutamine, Penicillin (100 IU/mL)/Streptomycin (100 μg/mL), 1× nonessential amino acids, and 250 μg/mL G418 ("Geneticin"). Reagents were all available through Life Technologies (Bethesda, Md.). The cells were plated at 0.5-1.0×10$^4$ cells/well in the 96 well plates and incubated for 24 hrs before adding test compound. The compounds were added to the cells to achieve a final concentration of 0.1 nM to 50 μM and a final DMSO (dimethylsulfoxide) concentration of 0.5%. Luciferase activity was measured 48 hours later by adding a lysis buffer and the substrate (Catalog number Glo-lysis buffer E2661 and Bright-Glo luciferase system E2620 Promega, Madison, Wis.). Cells should not be too confluent during the assay. Percent inhibition of replication data was plotted relative to no compound control. To determine the EC$_{50}$ (effective concentration at which 50% of the maximum inhibition was observed), a 10 point, 3-fold serial dilution for each compound was used, which spans a concentration range of 1000 fold. EC$_{50}$ values were calculated by fitting % inhibition at each concentration to the following equation:

$$\% \text{ inhibition}=100\%/[(EC_{50}/[I])^b+1]$$

where b was Hill's coefficient.

In some aspects, certain compounds of Formula (I), exhibited EC$_{50}$ of equal to or less than 50 μM when tested according to the assay of Example 2. In other aspects the EC$_{50}$ was equal to or less than 10 μM. In still other aspects the EC$_{50}$ was equal to or less than 1 μM.

Biological Example 3

Cloning and Expression of Recombinant HCV-NS5b

The coding sequence of NS5b protein was cloned by PCR from pFKI$_{389}$luc/NS3-3'/ET as described by Lohmann, V., et al. (1999) *Science* 285, 110-113 using the primers shown on page 266 of WO 2005/012288.

The cloned fragment was missing the C terminus 21 amino acid substituents. The cloned fragment was inserted into an IPTG-inducible (isopropyl-β-D-thiogalactopyranoside) expression plasmid that provides an epitope tag (His)6 at the carboxy terminus of the protein.

The recombinant enzyme was expressed in XL-1 cells and after induction of expression, the protein was purified using affinity chromatography on a nickel-NTA (nitrilotriacetic acid) column. Storage conditions were 10 mM Tris-HCl pH 7.5, 50 mM NaCl, 0.1 mM EDTA (ethylenediaminetetraacetic acid), 1 mM DTT (dithiothreotol), and 20% glycerol at −20° C.

Biological Example 4

HCV-NS5b Enzyme Assay Using Heteropolymer Substrate

The polymerase activity was assayed by measuring incorporation of radiolabeled UTP into a RNA product using a biotinylated, heteropolymeric template, which included a portion of the HCV genome. Typically, the assay mixture (50 μL) contained 10 mM Tris-HCl (pH 7.5), 5 mM $MgCl_2$, 0.2 mM EDTA, 10 mM KCl, 1 unit/μL RNAsin, 1 mM DTT, 10 μM each of NTP (nucleoside triphosphate), including [$^3$H]-UTP (uridine triphosphate), and 10 ng/μL heteropolymeric template. Test compounds were initially dissolved in 100% DMSO and further diluted in aqueous buffer containing 5% DMSO. Typically, compounds were tested at concentrations between 1 nM and 100 μM. Reactions were started with addition of enzyme and allowed to continue at 37° C. for 2 hours. Reactions were quenched with 8 μL of 100 mM EDTA and reaction mixtures (30 μL) were transferred to streptavidin-coated scintillation proximity microtiter plates (FlashPlates) and incubated at room temperature overnight. Incorporation of radioactivity was determined by scintillation counting.

Biological Example 5

HCV-NS5b Enzyme Assay Using Homopolymer Substrate

The polymerase activity was assayed by measuring incorporation of radiolabeled UTP into a RNA product using a biotinylated, homopolymeric template. The template was formed by annealing adenosine homopolymer to uridine 20-mer capped with a 5′-biotin group (biotin-$U^{20}$) in the ratio of 1:4. Typically, the assay mixture (50 μL) contained 25 mM Tris-HCl (pH 7.5), 40 mM KCl, 0.3 mM $MgCl_2$, 0.05 mM EDTA, 0.2 unit/μL Superase RNAse Inhibitor, 5 mM DTT, 30 μM UTP (Uridine triphosphate), including [$^3$H]-UTP (uridine triphosphate) at 0.4 μCi/μL with final concentration of 1 μM, and 50 nM of homopolymeric template. Test compounds were initially dissolved in 100% DMSO and further diluted in aqueous buffer containing 5% DMSO. Typically, compounds were tested at concentrations between 2 nM and 50 μM. Reactions were started with addition of enzyme and allowed to continue at 30° C. for 90 minutes. Reactions were quenched with 8 μL of 100 mM EDTA and reaction mixtures (30 μL) were transferred to streptavidin-coated scintillation proximity microtiter plates (FlashPlates) and incubated at room temperature overnight. Incorporation of radioactivity was determined by scintillation counting.

Inhibitor $IC_{50}$ values were determined by adding test compound as ten point, two-fold serial dilutions in 100% DMSO with a final reaction concentration of 5%. $IC_{50}$ values were calculated by plotting the % inhibition against compound concentration and fitting the data to a constrained four parameter sigmoidal curve, equivalent to the "four parameter logistic equation", where Bottom was the minimum Y value, Top was the maximum Y value, and Hillslope was the slope of the linear portion of the semi-log curve. Top and Bottom were constrained to values of 0% and 100%, respectively. These analyses were performed using Graphpad Prism v.4.0 (Graphpad Software, Inc.) in conjunction with DS Accord for EXCEL 6.0 (Accelrys, Microsoft Corp.).

Biological Example 6

The polymerase activity was also assayed by measuring incorporation of radiolabeled GTP into an RNA product using a biotinylated oligoG13 primer with a polycytidylic acid RNA template. Typically, the assay mixture (40 μL) contains 50 mM HEPES (pH 7.3), 2.5 mM magnesium acetate, 2 mM sodium chloride, 37.5 mM potassium acetate, 5 mM DTT, 0.4 U/mL RNasin, 2.5% glycerol, 3 nM NS5B, 20 nM polyC RNA template, 20 nM biotin-oligoG13 primer, and 0.2 μM tritiated guanosine triphosphate. Test compounds were initially dissolved and diluted in 100% DMSO and further diluted into aqueous buffer, producing a final concentration of 5% DMSO. Typically, compounds were tested at concentrations between 0.2 nM and 10 μM. Reactions were started with addition of tritiated guanosine triphosphate and allowed to continue at 30° C. for 2 hours. Reactions were quenched with 100 μL stop buffer containing 10 mM EDTA and 1 μg/mL streptavidin-coated scintillation proximity beads. Reaction plates were incubated at 4° C. for 10 hours and then incorporation of radioactivity was determined by scintillation counting.

Compounds in Table 1 supra have been tested in the polymerase assay of Biological Example 1 and the $IC_{50}$ values for each compound were provided in Table 3 infra. Most of the compounds of Table 1 exhibit an $IC_{50}$ of 1 μM or less or an $IC_{50}$ of 500 nM or less in the replicon assay of Biological Example 2 provided herein. For example, the compounds of Example numbers 2, 3, 5, 7, 8, 10, 11, 19, 35, 69, 74, 75, 76, 77, 78, 79, 80, 81, 82, 84, 85, 86, 87, 88, 89, 90, 91, 91, 92, 93, 94, 95, 96, 99, 118, 119, 120, 121, 122, 123, 125, 126, 127, 130, 135, 137, 138, 140, 141, 143, 145, 146, 147, 148, 149, 150, 151, 152, 154, 155, 156, 157, 158, 160, 161, 162, 163, 164, 165, 167, 168, 169, 170, 171, 172, 173, 176, 177, 179, 180, 182, 183, 184, 185, 186, 187, 188, 189, 190, 191, 192, 193, 194, 195, 196, 197, 198, 199, 200, 201, 202, 203, 208, 212, 213, 216, 217, 218, 219, 222, 224, 225, 226, 227, 228, 229, 231, 232, 233, 234, 235, 236, 238, 239, 240, 241, 243, 244, 246, 247, 248, 250, 251, 253, 256, 257, 258, 272, 273, 274, 275, 276, 277, 278, 279, 280, 281, 283, 284, 285, 286, 287, 288, 289, 290, 291, 292, 295, 296, 297, 298, 299, 301, 302, 303, 304, 305, 307, 308, 310, 311, 312, 313, 314, 315, 316, 318, 319, 320, 321, 322, 323, 325, 327, 328, 329, 330, 332, 334, 336, 337, 339, 340, 341, 342, 343 exhibit an $IC_{50}$ of 100 nM or less in the replicon assay of Biological Example 2. The compounds of Example numbers 1, 4, 6, 12, 13, 17, 18, 24, 26, 27, 29, 31, 36, 37, 38, 39, 40, 42, 45, 46, 47, 48, 49, 50, 51, 52, 53, 54, 55, 56, 58, 59, 60, 61, 62, 63, 64, 65, 66, 67, 70, 71, 72, 73, 83, 97, 98, 100, 101, 102, 103, 104, 105, 106, 107, 108, 109, 113, 114, 115, 116, 124, 128, 129, 131, 136, 139, 142, 144, 153, 159, 178, 181, 204, 205, 206, 207, 209, 211, 214, 215, 220, 221, 223, 230, 237, 242, 245, 249, 252, 254, 255, 259, 260, 262, 267, 282, 293, 294, 300, 206, 309, 317, 324, 326, 331, 333, 335, 338 exhibit an $IC_{50}$ between 100 nM and 5.0 uM in the replicon assay of Biological Example 2. The compounds of Example numbers 9, 15, 16, 20, 21, 22, 23, 25, 28, 30, 32, 33, 34, 41, 47, 57, 110, 111, 112, 117, 132, 166, 174, 175, 210, 271 exhibit an $IC_{50}$ of 5.0 μM or more in the replicon assay of Biological Example 2.

TABLE 3

| | NS5B-enzyme3 (uM) | MS [M + H⁺] | Retention time (min) | HPLC method |
|---|---|---|---|---|
| 1 | 0.1815 | 370.4 | 12.36 | A |
| 2 | 0.035 | 448.3 | 13.02 | A |
| 3 | 0.004 | 448.3 | 13.03 | A |
| 4 | 0.073 | 384.4 | 12.76 | A |
| 5 | 0.052 | 427.5 | 13.06 | A |
| 6 | — | 370.1 | 12.4 | A |
| 7 | 0.006 | 462.2 | 13.72 | A |
| 8 | 0.001 | 434.3 | 8.45 | A |
| 9 | 0.08 | 398.2 | 11.64 | A |
| 10 | 0.003 | 464.3 | 7.96 | A |
| 11 | 0.008 | 461.9 | 12.25 | A |
| 12 | 0.045 | 400.5 | 10.48/11.76 | A |
| 13 | 0.079 | 386.1 | 12.14 | A |
| 14 | 3.651 | 485.6 | 14.11 | A |
| 15 | 0.0735 | 385.3 | 6.12 | A |
| 16 | 0.4205 | 489.3 | 12.73 | A |
| 17 | 0.024 | 475.2 | 12.48 | A |
| 18 | 0.002 | 539.6 | 14.19 | A |
| 19 | 0.015 | 388.6 | 14.3 | A |
| 20 | 0.128 | 517.6 | 12.55/13.80 | A |
| 21 | 0.97 | 533.6 | 13.11 | A |
| 22 | 0.02 | 533.6 | 13.45 | A |
| 23 | 0.245 | 399.5 | 5.89 | A |
| 24 | 0.0445 | 503.6 | 13.46 | A |
| 25 | 0.173 | 503.4 | 12.66 | A |
| 26 | 0.067 | 463.3 | 12.13 | A |
| 27 | 0.022 | 539.3 | 13.7 | A |
| 28 | 0.226 | 399.5 | 7.01 | A |
| 29 | 0.001 | 599.3 | 12.76 | A |
| 30 | 0.003 | 569.3 | 13.09 | A |
| 31 | 0.047 | 519.6 | 14.34 | A |
| 32 | 0.241 | 544.6 | 13.79 | A |
| 33 | 0.038 | 587.3 | 12.8 | A |
| 34 | 1.05 | 388.6 | 14.34 | A |
| 35 | 0.0095 | 388.4 | 14.35 | A |
| 36 | 0.058 | 546.6 | 14.69 | A |
| 37 | 0.072 | 492.6 | 12.8 | A |
| 38 | 0.065 | 505.6 | 13.75 | A |
| 39 | 0.051 | 553.4 | 14.19 | A |
| 40 | 0.013 | 543.3 | 13.87 | A |
| 41 | 0.218 | 521.3 | 11.71 | A |
| 42 | 0.148 | 517.6 | 13.73 | A |
| 43 | | 553.6 | 15.49 | A |
| 44 | | 553.6 | 12.91 | A |
| 45 | 4.9 | 505.6 | 13.55 | A |
| 46 | 0.063 | 531.6 | 14.33 | A |
| 47 | 0.088 | 492.3 | 6.52 | A |
| 48 | 0.187 | 402.3 | 13.73 | A |
| 49 | 0.015 | 539.17 | 4.16 | C |
| 50 | 0.007 | 582.17 | 3.69 | C |
| 51 | 0.011 | 617.18 | 4.57 | C |
| 52 | 0.015 | 525.15 | 4.1 | C |
| 53 | 0.024 | 609.13 | 7.56 | B |
| 54 | 0.018 | 593.14 | 6.97 | B |
| 55 | 0.071 | 609.14 | 4.22 | C |
| 56 | 0.0071 | 553.18 | 4.4 | C |
| 57 | 0.26 | 578.18 | 8.23 | B |
| 58 | 0.088 | 539.17 | 6 | B |
| 59 | 0.039 | 609.13 | 6.75 | B |
| 60 | 0.009 | 601.18 | 4.73 | C |
| 61 | 0.003 | 578.18 | 8.98 | B |
| 62 | 0.011 | 529.16 | 7.84 | B |
| 63 | 0.042 | 617.19 | 9.78 | B |
| 64 | 0.031 | 578.17 | 9.18 | B |
| 65 | 0.045 | 601.18 | 7.23 | B |
| 66 | 0.049 | 611.13 | 4.39 | C |
| 67 | 0.1835 | 402.3 | 13.48 | A |
| 68 | | 593.14 | 6.77 | B |
| 69 | 0.002 | 597.4 | 16.51 | A |
| 70 | 0.067 | 402.5 | 15.7 | A |
| 71 | 0.052 | 398.5 | 16.1 | A |
| 72 | 0.064 | 412.6 | 16.77 | A |
| 73 | 0.021 | 418.5 | 16.91 | A |
| 74 | 0.012 | 581.19 | 8.44 | B |
| 75 | 0.008 | 623.24 | 2.28 | D |
| 76 | 0.004 | 595.6 | 17.16 | A |
| 77 | 0.003 | 625.6 | 17.66 | A |
| 78 | 0.005 | 599.2 | 7.91 | B |
| 79 | 0.004 | 627.18 | 17.35 | A |
| 80 | 0.006 | 657.24 | 9.57 | B |
| 81 | 0.009 | 612.23 | 4.74 | B |
| 82 | 0.006 | 609.22 | 7.11 | B |
| 83 | 0.003 | 629.21 | 7.16 | B |
| 84 | 0.004 | 609.22 | 16.76 | A |
| 85 | 0.002 | 583.5 | 16.78 | A |
| 86 | 0.006 | 585.18 | 7.1 | B |
| 87 | 0.005 | 639.23 | 17.73 | A |
| 88 | 0.002133 | 610.3 | 7.08 | A |
| 89 | 0.003 | 652.23 | 7.62 | B |
| 90 | 0.004 | 625.22 | 7.95 | B |
| 91 | 0.012 | 637.25 | 17.92 | A |
| 92 | 0.004 | 623.5 | 8.17 | B |
| 93 | 0.004 | 625.22 | 7.65 | B |
| 94 | 0.002 | 639.5 | 17.13 | A |
| 95 | 0.005 | 645.4 | 17.27 | A |
| 96 | | 623.4 | 17.53 | A |
| 97 | 0.027 | 550.3 | 11.24 | A |
| 98 | 0.003 | 582.3 | 9.34 | A |
| 99 | 0.002 | 597.3 | 10.73 | A |
| 100 | 0.004 | 567.3 | 13.4 | A |
| 101 | 0.011 | 591.3 | 11.52 | A |
| 102 | 0.0045 | 585.3 | 10.83 | A |
| 103 | 0.002 | 555.3 | 11.42 | A |
| 104 | 0.021 | 543.3 | 11.85 | A |
| 105 | 0.002 | 581.3 | 14.04 | A |
| 106 | 0.014 | 591.3 | 11.98 | A |
| 107 | <0.001 | 555.3 | 11.66 | A |
| 108 | 0.037 | 526.3 | 9.94 | A |
| 109 | 0.03 | 543.3 | 11.57 | A |
| 110 | 0.183 | 573.2] | 12.89 | A |
| 111 | 0.243 | 593.2 | 13.18 | A |
| 112 | 0.173 | 666.4 | 12.61 | A |
| 113 | 0.044 | 440.6 | 16.03 | A |
| 114 | 0.09 | 414.5 | 12.96 | A |
| 115 | 0.004 | 506.3 | 11.8 | A |
| 116 | 0.064 | 428.6 | 13.88 | A |
| 117 | 0.739 | 452.5 | 13.93 | A |
| 118 | 0.002 | 609.4 | 12.09 | A |
| 119 | 0.009 | 609.4 | 12.12 | A |
| 120 | 0.006 | 613.3 | 10.87 | A |
| 121 | 0.007 | 613.3 | 10.87 | A |
| 122 | 0.002 | 625.4 | 9.33 | A |
| 123 | 0.002 | 611.3 | 8.46 | A |
| 124 | 0.004 | 611.3 | 8.46 | A |
| 125 | 0.018 | 621.4 | 12.74 | A |
| 126 | 0.011 | 637.3 | 13.87 | A |
| 127 | 0.003 | 608.3 | 12.96 | A |
| 128 | 0.009 | 625.3 | 9.86, 10.06 | A |
| 129 | 0.096 | 409.2 | 12.3 | A |
| 130 | 0.001 | 609.3 | 14.24 | A |
| 131 | 0.261 | 609.3 | 14.27 | A |
| 132 | 0.108 | 610.3 | 7.09 | A |
| 133 | | 418.2 | 14.01 | A |
| 134 | | 398.5 | 13.56 | A |
| 135 | 0.002333 | 595.3 | 13.58 | A |
| 136 | 0.26 | 595.3 | 13.61 | A |
| 137 | 0.0015 | 624.3 | 7.15 | A |
| 138 | 0.001 | 638.3 | 7.21 | A |
| 139 | 0.001 | 640.3 | 7.05 | A |
| 140 | 0.001 | 624.3 | 7.2 | A |
| 141 | 0.002 | 610.3 | 7.02 | A |
| 142 | 0.002 | 624.3 | 7.21 | A |
| 143 | 0.0019 | 638.3 | 7.14 | A |
| 144 | 0.002 | 610.3 | 6.98 | A |
| 145 | 0.001 | 624.3 | 7.19 | A |
| 146 | 0.002 | 710.4 | 2.23 | D |
| 147 | 0.001 | 652.4 | 2.34 | D |
| 148 | 0.002 | 638.3 | 2.17/ | D |
| 149 | 0.003 | 738.4 | 2.40/ | D |
| 150 | 0.004 | 638.3 | 2.21/ | D |
| 151 | 0.003 | 724.4 | 2.40/ | D |
| 152 | 0.003 | 666.4 | 2.31/ | D |
| 153 | 0.004 | 738.4 | 2.43/ | D |
| 154 | 0.003 | 623.3 | 2.28/ | D |

TABLE 3-continued

| | NS5B-enzyme3 (uM) | MS [M + H$^+$] | Retention time (min) | HPLC method |
|---|---|---|---|---|
| 155 | 0.003 | 652.4 | 2.15 | D |
| 156 | 0.001 | 638.3 | 2.15 | D |
| 157 | 0.001 | 650.4 | 2.13 | D |
| 158 | 0.002 | 623.3 | 2.35 | D |
| 159 | 0.003 | 724.4 | 2.22 | D |
| 160 | 0.001 | 652.4 | 2.16 | D |
| 161 | 0.001 | 740.4 | 2.18 | D |
| 162 | 0.002 | 724.4 | 2.38 | D |
| 163 | 0.001 | 638.3 | 2.12 | D |
| 164 | 0.001 | 623.3 | 2.27 | D |
| 165 | 0.002 | 710.4 | 2.2 | D |
| 166 | 0.982 | 543.5 | 15.74 | A |
| 167 | 0.0035 | 639.3 | 14.32 | A |
| 168 | 3.8165 | 615.5 | 14.95 | A |
| 169 | 0.003 | 629.2 | 15.57 | A |
| 170 | 0.004 | 643.2 | 16.03 | A |
| 171 | 0.002 | 639.3 | 14.02 | A |
| 172 | 0.0012 | 609.6 | 13.8 | A |
| 173 | 0.001 | 623.6 | 15 | A |
| 174 | 5.113 | 493.2 | 15.41 | A |
| 175 | >10 | 389.2 | 6.89 | A |
| 176 | 1.41285 | 571.5 | 16.35 | A |
| 177 | 0.002 | 597.2 | 14.33 | A |
| 178 | 0.001 | 602.2 | 14.89 | A |
| 179 | 0.001 | 609.2 | 14.81 | A |
| 180 | <0.0002 | 623.2 | 14.74 | A |
| 181 | 0.003 | 376.4 | 14.22 | |
| 182 | 0.002 | 545.3 | 6.78 | A |
| 183 | 0.0018 | 623.5 | 15.31 | A |
| 184 | 0.0017 | 611.2 | 13.24 | A |
| 185 | 0.001 | 627.2 | 14.41 | A |
| 186 | 0.001 | 643.2 | 13.57 | A |
| 187 | 0.001 | 625.2 | 13.96 | A |
| 188 | 0.001 | 638.8 | 14.04 | A |
| 189 | 0.001 | 628.8 | 13.5 | A |
| 190 | 0.001 | 559.4 | 15.28 | A |
| 191 | 0.001 | 560.4 | 15.33 | A |
| 192 | 0.003 | 530.1 | 14.74 | A |
| 193 | 0.001 | 533.4 | 14.21 | A |
| 194 | 0.002 | 625.2 | 13.26 | A |
| 195 | 0.003 | 643.2 | 14.24 | A |
| 196 | 0.001 | 655.3 | 13.87 | A |
| 197 | 0.0046 | 639.2 | 14.58 | A |
| 198 | 0.001 | 651.3 | 14.21 | A |
| 199 | 0.002 | 645.2 | 14.63 | A |
| 200 | 0.001 | 659.3 | 14.75 | A |
| 201 | | 643.3 | 15.55 | A |
| 202 | 0.001 | 728.3 | 2.21 | D |
| 203 | 0.001 | 645.2 | 2.43 | D |
| 204 | 0.002 | 633.2 | 2.32 | D |
| 205 | 0.004 | 638.1 | 2.38 | D |
| 206 | 0.001 | 604.1 | 2.13 | D |
| 207 | | 603.1 | 2.21 | D |
| 208 | 0.0014 | 701.2 | 2.29 | D |
| 209 | 0.001 | 592.1 | 2.14 | D |
| 210 | 0.003 | 652.1 | 1.79 | D |
| 211 | 0.002 | 606.1 | 2.36 | D |
| 212 | 0.002 | 674.2 | 2.38 | D |
| 213 | 0.001 | 627.1 | 2.25 | D |
| 214 | 0.001 | 603.1 | 2.16 | D |
| 215 | 0.002 | 592.2 | 2.34 | D |
| 216 | 0.001 | 637.3 | 13.63 | A |
| 217 | 0.001 | 623.2 | 12.73 | A |
| 218 | 0.001 | 667.3 | 15.39 | A |
| 219 | | 623.2 | 14.75 | A |
| 220 | 0.015 | 374.2 | 14.17 | |
| 221 | 0.019 | 495.1 | 14.79 | A |
| 222 | 0.002 | 606.2 | 2.14 | D |
| 223 | 0.009 | 613.2 | 16.14 | A |
| 224 | | 701.3 | 7.4 | A |
| 225 | 0.001 | 625.2 | 13.72 | A |
| 226 | 0.009 | 659.2 | 15.15 | A |
| 227 | 0.001 | 671.2 | 14.94 | A |
| 228 | | 641.3 | 12.97 | A |
| 229 | 0.001 | 657.2 | 14.1 | A |
| 230 | 0.006 | 598.1 | 15.77 | A |
| 231 | 0.001 | 628.2 | 15.91 | A |
| 232 | 0.001 | 613.2 | 13.77 | A |
| 233 | 0.002 | 642.2 | 16.26 | A |
| 234 | 0.001 | 642.1 | 16.2 | A |
| 235 | | 627.2 | 14.99 | A |
| 236 | 0.003 | 390.1 | 13.86 | A |
| 237 | 0.042 | 403.2 | 1.16 | E |
| 238 | 0.002 | 554.2 | 7.65 | B |
| 239 | 0.002 | 547.2 | 7.8 | B |
| 240 | | 534.2 | 7.62 | B |
| 241 | 0.001 | 519.2 | 6.88 | B |
| 242 | 0.005 | 563.1 | 8.07 | B |
| 243 | 0.002 | 547.2 | 7.75 | B |
| 244 | 0.002 | 564.2 | 7.75 | B |
| 245 | 0.005 | 493.2 | 7.3 | B |
| 246 | 0.004 | 577.2 | 7.75 | B |
| 247 | 0.002 | 519.2 | 6.57 | B |
| 248 | 0.002 | 547.2 | 6.82 | B |
| 249 | 0.019 | 613.2 | 8.03 | B |
| 250 | 0.0055 | 597.2 | 8.06 | B |
| 251 | 0.004 | 565.2 | 7.73 | B |
| 252 | 0.002 | 586.2 | 7.22 | B |
| 253 | 0.002 | 586.2 | 7.13 | B |
| 254 | 0.015 | 533.2 | 7.49 | B |
| 255 | 0.005 | 547.2 | 6.57 | B |
| 256 | 0.001 | 557.2 | 8.07 | B |
| 257 | 0.002 | 559.2 | 7.74 | B |
| 258 | 0.007 | 559.2 | 7.54 | B |
| 259 | 0.007 | 554.2 | 15.23 | A |
| 260 | 0.008 | 547.1 | 14.54 | A |
| 261 | 0.199 | 540.1 | 2.44 | D |
| 262 | 0.025 | 558.1 | 2.14 | D |
| 263 | 0.108 | 489.2 | 2.39 | D |
| 264 | 0.538 | 503.2 | 2.43 | D |
| 265 | 0.601 | 481.2 | 2.49 | D |
| 266 | 0.142 | 578.2 | 2.39 | D |
| 267 | 0.064 | 510.1 | 2.2 | D |
| 268 | 0.62 | 489.2 | 2.36 | D |
| 269 | 0.33 | 489.2 | 2.37 | D |
| 270 | 0.019 | 518.2 | 2.34 | D |
| 271 | 2.47 | 482.2 | 2.12 | D |
| 272 | 0.001 | 609.2 | 14.15 | A |
| 273 | 0.001 | 641.4 | 12.87 | A |
| 274 | 0.001 | 657.2 | 14 | A |
| 275 | 0.002 | 547.4 | 14.31 | A |
| 276 | 0.002 | 607.5 | 15.04 | A |
| 277 | 0.002 | 589.2 | 14.81 | A |
| 278 | 0.001 | 657.3 | 14.46 | A |
| 279 | 0.0011 | 657.2 | 13.52 | A |
| 280 | 0.001 | 631.2 | 13.51 | A |
| 281 | 0.003 | 565.1 | 15.58 | A |
| 282 | 0.031 | 597.1 | 16.45 | A |
| 283 | 0.004 | 577.2 | 15.44 | A |
| 284 | 0.003 | 563.4 | 13.81 | A |
| 285 | 0.002 | 641.3 | 15.2 | A |
| 286 | 0.001 | 649.2 | 14.09 | A |
| 287 | 0.001 | 631.2 | 13.53 | A |
| 288 | 0.002 | 643.3 | 12.21 | A |
| 289 | 0.001 | 637.5 | 13.42 | A |
| 290 | 0.002 | 418.2 | 14.92 | A |
| 291 | 0.008 | 404.5 | 14.02 | |
| 292 | 0.0023 | 656.8 | 15.79 | A |
| 293 | 0.005 | 420.1 | 13.56 | A |
| 294 | 0.007 | 517.3 | 13.08 | A |
| 295 | 0.004 | 543.2 | 13.03 | A |
| 296 | 0.005 | 557.3 | 13.45 | A |
| 297 | 0.001 | 543.2 | 12.33 | A |
| 298 | 0.001 | 557.2 | 12.33 | A |
| 299 | 0.005 | 448.5 | 13.07 | |
| 300 | 0.031 | 564.1 | 14.79 | A |
| 301 | 0.004 | 585.2 | 14.32 | A |
| 302 | 0.003 | 554.2 | 13.74 | A |
| 303 | 0.004 | 596.2 | 15.55 | A |
| 304 | 0.005 | 568.2 | 14.3 | A |
| 305 | 0.004 | 568.2 | 14.05 | A |
| 306 | 0.0053 | 510.1 | 13.32 | |
| 307 | 0.006 | 477.2 | 7.32, 7.64 | A |
| 308 | 0.014 | 390.5 | 13.82 | |

TABLE 3-continued

| | NS5B-enzyme3 (uM) | MS [M + H+] | Retention time (min) | HPLC method |
|---|---|---|---|---|
| 309 | 0.054 | 467.1 | 17.57 | A |
| 310 | 0.004 | 489.2 | 7.35, 7.85 | A |
| 311 | 0.002 | 461.8 | 12.88 | A |
| 312 | 0.002 | 443.2 | 14.94 | A |
| 313 | 0.0315 | 404.2 | 13.55 | A |
| 314 | 0.006 | 427.8 | 13.88 | A |
| 315 | 0.006 | 448.1 | 14.44 | A |
| 316 | 0.003 | 432.3 | 14.19 | A |
| 317 | 0.0241 | 414.2 | 12.27 | A |
| 318 | 0.014 | 490.3 | 14.7 | A |
| 319 | 0.004 | 490.2 | 14.04 | A |
| 320 | 0.006 | 476.2 | 14.29 | A |
| 321 | 0.002 | 476.2 | 13.52 | A |
| 322 | 0.006 | 404.2 | 13.07 | A |
| 323 | 0.003 | 448.3 | 12.86 | A |
| 324 | 0.085 | 427.9 | 12.45 | A |
| 325 | 0.006 | 459.8 | 14.87 | A |
| 326 | 0.8815 | 446.3 | 13.68 | A |
| 327 | 0.004 | 478.6 | 12.57, 12.72 | A |
| 328 | 0.006 | 448.3 | 13.51 | A |
| 329 | 0.005 | 420.5 | 12.66 | A |
| 330 | 0.003 | 478.3 | 11.66, 11.93 | A |
| 331 | 0.008 | 464.3 | 7.92 | A |
| 332 | 0.012 | 434.2 | 8.32 | A |
| 333 | 0.01 | 478.3 | 11.7 | A |
| 334 | 0.003 | 403.8 | 13.5 | A |
| 335 | 0.024 | 402.1 | | A |
| 336 | 0.003 | 448.3 | 10.28 | A |
| 337 | 0.002 | 448.2 | 10.89 | A |
| 338 | 0.031 | 462.3 [M − H+] | 19.95 | A |
| 339 | 0.008 | 446 | 13.67 | A |
| 340 | 0.008 | 403.0 | 7.21 | A |
| 341 | 0.005 | 446 | 13.17 | A |
| 342 | 0.018 | 432 | 13.51 | A |
| 343 | 0.001 | 432 | 13.29 | A |

What is claimed is:

1. A compound of formula (I):

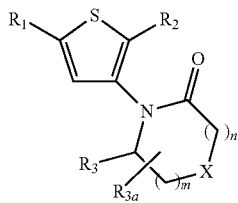

or a salt thereof, wherein m is 0, 1 or 2;

n is 0 or 1, wherein m+n is 1, 2 or 3;

$R_1$ is $C_3$-$C_{10}$alkynyl or phenyl, which phenyl is substituted with 0, 1, 2, or 3 substituents which are independently selected from the group consisting of halogen, hydroxy, cyano, $C_1$-$C_4$alkyl, halo$C_1$-$C_4$alkyl and $C_1$-$C_4$alkoxy, and which alkynyl is optionally substituted with a $C_3$-$C_7$cycloalkyl substituent, which cycloalkyl is optionally substituted with 1 or 2 independently selected $C_1$-$C_4$alkyl groups;

$R_2$ is $CO_2H$ or $C(O)N(H)S(O)_2CH_3$;

$R_3$ is $C_3$-$C_7$cycloalkyl which is substituted with 0, 1, 2 or 3 halogen atoms;

$R_{3a}$ represents 0, 1, 2, 3 or 4 residues independently selected at each occurrence from the group consisting of hydroxy, amino, cyano, halogen, $C_1$-$C_6$alkyl, and $C_1$-$C_6$alkoxy, wherein each alkyl or alkoxy substituent is substituted with 0, 1 or 2 substituents independently selected from hydroxy, cyano, $C_1$-$C_4$alkoxy, $C_1$-$C_4$alkylsulfone, $N(R_{3b})_2$, $C(O)N(R_{3b})$, heterocycle having 4 to 7 ring atoms and 1 or 2 ring heteroatoms selected from N, O and S and 5 or 6 member heteroaryl; or two geminal $R_{3a}$ substituents, taken in combination form a spirocyclic 3 to 6 member cycloalkyl or heterocycle;

$R_{3b}$ is independently selected at each occurrence from hydrogen, $C_1$-$C_4$alkyl, $C_1$-$C_4$alkoxy$C_1$-$C_4$alkyl and $C_1$-$C_4$alkanoyl; or $N(R_{3b})_2$, taken in combination, form a 4 to 6 member heterocycle having 0 or 1 additional ring heteroatoms selected from N, O and S;

X is O, N-L-$R_4$ or $CR_5R_6$;

L is a bond, $S(O)_2$ or $C(O)$;

$R_4$ is $C_1$-$C_6$alkyl or $C_3$-$C_7$cycloalkyl each of which is substituted with 0, 1, or 2 hydroxy and 0 or 1 substituents selected from cyano, $S(O)_2$—$C_1$-$C_4$alkyl, $CO_2H$ or $NR_{4a}R_{4b}$ or phenyl;

$R_4$ is naphthyl or phenyl, which phenyl is substituted with 0, 1, 2, or 3 substituents independently selected form the group consisting of halogen, cyano, $C_1$-$C_6$alkyl, halo$C_1$-$C_6$alkyl, $C_1$-$C_6$alkoxy, halo$C_1$-$C_6$alkoxy, amino, hydroxy, mono- and di-$C_1$-$C_6$alkylamino, hydroxy$C_1$-$C_4$alkyl, amino$C_1$-$C_4$alkyl, $C_1$-$C_6$alkyl-OC(O)NH—, $C_1$-$C_4$alkyl-C(O)NH—, —C(O)$NR_{4a}R_{4b}$, phenyl, phenoxy, heteroaryl having one or two ring nitrogen atoms and having 0, 1, or 2 $C_1$-$C_4$alkyl substituents, or two substituents combine to form a fused heterocyclic ring, which heterocycle has 5, 6 or 7 ring atoms, 1 or 2 ring heteroatoms selected from N, O and S and which heterocycle is substituted with 0, 1 or 2 substituents independently selected from $C_1$-$C_6$alkyl; or $R_4$ is a 5 or 6 member heteroaryl having 1 to 3 heteroatoms selected from N, O and S, which heteroaryl is substituted with 0, 1, or 2 substituents independently selected from the group consisting of halogen, cyano, $C_1$-$C_6$alkyl, halo$C_1$-$C_6$alkyl, $C_1$-$C_6$alkoxy, halo$C_1$-$C_6$alkoxy, hydroxy, $NR_{4a}R_{4b}$, hydroxy$C_1$-$C_4$alkyl, amino$C_1$-$C_4$alkyl, $C_1$-$C_6$alkyl-OC(O)NH—, $C_3$-$C_7$cycloalkyl, $C_5$-$C_7$cycloalkenyl, phenyl, 5 or 6 membered heteroaryl having 1 or 2 ring heteroatoms selected from N, O and S, and saturated or partially unsaturated monocyclic or bicyclic heterocycle which heterocycle has 1 or 2 ring N, O or S atoms, 5 to 7 ring atoms in each ring and is substituted with 0, 1 or 2 substituents independently selected from the group consisting of halogen, $C_1$-$C_6$alkyl, $C_1$-$C_6$alkanoyl, $C_1$-$C_6$alkoxyC(O)N(H)CH_2, amino$C_1$-$C_4$alkyl, $C_1$-$C_4$alkoxy$C_1$-$C_4$alkyl and $NR_{4a}R_{4b}$, and wherein the phenyl or heteroaryl substituent is unsubstituted or substituted with 1 or 2 independently selected substituents selected from halogen, $CO_2H$, cyano, $C_1$-$C_4$alkyl, $C_1$-$C_4$alkoxy, $CH_2NR_{4a}R_{4b}$ and $C(O)NR_{4a}R_{4b}$; or $R_4$ is a saturated heterocycle having 1 ring nitrogen and 0 or 1 additional ring heteroatom selected from N, O and S, which heterocyclic ring is substituted with 0, 1, or 2 substituents independently selected from the group consisting of $C_1$-$C_6$alkyl, $CO_2C_1$-$C_6$alkyl and $CO_2$-benzyl;

$R_{4a}$ is independently selected at each occurrence from the group consisting of hydrogen and $C_1$-$C_6$alkyl, wherein the alkyl substituent is unsubstituted or substituted with hydroxy, $C_1$-$C_4$alkoxy, amino or mono- and di-$C_1$-$C_4$alkylamino;

$R_{4b}$ is independently selected at each occurrence from the group consisting of hydrogen, $C_1$-$C_6$alkyl and $C_1$-$C_4$alkanoyl, wherein the alkyl substituent is unsubstituted or substituted with hydroxy, $C_1$-$C_4$alkoxy, amino or mono- and di-$C_1$-$C_4$alkylamino; or $NR_{4a}R_{4b}$, taken in combination, form a heterocyclic ring having one ring nitrogen atom and 0 or 1 additional ring heteroatom selected from N, O and S, which heterocyclic ring is substituted with 0, 1, 2 or 3 substituents independently selected from the group consisting of halogen, hydroxy, amino, $C_1$-$C_4$alkyl, halo$C_1$-$C_4$alkyl, hydroxy$C_1$-$C_4$alkyl, amino$C_1$-$C_4$alkyl, $C_1$-$C_4$alkoxy, $C_1$-$C_4$alkoxy$C_1$-$C_4$alkyl, and mono- and di-$C_1$-$C_4$alkylamino;

$R_5$ is absent or is selected from the group consisting of hydrogen and $C_1$-$C_6$alkyl;

$R_6$ is oxo, hydrogen, hydroxy, amino, N(H)-J-$R_7$;

J is absent, C(O) or $S(O)_2$; and $R_7$ is $C_1$-$C_6$alkyl, phenyl or benzyl, each of is optionally substituted with $C_1$-$C_6$alkyl, $C_1$-$C_6$alkoxy, halogen, phenyl or phenoxy.

2. The compound of claim 1, wherein the compound is a compound of formula II, or a salt thereof:

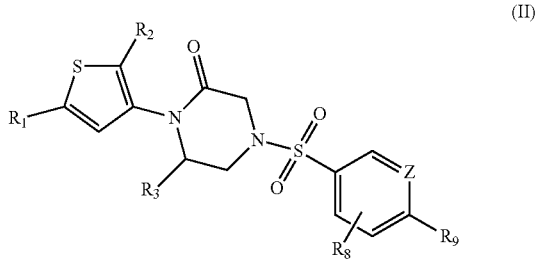

(II)

wherein

Z is CH or N;

$R_8$ is selected from hydrogen, $CO_2H$, $C_1$-$C_4$alkyl, C-$C_4$alkoxy, cyano and halogen;

$R_9$ is selected from $C_1$-$C_6$alkyl, $C_1$-$C_6$alkoxy, phenyl, $NR_{9a}R_{9b}$, N(H)—C(O)—O—$C_1$-$C_4$alkyl, and heterocycle, wherein the heterocycle has one or two rings, each ring having 5, 6, or 7 ring atoms, one ring nitrogen atom and 0 or 1 additional ring heteroatom selected from N, O and S, and wherein the heterocycle is unsubstituted or substituted with 1, 2 or 3 substituents independently selected from the group consisting of halogen, hydroxy, amino, $C_1$-$C_4$alkyl, halo$C_1$-$C_4$alkyl, hydroxy$C_1$-$C_4$alkyl, amino$C_1$-$C_4$alkyl, $C_1$-$C_4$alkoxy, $C_1$-$C_4$alkoxy$C_1$-$C_4$alkyl, and mono- and di-$C_1$-$C_4$alkylamino;

$R_{9a}$ is selected from the group consisting of hydrogen and $C_1$-$C_6$alkyl, wherein the alkyl substituent is unsubstituted or substituted with hydroxy, $C_1$-$C_4$alkoxy, amino or mono- and di-$C_1$-$C_4$alkylamino; and $R_{9b}$ is selected from the group consisting of hydrogen, $C_1$-$C_6$alkyl and $C_1$-$C_4$alkanoyl, wherein the alkyl substituent is unsubstituted or substituted with hydroxy, $C_1$-$C_4$alkoxy, amino or mono- and di-$C_1$-$C_4$alkylamino.

3. The compound of claim 1, wherein the compound is a compound of formula III, or a salt thereof:

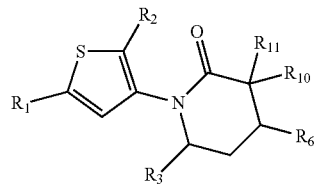

(III)

wherein $R_6$ is hydrogen, hydroxy, amino or N(H)-J-$R_7$;

J is C(O) or $S(O)_2$;

$R_7$ is (a) $C_1$-$C_4$alkyl optionally substituted with phenyl or phenoxy, or (b) phenyl optionally substituted with $C_1$-$C_4$alkyl, halogen or $C_1$-$C_4$alkoxy;

$R_{10}$ is selected from hydrogen and $C_1$-$C_6$alkyl which alkyl is substituted with 0, 1, or 2 hydroxy and 0 or 1 substituents selected from cyano, $SO_2CH_3$, methoxy, ethoxy, $N(R_{10a})_2$ and $C(O)(NR_{10a})_2$;

$R_{10a}$ is selected at each occurrence from the group consisting of hydrogen and $C_1$-$C_4$alkyl which is substituted with 0 or 1 substituents selected from hydroxy, methoxy and ethoxy;

$R_{11}$ is selected from the group consisting of hydrogen, fluoro, cyano, hydroxy and $C_1$-$C_4$alkyl.

4. The compound of claim 1, wherein the compound is a compound of formula IV, or a salt thereof:

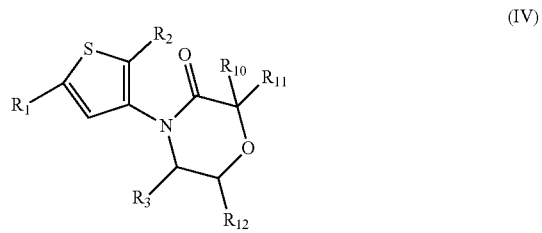

(IV)

wherein $R_{10}$ and $R_{11}$ are independently selected from hydrogen and $C_1$-$C_6$alkyl which alkyl is substituted with 0, 1, or 2 hydroxy and 0 or 1 substituents selected from $SO_2CH_3$, cyano, methoxy, ethoxy, $N(R_{10a})_2$ and $C(O)N(R_{10a})_2$;

$R_{10a}$ is selected at each occurrence from the group consisting of hydrogen and $C_1$-$C_4$alkyl which is substituted with 0 or 1 substituents selected from hydroxy, methoxy and ethoxy, or $N(R_{10a})_2$, taken in combination forms a 4 to 6 member heterocyclic ring;

$R_{12}$ is selected from the group consisting of hydrogen and $C_1$-$C_4$alkyl.

5. The compound of claim 1, wherein $R_1$ is tert-butylethynyl, phenyl, or phenyl para-substituted with F, Cl, or Me.

6. The compound of claim 5, wherein $R_1$ is tert-butylethynyl.

7. The compound of claim 1, wherein $R_2$ is $CO_2H$.

8. The compound of claim 1, wherein $R_3$ is cyclohexyl.

9. The compound of claim 3, wherein $R_6$ is hydrogen; $R_{10}$ is hydrogen or hydroxy$C_1$-$C_6$alkyl; and $R_{11}$ is hydrogen, methyl, hydroxy or fluoro.

10. The compound of claim 4, wherein $R_{10}$ is hydroxy$C_1$-$C_6$alkyl; $R_{11}$ is hydrogen or methyl; and $R_{12}$ is hydrogen or methyl.

11. The compound of claim 1, or a pharmaceutically acceptable salt thereof, selected from the group consisting of:

3-((S)-2-Cyclohexyl-5-oxo-pyrrolidin-1-yl)-5-phenyl-thiophene-2-carboxylic acid;

3-(2-Cyclohexyl-6-oxo-piperidin-1-yl)-5-phenyl-thiophene-2-carboxylic acid;

3-(3-Cyclohexyl-5-oxo-morpholin-4-yl)-5-phenyl-thiophene-2-carboxylic acid;

3-[(R)-2-Cyclohexyl-6-oxo-4-(toluene-4-sulfonyl)-piperazin-1-yl]-5-phenyl-thiophene-2-carboxylic acid;

3-(2-Cyclohexyl-6-oxo-piperidin-1-yl)-5-(3,3-dimethyl-but-1-ynyl)-thiophene-2-carboxylic acid;

3-((S)-2-Cyclohexyl-6-oxo-piperidin-1-yl)-5-(3,3-dimethyl-but-1-ynyl)-thiophene-2-carboxylic acid;

3-(2-Cyclohexyl-6-oxo-piperidin-1-yl)-5-(4-fluoro-phenyl)-thiophene-2-carboxylic acid;

3-(2-Cyclohexyl-6-oxo-piperidin-1-yl)-5-p-tolyl-thiophene-2-carboxylic acid;

5-(4-Chloro-phenyl)-3-(2-cyclohexyl-6-oxo-piperidin-1-yl)-thiophene-2-carboxylic acid;

3-[2-Cyclohexyl-4-(6-dipropylamino-pyridine-3-sulfonyl)-6-oxo-piperazin-1-yl]-5-phenyl-thiophene-2-carboxylic acid;

3-{(R)-2-Cyclohexyl-4-[6-((R)-2-methyl-pyrrolidin-1-yl)-pyridine-3-sulfonyl]-6-oxo-piperazin-1-yl}-5-phenyl-thiophene-2-carboxylic acid;

3-[(R)-2-Cyclohexyl-6-oxo-4-(6-pyrrolidin-1-yl-pyridine-3-sulfonyl)-piperazin-1-yl]-5-phenyl-thiophene-2-carboxylic acid;

3-{(R)-2-Cyclohexyl-4-[6-((2S,5R)-2,5-dimethyl-pyrrolidin-1-yl)-pyridine-3-sulfonyl]-6-oxo-piperazin-1-yl}-5-phenyl-thiophene-2-carboxylic acid;

3-[2-Cyclohexyl-6-oxo-4-(toluene-4-sulfonyl)-piperazin-1-yl]-5-(3,3-dimethyl-but-1-ynyl)-thiophene-2-carboxylic acid;

3-{(R)-2-Cyclohexyl-4-[6-((2R,6S)-2,6-dimethyl-morpholin-4-yl)-pyridine-3-sulfonyl]-6-oxo-piperazin-1-yl}-5-phenyl-thiophene-2-carboxylic acid;

3-[2-Cyclohexyl-4-(6-morpholin-4-yl-pyridine-3-sulfonyl)-6-oxo-piperazin-1-yl]-5-(3,3-dimethyl-but-1-ynyl)-thiophene-2-carboxylic acid;

3-[(R)-2-Cyclohexyl-4-(6-diethylamino-pyridine-3-sulfonyl)-6-oxo-piperazin-1-yl]-5-phenyl-thiophene-2-carboxylic acid;

3-[(R)-2-Cyclohexyl-6-oxo-4-(3,4,5,6-tetrahydro-2H-[1,2']bipyridinyl-5'-sulfonyl)-piperazin-1-yl]-5-phenyl-thiophene-2-carboxylic acid;

3-((R)-4-Cyclohexyl-2-oxo-oxazolidin-3-yl)-5-(3,3-dimethyl-but-1-ynyl)-thiophene-2-carboxylic acid;

3-[(R)-2-Cyclohexyl-4-(6-morpholin-4-yl-pyridine-3-sulfonyl)-6-oxo-piperazin-1-yl]-5-phenyl-thiophene-2-carboxylic acid;

3-[(R)-2-Cyclohexyl-4-(4-methoxy-benzenesulfonyl)-6-oxo-piperazin-1-yl]-5-(3,3-dimethyl-but-1-ynyl)-thiophene-2-carboxylic acid;

3-[(R)-2-Cyclohexyl-4-(6-methoxy-pyridine-3-sulfonyl)-6-oxo-piperazin-1-yl]-5-(3,3-dimethyl-but-1-ynyl)-thiophene-2-carboxylic acid;

3-[(R)-2-Cyclohexyl-4-(1-methyl-1H-pyrazole-3-sulfonyl)-6-oxo-piperazin-1-yl]-5-(3,3-dimethyl-but-1-ynyl)-thiophene-2-carboxylic acid;

3-{(R)-2-Cyclohexyl-4-[6-(8-oxa-3-aza-bicyclo[3.2.1]oct-3-yl)-pyridine-3-sulfonyl]-6-oxo-piperazin-1-yl}-5-p-tolyl-thiophene-2-carboxylic acid;

3-(2-Cyclohexyl-5-oxo-pyrrolidin-1-yl)-5-(3,3-dimethyl-but-1-ynyl)-thiophene-2-carboxylic acid;

3-((R)-3-Cyclohexyl-5-oxo-morpholin-4-yl)-5-(3,3-dimethyl-but-1-ynyl)-thiophene-2-carboxylic acid;

3-((4S,5R)-5-Cyclohexyl-3,4-dimethyl-2-oxo-imidazolidin-1-yl)-5-(3,3-dimethyl-but-1-ynyl)-thiophene-2-carboxylic acid;

5-(4-Chloro-phenyl)-3-((R)-3-cyclohexyl-5-oxo-morpholin-4-yl)-thiophene-2-carboxylic acid;

3-[(R)-5-Cyclohexyl-2-(2-morpholin-4-yl-2-oxo-ethyl)-3-oxo-morpholin-4-yl]-5-(3,3-dimethyl-but-1-ynyl)-thiophene-2-carboxylic acid;

3-[(R)-5-Cyclohexyl-2-(3-hydroxy-propyl)-3-oxo-morpholin-4-yl]-5-(3,3-dimethyl-but-1-ynyl)-thiophene-2-carboxylic acid;

3-[(R)-5-Cyclohexyl-2-(3-methanesulfonyl-propyl)-3-oxo-morpholin-4-yl]-5-(3,3-dimethyl-but-1-ynyl)-thiophene-2-carboxylic acid;

3-{(R)-5-Cyclohexyl-2-[(2-methoxy-ethylamino)-methyl]-3-oxo-morpholin-4-yl}-5-(3,3-dimethyl-but-1-ynyl)-thiophene-2-carboxylic acid;

3-(4-Cyclohexyl-2-oxo-[1,3]oxazinan-3-yl)-5-(3,3-dimethyl-but-1-ynyl)-thiophene-2-carboxylic acid;

3-((R)-5-Cyclohexyl-2-morpholin-4-ylmethyl-3-oxo-morpholin-4-yl)-5-(3,3-dimethyl-but-1-ynyl)-thiophene-2-carboxylic acid;

3-[(2R,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid;

3-((2S,5R)-2-Cyanomethyl-5-cyclohexyl-2-methyl-3-oxo-morpholin-4-yl)-5-(3,3-dimethyl-but-1-ynyl)-thiophene-2-carboxylic acid;

3-(6-Cyclohexyl-3-hydroxy-2-oxo-piperidin-1-yl)-5-(3,3-dimethyl-but-1-ynyl)-thiophene-2-carboxylic acid;

3-((R)-5-Cyclohexyl-2,2-dimethyl-3-oxo-morpholin-4-yl)-5-p-tolyl-thiophene-2-carboxylic acid;

3-(6-Cyclohexyl-3-hydroxy-2-oxo-piperidin-1-yl)-5-p-tolyl-thiophene-2-carboxylic acid;

3-[(2S,5R)-5-Cyclohexyl-2-(3-hydroxy-3-methyl-butyl)-2-methyl-3-oxo-morpholin-4-yl]-5-(3,3-dimethyl-but-1-ynyl)-thiophene-2-carboxylic acid;

3-[(2R,5R)-5-Cyclohexyl-2-(3-hydroxy-3-methyl-butyl)-2-methyl-3-oxo-morpholin-4-yl]-5-(3,3-dimethyl-but-1-ynyl)-thiophene-2-carboxylic acid;

3-[(2S,5R)-5-Cyclohexyl-2-((R)-3-hydroxy-butyl)-2-methyl-3-oxo-morpholin-4-yl]-5-(3,3-dimethyl-but-1-ynyl)-thiophene-2-carboxylic acid;

3-[(2R,5R)-5-Cyclohexyl-2-((R)-3-hydroxy-butyl)-2-methyl-3-oxo-morpholin-4-yl]-5-(3,3-dimethyl-but-1-ynyl)-thiophene-2-carboxylic acid;

3-((S)-6-Cyclohexyl-3-hydroxy-2-oxo-piperidin-1-yl)-5-(3,3-dimethyl-but-1-ynyl)-thiophene-2-carboxylic acid;

3-[(2R,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid;

3-(6-Cyclohexyl-3-hydroxy-3-methyl-2-oxo-piperidin-1-yl)-5-p-tolyl-thiophene-2-carboxylic acid;

3-((R)-3-Cyclohexyl-5-oxo-1,9-dioxa-4-aza-spiro[5.5]undec-4-yl)-5-(3,3-dimethyl-but-1-ynyl)-thiophene-2-carboxylic acid;

3-[6-Cyclohexyl-3-(3-hydroxy-propyl)-2-oxo-piperidin-1-yl]-5-(3,3-dimethyl-but-1-ynyl)-thiophene-2-carboxylic acid;

3-[(2S,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid;

3-[(2S,5R)-5-Cyclohexyl-2-(2-hydroxy-ethyl)-2-methyl-3-oxo-morpholin-4-yl]-5-(3,3-dimethyl-but-1-ynyl)-thiophene-2-carboxylic acid;

3-((R)-5-Cyclohexyl-2-hydroxymethyl-3-oxo-morpholin-4-yl)-5-(3,3-dimethyl-but-1-ynyl)-thiophene-2-carboxylic acid;

3-[(2R,5R)-5-Cyclohexyl-2-(2,3-dihydroxy-propyl)-2-methyl-3-oxo-morpholin-4-yl]-5-(3,3-dimethyl-but-1-ynyl)-thiophene-2-carboxylic acid;

3-[(2S,5R)-5-Cyclohexyl-2-(2,3-dihydroxy-propyl)-3-oxo-morpholin-4-yl]-5-(3,3-dimethyl-but-1-ynyl)-thiophene-2-carboxylic acid;

3-[(2S,5R)-5-Cyclohexyl-2-(2-hydroxy-ethyl)-3-oxo-morpholin-4-yl]-5-(3,3-dimethyl-but-1-ynyl)-thiophene-2-carboxylic acid;

3-[6-Cyclohexyl-3-hydroxy-3-(3-hydroxy-propyl)-2-oxo-piperidin-1-yl]-5-(3,3-dimethyl-but-1-ynyl)-thiophene-2-carboxylic acid;

3-[(2R,5R)-5-Cyclohexyl-2-(2,3-dihydroxy-propyl)-3-oxo-morpholin-4-yl]-5-(3,3-dimethyl-but-1-ynyl)-thiophene-2-carboxylic acid;

3-[(2R,5R)-5-Cyclohexyl-2-(2-hydroxy-ethyl)-3-oxo-morpholin-4-yl]-5-(3,3-dimethyl-but-1-ynyl)-thiophene-2-carboxylic acid;

3-[(2S,5R)-5-Cyclohexyl-2-(3-hydroxy-propyl)-2-methyl-3-oxo-morpholin-4-yl]-5-(3,3-dimethyl-but-1-ynyl)-thiophene-2-carboxylic acid;

3-((S)-6-Cyclohexyl-3-hydroxy-2-oxo-piperidin-1-yl)-5-(3,3-dimethyl-but-1-ynyl)-thiophene-2-carboxylic acid;

3-[(2R,5R)-5-Cyclohexyl-2-(3-hydroxy-propyl)-3-oxo-morpholin-4-yl]-5-(3,3-dimethyl-but-1-ynyl)-thiophene-2-carboxylic acid;

3-[(2S,5R)-5-Cyclohexyl-2-(3-hydroxy-propyl)-3-oxo-morpholin-4-yl]-5-(3,3-dimethyl-but-1-ynyl)-thiophene-2-carboxylic acid;

3-[(2R,5R)-5-Cyclohexyl-2-((R)-2-hydroxy-propyl)-3-oxo-morpholin-4-yl]-5-(3,3-dimethyl-but-1-ynyl)-thiophene-2-carboxylic acid;

3-[(2R,5R)-5-Cyclohexyl-2-((S)-2-hydroxy-propyl)-3-oxo-morpholin-4-yl]-5-(3,3-dimethyl-but-1-ynyl)-thiophene-2-carboxylic acid;

3-[(S)-6-Cyclohexyl-3-(3-hydroxy-propyl)-2-oxo-piperidin-1-yl]-5-(3,3-dimethyl-but-1-ynyl)-thiophene-2-carboxylic acid;

3-((S)-3-Amino-6-cyclohexyl-2-oxo-piperidin-1-yl)-5-(3,3-dimethyl-but-1-ynyl)-thiophene-2-carboxylic acid; and 3-[(S)-6-Cyclohexyl-3-(2-hydroxy-ethyl)-2-oxo-piperidin-1-yl]-5-(3,3-dimethyl-but-1-ynyl)-thiophene-2-carboxylic acid.

12. A pharmaceutical composition, comprising:
a therapeutically effective amount of a compound according to claim 1 and
one or more pharmaceutically acceptable carriers.

13. A pharmaceutical combination, comprising:
a therapeutically effective amount of the compound according to claim 1 and
one or more therapeutically active agents.

* * * * *